US012529036B2

(12) United States Patent
Evans et al.

(10) Patent No.: US 12,529,036 B2
(45) Date of Patent: Jan. 20, 2026

(54) SYNTHETIC CHIMERIC VACCINIA VIRUS

(71) Applicant: TONIX PHARMA LIMITED, Dublin (IE)

(72) Inventors: David Evans, Edmonton (CA); Ryan Noyce, Edmonton (CA); Seth Lederman, Austin, TX (US)

(73) Assignee: TONIX PHARMA LIMITED, Dun Laoghaire (IE)

( * ) Notice: Subject to any disclaimer, the term of this patent is extended or adjusted under 35 U.S.C. 154(b) by 1035 days.

(21) Appl. No.: 17/050,946

(22) PCT Filed: May 2, 2019

(86) PCT No.: PCT/US2019/030486
§ 371 (c)(1),
(2) Date: Oct. 27, 2020

(87) PCT Pub. No.: WO2019/213452
PCT Pub. Date: Nov. 7, 2019

(65) Prior Publication Data

US 2021/0230560 A1 Jul. 29, 2021

Related U.S. Application Data

(60) Provisional application No. 62/665,973, filed on May 2, 2018.

(51) Int. Cl.
*C12N 7/00* (2006.01)
*A61K 35/768* (2015.01)
(Continued)

(52) U.S. Cl.
CPC .............. *C12N 7/00* (2013.01); *A61K 35/768* (2013.01); *A61K 39/285* (2013.01);
(Continued)

(58) Field of Classification Search
None
See application file for complete search history.

(56) References Cited

U.S. PATENT DOCUMENTS

| | | | |
|---|---|---|---|
| 2,787,577 | A | 4/1957 | Allisbaugh |
| 4,683,195 | A | 7/1987 | Mullis |

(Continued)

FOREIGN PATENT DOCUMENTS

| | | | |
|---|---|---|---|
| CN | 105121635 | A | 12/2015 |
| EP | 3045181 | | 7/2016 |

(Continued)

OTHER PUBLICATIONS

Domi et al., "Engineering of a vaccinia virus bacterial artificial chromosome in *Escherichia coli* by bacteriophage λ-based recombination," Nature Methods, vol. 2, No. 2: 95-97 (Year: 2005).*

(Continued)

*Primary Examiner* — M Franco G Salvoza
(74) *Attorney, Agent, or Firm* — HALEY GUILIANO LLP; James F. Haley, Jr.; Maha M. Saber

(57) ABSTRACT

The invention relates in various aspects to a synthetic chimeric vaccinia virus or compositions comprising such viruses, and the development and use of systems and methods for producing such synthetic chimeric vaccinia viruses. The synthetic chimeric vaccinia viruses are well suited, among others, as virus vaccines or to generate an oncolytic response and pharmaceutical formulations.

15 Claims, 13 Drawing Sheets
(4 of 13 Drawing Sheet(s) Filed in Color)
Specification includes a Sequence Listing.

(51) Int. Cl.
*A61K 39/285* (2006.01)
*A61K 39/00* (2006.01)

(52) U.S. Cl.
CPC .................. *A61K 2039/525* (2013.01); *C12N 2710/24132* (2013.01); *C12N 2710/24134* (2013.01); *C12N 2710/24143* (2013.01); *C12N 2710/24151* (2013.01)

(56) References Cited

U.S. PATENT DOCUMENTS

| | | | | |
|---|---|---|---|---|
| 4,683,202 | A | 7/1987 | Mullis | |
| 4,754,065 | A | 6/1988 | Levenson | |
| 4,800,159 | A | 1/1989 | Mullis | |
| 6,004,777 | A | 12/1999 | Tartaglia | |
| 6,723,325 | B1 | 4/2004 | Weltzin | |
| 8,795,667 | B2 | 8/2014 | Johnson et al. | |
| 11,345,896 | B2 | 5/2022 | Evans | |
| 12,365,879 | B2 | 7/2025 | Evans et al. | |
| 2004/0014034 | A1* | 1/2004 | Evans | C12N 15/86 435/456 |
| 2009/0053244 | A1 | 2/2009 | Chen et al. | |
| 2013/0216566 | A1 | 8/2013 | Anderson | |
| 2016/0010064 | A1 | 1/2016 | Qin et al. | |
| 2018/0251736 | A1 | 9/2018 | Evans | |
| 2018/0326039 | A1 | 11/2018 | Haruta | |
| 2023/0002741 | A1 | 1/2023 | Evans et al. | |

FOREIGN PATENT DOCUMENTS

| | | | | |
|---|---|---|---|---|
| WO | WO2005028634 | | 3/2005 | |
| WO | WO2005103259 | | 11/2005 | |
| WO | 2006/022215 | A1 | 3/2006 | |
| WO | WO2007093133 | | 8/2007 | |
| WO | WO-2012142529 | A2 * | 10/2012 | A61K 35/768 |
| WO | WO2013038066 | | 3/2013 | |
| WO | WO2014160475 | | 10/2014 | |
| WO | WO2017027757 | | 2/2017 | |
| WO | WO2018057755 | | 3/2018 | |
| WO | WO2018085582 | | 5/2018 | |
| WO | WO2019043282 | | 3/2019 | |
| WO | WO2019213452 | | 11/2019 | |

OTHER PUBLICATIONS

Zhu et al., "The attenuation of vaccinia Tian Tan strain by removal of the viral M1L-K2L genes," Journal of Virological Methods 144: 17-26 (Year: 2007).*

Buller et al., "Decreased virulence of recombinant vaccinia virus expression vectors is associated with a thymidine kinase-negative phenotype," Nature, 317:813-815 (1985).

Baxby, "The origins of vaccinia virus," Journal of Infectious Disease, 136(3):453-455 (1977).

Hendrickson et al., "Orthopoxvirus genome evolution: the role of gene loss," Viruses, 2:1933-1967 (2010).

Josiah et al., "Adipose-derived stem cells as therapeutic delivery vehicles of an oncolytic virus for glioblastoma,"' Molecular Therapy, 18(2):377-385 (2010).

Tonix Pharmaceuticals Press Release "Tonix Pharmaceuticals Announces Demonstrated Vaccine Activity in First-Ever Synthesized Chimeric Horsepox Virus Pre-Clinical Smallpox-Preventing Vaccine Candidate TNX-801 May Qualify for Priority Review Voucher if FDA-Approved Under Provisions in the 21st Century Cures Act," May 2, 2017 (3 pages).

Czub et al., "Evaluation of modified vaccinia virus Ankara based recombinant SARS vaccine in ferrets," Vaccine, 23(17-18):2273-2279 (2005).

Gomez et al., "The Poxvirus Vectors MVA and NYVAC as Gene Delivery Systems for Vaccination Against Infectious Diseases and Cancer," Current Gene Therapy, 8(2):97-120 (2008).

Antoine et al., "The complete genomic sequence of the modified vaccinia Ankara strain: comparison with other orthopoxviruses," Virology, 244(2):365-396 (1998).

Chan et al., "Oncolytic Poxviruses," Annual Review of Virology, 1:191-214 (2014).

Kerrigan et al., "Mesenchymal stromal cells for the delivery of oncolytic viruses in gliomas," Cytotherapy, 19(4):445-457 (2017).

Du et al., "Vaccinia virus DNA replication: two hundred base pairs of telomeric sequence confer optimal replication efficiency on minichromosome templates," PNAS, 93(1):9693-9698 (1996).

Chakrabarti et al., "Compact, synthetic, vaccinia virus early/late promoter for protein expression, " BioTechniques, 23(6):1094-1097 (1997).

Di Pilato et al., "Modification of promoter spacer length in vaccinia virus as a strategy to control the antigen expression," Journal of General Virology, 96(8):2360-2371 (2015).

Earl et al., "Removal of cryptic poxvirus transcription termination signals from the human immunodeficiency virus type 1 envelope gene enhances expression and immunogenicity of a recombinant vaccinia virus," Journal of Virology, 64(5):2448-2451 (1990).

Esparza et al., "Investigations on the historical origin and evolution of the smallpox vaccine," Gac Med Caracas, 128(Supl 1):S88-S97 (2020).

Falkner et al., "*Escherichia coli* gpt gene provides dominant selection for vaccinia virus open reading frame expression vectors," Journal of Virology, 62(6):1849-54 (1988).

Gammon et al., "Vaccinia Virus-Encoded Ribonucleotide Reductase Subunits Are Differentially Required for Replication and Pathogenesis," Plos Pathogens, 6(7):e1000984, pp. 1-20, 2010.

Hartman et al., "SARS-CoV-2 infection of African green monkeys results in mild respiratory disease discernible by PET/CT imaging and shedding of infectious virus from both respiratory and gastrointestinal tracts," PLOS Pathogens, 16(9):e1008903 (2020).

Himly et al., "The DF-1 chicken fibroblast cell line: transformation induced by diverse oncogenes and cell death resulting from infection by avian leukosis viruses," Virology, 248(2):295-304 (1998).

Jenner, "An Inquiry into the Causes and Effects of the Variolae Vaccinae, a Disease Discovered in Some of the Western Counties of England, Particularly Gloucestershire, and Known by the Name of The Cow Pox," Springfield, e-Printed for Dr. Samuel Cooley, by Ashley & Brewer, 1802 (1800) (134 pages) (6 parts).

Kolb et al., "Improvements in the rabbit scarification method for the assay of smallpox vaccine," Bulletin of the World Health Organization, 25(1):19-24 (1961).

Korber et al., "Spike mutation pipeline reveals the emergence of a more transmissible form of SARS-CoV-2," bioRxiv 2020.04.29. 069054 (2020) (33 pages).

Kremer et al., "Vaccinia virus and poxvirology, Methods and Protocols," Second Edition, vol. 890, Humana Press, Totowa, NJ, pp. 59-92 (2012) (339 pages).

Leon et al., "The EB66® cell line as a valuable cell substrate for MVA-based vaccines production," Vaccine, 34(48):5878-5885 (2016).

Lohr et al., "New avian suspension cell lines provide production of influenza virus and MVA in serum-free media: studies on growth, metabolism and virus propagation," Vaccine, 27(36):4975-4982 (2009).

Pallesen et al., "Immunogenicity and structures of a rationally designed prefusion MERS-CoV spike antigen," PNAS, 114(35):E7348-E7357 (2017).

Ralph et al., "2019-nCoV (Wuhan virus), a novel Coronavirus: human-to-human transmission, travel-related cases, and vaccine readiness," Journal of Infection in Developing Countries, 31:14(1):3-17 (2020).

Rice et al., "An efficient method for generating poxvirus recombinants in the absence of selection," Viruses, 3(3): 217-232 (2011).

Roberts et al., "A mouse-adapted SARS-coronavirus causes disease and mortality in BALB/c mice, " PLoS Pathogens, 3(1):e5.doi:10. 1371 (2007).

Sadoff et al., "Interim Results of a Phase 1-2a Trial of Ad26. COV2.S Covid-19 VaccineInterim Results of a Phase 1-2a Trial of Ad26.COV2.S Covid-19 Vaccine," New England Journal of Medicine, 384(19):1824-1835 (2021).

(56) References Cited

OTHER PUBLICATIONS

Subbarao et al., "Prior infection and passive transfer of neutralizing antibody prevent replication of severe acute respiratory syndrome coronavirus in the respiratory tract of mice," Journal of Virology, 78(7):3572-3577 (2004).
Yager et al., "Pathology of Domestic Animals," The skin and appendages, K. V. F. Jubb, p. C. Kennedy, N. Palmer, 4th Edition, vol. 1., Academic Press, San Diego, CA, pp. 531-738 (1993) (787 pages) (4 Parts).
Alzhonova et al., "T cell inactivation by poxviral B22 family proteins increases viral virulence, " PLOS, 10(5):e1004123 (2014) (19 pages).
Aragon et al., "Risks of serious complications and death from smallpox vaccination: a systematic review of the United States experience, 1963-1968," BMC Public Health 3:26 1-12 (2003).
Aragon et al., "The risks and benefits of pre-event smallpox vaccination: where you stand depends on where you sit," Annals of Emergency Medicine, 42(5):681-684 (2003).
Artenstein et al., "A novel, cell culture-derived smallpox vaccine in vaccinia-naive adults," Vaccine, 23: 3301-3309 (2005).
Attwood, "Genomics. The Babel of bioinformatics," Science, 290(5491):471-473 (2000).
Baker, et al., "Protein structure prediction and structural genomics," Science, 294(5540):93-96 (2001).
Baroudy et al., "Incompletely base-paired flip-flop terminal loops link the two DNA strands of the vaccinia virus genome into one uninterrupted polynucleotide chain," Cell, 28(2):315-24 (1982).
Brickmann et al., "Re-assembly of nineteenth-century smallpox vaccine genomes reveals the contemporaneous use of horsepox and horsepox-related viruses in the USA," Genome Biology, 21:286 (2020) (6 pages).
Child et al., "Insertional inactivation of the large subunit of ribonucleotide reductase encoded by vaccinia virus is associated with reduced virulence in vivo," Virology, 174:625-629 (1990).
Couko et al., "Use of carrier cells to deliver a replication-selective herpes simplex virus-1 mutant for the intraperitoneal therapy of epithelial ovarian cancer," Clinical Cancer Research, 5(6):1523-37 (1999).
Damaso, "Revisiting Jenner's mysteries, the role of the Beaugency lymph in the evolutionary path of ancient smallpox vaccines," Lancet, S1473-3099(17)30445 (2017) (9 pages).
DiEuliis, et al., "A Holistic Assessment of the Risks and Benefits of the Synthesis of Horsepox Virus," mSphere, 3(2)e00074-18 (2018)(8 pages).
Draganov, et al., "Delivery of oncolytic vaccinia virus by matched allogeneic stem cells overcomes critical innate and adaptive immune barriers," Journal of Translational Medicine, 17(1):100 (2019).
FDA Briefing Document, "Vaccines and Related Biological Products Advisory Committee Meeting," Sep. 19, 2012 (30 pages).
Frey et al. "Comparison of the safety and immunogenicity of ACAM1000, ACAM2000 and Dryvax in healthy vaccinia-naive adults," Vaccine 27:1637-1644 (2008).
Frey et al., "Clinical responses to undiluted and diluted smallpox vaccine," New England Journal of Medicine, 346:1265-1274 (2002).
Garcel et al. "Phenotypic and genetic diversity of the traditional Lister smallpox vaccine," Vaccine, 27:708-17 (2009).
Garcia-Castro et al., "Treatment of metastatic neuroblastoma with systemic oncolytic virotherapy delivered by autologous mesenchymal stem cells: an exploratory study," Cancer Gene Therapy, 17(7): 476-83 (2010).
GenBank Accession No. AY313847.1, "Vaccinia virus strain Acambis clone 2000, complete genome" (2010) (82 pages).
Greenberg et al., "ACAM2000: a newly licensed cell culture-based live vaccinia smallpox vaccine,"Expert Opinion on Investigational Drugs, 17:555-564 (2008).
Guo, et al., "Oncolytic virotherapy: molecular targets in tumor-selective replication and carrier cell-mediated delivery of oncolytic viruses," Biochimica et Biophysica Acta, 1785: 217-231 (2008).
Hammad et al., "Neural Stem Cell Delivery of a Chimeric Orthopoxvirus in Combination with PD-1 Antibody for the Treatment of Metastatic Ovarian Cancer in Mice," Molecular Therapy, 27(4S1):127-128 (2019).
Imperiale, "Re-creation of Horsepox Virus," mSphere, 3(2)e00079-18 (2018)(1 page).
Jefferson, et al., "The mechanisms of genetically modified vaccinia viruses for the treatment of cancer," Critical Reviews in Oncology/Hematology, 95(3):407-416 (2015).
Kennedy et al., "T-Cell epitope discovery for variola and vaccinia viruses," Reviews in Medical Virology,17: 93-113 (2007).
Kim, et al., "Stem Cell-Based Cell Carrier for Targeted Oncolytic Virotherapy: Translational Opportunity and Open Questions," Viruses, 7(12):6200-6217 (2015).
Koblentz, "A Critical Analysis of the Scientific and Commercial Rationales for the De Novo Synthesis of Horsepox Virux," mSphere, 3(2)e00040-18 (2018)(10 pages).
Koblentz, "The De Novo Synthesis of Horsepox Virus: Implications for Biosecurity and Recommendations for Preventing the Reemergence of Smallpox," Health Security, 15(5):620-628 (2017).
Komarova et al., "Mesenchymal progenitor cells as cellular vehicles for delivery of oncolytic adenoviruses," Molecular Cancer Therapeutics, 5(30:755-766 (2006).
Kupferschmidt, "A paper showing how to make a smallpox cousin just got published. Critics wonder why," downloaded from http://www.sciencemag.org/news/2018/01/paper-showing-how-make-smallpox-cousin-just-got-published-critics-wonder-why on May 25, 2018 (Jan. 19, 2018) (11 pages).
Kupferschmidt, "How Canadian researchers reconstituted an extinct poxvirus for $100,000 using mail-order DNA," Science Magazine (2017) (5 pages).
Kushner, "Synthetic Biology Could Bring a Pox on Us All," Science, (18 pages) (2019).
Li et al., Genomic sequence and analysis of a vaccinia virus isolate from a patient with a smallpox vaccine-related complication, Virology Journal, 3:88; 9 pages (2006).
Li et al., "Recovery of a chemically synthesized Japanese encephalitis virus reveals two critical adaptive mutations in NS2B and NS4A," Journal of General Virology, 94(Pt. 4):806-815 (2014).
Li et al., "On the origin of smallpox: correlating variola phylogenies with historical smallpox records," PNAS, 104:15787-15792 (2007).
Loy, "An Account of Some Experiments on the Origin of the Cow-Pox," Webster (1801) (29 Pages).
Mack et al., "A prospective study of serum antibody and protection against smallpox,"The American Journal of Tropical Medicine and Hygiene, 21: 214-218 (1972).
Marriott et al., "Clonal vaccinia virus grown in cell culture fully protects monkeys from lethal monkeypox challenge," Vaccine, 26: 581-588 (2008).
Medaglia, et al., "Genomic analysis, phenotype, and virulence of the historical Brazilian smallpox vaccine strain IOC: Implications for the origins and evolutionary relationships of vaccinia virus," Journal of Virology, 89:11909-11925 (2015).
Merkel et al., "Development of a highly efficacious vaccinia-based dual vaccine against smallpox and anthrax, two important bioterror entities," PNAS, 107:18091-18096(2010).
Monath et al., "ACAM2000 clonal Vero cell culture vaccinia virus (New York City Board of Health strain)—a second-generation smallpox vaccine for biological defense," International Journal of Infectious Diseases, 8(Supp 2)S31-S44 (2004).
Morikawa et al., "An attenuated LC16m8 smallpox vaccine: analysis of full-genome sequence and induction of immune protection," Journal of Virology, 79:11873-11891 (2005).
Murphy et al., "Adventitious Agents and Smallpox Vaccine in Strategic National Stockpile," Emerging Infectious Diseases, 11(7):1086-1089 (2005).
Nalca et al., "ACAM2000: the new smallpox vaccine for United States Strategic National Stockpile," Drug Design, Development Therapy, 4:71-79 (2010).
Noyce et al., "Construction of an infectious horsepox virus vaccine from chemically synthesized DNA Fragments," PLOS One, 13(1):e0188453 (2018) (16 pages).

(56) References Cited

OTHER PUBLICATIONS

Noyce, et al., "Synthetic horsepox viruses and the continuing debate about dual use research," PLoS Pathogens, 14(10):e1007025 (2018) (5 pages).
Oldfield et al., "Genome-wide engineering of an infectious clone of herpes simplex virus type 1 using synthetic genomics assembly methods," PNAS, 114(42):e8885-e8894 (2017).
Osborne et al., "Genomic differences of Vaccinia virus clones from Dryvax smallpox vaccine: the Dryvax-like ACAM2000 and the mouse neurovirulent Clone-3," Vaccine, 25:8807-8832 (2007).
Paez et al., "Stability of vaccinia virus DNA during persistent infections: accumulation of left-end deletions and of tandem repeats at both ends of the viral genome and prevention by interferon," Virology, 163(1):145-154 (1988).
Park et al., "Phase 1b Trial of Biweekly Intravenous Pexa-Vec (JX-594), an Oncolytic and Immunotherapeutic Vaccinia Virus in Colorectal Cancer," Molecular Therapy, 23(9):1532-2540 (2015).
Qin et al., "Evolution of and evolutionary relationships between extant vaccinia virus strains," Journal of Virology, 89(3):1809-1824 (2015).
Qin et al., "Genomic analysis of the vaccinia virus strain variants found in Dryvax vaccine," Journal of Virology, 85(24):13049-013060 (2011).
Ramírez, et al., "Patient-derived mesenchymal stem cells as delivery vehicles for oncolytic virotherapy: novel state-of-the-art technology," Oncolytic Virotherapy, 4:149-155 (2015).
Sam et al., "Expression of poxvirus DNA in coinfected cells and marker rescue of thermosensitive mutants by subgenomic fragments of DNA," Annales de 1Institut Paseur/Virologie, 132(2):135-150 (1981).
Sarkar et al., "The minimum protective level of antibodies in smallpox," Bull World Health Organ, 52:307-311 (1975).
Scheiflinger et al., "Construction of chimeric vaccinia viruses by molecular cloning and packaging, " PNAS, 89(21):9977-81 (1992).
Schrick et al., An Early American Smallpox Vaccine Based on Horsepox, New England Journal of Medicine, 377(15):1491-1492 (2017).
Shvalov et al., "Complete Genome Sequence of Vaccinia Virus Strain L-IVP," Genome Announcements, 4(3):e00372-16 (2016).
Tcherepanov et al., "Genome Annotation Transfer Utility (GATU): rapid annotation of viral genomes using a closely related reference genome," BMC Genomics, 7:150 (2006) (10 pages).
Tonix Pharmaceuticals Press Release "Tonix Pharmaceuticals Announces Publication Reporting Synthesis, Construction and Characterization of a Potential Smallpox-Preventing Vaccine Candidate TNX-801 (Live Horsepox Virus from Cell Culture), " Jan. 19, 2018 (4 pages).
Tulman et al., "Genome of horsepox virus," Journal of Virology, 80(18):9244-9258 (2006).
Walsh et al., "Vaccinia viruses: vaccines against smallpox and vectors against infectious diseases and tumors," Expert Review of Vaccines, 10:1221-1240 (2011).
Weltzin et al., "Clonal vaccinia virus grown in cell culture as a new smallpox vaccine," Nature Medicine, 9(9):1125-1130 (2003).
WHO Advisory Committee on Variola Virus Research: Report of the Eighteenth Meeting, Nov. 2-3, 2016, Geneva, Switzerland, World Health Organisation, ww.who.int/csr/resources/publications/smallpox/variola-research-november-2016, Chapter 18, pp. 29-31 (downloaded Jan. 30, 2017) (58 pages).
Yao et al., "Construction of recombinant vaccinia viruses using leporipoxvirus-catalyzed recombination and reactivation of orthopoxvirus DNA," Methods in Molecular Biology, 269:51-64 (2004).
Yao et al., "High-frequency genetic recombination and reactivation of orthopoxviruses from DNA fragments transfected into leporipoxvirus-infected cells," Journal of Virology, 77(13):7281-7290 (2003).
Zhang et al., "Eradication of Solid Human Breast Tumors in Nude Mice with an Intravenously Injected Light-Emitting Oncolytic Vaccinia Virus," Cancer Research, 67(20):10038-46 (2007).
Willer et al., "The complete genome sequence of shope (rabbit) fibroma virus," Virology, 264(2):319-343 (1999).
Becker et al., "Synthetic recombinant bat SARS-like coronavirus is infectious in cultured cells and in mice," PNAS, 105(50):19944-9 (2008).
Cello et al., "Chemical Synthesis of Poliovirus cDNA: Generation of Infectious Virus in the Absence of Natural Template," Science, 297:1016-1018 (2002).
Tumpey et al., "Characterization of the Reconstructed 1918 Spanish Influenza Pandemic Virus," Science, 310:77-80 (2005).
Wimmer et al., "Synthetic viruses: a new opportunity to understand and prevent viral disease," Nature Biotechnology, 27(12):1163-72 (2009).
Kettle et al., "Vaccinia virus serpins B13R (SPI-2) and B22R (SPI-1) encode Mr 38.5 and 40K, intracellular polypeptides that do not affect virus virulence in a murine intranasal model," Virology, 206:136-147 (1995).

* cited by examiner

VACV WR 70bp repeat region in the ITR

FIG. 3A

WR DUPLEX DNA

*Duplex Sequences*

5'-/5Phos/TGTGTGACCCATGACTGTAGGAAACTCTAGAGTGTAAGAAAGATCGATCGCTTTATAGAGA-3'

5'-/5Phos/TGGTCTCTATAAAGCGATCGATCTTTCTTACACTCTAGAGTTTCCTACAGTCATGGGTCAC-3'

```
5'- TGTGTGACCCATGACTGTAGGAAACTCTAGAGTGTAAGAAAGATCGATCGCTTTATAGAGA -3'
       ||||||||||||||||||||||||||||||||||||||||||||||||||||||||||
   3'- CACTGGGTACTGACATCCTTTGAGATCTCACATTCTTTCTAGCTAGCGAAATATCTCTGGT -5'
```

FIG. 9

A VACV strains nucleotide sequence variations within the duplex region in the ITRs

```
WR          GTCACCCATGACTGTAGGAAACTCTACAGTGTAAGAAAGATCGATCGCTTTATAGACA   58
ACAM2000    GTCACCAACGACCCTAGGAAACTCTACAGGGTAAGAAAAATCAATCGCTTTATAGACA   58
Dryvax      GTCACCAACGACCCTAGGAAACTCTACAGGGTAAGAAAAATCAATCGCTTTATAGACA   58
Copenhagen  GTCACCAACGACCCTAGGAAACTCTACAGGGTAAGAAAAATCAATCGCTTTATAGACA   58
            ****** * *** **************** ******** *** **************
```

B ACAM2000 terminal hairpin loop sequences

S Form

5'- ACATTTTTTTCTAGACACTAAATAAATATTTAAAATATAATATTAATATACTAAAATTTATGTAT
TATTAATTTATCTAACTAAAGTTAGTAAATTATATACATAATTTTATAATTAATTTAATTTTACT
ATTTATTTAGTGTCTAGAAAAAAA -3'

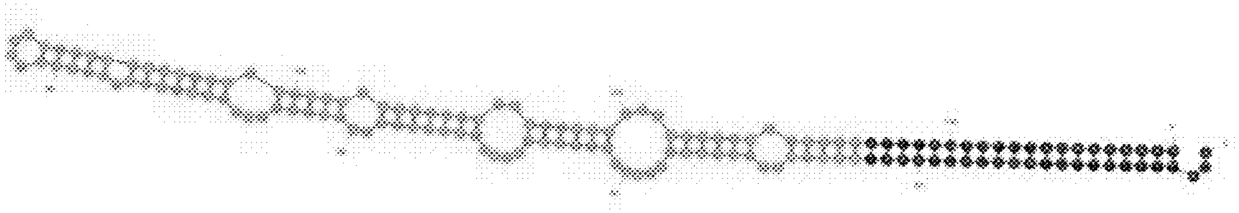

F Form

5'- ACATTTTTTTCTAGACACTAAATAAATAGTAAAATTAAATTAATTATAAAATTATGTATATAATT
TACTAACTTTAGTTAGATAAATTAATAATACATAAATTTTAGTATATTAATATTATATTTTAAAT
ATTTATTTAGTGTCTAGAAAAAAA-3'

SEQUENCE LISTING

```
<160> NUMBER OF SEQ ID NOS: 22

<210> SEQ ID NO 1
<211> LENGTH: 18525
<212> TYPE: DNA
<213> ORGANISM: Vaccinia virus

<400> SEQUENCE: 1

tagggataac agggtaatga agaagctctt cgccagaagc tagcaagagg tttaatattt     60

ttgtgagacc atcgaagaga gaaagagaat aaaaatattt tatgactcca ttgaagagag    120

aaagagaaaa tgagaatgag aataaaaata ttttagtgac accatcagaa agaggtttaa    180

tatttttgtg agaccatcga agagagaaag agaataaaaa tattttatga ctccattgaa    240

gagagaaaga gaaaatgaga atgagaataa aaatatttta gtgacaccat cagaaagagg    300

tttaatattt tttatgagac catcaaagag agaaagagaa taaaaatatt tttgtaaaac    360
```

```
tttttttatg agaccatcaa agagagaaag agaataaaaa tatttttgta aaactttttt    420
tatgagacca tcaaagagag aaagagaata aaaatatttt tgtaaaactt tttttatgag    480
accatcaaag agagaaagag aataaaaata tttttgtaaa acttttttta tgagaccatc    540
aaagagagaa agagaataaa aatatttttg taaaactttt tttatgagac catcaaagag    600
agaaagagaa taaaaatatt tttgtaaaac tttttttatg agaccatcaa agagagaaag    660
agaataaaaa tatttttgta aaactttttt tatgagacca tcaaagagag aaagagaata    720
aaaatatttt tgtaaaactt tttttatgag accatcagaa agaggtttaa tatttttgtg    780
ataccctgaa aggaaatagg aataggaata ggaatagtgt cataatcgta tcacactatt    840
gagacagaaa aagaagaagt cgcgagaggt aactttttgt gaatgtagtt aagaacattt    900
ttgttttgca aaccggaata tagtgtccgg tacacttttt taattcgtgg tgtgcctgaa    960
tcgttcgatt aaccctactc atccaatttc agatgaatag agttatcgat tcagacacac   1020
gctttgagtt ttgttgaatc gatgagtgaa gtatcatcgg ttgcaccttc agatgccgat   1080
ccgtcgacat acttgaatcc atccttgacc tcaagttcag atgattcctt gcacatgtct   1140
ccgatacgaa cgctaaactc tagattcttg acgcattttg tatcgacgat cgttgaaccg   1200
atgatatctt cgtaactcac tttcttatga gagatgttag acccgagtac tggatgggtc   1260
ttgatgtcgc tgtctttctc ttcttcgcta catctgatgt cgatagacac ctcacagtct   1320
ttgatcatag caagagcttc ttcatgagtg atcgcgggag agtccttacc ttgtcctggg   1380
gacacgctgg acaatctagc attcactgtg tttccatcag cggattctga gatggattta   1440
atctgaggac atttggtgaa tccaaagttc attctcagac ctccaccgat gatggagtaa   1500
taagtggtag gaggatctac atcctcgact gatgtggaat catcttctga ttccacctcg   1560
ggatctggat ctgactcgga ctctgtaatt tccgttacgg attggcaaat cttatcattg   1620
gtcggtgttt ggtcttgctt tgtgactttg ataataacat cgattcccat atgatgtttg   1680
ttttcttctt ccgtacacga ggaggaggat tgctgaagac tggcaggcac atgcatgcca   1740
ggacgatata ttgtttcatg attgctattg attgattact gttctttatg attctacttc   1800
cttaccgtgc aataaattag aatatatttt ctacttttac gagaaattaa ttattgtatt   1860
tatgggtgaa aaacttacta taaaaagcgg gtgggtttgg aattagtgat cagtttatgt   1920
atatcgcaac taccgggcat atggctatcg acatcgagaa cattacccac atgataagag   1980
attgtatcag tttcgtagtc ttgagtattg gtattactat atagtatata gatgtcgacg   2040
ctagatagac agtctccgaa tgcggcatga tagtatcatt ctttgctttc gttaactgtt   2100
tggaggaaga atctttgtta ttgcatttaa tctcgaaatt cagagtgcac acctttctcc   2160
tgtaaagaaa cctgaagttg ctaccttatt aaggacagag aagtatccat cacgaaagac   2220
gggatcgcag tctttatgat tcatagtaat agttagttcc gacgttgaga tggattcgct   2280
gagaccggta gtggtcgtcc gagtacacga tgtgtcgtta actggataca ggttaatttc   2340
cacatcgata tagttaaacg tatttctggg tacgggttcg catttatctg cggaagagac   2400
ggtgtgagaa tatgttccga gaccacacgg agaacagatg acgtctccgg atactccgta   2460
tcctattcca cattttgttt gggaaacaca tgccttgcat ccggatgatc ctttgagaag   2520
acaataatat ccgggagagc attcacagat tctattgtga gtagtgttac acgatcgcat   2580
cttccgttac aacttagaca agcgggtaaa tgattattgc gagatgtgaa ggtacccgaa   2640
ccacacggcg tacattgtgt gttagtcttg ctatcgcata atctggaagc gtatgttccc   2700
ggacacaaat tatggcgttt gtattcgttg tctttacact ttccatcgga tggtgcatgc   2760
```

```
ggtgctatat ctcttccgtt tattattata catgagagaa acaatatata cgagtataat   2820
acggacttca taatttaata atgtagtaat cgttgtcttg ttcctgtttc ctacttctcc   2880
aatcatatag atattttctt tctatcatgg ataatatttg taatggttct ttccgtacaa   2940
catactgttt agatgatatt gcgcataatt tccggaggca aatacgatag tctagattgg   3000
ccatcgatgg tagactctaa tttattgagt gctttgtcga cgagtttact tttacgctcc   3060
atcgatagat ggcactgttc tatgagatcg tcgtacatgg gaaatgaaat gtgactgtct   3120
gaatgtatgg ctttaagata gctgtgatac cgtatacagg tcggtgtcgg agattcgaat   3180
ctctttaagg cgacttatgt cacgatgatg gaatctatct tatcgaatga tatatttttc   3240
ataaatacac ttttatagtc ctcgtttaaa cagaatttac tatgtagttc cgcgaatgac   3300
tcgtccctta ataggcagta ggctagtatc ttttttacgt agtaatcgtc gtagggagag   3360
aattctgaca tcttgtagaa caacgattta atcataggta ctttcagtct gtggtggatg   3420
atgtcattca caacatccgc cttgtatatg atgtttctgt tttcaaacac caagtcgaat   3480
accgtcttta gtcggaaggt tgatgtcgta tccgatgtat gaggcaacat tgttgttaca   3540
attttgaaag gcggtattat aatattcgtc tttctgaatg tcgaacctat ctagtagata   3600
ccgtagtata ttgagagtgt atccttgatt atgttttatg aatagataaa gtagatgttg   3660
tccttcttcc ttttgttcgt gccaattgag taacattatg agaatatgac ctgttgcaca   3720
atcgttccat gatgggtgta caatcaagat tattacgtat cctcgagata aaagagcata   3780
caccacacga ggactatgtt tggtatactg ttgaaggtaa gtgtgtaacg gcgttaatgt   3840
ttgctccata atctattatc gcgtagatga atcgcttctc ggctcgcatc ttagtgtgac   3900
ttgacttgta ataattgctt ttgtagaacg tggatatgtg tttacagtag taatgaagag   3960
aagtgagttc atcctcgtcg gcgcaattag ggtcggatcc tttgtacaga acgtaatagt   4020
ttaagctccc attgaattta tatctaagat aacacagcaa tagatcggat gatttactaa   4080
agtcatcaat ggtgtccgtt agtatatcaa agatcttgtt atcgattgat agtggtcatc   4140
cttgctatca aagttacgca tgccgtggtg taacaatatc tttaatacag atggattaaa   4200
tcgtgtattc atcgtatagc aatgtaatgg agagttacct cgtttattca gatcgcagtg   4260
tttaataact agcttaaaca gatgagacga tgtatccaca tcaaagaacg taaaatacat   4320
atgacaaaca ttgttgacag aaacgtgacc ttcattctta ccgtcgtcca taaatacgtt   4380
aggtatgtac cacatactgt cgcgaacgat gcgtacaatc tcgtccatct cataatgatt   4440
tactttttca taattaaaga tgtgaaagaa aaccgaacaa tatatttttt tagtaatgtt   4500
tatgcgagac atataaaata aactccgtgt ttatgatgcc ggtaaatgtt tttatcatct   4560
tggacggaat cgattttgta atatgtcatg gaaacaaatg aaacaggaca ttatcgctcc   4620
atgataaatt atttaatgga gtaataaagt atctccatgg gtaatttcga aatcaagtta   4680
tcgtctgtat taatgttgtc cactatggag tcgatcctct cattgttctt tacagtttct   4740
gtaatgatgg acgttagttc ttttttgtac catttgatgt cggattcttt gcgtatctca   4800
atctgtggcg tttgcttcgt ttaaataata tatcaaacat ggagacgcct gatatgtagg   4860
cattcttcat tctattaatg tctactctat agcgctttag ttccttatga cgaccggcga   4920
tatcatactt tactttagaa ggaaaatcat catctatgat taaggcgtat ctgatacagg   4980
cgaataatgg ttcaggatat agatagcgta tatctctatt aaatgcgtca atcatagtct   5040
ctagagtggg atggtagcta agtaataaat caactagctt cgttttgttt tctcttctgt   5100
```

-continued

```
aactactttt ctggatggcc gtattgatta tcgagcgtga tgttgtaaca ctcgctccat   5160
attccaataa ccgctttgca aattgtatat tattgacatc gaccgcgtaa tatagtagag   5220
ttttattctc attatcgatc atatctatat tatccatgta cttgcttagt atatcaaata   5280
catctattag tatggtttca taacagtgat acccgcaatt attaaatctc gataatatca   5340
gaccgtacat acatagacgg ccattgttag atatgtgatt tacagccgcg tgtccatatt   5400
ttccacgata aaccttacga cgtttacatc gacgagatta ttattaacaa agtagtcgtg   5460
cagaggatag ttgttgtccg ttatctaaca tgcatcgaac gaccatatcg ccgtaatgta   5520
agtagtttat caacatggct tgtacgatgg attcatcctg ttgtctaaat ctctttagaa   5580
tgttatcgat gatgtagtgg ttatattctc tggaatcgta cgaagtaata ctacgcatta   5640
cgtcgacaag agtatgacgt ctctcaataa gaagattaac gatttccatg tctacattat   5700
atggggttac tctaaatcgc ttgtttagat aatacgcctc taatataggg ctgacgtcgt   5760
atactctaca cgtgtccaca tcctttatta ataataattt aacaatctct atatctatgg   5820
ttgagaaaga ccagtagtat tggatgggta aagatcctcc ttcgtctctg ccatggatgg   5880
aaacattgtt attgatcaaa catttaatta catccttgga tagagattga gattctctat   5940
gagacgatat atagtaatga agagagttct tacacatatc actgttgtac atacaggtac   6000
gaaatacgta accggtgctg taacattctg atttaagaag ccatagcaat acttctggtc   6060
tcggattagg cgtcgttacg tatatatcca ccaatccgag accattgatt gcataattcg   6120
tattcttgga cggacgtatc cgtttatcca caattaggta ttttagcaga cgtaagtcga   6180
tattatccga atacagatcg aaatcattta tattcgactt gagttcgtta gaggaattcg   6240
aatagctgga tatcagtaga tgcacaattt gagatttgac gtatctatgc ttactgtata   6300
ctcctagcgg agttaatcct tcgttgtttc tacaaagtct ctcgactccg cgagagagta   6360
acagtcgaac aatcttaatg tctgtatcgc atttattgaa gacgtaacaa tgtagcgcat   6420
tgtttcctcg tctatctata tgttttgata agttgtgaca cgtttcaatt tctagtttta   6480
tttttttgta cgtcacatct tcatccagta gacgacatag aatacatgtg caatccatag   6540
ctattctggt gctaattatt cctatttcac gaaaaatgat gaaggcaatc attcctcata   6600
agatgataaa aagtgtagtg agagagcatg aaggagattt agtatttagc agtgcggata   6660
tgatccaaga gggtgagata gtcgttctcg ttcagaatct ttcgcagcat aagtagtatg   6720
tcgatatact tatcgttgaa gactcttcca gagacgatag ctgattgagt acaaagtcca   6780
atgattgcac gaagttcttc ggcggttttc atggagtcat ttctgatgaa acatttaatg   6840
atctccacgc aattgtcgat attgtcccac ggaagtgaat ccttcaactc accaccaaag   6900
agctccgttg catcagttct gaaagagatg agaagcctgt agagaggccc tgcagtttct   6960
ctatgggtcc atctatgaga aacccacagg atgtattcag tcagacaatg tctgacgtcg   7020
gccacggtat tcagggagtc cttagtagcg tggcaatgac agggtctgaa ctgggcacaa   7080
ggaaaggcca ttgtaaaggt agacctgtag ccgtttatgc taatagaggg ctttaatttc   7140
catttttta atgggttgtg gatgaggaat gagagtgata tcatattgag atacgtagtt   7200
atgtagaggt gtatttccta tattatttac tttcggtttc atattttacc aactctttaa   7260
taaatttctt ttcacgatgc atcttattaa atgacgtttt ctcataagtg gacatataga   7320
tgcagaagta atgaagaaaa gtattacctc tatcatctgc ataattaggg tctgctcctt   7380
ttcttaacaa cttatacagt acgtagtagt ttatcggttt taaatcaagt ctagaatata   7440
tagtggatta atatattttt atattagcta aagctatcta tactatcaga aagcatatca   7500
```

ttctcaactt catcatgagt taaatatttg tgtaatggaa tgtgaccatc actgtcatga 7560
catactcctt taataggttt tttaaaacag atgattcaaa tccttcattc attagataac 7620
agtgtaacgg agtcgtacct tctactagtt tgtttatatc acagcattct acaaacagtc 7680
taaacaatag agaagacgga cagactttaa cgtataaatg acacatgtta tcgatattcg 7740
ttgatgaatt attattaaac gtagttatga taaatgattc taacgacatc tctcgctaga 7800
gataaaatct agtatcgtat cattaaacat ctttgcatca tactcgcata gcatagtttt 7860
tcataattaa tacaatattt aaaagactta ttcggaaagt attttaatac atgtatcatc 7920
gatggagatc catatgagga gtcacttgta gttcttcagt agtaataaca gtgctatcat 7980
cgatagtata attatatgta gaaggttcat atgttgttgt aattggagta actgttggta 8040
gttcttccgt ggaatcaata attatactaa cagcaatagt ataattatat aaatatgttc 8100
cgttgatatc acatatttta atgaactcat ttctaacacc ctcagctata tctgtccaat 8160
taaatgtagc caacaatcta ctacgttctc tttgattgac tacttgtacg gtagcgacgc 8220
tacactatct ttattgtctt ctacatgctc caattgaatg tcatgataca acgcagtttt 8280
tcttatgcat gtttcataac accacgaaca tgtcgcagta agatatatag ccagagataa 8340
tttctgtaaa ttcatgattg ccggtcataa acaagcccgt caataattgt ggctatatat 8400
tcagtttata gagcaaaata attaagcaca atagcgctta atctcaaaat atgttatgtt 8460
tatttttttc atattaaaca tactggttaa aatcctctaa aggctgatct tcatctataa 8520
atcaagatca taattacatt tagacagtgg tttcatgttt ataaaaatgt tctttttgtg 8580
tgaataagga atatactaat caataatcaa ccatcgaccc cattacgata gtatgcaggc 8640
aaccccccat tagagaggta cgtgtaatca gtctctccag ttttagtatt tttataagtc 8700
attgttacat aaacggcttt taaacagtct cctcgataat aagccatatc tggaaattta 8760
ttaaatactc gagtcatttt acgcacggtc aaaaaagtaa gtaatgtcga cgacttctta 8820
cattctatag aaacacctag aatactcatt ttcttttgga aaatatcctc agactctgat 8880
ttgaacaatg cacgacctat agtaaaccgt gaccaataag ttatattagt caatggtata 8940
tccaaaccat caggtgtgga tagtacgccg atagtccagt ctttggtatc gatagtgtag 9000
ttattgaact gagaagttac cgtatagtct ttttggtcat ctctaaacaa ggaaactaat 9060
acctctacac tattgaacga tttatcttcc gtaatgggtg gaataacggg aatataaagt 9120
ggactagcga tggatgaagt cacgaatata agacacgcta ttaatccgta tatcatcatt 9180
ttgatattac ttataataac gatttgttta atttttagtt tatactatta attgtaaatg 9240
atattattat ttttttaagt attatcagct ttagtttata ctatttgtaa tatttagaca 9300
tagataaacg tgataaaagt ctatttgttt atatttattg cggatagcag tatttcccta 9360
taaaaagtat acgtcctgtg ttgtctttaa tcatgtacat gaatggatgg tttatgtaga 9420
ccttcgtacg atataccatc gaaaagttag tcataaatac tcctgtaacg gccgatgctt 9480
ctgtatactc ctcattaaca tctataaacg tcgtatgtag aaatttttct acagtgatag 9540
tttcattaca catcttgcta aaatctgcat aatatccgaa tatattagta agtcctaaat 9600
tttctagaat aggtaccaga ttatacggtt ctgtcatttc cactttaaac tttggcatat 9660
acaagtctat acttttagta gataacatac cacaccattt tttaaatttt tcatctgtta 9720
tatttttttc tatgttatat ataccttcta tgtcgtccgg tagtataatc accatactag 9780
agtttccctc gtatggaata tcgataatag agaatcctcc gaataattca ttaatatgta 9840

```
catattgcaa gttattctcg gtacccacca tcatatcaac gctggtaact atattcttag   9900
aaatataaaa cttgtctgta tatgtaagat gtttagaaaa tggatatttc cacattgctt   9960
taaaatggac ggcgctaaca actgtcatac gagtattaat ggatagcgga ctagtcaata  10020
aggaattaat tttaccattt gtcattgtct taacccattc gttgattagt tcctttgttt  10080
ggttagcatt attaaagttt acagtttgaa aatcgtcttt tattttttgt aggaaggagg  10140
catggaactc gatactatcg ctaccgtata ttttatttgc ggtagctagt gtcgcacaat  10200
acggaatatc tacgtccatg tcattattgt catccttctt atcatcgggt gtattctcat  10260
tcatattctc tatatatttt gatagttgtt cagctgtaga accagctgct ccatgattta  10320
gaatagataa agtagataaa atggaaactg gagaaatcaa aacattttca tcagggtgtt  10380
ttacgattag ttctttaaag atatccatgg tatagaccaa acaataacga taacgatata  10440
tatcataaat aaataatgtt aaatttcagt ttatgtttgt accccgtatt catacttaac  10500
aaattggtat tacataccat taataatgca agcataaaaa atcgttagta gatgtttcta  10560
aatataggtt ccgtaagcaa agaatataag aatgaagggt aatgataaaa tcaatcgtta  10620
tctaaaatga tcatactcat ttattttatt ctattatatt aacacataca tttttaacag  10680
caacacattc aatattgtat tgttattttt atattattta cacaattaac aatatattat  10740
tagtttatat tactgaatta ataatataaa attcccaatc ttgtcataaa cacacactga  10800
gaaacagcat aaacacagaa tccatcaaaa atgtcgatga aatatctgat gttgttgttc  10860
gctgctatga taatcagatc attcgccgat agtggtaacg ctatcgaaac gacattgcca  10920
gaaattacaa acgctacaac agatattcca gctatcagat tatgcggtcc agagggagat  10980
ggatattgtt tacacggtga ctgtatccac gctagagata tcgacggtat gtattgtaga  11040
tgctctcatg gttatacagg cattagatgt cagcatgtag tattagtaga ctatcaacgt  11100
tcagaaaaac caaacactac aacgtcatat atcccatctc ccggtattat gcttgtatta  11160
gtaggcatta ttattatgtg ttgtctatta tctgtttata ggttcactcg acgaactaaa  11220
ctacctctac aagatatggt tgtgccataa tttttataaa ttttttttat gagtattttt  11280
acaaaaatgt ataaagtgta tgtcttatgt atatttataa aaatgctaaa tatgcgatgt  11340
atctatgtta tttgtattta tctaaacaat acctctacct ctagatatta tacaaaaatt  11400
ttttatttca gcatattaaa gtaaaatcta gttaccttga aatgaatac agtgggtggt   11460
tccgtatcac cagtaagaac ataatagtcg aatacagtat ccgattgaga ttttgcatac  11520
aatactagtc tagaaagaaa tttgtaatca tcttctgtga cgggagtcca tatatctgta  11580
tcatcgtcta gtttatcagt gtcccatgct atatttctgt tatcatcatt agttaatgaa  11640
aataactctc gtgcttcaga aaagtcaaat attgtatcca tacatacatc tccaaaacta  11700
tcgcttatac gtttatcttt aacgatacct atacctagat ggttatttac taacagacat  11760
tttccagatc tattgactat aactcctata gtttccacat caaccaagta atgatcatct  11820
attgttatat aacaataaca taactctttt ccatttttat cagtatgtat atctatatca  11880
acgtcgtcgt tgtagtgaat agtagttatt gatctattat atgaaacgga tatgtctaga  11940
acggcaattg tcttacgtcc agttaacact ttctttgatt taaagtctag agtctttgca  12000
aacataatat ccttatccga ctttatattt cctgtagggt ggtataattt tattttgcct  12060
ccacatatcg gtgtttccaa atatattact agacaatatt ccatatagtt attagttaag  12120
ggtacccaat tagaacacgt acgcttatta tcatcatttg gatcgtattt cataaaagtt  12180
attgtgttat cgatgtcaac acattctaca ttttttaatc gtctatatag tatttttctg  12240
```

```
atattttcta taatatcaga attgtcttcc atcggaagtt gtatactatc ggaatcagtt  12300
acatgtttaa ataattctct gatgtcattc cttatacaat caaattcatt attaaacagt  12360
ttaatagtct gtagaccttt atcgtcgtaa atatccattg tcttattagt tacgcttatt  12420
tttatgtgtt tttacgttga tttattatat tttataagaa tgattgtttg acgaatcacg  12480
agaactatta agacacatta ttaggtatat attataaaaa agtttttgat tacgatgtta  12540
taagaggaaa gaggacacat taacatcata catcaattaa ctacattctt ataacatcgt  12600
aatcaaaaga attgcaattt tgatgtataa caactgtcaa tgggttatgg aattgtatat  12660
tacatattat acggtatgtt ggtaacgaca aataccgatc ggtaattgtc tgccggtgta  12720
atagaattat atatatctat ctattacacc ggccttgtat acataataat aagttgtggt  12780
agtatgatct ccatatttat aatttaggac tttgtattca gtatttttgg aatcataaaa  12840
aataaaaaaa agttttacta atttaaaatt taaaaagtat ttacattttt ttcactgttt  12900
agtcgcggat atggaattcg atcctgccaa aatcaataca tcatctatag atcatgtaac  12960
aatattacaa tacatagatg aaccaaatga tataagacta acagtatgca ttatccgaaa  13020
tattatatca atatcacaaa aataaatcca catttggcta atcaatttcg ggcttggaaa  13080
aaacgtatcg ccggaaggga ctatatgact aacttatcta gagatacagg aatacaacaa  13140
tcaaaactta ctgaaactat acgtaactgt caaaaaaata gaaacatata tggtctatat  13200
atacactaca atttagttat taattggata accgatgtga ttatcaatca atattaagaa  13260
ggttggtaaa ttggtacata gctaataata cctatacacc caataataca acaaccattt  13320
ctgagttgga tatcatcaaa atactggata aatacgagga cgtgtataga gtaagtaaag  13380
aaaaagaatg tggaatttgc tatgaagttg tttactcaaa acgatagata ctttggttta  13440
ttggattcgt gtaatcatat attttgcata acatgtatca atatatggca taaaacacga  13500
agagaaaccg gtgcgtcgga taattgtcct atatgtcgta cccgttttag aaacataaca  13560
atgagcaagt tctataagct agttaactaa taaataaaaa gtttaatttg ttgacgacgt  13620
atgtcgttat ttttctcgta tgaaagatta aattcaattc aattcgttgt ttctaatata  13680
atctgccgta ttggatggat tctcaagaca attgcattta gattatatca taaataaaaa  13740
tagtagcaca caactacttc agcaaacatt ctttttataa atgccatcta tcgtagtgag  13800
gacacaagtg aacctataat gagcaaattt attagtatcg gttacatgaa ggactttctg  13860
tagagtgacg attctaccat ctatggtacg aacggtttca tcttctttga tgccatcacc  13920
cagatgttct ataaacttgg tatcctcgtc cgatctcata tcctttgcca accaatacat  13980
gtagctaaaa ttaggcataa atttcacaca tccagtgcaa cgaaattctc cagaagatgt  14040
tacgatgttt aggttaggac atttgatttc gtcggcatta acatatgggt gaacacaccc  14100
atacatgaag gcgatgagaa ataggattct catcttgcca aaatatcact agaaaaaatt  14160
tatttatcaa ttttaaaggt ataaaaaata cttattgttg ctcgaatatt ttgtatttga  14220
tggtatacgg aagattagaa atgtaggtat tatcatcaac tgattctatg gttttatgta  14280
ttctatcatg tttcactatt gcgttggaaa taatatcata tgcttccaca tatattttat  14340
tttgttttaa ctcataatac tcacgtaatt ctggattatt ggcatatcta tgaataattt  14400
tagctccatg atcagtaaat attaatgaga acatagtatt accacctacc attatttttt  14460
tcatctcatt caattcttaa ttgcaaagat ctatataatc attatagcgt tgacttatgg  14520
actctggaat cttagacgat gtacagtcat ctataatcat ggcatattta atacattgtt  14580
```

```
ttatagcata gtagttatct acgatgttag atatttctct caatgaatca atcacataat  14640
ctaatgtagg tttatgacat aatagcattt tcagcagttc aatgttttta gattcgttga  14700
tggcaatggc tatacatgta tatccgttat ttgatctaat gttgacatct gaaccggatt  14760
ctagcagtaa agatactaga gattgtttat tatatctaac agccttgtga agaagtgttt  14820
ctcctcgttt gtcaatcatg ttaatgtctt taagataagg taggcaaatg tttatagtac  14880
taagaattgg gcaagcataa gacatgtcac aaagaccctt tttgtatgta taagtgtaaa  14940
aattataaca ttcatagttg gatttacata ggtgtccaat cgggatctct ccatcatcga  15000
gataattgat ggcatctccc ttcctttttt agtagatatt tcatcgtgta agaatcaata  15060
ttaatatttc taaagtatcc gtgtatagcc tctttattta ccacagttcc atattccact  15120
agagggatat cgccgaatgt catatactca attagtatat gttggaggac atccgagttc  15180
attgttttca atatcaaaaa gatggtttcc ttatcatttc tccatagtgg tacaatacta  15240
cacattattc cgtgaggctt tccattctcc aaaaacaatt tgaccaaatc tacatcttta  15300
ttgtatctat aatcactatt tagataatca gccataattc ctcgagtgca acatgttaga  15360
tcgtctatat atgaataagc agtgttatct attcctttca ttaacaattt aacgatgtct  15420
atatctatat gagatgactt aatataatat tgaagacctg tacaatagtt tttatctata  15480
aaagacggct tgattccgtg attaattaga catttaacaa cttccggacg cacatatgct  15540
ctcgtatccg actttgaata cagatgcaat acggtaccgc aatttcgtag ttgataatca  15600
tcatacgcgt atcagtactc gtcctcataa agaacactgc agccattttc tatgaacaaa  15660
tcaataattt taggaacagg atcattgtca ttacataatt ttctataact gaacgatggt  15720
tttcacattt aacactcaag tcaaatccat gttctaccaa cacctttatc aagtcaacgt  15780
ctacattttt ggatttcata tagctgaata tattaaagtc atttatgttg ctaaatccag  15840
tggcttctag tagagccatc gctatatcct ttaactttaa catgtctact atttgtgtat  15900
tcttctaatg gggtagctgt ctccaatttt tgcgtaatgg attagtgcca ctgtctagta  15960
gtagtttgac gacctcgaca ttattacaat gctcattaaa aaggtatgcg tgtaaagcat  16020
tattcttgaa ttggttcctg gtatcattag gatctctgtc tctcaacatc tgtttaagtt  16080
catcgagagc cacctcctca ttttccaaat agtcaaacat tttgactgaa tgagctactg  16140
tgaactctat acacccacac aactaatgtc attaaatatc atgtcaaaaa cttgtacaat  16200
tattaataaa aataatttag tgtttaaatt ttaccagttc cagattttac acctccgtta  16260
accccactgg acgatcctcc tccccacatt ccaccgccac cagatgtata agttttagat  16320
cctttattac taccatcatg tccatggata aagacactcc acatgccgcc actaccccct  16380
ttagaagaca tattaataag acttaaggac aagtttaaca ataaaattaa tcacgagtac  16440
cctactacca acctacacta ttatatgatt atagtttcta tttttacagt accttaacta  16500
aagtctctag tcacaagagc aatactacca acctacacta ttatatgatt atagtttcta  16560
tttttatagg aacgcgtacg agaaaatcaa atgtctaatt tctaacggta gtgttgataa  16620
acgattatcg tcaatggata cctcctctat catgtcgtct attttcttac tttgttctat  16680
taacttatta gcattatata ttatttgatt ataaaactta tattgcttat tagcccaatc  16740
tgtaaatatc ggattattaa catatcgttt ctttgtaggt ttatttaaca tgtacatcac  16800
tgtaagcatg tccgtaccat ttattttaat ttgacgcata tccgcaattt ctttttcgca  16860
gtcggttata aattctatat atgatggata catgctacat gtgtacttat aatcgactaa  16920
tatgaagtac ttgatacata ttttcagtaa cgatttatta ttaccaccta tgaataagta  16980
```

```
cctgtgatcg tctaggtaat caactgtttt cttaatacat tcgatggttg gtaatttact  17040
cagaataatt tccaatatct taatatataa ttctgctatt tctggaatat atttatctgc  17100
cagtataaca caaatagtaa tacatgtaaa cccatatttt gttattatat taatgtctgt  17160
gccattatct attaaccatt ctactaggct gacactatgc gacttaatac aatgataaag  17220
tatactacat ccatgtttat ctattttgtt tatatcatta atatacggct tacaaagttt  17280
tagtatcgat aacacatcca actcacgcat agagaaggta gggaataatg gcataatatt  17340
tattaggtta tcatcattgt cattatttac aactaagttt ccatttttta aaatatactc  17400
gacaacttta ggatctctat tgccaaattt ttgaaaatat ttatttatat gcttaaatct  17460
atataatgta gctccttcat caatcataca tttaataaca ttgatgtata ctgtatgata  17520
agatacatat tctaacaata gatcttgtat agaatctgta tatcttttaa gaattgtgga  17580
tattaggata ttattacgta aactattaca caattctaaa atataaaacg tatcacggtc  17640
gaataatagt tgatcaacta tataattatc gattttgtga tttttcttcc taaactgttt  17700
acgtaaatag ttagatagaa tattcattag ttcatgacca ctatagttac tatcgaataa  17760
cgcgtcaaat atttcccgtt taatatcgca tttgtcaaga taataataga gtgtggtatg  17820
ttcacgataa gtataataac gcatctcttt ttcgtgtgaa attaaatagt ttatcacgtc  17880
caaagatgta gcataaccat cttgtgacct agtaataata taataataga gaactgtttt  17940
acccattcta tcatcataat cagtggtgta gtcgtaatcg taatcgtcta attcatcatc  18000
ccaattataa tattcaccag cacgtctaat ctgttctatt ttgatcttgt atccatactg  18060
tatgttgcta catgtaggta ttcctttatc caataatagt ttaaacacat ctacattggg  18120
atttgatgtt gtagcgtatt tttctacaat attaatacca tttttgatac tatttatttc  18180
tatacctttc gaaattagta atttcaataa gtctatatcg atgttatcag aacatagata  18240
ttcgaatata tcaaaatcat tgatattttt atagtcgact gacgacaata acaaaatcac  18300
aacatcgttt ttgatattat tatttttctt ggtaacgtat gcctttaatg gagtttcacc  18360
atcatactca tataatggat ttgcaccact ttctatcaat gattgtgcac tgctggcatc  18420
gatgttaaat gttttacaac tatcatagag tatcttatcg ttaaccatga ttggttgttg  18480
atgctatcgc atttttggt ttctttctag ggataacagg gtaat                   18525
```

<210> SEQ ID NO 2
<211> LENGTH: 24931
<212> TYPE: DNA
<213> ORGANISM: Vaccinia virus

<400> SEQUENCE: 2

```
tagggataac agggtaattg tttaaatttt accagttcca gattttacac ctccgttaac     60
cccactggac gatcctcctc cccacattcc accgccacca gatgtataag ttttagatcc    120
tttattacta ccatcatgtc catggataaa gacactccac atgccgccac tacccccttt    180
agaagacata ttaataagac ttaaggacaa gtttaacaat aaaattaatc acgagtaccc    240
tactaccaac ctacactatt atatgattat agtttctatt tttacagtac cttaactaaa    300
gtctctagtc acaagagcaa tactaccaac ctacactatt atatgattat agtttctatt    360
tttataggaa cgcgtacgag aaaatcaaat gtctaatttc taacggtagt gttgataaac    420
gattatcgtc aatggatacc tcctctatca tgtcgtctat tttcttactt tgttctatta    480
acttattagc attatatatt atttgattat aaaacttata ttgcttatta gcccaatctg    540
```

```
taaatatcgg attattaaca tatcgtttct ttgtaggttt atttaacatg tacatcactg    600
taagcatgtc cgtaccattt attttaattt gacgcatatc cgcaatttct ttttcgcagt    660
cggttataaa ttctatatat gatggataca tgctacatgt gtacttataa tcgactaata    720
tgaagtactt gatacatatt ttcagtaacg atttattatt accacctatg aataagtacc    780
tgtgatcgtc taggtaatca actgttttct taatacattc gatggttggt aatttactca    840
gaataatttc caatatctta atatataatt ctgctatttc tggaatatat ttatctgcca    900
gtataacaca aatagtaata catgtaaacc catattttgt tattatatta atgtctgtgc    960
cattatctat taaccattct actaggctga cactatgcga cttaatacaa tgataaagta   1020
tactacatcc atgtttatct attttgttta tatcattaat atacggctta caaagtttta   1080
gtatcgataa cacatccaac tcacgcatag agaaggtagg gaataatggc ataatattta   1140
ttaggttatc atcattgtca ttatttacaa ctaagtttcc attttttaaa atatactcga   1200
caactttagg atctctattg ccaaattttt gaaaatattt atttatatgc ttaaatctat   1260
ataatgtagc tccttcatca atcatacatt taataacatt gatgtatact gtatgataag   1320
atacatattc taacaataga tcttgtatag aatctgtata tcttttaaga attgtggata   1380
ttaggatatt attacgtaaa ctattacaca attctaaaat ataaaacgta tcacggtcga   1440
ataatagttg atcaactata taattatcga ttttgtgatt tttcttccta aactgtttac   1500
gtaaatagtt agatagaata ttcattagtt catgaccact atagttacta tcgaataacg   1560
cgtcaaatat ttcccgttta atatcgcatt tgtcaagata ataatagagt gtggtatgtt   1620
cacgataagt ataataacgc atctcttttt cgtgtgaaat taaatagttt atcacgtcca   1680
aagatgtagc ataaccatct tgtgacctag taataatata ataatagaga actgttttac   1740
ccattctatc atcataatca gtggtgtagt cgtaatcgta atcgtctaat tcatcatccc   1800
aattataata ttcaccagca cgtctaatct gttctatttt gatcttgtat ccatactgta   1860
tgttgctaca tgtaggtatt cctttatcca ataatagttt aaacacatct acattgggat   1920
ttgatgttgt agcgtatttt tctacaatat taataccatt tttgatacta tttatttcta   1980
tacctttcga aattagtaat ttcaataagt ctatatcgat gttatcagaa catagatatt   2040
cgaatatatc aaaatcattg atatttttat agtcgactga cgacaataac aaaatcacaa   2100
catcgttttt gatattatta tttttcttgg taacgtatgc ctttaatgga gtttcaccat   2160
catactcata taatggattt gcaccacttt ctatcaatga ttgtgcactg ctggcatcga   2220
tgttaaatgt tttacaacta tcatagagta tcttatcgtt aaccatgatt ggttgttgat   2280
gctatcgcat tttttggttt ctttcatttc agttatgtat ggatttagca cgtttgggaa   2340
gcatgagctc atatgatttc agtactgtag tgtcagtact attagtttca ataagatcaa   2400
tctctagatc tatagaatca aaacacgata ggtcagaaga taatgaatat ctgtaggctt   2460
cttgttgtac tgtaacttct cgttttgtta gatgtttgca tcgtgcttta acatcaatgg   2520
tacaaatttt atcctcgctt tgtgtatcat attcgtccct actataaaat tgtatattca   2580
gattatcatg cgatgtgtat acgctaacgg tatcaataaa cggagcacac catttagtca   2640
taacagtaat ccaaaatttt ttaaagtata tcttaacgaa agaagttgtg tcattgtcta   2700
cggtgtatgg tactagatcc tcataagtgt atatatctag agtaatgttt aatttatcaa   2760
atggttgata atatggatcc tcatgacaat ttccgaagat ggaaatgaga tatagacacg   2820
caataaatct aattgcggac atggttactc cttaaaaaaa tacgaataat caccttggct   2880
atttagtaag tgtcatttaa cactatactc atattaatcc atggactcat aatctctata   2940
```

```
cgggattaac ggatgttcta tatacgggga tgagtagttc tcttctttaa ctttatactt   3000
tttactaatc atatttagac tgatgtatgg gtaatagtgt ttgaagagct cgttctcatc   3060
atcagaataa atcaatatct ctgttttttt gttatacaga tgtattacag cctcatatat   3120
tacgtaatag aacgtgtcat ctaccttatt aactttcacc gcatagttgt ttgcaaatac   3180
ggttaatcct ttgacctcgt cgatttccga ccaatctggg cgtataatga atctaaactt   3240
taatttcttg taatcattcg aaataatttt tagtttgcat ccgtagttat cccctttatg   3300
taactgtaaa tttctcaacg cgatatctcc attaataatg atgtcgaatt cgtgctgtat   3360
acccatactg aatggatgaa cgaataccga cggcgttaat agtaatttac tttttcatct   3420
ttacatattg ggtactagtt ttactatcat aagtttataa attccacaag ctactatgga   3480
ataagccaac catcttagta taccacacat gtcttaaagt ttattaatta attacatgtt   3540
gttttatata tatcgctacg aatttaaaca gagaaatcag tttaggaaaa aaaattatct   3600
atctacatca tcacgtctct gtattctacg atagagtgct actttaagat gcgacagatc   3660
tgtgtcatca aaaatatact ccattaaaat gattattccg gcagcgaact tgatattgga   3720
tatatcacaa cctttgttaa tatctacgac aatagacagc agtcccatgg ttccataaac   3780
agtgagttta tctttctttg aagagatatt ttgtagagat cttataaaac tgtcgaatga   3840
catcgcattt atatctttag ctaaatcgta tatgttacca tcgtaatatc taaccgcgtc   3900
tatcttaaac gtttccatcg ctttaaagac gtttccgata gatggcctca tttcatcagt   3960
catactgagc caacaaatat aatcgtgtat aacatctttg atagaatcag actctaaaga   4020
aaacgaatcg gctttattat acgcattcat gataaactta atgaaaaatg tttttcgttg   4080
gatgaatagt atgtcttaat aattgttatt attttcatta attaatattt agtaacgagt   4140
acactctata aaaacgagaa tgacataact agttatcaaa gtgtctagga cgcgtaattt   4200
tcatatggta tagatcctgt aagcattgtc tgtattctgg agctattttc tctatcgcat   4260
tagtgagttc agaatatgtt ataaatttaa atcgaataac gaacataact ttagtaaagt   4320
cgtctatatt aactctttta ttttctagcc atcgtaatac catgtttaag atagtatatt   4380
ctctagttac tacgatctca tcgttgtcta gaatatcaca tactgaatct acatccaatt   4440
ttagaaattg gtctgtgtta catatctctt ctatattatt gttgatgtat tgtcgtagaa   4500
aactattacg tagaccattt tctttataaa acgaatatat agtactccaa ttatctttac   4560
cgatatattt gcacacataa tccattctct caatcactac atctttaaga ttttcgttgt   4620
taagatattt ggctaaacta tataattcta ttagatcatc aacagaatca gtatatattt   4680
ttctagatcc aaagacgaac tctttggcgt cctctataat attcccagaa aagatatttt   4740
cgtgttttag tttatcgaga tctgatctgt tcatatacgc catgattgta cggtacgtta   4800
tgataaccgc ataaaataaa aatccatttt catttttaac caatactatt cataattgag   4860
attgatgtaa tactttgtta ctttgaacgt aaagacagta cacggatccg tatctccaac   4920
aagcacgtag taatcaaatt tggtgttgtt aaacttcgca atattcatca atttagatag   4980
aaacttatac tcatcatctg ttttaggaat ccatgtatta ttaccacttt ccattatccc   5040
aggctatgtt tcgtccatca tcgttgcgca gagtgaataa ttcttttgta ttcggtagtt   5100
caaatatata atccatgcat agatcggtaa agctattgta gatgtgattt ttcctaaatc   5160
taatataaaa ctcgtttact agcaaacact ttcctgattt atcgaccaag acacatatgg   5220
tttctaaatc tatcaagtgg tggggatcca tagttatgac gcagtaacat atattattac   5280
```

```
attcttgact gtcgctaata tctaaatatt tattgttatc gtattggatt ctgcatatag   5340
atggcttgta tgtcaaagat atagaacaca taaccaattt atagtcgcgc tttacattct   5400
cgaatctaaa gttaagagat ttagaaaaca ttatatcctc ggatgatgtt atcactgttt   5460
ctggagtagg atatattaaa gtctttacag atttcgtccg attcaaataa attactaaat   5520
aatatcccac attatcatct gttagagtag tatcattaaa tctattatat tttatgaaaa   5580
atatatcact tgctcacctc tatatttcgt acatttttaa actgtttgta taatatctct   5640
ctgatatatt tattgtgtcg gtagacgata ccgttacatt tgaattaatg gtgttccatt   5700
ttacaacttt taacaagttg accaattcat ttctaatagt atcaaactct ccatgattaa   5760
atattttaat agtatccatt ttatatcact acggacacaa agtagctgac ataaaccatt   5820
gtataatttt tatgttttat gtttattagc gtacacattt tggaagttcc ggctgccatg   5880
tatttcctgg agagcaagta gatgatgagg aaccagatag tttatatccg tacttgcact   5940
taaagtctac attgtcgttg tatgagtatg atcttttaaa cccgctagac aagtatccgt   6000
ttgatattgt aggatgtgga catttaacaa tctgacacgt gggtggatcg gaccattctc   6060
ctcctgaaca caggacacca gagttaccaa tcaacgaata tccactattg caactataag   6120
ttacaacgct cccatcggta taaaaatcct cgtatccgtt atgtcttccg ttggatatag   6180
atggaggga ttggcattta acagattcac aaataggtgc ctcgggattc cataccatag   6240
atccagtaga tcctaattca caatacgatt tagattcacc gatcaaatga tatccgctat   6300
tacaagagta cgttatacta gagccaaagt ctactccacc aatatcaagt tggccattat   6360
cgatatctcg aggcgatggg catctccgtt taatacattg attaaagagt gtccatccag   6420
tacctgtaca tttagcatat ataggtccca tttttgctt tctgtatcca ggtagacata   6480
gatattctat agtgtctcct atgttgtaat tagcattagc atcagtctcc acactattct   6540
taaatttcat attaatgggt cgtgacggaa tagtacagca tgatagaacg catcctattc   6600
ccaacaatgt caggaacgtc acgctctcca ccttcatatt tatttatccg taaaaatgtt   6660
atcctggaca tcgtacaaat aataaaaaag cccatatatg tttgctattg tagaaattgt   6720
ttttcacagt tgctcaaaaa cgatggcagt gacttatgag tttcatcttt agtaaacata   6780
tcataatatt cgatattacg agttgacata tcgaacaaat tccaagtatt tgattttgga   6840
taatattcgt attttgcatc tgctataatt aagatataat caccgcaaga acacacgaac   6900
atctttccta catggttaaa gtacatgtac aattctatcc atttgtcttc cttaactata   6960
tatttgtata gataattacg agtctcgtga gtaattccag taattacata gatgtcgccg   7020
tcgtactcta cagcataaac tatactatga tgtctaggca tgggagactt ttttatccaa   7080
cgatttttag tgaaacattc cacatcgttt aatactacat atttttcata cgtggtataa   7140
actccaccca ttacatatat atcatcgttt acgaataccg acgcgcctga atatctagga   7200
gtaattaagt ttggaagtct tatccatttc gaagtgccgt gtttcaaata ttctgccaca   7260
cccgttgaaa tagaaaattc taatcctcct attacatata actttccatc gttaacacaa   7320
gtactaactt ctgattttaa cgacgacata ttagtaaccg ttttccattt tttcgtttta   7380
agatctaccc gcgatacgga ataaacatgt ctattgttaa tcatgccgcc aataatgtat   7440
agacaattat gtaaaacatt tgcattatag aattgtctat ctgtattacc gactatcgtc   7500
caatattctg ttctaggaga gtaatgggtt attgtggata tataatcaga gtttttaatg   7560
actactatat tatgttttat accatttcgt gtcactggct ttgtagattt ggatatagtt   7620
aatcccaaca atgatatagc attgcgcata gtattagtca taaacttggg atgtaaaatg   7680
```

```
ttgatgatat ctacatcgtt tggattttta tgtatccact ttaataatat catagctgta   7740
acatcctcat gatttacgtt aacgtcttcg tgggataaga tagttgtcag ttcatccttt   7800
gataattttc caaattctgg atcggatgtc accgcagtaa tattgttgat tatttctgac   7860
atcgacgcat tatatagttt tttaattcca tatcttttag aaaagttaaa catccttata   7920
caatttgtgg aattaatatt atgaatcata gtttttacac atagatctac tacaggcgta   7980
acatcaatta ttacggcagc aactagtatc atttctacat tgtttatggt gatgtttatc   8040
ttcttccagc gcatatagtc taatagcgat tcaaacgcgt gatagtttat accattcaat   8100
ataatcactt catcatttat atggtgctcc tgaatgcgtt taaaaaaatt atacggagac   8160
gccgtaataa tttccttatt cacttgtata atttccccat tgatagaaaa tatcacgctt   8220
tccattcttg aagtactata agtaattata gtataatgta aaggtttata tattcaatat   8280
tttttataaa aaaatcattt cgacattaat tcctttttaa atttccgtct atcatctata   8340
gaaacgtatt ctatgaattt ataaaatgct tttacgtgtc ctatcgtagg cgatagaacc   8400
gctaaaaagc ctatcgaatt tctacaaaag aatctgttat atggtatagg gagagtataa   8460
aacattaaat gcccgtactt attaaagtat tcagtagcca atcctaactc tttcgaatac   8520
ttattaatgg ctcttgttct gtacgaatct atttttttga acaacggacc tagtggtata   8580
tcttgttcta tgtatctaaa ataatgtctg actagatccg ttagtttaat atcctcagtc   8640
atcttgtcta gaatggcaaa tctaactgcg ggtttaggct ttagtttagt ttttatatct   8700
acatctatgt ctttatctaa caccaaaaat ataatagcta atattttatt acaatcatcc   8760
ggatattctt ctacgatctc actaactaat gtttctttgg ttatactagt atagtcacga   8820
tcagacaaat aaagaaaatc agatgatcga tgaataatac atttaaattc atcatctgta   8880
agatttttga gatgtctcat taaaatatta ttagggttag tactcattat cattcggcag   8940
ctattactta ttttattatt tttcaccata tagatcaatc attagatcat caaaatatgt   9000
ttcaatcatc ctaaagagta tggtgaatga ctcttcccat ctaatttctg aacgttcacc   9060
aatgtctcta gccactttgg cactaatagc gatcattcgc ttagcgtctt ctatattatt   9120
aactggttga ttcaatctat ctagcaatgg accgtcggac agcgtcattc tcatgttctt   9180
aatcaatgta catacatcgc cgtcatctac caattcatcc aacaacataa gctttttaaa   9240
atcatcatta taataggttt gatcgttgtc atttctccaa agaatatatc taataagtag   9300
agtcctcatg attagttaac aactattttt tatgttaaat caattagtac accgctatgt   9360
ttaatactta ttcatatttt agtttttagg attgagaatc aatacaaaaa ttaatgcatc   9420
attaatttta gaaatactta gtttccacgt agttaatgaa acatttgaac tcatcgtaca   9480
ggacgttctc gtacaggacg taactataaa ccggtttata tttgttcaag atagatacaa   9540
atccgataac tttttttgacg aattctacgg gatccacttt aaaagtgtca taccgggttc   9600
tttttatttt tttaaacaga tcaatggtgt gatgttgatt aggtctttta cgaatttgat   9660
atagaatagc gttcacatat cctccataat ggtcaatcgc catttgttcg tatgtcataa   9720
attctttaat tatatgacac tgtgtattgt ttagttcatc cttgttcatt gttaggaatc   9780
tatccaaaat ggcaattata ctagaactat aggtgcgttg tatacacata ttgatgtgtc   9840
tgtttataca atcaatgata tttggatcca tgctactacc ttcgggtaaa attgtagcat   9900
catataccat ttctagtact ttaggttcat tattatccat tgcagaggac gtcatgatcg   9960
aatcataaaa aaatatatta tttttatgtt attttgttaa aaataatcat cgaatacttc  10020
```

```
gtaagatact ccttcatgaa cataatcagt tacaaaacgt ttatatgaag taaagtatct  10080
acgattttta caaaagtccg gatgcataag tacaaagtac gcgataaacg gaataataat  10140
agatttatct agtctatctt tttctatagc tttcatagtt agatacatgg tttcagaagt  10200
aggattatgt aacatcagct tcgataaaat gactgggtta tttagtctta cacattcgct  10260
catacatgta tgaccgttaa ctacagagtc tacactaaaa tgattgaaca atagatagtc  10320
taccattgtt ttgtattcag atagtacagc gtagtacata gcatcttcac aaattatatc  10380
attgtctaat agatatttga cgcatcttat ggatcccact tcaacagcca tcttaaaatc  10440
atattgcttt cctttatcat taataatttc tagaacatca tctctatcat aaaagataca  10500
aatattaact gtttgatccg taataacatt gctagtcgat agcaatttgt taataagatg  10560
cgctaggctc aatgtcttaa taagaagtgt aagaggacta tctccgaatt tgttttgttt  10620
attaacatcc gttgatggaa gtaaaagatc tataatgtct acatacttaa ctgttttaga  10680
gcatacaata tggagaggtg tatttccatc atgatctggt tttgagggac taattcctag  10740
tttcatcatc catgagattg tagaagcttt tggattgtct gacataagat gtctatgaat  10800
atgattttg ccaaatttat ccactatcct ggcttcgaat ccgatggaca ttattttttt  10860
aaacactctt tctgaaggat ctgtacacgc caacaacgga ccacatcctt cttcatcaac  10920
cgagttgtta atcttggctc catactgtac caataaattt attctctcta tgacttcatc  10980
atctgttccc gagagataat atagaggtgt tttattatgt ttatcacacg cgtttggatc  11040
tgcgccgtgc gtcagcagca tcgcgactat tctattatta ttaattttag aagctatatg  11100
caatggataa tttccatcat catccgtctc atttggagag tatcctctat gaagaagttc  11160
ttcgacaaat cgttcatcta gtcctttaat tccacaatac gcatgtagaa tgtgataatt  11220
atttccagaa ggttcgatag cttgtagcat attcctaaat acatctaaat ttttactatt  11280
atatttggca taaagagata gataatactc ggccgacata atgttgtcca ttgtagtata  11340
aaaattaata tttctatttc tatttctgta tatttgcaac aatttactct ctataacaaa  11400
tatcataact tagttctttt atgtcaagaa ggcactggtt tagttcatct ataaatgtca  11460
cgccataact accacgcatg ccatactcag aattatgata aagatattta tccttggggt  11520
gtaggtaatg gggattaatc tttgttggat cagtctctaa gttaacacat gtcacacatg  11580
atccatttat agttatatca cacgatgatg atttatgaat tgattccgga agatcgctat  11640
cgtattttgt ggttccacaa ttcatttcca tacatgttat tgtcacacta atattgtgat  11700
gaactttatc tagccgctga gtggtaaaca acagaacaga tagtttatta tctttaccaa  11760
caccctcagc cgctgccaca aatctctgat ccgtatccat gatggtcatg tttatttcta  11820
gtccgtatcc agtcaacact atgttagcat ttctgtcgat atagctttca ctcatatgac  11880
actcaccaat aatagtagaa ttaatgtcat aatttacacc aatagtgagt tcggcggcaa  11940
agtaccaata ccggtaatct tgtcgaggag gacatatagt attcttgtat tctaccgaat  12000
acccgagaga tgcgatacaa aagagcaaga ctaatttgta aaccatctta ctcaaaatat  12060
gtaacaatag tacgatgcaa tgagtaagac aataggaaat ctatcttata tacacataat  12120
tattctatca attttaccaa ttagttagtg taatgttaac aaaaatgtgg gagaatctaa  12180
ttagtttttc tttacacaat tgacgtacat gagtctgagt tccttgtttt tgctaattat  12240
ttcatccaat ttattattct tgactatatc gagatctttt gtataggagt cagacttgta  12300
ttcaacatgc ttttctataa tcattttagc tatttcggca tcatccaata gtacattttc  12360
cagattagca gaatagatat taatgtcgta tttgaacaga gcctgtaaca tctcaatgtc  12420
```

```
tttattatct atagccaatt taatgtccgg aatgaagaga agggaattat tggtgtttgt  12480
cgacgtcata tagtcgagca agagaatcat catatccacg tgtccatttt ttatagtgat  12540
gtgaatacaa ctaaggagaa tagccagatc aaaagtagat ggtatctctg aaagaaagta  12600
ggaaacaata cttacatcat taagcatgac ggcatgataa aatgaagttt tccatccagt  12660
tttcccatag aacatcagtc tccaattttt cttaacaaac agttttaccg tttgcatgtt  12720
accactatca accgcataat acaatgcggt gtttcccttg tcatcaaatt gtgaatcatc  12780
cagtccactg aatagcaaaa tctttactat tttggtatct tccaatgtgg ctgcctgatg  12840
taatggaaat tcattctcta gaagattttt caatgctcca gcgttcaaca acgtacatac  12900
tagacgcacg ttattatcag ctattgcata atacaaggca ctatgtccat ggacatccgc  12960
cttaaatgta tctttactag agagaaagct tttcagctgc ttagacttcc aagtattaat  13020
tcgtgacaga tccatgtctg aaacgagacg ctaattagtg tatatttttt catttttat  13080
aattttgtca tattgcacca gaattaataa tatctctaat agatctgatt agtagataca  13140
tggctatcgc aaaacaacat atacacattt aataaaaata atatttatta agaaaattca  13200
gatttcacgt acccatcaat ataaataaaa taatgattcc ttacaccgta cccatattaa  13260
ggagattcca ccttacccat aaacaatata aatccagtaa tatcatgtct gatgatgaac  13320
acaaatggtg tattaaattc cagtttttca ggagatgatc tcgccgtagc taccatgata  13380
gtagatgcct ctgctacagt tccttgttcg tcgacatcta tctttgcatt ctgaaacatt  13440
ttataaatat ataatgggtc cctagtcata tgtttaaacg acgcattatc tggattaaac  13500
atactaggag ccatcatttc ggctatcgac ttaatatccc tcttattttc gatagaaaat  13560
ctagggagtt taagattgta cactttattc cctaattgaa acgaccaata gtctaatttt  13620
gcagccgtaa tagaatctgt gaaatgggtc atattatcac ctattgccag gtacatacta  13680
atattagcat ccttatacgg aaggcgcacc atatcatatt cttcgtcatc gattgtgatt  13740
gtatttcctt gcaatttagt aactacgttc atcatgggaa ccgttttcgt accgtactta  13800
ttagtaaaac tagcattgcg tgttttagtg atatcaaacg gatattgcca tataccttta  13860
aaatatatag tattaatgat tgcccataga gtattattgt cgagcatatt agaatctact  13920
acattagaca taccggatct acgttctact atagaattaa ttttattaac cgcatctcgt  13980
ctaaagttta atctatatag gccgaatcta tgatattgtt gataatacga cggtttaata  14040
cacacagtat tatctacgaa actttgataa gttagatcag tgtacgtata tttagatgtt  14100
ttcagcttag ctaatcctga tattaattct gtaaatgctg gacccagatc tctttttctc  14160
aaatccatag tcttcaataa ttctattcta gtattacctg atgcaggcaa tagcgacata  14220
aacatagaaa acgaataacc aaacggtgag aagacaatat tatcatcttg aatattttta  14280
tacgctacta taccggcatt ggtaaatcct tgcagacgat aggtagacac tgaacacgtt  14340
aacgatagta tcaataacgc aatcatgatt ttatggtatt aataattaac cttattttta  14400
tgttcggtat aaaaattatt gatgtctaca catccttttg taattgacat ctatatatcc  14460
ttttgtataa tcaactctaa tcactttaac ttttacagtt ttccctacca gtttatccct  14520
atattcaaca tatctatcca tatgcatctt aacactctcc gccaagatag cttcaaagtg  14580
aggatagtca aaaagataaa tatatagagc ataatcattc tcgtatactc tgccctttat  14640
tacatcaccc gcattgggca acgaataaca aaatgcaagc atcttgttaa cgggctcgta  14700
aattgggata aaaattatgt ttttatatct attttattca agagaatatt caggaatttc  14760
```

-continued

```
tttttccggt tgtatctcat cgcagtatat atcatttgta cattgtttca tatttttttaa  14820
tagtttacac cttttagtag gactagtatc gtacaattca tagctgtatt ttgaattcca  14880
atcacgcata aaaatatctt ccaattgttg acgaagacct aatccatcat ccggtgtaat  14940
attaatagat gctccacatg tatccgtaaa gtaatttcct gtccaatttg aggtacctat  15000
ataggccgtt ttatcggtta ccatatattt ggcatggttt accctagaat acggaatggg  15060
aggatcagca tctggtacaa taaatagctt tacttctata tctatgtttt tagattttag  15120
catagcgata gatcttaaaa agtttctcat gataaacgaa gatcgttgcc agcaactaat  15180
caatagctta acggatactt gtctgtctat agcggatctt cttaattcat cttctatata  15240
aggccaaaac aaaattttac ccgccttcga ataaataata gggataaagt tcataacaga  15300
tacataaacg aatttactcg catttctaat acatgacaat aaagcggtta aatcattggt  15360
tctttccata gtacatagtt gttgcggtgc agaagcaata aatacagagt gtggaacacc  15420
acttacgtta atactaagag gatgatctgt attataatac gacggataaa agtttttcca  15480
attatatggt agattgttaa ctccaagata ccagtatacc tcaaaaattt gagtgagatc  15540
cgctgccaag ttcctattat tgaagatcgc aatacccaat tctttgacct gagttagtga  15600
tctccaatcc atgttagcgc ttcctaaata aatatgtgta ttatcagata tccaaaattt  15660
tgtatgaaga actcctccta ggatatttgt aatatctatg tatcgtactt caactccggc  15720
catttgtagt ctttcaacat cctttaatgg tttgttagat ttattgacgg ctactctaac  15780
tcttactcct cttttgggta attgtacaat ctcgtttaat attatcgtgc cgaaattcgt  15840
acccacttca tccgataaac tccaataaaa agatgatata tctagtgttt ttgtggtatt  15900
ggatagaatt tccctccaca tgttaaatgt agacaaatat actttatcaa attgcatacc  15960
tataggaata gtctctgtaa tcactgcgat tgtattatcc ggattcattt tatttgttaa  16020
aaaataatcc tatatcactt cactctatta aaaatccaag tttctatttc tttcatgact  16080
gatttttttaa cttcatccgt ttccttatga agatgatgtt tggcaccttc ataaattttt  16140
atttctctat tacaatttgc atgttgcatg aaataatatg cacctgaaac atcactaatc  16200
tcattgtttg ttccctggag tatgagagtc gggggggtgtt aatcttggaa attatttttc  16260
taaccttgtt ggtagccttc aagacctgac tagcaaatcc agccttaatt ttttcatgat  16320
tgattaatgg gtcgtattgg tatttataaa ctttatccat atctctagat actgattctg  16380
gacatagctt tccgactggc gcatttggtg tgatggttcc cataagtttg gcagctagca  16440
gattcagttt tgaaacagca tctgcattaa ctagaggaga cattagaatc attgctgtaa  16500
acaagtttgg attatcgtaa gaggctagta tagaaattgt tgctcccatg gaatgaccca  16560
ataagtagat ttaatagtta ccacgtgctg taccaaagtc atcaatcatc atttttttcac  16620
cattacttct tccatgtcca atatgatcat gtgagaatac taaaattcct aacgatgata  16680
tgttttcagc tagttcgtca taacgtccag aatgtttacc agctccatga cttatgaata  16740
ctaatgcctt aggatatgta ataggtttcc aatatatgta atcattgtcc agattgaaca  16800
tacagtttgc actcatgatt cacgttatat aactatcaat attaacagtt cgtttgatga  16860
tcatattatt tttatgtttt attgataatt gtaaaaacat acaattaaat caatatagag  16920
gaaggagacg gctactgtct tttgtgagat agtcatggcg actaaattag attatgagga  16980
tgctgttttt tactttgtgg atgatgataa aatatgtagt cgcgactcca tcatcgatct  17040
aatagatgaa tatattacgt ggagaaatca tgttatagtg tttaacaaag atattaccag  17100
ttgtggaaga ctgtacaagg aattgatgaa gttcgatgat gtcgctatac ggtactatgg  17160
```

tattgataaa attaatgaga ttgtcgaagc tatgagcgaa ggtgaccact acatcaattt 17220
tacaaaagtc catgatcagg aaagtctatt cgctaccata ggaatatgtg ctaaaatcac 17280
tgaacattgg ggatacaaaa agatttcaga atctagattc caatcattgg gaaacattac 17340
agatctgatg accgacgata atataaacat cttgatactt tttctagaaa aaaaattgaa 17400
ttgatgatat aggggtcttc ataacgcata attattacgt tagcattcta tatccgtgtt 17460
aaaaaaaatt atcctatcat gtatttgaga gttttatatg tagcaaacat gatagctgtg 17520
atgccaataa gctttagata ttcacgcgtg ctagtgttag ggatggtatt atctggtggt 17580
gaaatgtccg ttatataatc tacaaaacaa tcatcgcata tagtatgcga tagtagagta 17640
aacattttta tagtttttac tggattcata catcgtctac ccaatttggt tataaatgaa 17700
attgtcgcca atcttacacc caaccccttg ttatccatta gtatagtatt aacttcgtta 17760
tttatgtcat aaactgtaaa tgattttgta gatgccatat catacatgat attcatgtcc 17820
ctattataat cattactaac tttatcacaa tatatgttga taatatctat atatgatcta 17880
gtctttgtgg gcaactgtct atacaagtcg tctaaacgtt gtttactcat atagtatcga 17940
acagccatca ttacatggtc ccgttccgtt gatagataat cgagtatgtt agtggacttg 18000
tcaaatctat ataccatatt ttctggaagt ggatatacat agtcgtgatc aacattattg 18060
ctagcctcat cttctatatc atgtactata ccattatcta tatcatctac ataatctacg 18120
atattattac acataaacat cgacaacata ctattgttta ttatctaagt cctgttgatc 18180
caaacccttg atctcctcta tttgtactat ctagagattg tacttcttcc agttctggat 18240
aatatatacg ttgatagatt agctgagcta ttctatctcc agtatttaca ttaaacgtac 18300
attttccatt attaataaga atgactccta tgtttcccct ataatcttcg tctattacac 18360
cacctcctat atcaatgcct tttagtgaca gaccagacct aggagctatt ctaccatagc 18420
aaatcttagg catggacata ctaatatctg tcttaattaa ctgtctttct cctggaggga 18480
tagtataatc gtaagcgcta tacaaatcat atccggcagc acccggcgat tgcctagtag 18540
gagatttagc tctgttagtt tccttaacaa atctaactgg tgagttaata ttcatgttga 18600
acataaaact aatattttat ttcaaaatta tttaccatcc catatattcc atgaataagt 18660
gtgatgattg tacacttcta tagtatctat atacgattca cgataaaatc ctcctatcaa 18720
tagcagttta ttatccacta tgatcaattc tggattatcc ctcggataaa taggatcatc 18780
tatcagagtc catgtattgc tggattcaca ataaaattcc gcatttctac caaccaagaa 18840
taaccttcta ccgaacacta acgcgcatga tttataatga ggataataag tggatggtcc 18900
aaactgccac tgatcatgat tgggtagcaa atattctgta gttgtatcag tttcagaatg 18960
tcctcccatt acgtatataa cattgtttat ggatgccact gctggattac atctaggttt 19020
cagaagactc ggcatattaa cccaagcagc atccccgtgg aaccaacgct caacagatgt 19080
gggatttggt agacctccta ctacgtataa tttattgtta gcgggtatcc cgctagcata 19140
cagtctgggg ctattcatcg gaggaattgg aatccaattg tttgatatat aatttacagc 19200
tatagcattg ttatgtattt cattgttcat ccatccaccg atgagatata ctacttctcc 19260
aacatgagta cttgtacaca tatggaatat atctataatt tgatccatgt tcataggata 19320
ctctatgaat ggatacttgt atgatttgcg tggttgttta tcacaatgaa atattttggt 19380
acagtctagt atccatttta cattatttat acctctggga gaaagataat ttgacctgat 19440
tacatttttg ataaggagta gcagatttcc taatctattt cttcgcttta tataccactt 19500
aatgacaaaa tcaactacat aatcctcatc tggaacattt agttcatcgc tttctagaat 19560
aagtttcata gatagataat caaaattgtc tatgatgtca tcttccagtt ccaaaaagtg 19620
tttggcaata aagtttttag tatgacataa gagattggat agtccgtatt ctatacccat 19680
catgtaacac tcgacacaat attcctttct aaaatctcgt aagataaagt ttatacaagt 19740
gtagatgata aattctacag aggttaatat agaagcacgt aataaattga cgacgttatg 19800
actatctata tatacctttc cagtatacga gtaaataact atagaagtta aactgtgaat 19860
gtcaaggtct agacaaaccc tcgtaactgg atctttattt ttcgtgtatt tttgacgtaa 19920
atgtgtgcga aagtaaggag ataacttttt caatatcgta gaattgacta ttatattgcc 19980
acctatagca tcaataattg ttttgaattt cttagtcata gacaatgcta atatattctt 20040
acagtacaca gtattaacaa atatcggcat ttatgtttct ttaaaagtca acatctagag 20100
aaaaatgatt atctttttga gacataactc ccattttttg gtattcaccc acacgttttt 20160
cgaaaaaatt agtttttcct tccaatgata tattttccat gaaatcaaac ggattggtaa 20220
cattataaat tttttaaat cccaattcag aaatcaatct atccgcgacg aattctatat 20280
atgttttcat catttcacaa ttcattccta taagtttaac tggaagagcc gcagtaagaa 20340
attcttgttc aatggatact gcatctgtta taatatatct aacggtttct tcactcggtg 20400
gatacaataa atgtttaaac atcaaacatg cgaaatcgca gtgcagaccc tcgtctctac 20460
taattagttc gttggaaaac gtgagtccgg gcattaggcc acgcttttta agccaaaata 20520
tggaagcgaa tgatccggaa aagaagattc cttctactgc agcaaaggca ataagtctct 20580
ctccataacc ggcgctgtca tgtatccact tttgagccca atcggccttc tttttacac 20640 aaggcatcgt ttctatggca ttaaagagat agtttttttc attactatct ttaacataag 20700
tatcgatcaa aagactatac atttccgaat gaatgttttc aatggccatc tgaaatccgt 20760
agaaacatct agcctcggta atctgtactt ctgtacaaaa tcgttccgcc aaattttcat 20820
tcactattcc gtcactggct gcaaaaaacg ccaatacatg ttttataaaa tatttttcgt 20880
ctggtgttag tttattccaa tcattgatat ctttagatat atctacttct tccactgtcc 20940
aaaatgatgc ctctgccttt ttatacatgt tccagatgtc ataatattgg attgggaaaa 21000
taacaaatct atttggattt ggtgcaagga tgggttccat aactaaatta acaatatcaa 21060
taaatttttt ttcagttatc tatatgcctg tacttggatt ttttgtacat cgatatcgcc 21120
gcaatcacta caataattac aagtattatt gatagcattg ttattagtac tatcataatt 21180
aaattatcga cattcatggg tgctgaataa tcgttattat catcattatc attttgtaat 21240
tgtgacatca tactaaataa atcgtttgcg agattgttgt gggaagcggg catggaggat 21300
gcattatcat tattatttaa cgccttccat ttggattcac aaatgttacg cacattcaac 21360
attttatgga aactataatt ttgtgaaaac agataacaag aaaactcgtc atcgttcaaa 21420
tttttaacga tagtaaaccg attaaacgtc gagctaattt ctaacgctag cgactctgtt 21480
ggatatgggt ttccagatat atatcttttc agttccccta cgtatctata atcatctgta 21540
ggaaatggaa gatatttcca tttatctact gttcctaata tcatatgtgg tggtgtagta 21600
gaaccattaa gcgcgaaaga tgttatttcg catcgtattt taacttcgca ataatttctg 21660
gttagataac gcactctacc agtcaagtca atgatattag cctttacaga tatattcata 21720
gtagtcgtaa cgatgactcc atcttttaga tgcgatactc ctttgtatgt accagaatct 21780
tcgtacctca aactcgatat atttaaacaa gttaatgaga tattaacgcg ttttatgaat 21840
gatgatatat aaccagaagt tttatcctcg gtggctagcg ctataacctt atcattataa 21900
taccaactag tgtgattaat atgtgacacg ttagtgtggg tacaaatatg tacattatcg 21960
tctacgtcgt attcgataca tccgcataca gccaacaaat ataaaatgac aaatactcta 22020
acgccgttcg tacccatctt gatgcggttt aataaatgtt ttgatttcaa tttattgtaa 22080
aaaaagattc ggttttatac tgttcgatat tctcattgct tatattttca tctatcatct 22140
ccacacagtc aaatccgtgg ttagcatgca cctcatcaac cggtaaaaga ctatcggact 22200
cttctatcat tataactcta gaatatttaa tttggtcatt attaatcaag tcaattatct 22260
tatttttaac aaacgtgagt attttactca ttttttataa aaacttttag aaatatacag 22320
actctatcgt gtgtctatat cttcttttta tatccaatgt atttatgtct gatttttctt 22380
catttatcat atataatggt ccaaattcta cacgtgcttc ggattcatcc agatcattaa 22440
ggttcttata attgtaacat ccttctcttc cctcttctac atcttccttc ttattcttat 22500
tcttagcgtc acagaatcta ccacagcagg atcccatgac gagcgtcata ttaaactaat 22560
tcattttcaa ttataatata ctggtaatga ccattaaaat aaaaatattc ttcataaccg 22620
gtaagaaagt gaaaagttca cattgaaact atgtcagtag tatacatcat gaaatgatga 22680
tatatatata ctctattttg gtggaggatt atatgatata attcgtggat aatcattttt 22740
aagacacatt tctttattcg taaatctttt cacgttaaat gagtgtccat attttgcaat 22800
ttcttcatat gatggcggtg tacgtggacg aggctgctcc tgttcttgtt gtggtcgccg 22860
actgtcgtgt ctgcgtttag atccctccat tatcgcgatt gcgtagatgg agtactatta 22920
tataccttgt aattaaattt ttttattaat taaacgtata aaaacgttcc gtatctgtat 22980
ttaagagcca gatttcgtct aatagaacaa atagctacag taaaaataac tagaataatt 23040
gctacaccca ctagaaacca cggatcgtaa tacggcaatc ggttttcgat aataggtgga 23100
acgtatattt tatttaagga cttaacaatt gtctgtaaac cacaatttgc ttccgcggat 23160
cctgtattaa ctatctgtaa aagcatatgt tggccgggcg gagccgaaca ttctccgata 23220
tccaatttct gtatatctat aatattatta acctccgcat acgcattaca gttcttttct 23280
agcttggata ctacactagg tacatcatct agatctattc ctatttcctc agcgatagct 23340
cttctatcct tttccggaag caatgaaatc acttcaataa atgattcaac catgagtgtg 23400
aaactaagtc gagaattact catgcatttg ttagttattc ggagcgcgca atttttaaac 23460
tgtcctataa cctctcctat atgaatagca caagtgacat tagtagggat agaatgttga 23520
gctaattttt gtaaataact atctataaaa agattataca aagttttaaa ctctttagtt 23580
tccgccattt atccagtctg agaaaatgtc tctcataata aatttttcca agaaactaat 23640
tgggtgaaga atggaaacct ttaatctata tttatcacag tctgttttgg tacacatgat 23700
gaattcttct aatgctgtac taaattcgat atctttttcg atttctggat atgtttttaa 23760
taaagtatga acaaagaaat ggaaatcgta ataccagtta tgtttaactt tgaaattgtt 23820
ttttattttc ttgttaatga ttccagccac ttgggaaaag tcaaagtcgt ttaatgccga 23880
tttaatacgt tcattaaaaa caaacttttt atcctttaga tgaattatta ttggttcatt 23940
ggaatcaaaa agtaagatat tatcgggttt aagatctgcg tgtaaaaagt tgtcgcagca 24000
tggtagttcg taaattttaa tgtataacag agccatctgt aaaaagataa actttatgta 24060
ttgtaccaaa gatttaaatc ctaatttgat agctaactcg gtatctactt tatctgcaga 24120
atacagtgct aggggaaaaa ttataatatt tcctctttcg tattcgtagt tagttctctt 24180
ttcatgttcg aaaaagtgaa acatgcggtt aaaatagttt ataacattaa tattactgtt 24240
aataactgcc gggtaaaagt gggatagtaa tttcacgaat ttgatactgt cctttctctc 24300
gttaaacgcc tttaaaaaaa ctttagaaga atatctcaat gagagttcct gaccatccat 24360
agtttgtatc aataatagca acatatgaag aacccgttta tacagagtat gtaaaaatgt 24420
taatttatag tttaatccca tggcccacgc acacacgatt aatttttttt catctccctt 24480
tagattgttg tatagaaatt tgggtactgt gaactccgcc gtagtttcca tgggactata 24540
taattttgtg gcctcgaata caaattttac tacatagtta tctatcttaa agactatacc 24600
atatcctcct gtagatatgt gataaaaatc gtcgtttata ggataaaatc gtttatcctt 24660
ttgttggaaa aaggatgaat taatgtaatc attctcttct atctttagta gtgtttccct 24720
attaaaattc ttaaaataat ttaacaatct aactgacgga gcccaatttt ggtgtaaatc 24780
taattgggac attatattgt taaaatacaa acagtctcct aatataacag tatctgataa 24840
tctatgggga gacatccatt gatattcagg ggatgaatca ttggcaacac ccatttattg 24900
tacaaaaagc ccctagggat aacagggtaa t 24931

<210> SEQ ID NO 3
<211> LENGTH: 23333
<212> TYPE: DNA
<213> ORGANISM: Vaccinia virus

<400> SEQUENCE: 3
tagggataac agggtaattc tttagtttcc gccatttatc cagtctgaga aaatgtctct 60
cataataaat ttttccaaga aactaattgg gtgaagaatg gaaaccttta atctatattt 120
atcacagtct gttttggtac acatgatgaa ttcttctaat gctgtactaa attcgatatc 180
tttttcgatt tctggatatg tttttaataa agtatgaaca aagaaatgga aatcgtaata 240
ccagttatgt ttaactttga aattgttttt tattttcttg ttaatgattc cagccacttg 300
ggaaaagtca aagtcgttta atgccgattt aatacgttca ttaaaaacaa actttttatc 360
ctttagatga attattattg gttcattgga atcaaaaagt aagatattat cgggtttaag 420
atctgcgtgt aaaaagttgt cgcagcatgg tagttcgtaa attttaatgt ataacagagc 480
catctgtaaa aagataaact ttatgtattg taccaaagat ttaaatccta atttgatagc 540
taactcggta tctactttat ctgcagaata cagtgctagg ggaaaaatta taatatttcc 600
tctttcgtat tcgtagttag ttctcttttc atgttcgaaa aagtgaaaca tgcggttaaa 660
atagtttata acattaatat tactgttaat aactgccggg taaaagtggg atagtaattt 720
cacgaatttg atactgtcct ttctctcgtt aaacgccttt aaaaaaactt tagaagaata 780
tctcaatgag agttcctgac catccatagt ttgtatcaat aatagcaaca tatgaagaac 840
ccgtttatac agagtatgta aaaatgttaa tttatagttt aatcccatgg cccacgcaca 900
cacgattaat ttttttcat ctccctttag attgttgtat agaaatttgg gtactgtgaa 960
ctccgccgta gtttccatgg gactatataa ttttgtggcc tcgaatacaa attttactac 1020
atagttatct atcttaaaga ctataccata tcctcctgta gatatgtgat aaaaatcgtc 1080
gtttatagga taaaatcgtt tatccttttg ttggaaaaag gatgaattaa tgtaatcatt 1140
ctcttctatc tttagtagtg tttccctatt aaaattctta aaataattta acaatctaac 1200
tgacggagcc caattttggt gtaaatctaa ttgggacatt atattgttaa aatacaaaca 1260
gtctcctaat ataacagtat ctgataatct atggggagac atccattgat attcagggga 1320
tgaatcattg gcaacaccca tttattgtac aaaaagcccc aatttacaaa cgaaagtcca 1380
ggtttgatag agacaaacta ttaactattt tgtctctgtt tttaatttct ttagtaatga 1440

```
aattattcac aatatcagta tcttctttat ctaccagaga ttttactaac ttgataacct   1500
tggctgtctc attcaatagg gtagtaatat ttgtatgtgt gatattgata tctttttgaa   1560
ttgtttcttt tagaagtgat tctttgatgg tgccagcata cgaattacaa taatgcagaa   1620
actcggttaa catgcaggaa ttatagtaag ccaattccaa ttgttgcctg tgttgtatta   1680
gagtgtcaat atgagcaatg gtgtccttgc gtttctctga tagaatgcga gcagcgattt   1740
tggcgttatc atttgacgat atttctggaa tgacgaatcc tgtttctact aactttttgg   1800
taggacaaag tgaaacaatc aagaagatag cttctcctcc tatttgtgga agaaattgaa   1860
ctcctctaga tgatctactg acgatagtat ctccttgaca gatattggac cgaattacag   1920
aagtacctgg aatgtaaagc cctgaaaccc cctcattttt taagcagatt gttgccgtaa   1980
atcctgcact gtgaccaaga tagagagctc ctttggtgaa tccatctcta tgtttcagtt   2040
taaccaagaa acagtcagct ggtctaaaat ttccatctct atctaataca gcatctaact   2100
tgatgtcagg aactatgacc ggtttaatgt tatatgtaac attgagtaaa tccttaagtt   2160
cataatcatc actgtcatca gttatgtacg atccaaacaa tgtttctacc ggcatagtgg   2220
atacgaagat gctatccatc agaatgtttc cctgattagt attttctata tagctattct   2280
tctttaaacg attttccaaa tcagtaacta tgttcatttt tttaggagta ggacgcctag   2340
ccagtatgga agaggatttt ctagatcctc tcttcaacat ctttgatctc aatggaatgc   2400
aaaaccccat agtgaaacaa ccaacgataa aaataatatt gtttttcact ttttataatt   2460
ttaccatctg actcatggat tcattaatat ctttataaga gctactaacg tataattctt   2520
tataactgaa ctgagatata tacaccggat ctatggtttc cataattgag taaatgaatg   2580
ctcggcaata actaatggca aatgtataga acaacgaaat tatactagag ttgttaaagt   2640
taatattttc tatgagctgt tccaataaat tatttgttgt gactgcgttc aagtcataaa   2700
tcatcttgat actatccagt aaacagtctt taagttctgg aatattatca tcccattgta   2760
aagcccctaa ttcgactatc gaatatcctg ctctgatagc agtttcaata tcgacggacg   2820
tcaatactgt aataaaggtg gtagtattgt catcatcgtg ataaactact ggaatatggt   2880
cgttagtagg tacggtaact ttacacaacg cgatatataa ctttcctttt gtaccatttt   2940
taacgtagtt gggacgtcct gcagggtatt gttttgaaga aatgatatcg agaacagatt   3000
tgatacgata tttgttggat tcctgattat ttactataat ataatctaga cagatagatg   3060
attcgataaa tagaaaaggt atatcgttgg taggataata catccccatt ccagtattct   3120
cggatactct attaatgaca ctagttaaga acatgtcttc tattctagaa aacgaaaaca   3180
tcctacatgg actcattaaa acttctaacg ctcctgattg tgtctcgaat gcctcgtaca   3240
aggatttcaa ggatgccata gattctttga ccaacgattt agaattgcgt ttagcatctg   3300
atttttttat taaatcgaat ggtcggctct ctggtttgct accccaatga taacaatagt   3360
cttgtaaaga taaaccgcaa gaaaatttat acgcatccat ccaaataacc ctagcaccat   3420
cggatgatat taatgtatta ttatagattt tccatccaca gttattgggc cagtatactg   3480
ttagcaacgg tatatcgaat agattactca tgtaacctac tagaatgata gttcgtgtac   3540
tagtcataat atctttaatc caatctaaga aatataaaat tagatctttt acactgttaa   3600
agttaacaaa ggtattaccc gggtacgtgg atatcatata tggtattggt ccattatcag   3660
taatagctcc ataaactgat acggcgatgg tttttatatg tgtttgatct aacgaggaag   3720
aaattcgcgc ccacaattca tctctagata tgtatttaat atcaaacggt aacacatcaa   3780
```

-continued

```
tttcgggacg cgtatatgtt tctaaatttt taatccaaat ataatgatga cctatatgcc   3840
ctattatcat actgtcaact atagtacacc tagagaactt acgatacatc tgtttcctgt   3900
aatcgttaaa ttttacaaat ctataacatg ctaaaccttt tgacgacaac cattcattaa   3960
tttctgatat ggaatctgta ttctcgatac cgtattgttc taaagccagt gctatatctc   4020
cctgttcgtg ggaacgcttt cgtataatat cgatcaacgg ataatctgaa gtttttggag   4080
aataatatga ctcatgatct atttcgtcca taaacaatct agacatagga attggaggcg   4140
atgatcttaa ttttgtgcaa tgagtcgtca atcctataac ttctaatctt gtaatattca   4200
tcatcgacat aatactatct atgttatcat cgtatattag tataccatga ccttcttcat   4260
ttcgtgccaa aataatatac agtcttaaat aattacgcaa tatctcaata gtttcataat   4320
tgttagctgt tttcatcaag gtttgtatcc tgtttaacat gatggcgttc tatacgtttc   4380
tattttctat tttttaaatt tttaacgatt tactgtggct agatacccaa tctctctcaa   4440
atattttttt agcctcgctt acaagctgtt tatctatact attaaaactg acgaatccgt   4500
gattttggta atgggttccg tcgaaatttg ccgaagtgat atgaacatat tcgtcgtcga   4560
ctatcaacaa ttttgtatta ttctgaatag tgaaaacctt cacagataga tcattttgaa   4620
cacacaacgc gtctagactt ctggcggttg ccatagaata tacgtcgttc ttatcccaat   4680
taccaactag aagtctgatc ttaactcctc tattaatggc tgcttctata atggagttgt   4740
aaatgtcggg ccaatagtag ctattaccgt cgacacgtgt agtgggaact atggccaaat   4800
gttcaatatc tatactagtc ttagctgacc tgagtttatc aataactaca tcggtatcta   4860
aatctctaga atatcccaat aggtgttccg gagaatcagt aaagaacact ccacctatag   4920
gattcttaat atgatacgca gtgctaactg gcaaacaaca agccgcagag cataaattca   4980
accatgaatt ttttgcgcta ttaaaggctt taaaagtatc aaatcttcta cgaagatctg   5040
tggccagcgg gggataatca gaatatacac ctaacgtttt aatcgtatgt atagatcctc   5100
cagtaaatga cgcgtttcct acataacatc tttcatcatc tgacacccaa aaacaaccga   5160
gtagtagtcc cacattattt tttttatcta tattaacggt tataaaattt atatccgggc   5220
agtgactttg tagctctccc agatttcttt tccctcgttc atctagcaaa actattattt   5280
taatcccttt ttcagatgcc tcttttagtt tatcaaaaat aagcgctccc ctagtcgtac   5340
tcagaggatt acaacaaaaa gatgctatgt atatatattt cttagctaga gtgataattt   5400
cgttaaaaca ttcaaatgtt gttaaatgat cggatctaaa atccatattt tctggtagtg   5460
tttctaccag cctacatttt gctcccgcag gtaccgatgc aaatggccac atttagttaa   5520
cataaaaact tatacatcct gttctatcaa cgattctaga atatcatcgg ctatatcgct   5580
aaaattttca tcaaagtcga catcacaacc taactcagtc aatatattaa gaagttccat   5640
gatgtcatct tcgtttattt ctatatccgt atccattgta gattgttgac cgattatcga   5700
gtttaaatca ttactaatac tcaatccttc agaatacaat ctgtgtttca ttgtaaattt   5760
ataggcggtg tatttaagtt ggtagatttt caattatgta tcaatatagc aacagtagtt   5820
cttgctcctc cttgattcta gcatcctctt cattattttc ttctacgtac ataaacatgt   5880
ccaatacgtt agacaacaca ccgacgatgg cggccgccac agacacgaat atgactaaac   5940
cgatgaccat ttaaaaaccc ctctctagct ttcacttaaa ctgtatcgat tattctttta   6000
gaacatgtat aatataaaaa cattattcta tttcgaattt aggcttccaa aaatttttca   6060
tccgtaaacc gataataata tatatagact tgttaatagt cggaataaat agattaatgc   6120
ttaaactatc atcatttcca cgattagaga tacaatattt acattttttt tgctgtttcg   6180
```

aaactttatc aatacacgtt aatacaaacc caggaaggag atattgaaac tgaggctgtt 6240
gaaaatgaaa cggtgaatac aataattcag ataatgtaaa atcatgattc cgtattctga 6300
tgatattaga actgctaatg gatgtcgatg gtatgtatct aggagtatct attttaacaa 6360
agcatcgatt tgctaatata caattatcct tttgattaat tgttatttta ttcatattct 6420
taaaaggttt catatttatc aattcttcta cattaaaaat ttccattttt aatttatgta 6480
gccccgcaat actcctcatt acgtttcatt ttttgtctat aatatccatt ttgttcatct 6540
cggtacatag attatccaat tgagaagcgc atttagtagt tttgtacatt ttaagtttat 6600
tgacaaatcg tcgaaaacta gttatagtta acattttatt atttgatacc ctgatattaa 6660 taccccctgcc gttactatta tttataactg atgtaaccca cgtaacatta gaattaatta 6720
tcgatagtaa tgcatcaacg cttccaaaat tgtctattat aaactcaccg ataatttttt 6780
tattacatgt tttcatattc attaggatta tcaaatcttt aatcttacta cgattgtatg 6840
cgttgatatt gcaagacgtc attctaaaag acggaggatc tccatcaaat gccaaacaat 6900
cacgtacaaa gtacatggaa ataggttttg ttctattgcg catcatagat ttatatagaa 6960
cacccgtaga aatactaatt tgttttactc tataaaatac taatgcatct atttcatcgt 7020
tttgtataac gtctttccaa gtgtcaaatt ccaaattttt ttcattgata gtaccaaatt 7080
cttctatctc tttaactact tgcatagata ggtaattaca gtgatgccta catgccgttt 7140
tttgaaactg aatagatgcg tctagaagcg atgctacact agtcacaatc accactttca 7200
tatttagaat atatgtatgt aaaaatatag tagaatttca ttttgttttt ttctatgcta 7260
taaatgaatt ctcattttgc atctgctcat actccgtttt atatcaatac caaagaagga 7320
agatatctgg ttctaaaagc cgttaaagta tgcgatgtta gaactgtaga atgcgaagga 7380
agtaaagctt cctgcgtact caaagtagat aaaccctcat cacccgcgtg tgagagaaga 7440
ccttcgtccc cgtccagatg cgagagaatg aataaccctg gaaaacaagt cccgtttatg 7500
agaacggaca tgctacaaaa tatgttcgcg gctaatcgcg acaacgtggc gtcgagactt 7560
ttgaactaaa atacaattat atctttttcg atattaataa atccgtgtcg cccgggtttt 7620
ttatctcttt cagtatgtga atagataggt attttatctc tattcatcat cgaatttaag 7680
agatccgata aacattgttt gtattctcca gatgtcagca tctgatacaa caatatatgt 7740
gcacataaac ctctggcact tatttcatgt accttcccct tatcactaag gagaatagta 7800
tttgagaaat atgtatacat gatattatca tgaattagat atacagaatt tgtaacactc 7860
tcgaaatcac acgatgtgtc ggcgttaaga tctaatatat cactcgataa cacattttca 7920
tctagataca ctagacattt tttaaagcta aaatagtctt tagtagtgac agtaactatg 7980
cgattatttt catcgatgat acatttcatc ggcatattat tacgcttacc atcaaagact 8040
ataccatgtg tatatctaac gtattctagc atggttgcca tacgcgcatt aaacttttca 8100
ggatctttgg atagatcttc caatctatct atttgagaaa acatttttat catgttcaat 8160
agttgaaacg tcggatccac tatatagata ttatctataa agattttagg aactacgttc 8220
atggtatcct ggcgaatatt aaaactatca atgatatgat tatcgttttc atcttttatc 8280
accatatagt ttctaagata tggatttta cttaatataa tattatttcc cgtgataaat 8340
tttattagaa aggccaaatc tataagaaaa gtcctagaat tagtctgaag aatatctata 8400
tcgccgtata gtatatttgg attaattaga tatagagaat atgatccgta acatatacaa 8460
cttttattat ggcgtctaag atattcttcc atcaacttat taacattttt gactagggaa 8520

-continued

```
gatacattat gacgtcccat tacttttgcc ttgtctatta ctgcgacgtt catagaattt   8580
agcatatctc ttgccaattc ttccattgat gttacattat aagaaatttt agatgaaatt   8640
acatttggag ctttaatagt aagaactcct aatatgtccg tgtatgtggt cactaataca   8700
gattgtagtt ctataatcgt aaataattta cctatattat atgtttgagt ctgtttagaa   8760
aagtagctaa gtatacgatc ttttatttct gatgcagatg tatcaacatc ggaaaaaaat   8820
cttttttat tctttttac taaagataca aatatgtctt tgttaaaaac agttattttc   8880
tgaatatttc tagcttgtaa ttttaacata tgatattcgt tcacactagg tactctgcct   8940
aaataggttt ctataatctt taatgtaata ttaggaaaag tattctgatc aggattccta   9000
ttcattttga ggatttaaaa ctctgattat tgtctaatat tgtctctacg caaacttttt   9060
cacagagcga tagagttttt gataactcgt ttttcttaag aaatataaaa ctactgtctc   9120
cagagctcgc tctatctttt attttatcta attcgataca aactcctgat actggttcag   9180
aaagtaattc attaattttc agtcctttat agaagatatt taatatagat aatacaaaat   9240
cttcagtttt tgatatcgat ctgattgatc ctagaactag atatattaat aacgtgctca   9300
ttaggcagtt tatggcagct tgataattag atatagtata ttccagttca tatttattag   9360
ataccgcatt gcccagattt tgatattcta tgaattcctc tgaaaataaa tccaaaataa   9420
ctagacattc tatttttgt ggattagtgt actctcttcc ctctatcatg ttcactactg   9480
gtgtccacga tgataaatat ctagagggaa tataatatag tccataggat gccaatctag   9540
caatgtcgaa taactgtaat tttattcttc gctcttcatt atgaattgat tcttgaggta   9600
taaacctaac acaaattata ttattagact tttcgtatgt aatgtctttc atgttataag   9660
tttttaatcc tggaatagaa tctattttaa tgaggctttt aaacgcagag ttctccaacg   9720
agtcaaagca taatactctg ttgtttttct tatatacgat gttacgattt tcttctttga   9780
atggaatagg tttttgaatt agtttataat tacaacataa tagataagga agtgtgcaaa   9840
tagtacgcgg aaaaaacata atagctcccc tgttttcatc catggtttta agtaaatgat   9900
cactggcttc tttagtcaat ggatattcga acattaaccg tttcatcatc attggacaga   9960
atccatattt cttaatgtaa agagtgatca aatcattgtg tttattgtac catcttgttg  10020
taaatgtgta ttcggttatc ggatctgctc cttttctat taaagtatcg atatcgatct  10080
cgtctaagaa ttcaactata tcgacatatt tcatttgtat acacataacc attactaacg  10140
tagaatgtat aggaagagat gtaacgggaa cagggtttgt tgattcgcaa actattctaa  10200
tacataattc ttctgttaat acgtcttgca cgtaatctat tatagatgcc aagatatcta  10260
tataattatt ttgtaagatg atgttaacta tgtgatctat ataagtagtg taataattca  10320
tgtattttga tatatgttcc aactctgtct ttgtgatgtc tagtttcgta atatctatag  10380
catcctcaaa aaatatattc gcatatattc ccaagtcttc agttctatct tctaaaaaat  10440
cttcaacgta tggaatataa taatctattt tacctcttct gatatcatta atgatatagt  10500
ttttgacact atcttctgtc aattgattct tattcactat atctaagaaa cggatagcgt  10560
ccctaggacg aactactgcc attaatatct ctattatagc ttctggacat aattcatcta  10620
ttataccaga attaatggga actattccgt atctatctaa catagtttta agaaagtcag  10680
aatctaagac ttgatgttca tatattggtt catacatgaa atgatctcta ttgatgatag  10740
tgactatttc gttctctgaa aattggtaac tcattttata tatgctttcc ttgttgatga  10800
aggataggat atactcaata gaatttgtac caacaaactg ttctcttatg aatcgtatat  10860
catcatctga aataatcatg taaggcatac atttaacaat tagagacttg tctcctgtta  10920
```

tcaatatact attcttgtga taatttatgt gtgaggcaaa tttgtccacg ttctttaatt 10980
ttgttatagt agatatcaaa tccaatggag ctacagttct tggcttaaac agatatagtt 11040
tttctggaac gaattctaca acattattat aaaggacttt gggtagataa gtgggatgaa 11100
atcctatttt aattaatgct atcgcattgt cctcgtgcaa atatccaaac gcttttgtga 11160
tagtatgaca ttcattatct agaaacgctc tacgaatatc tgtcacagat atcatcttta 11220
gagaatacta gttgcgttaa tagtactaaa atttgtattt tttttaatat atctcaaaaa 11280
aaattaatat ttatggatcc gatgtataat tagaatcaga atctaatgat gacgtaccca 11340
agaagtttat ctacagccaa tttagctgca ttatttttag catctcgttt agattttcca 11400
tcggccttat cgaatactct tccgtcgata tctacacagg cataaaatgt aggagagtta 11460
ctaggcccaa ctgattcaat acgaaaagac caatctctct tagttatttg gcagtactca 11520
ttaataatgg tgacagggtt agcatctttc caatcaataa ttttttagc cggaataaca 11580 tcatcaaaag acttatgatc ctctctcatt gatttttcgc gggatacatc atctattatg 11640
gcgtcagcca taacatcagc atccggctta tccgcctccg ttgtcataaa ccaacgagga 11700
ggaatatcgt cggagctgta caccatagca ctacgttgaa gatcgtacag agctttatta 11760
acttctcgct tctccatatt aagttgtcta gttagttgtg cagcagtagc tccttcgatt 11820
ccaatgtttt taatagccgc acacacaatc tctgcgtcag aacgctcgtc aatatagatc 11880
ttagacattt ttagagagaa ctaacacaac cagcaataaa actgaaccta ctttatcatt 11940
tttttattca tcatcctctg gtggttcgtc gttcctatcg aatgtggatc tgattaaccc 12000
gtcatctata ggtgatgctg gttctggaga ttctggagga gatggattat tatctggaag 12060
aatctctgtt atttccttgt tttcatgtat cgattgcgtt gtaacattaa gattgcgaaa 12120
tgctctaaat ttgggaggct taaagtgttg tttgcaatct ctacacgcat gtctaactag 12180
tggaggttcg tcagcggctc tagtttgaat catcatcggc gtagtattcc tacttttaca 12240
gttaggacac ggtgtattgt atttctcgtc gagaacgtta aaataatcgt tgtaactcac 12300
atcctttatt ttatctatat tgtattctac tcctttctta atgcatttta taccgaataa 12360
gagatagcga aggaattctt tttcggtgcc gctagtaccc ttaatcatat cacatagtgt 12420
tttatattcc aaatttgtgg caatagacgg tttatttcta tacgatagtt tgtttctgga 12480
atcctttgag tattctatac caatattatt ctttgattcg aatttagttt cttcgatatt 12540
agattttgta ttacctatat tcttgatgta gtactttgat gatttttcca tggcccattc 12600
tattaagtct tccaagttgg catcatccac atattgtgat agtaattctc ggatatcagt 12660
agcggctacc gccattgatg tttgttcatt ggatgagtaa ctactaatgt atacattttc 12720
catttataac acttatgtat taactttgtt catttatatt ttttcattat tatgttgata 12780
ttaacaaaag tgaatatata tgttaataat tgtattgtgg ttatacggct acaatttcat 12840
aatgagtgga agtcagtgtc cgatgatcaa tgacgatagc tttactctga aaagaaagta 12900
tcaaatcgat agtgcggagt caacaatgaa aatggataag aagaggacaa agtttcagaa 12960
tagagccaaa atggtaaaag aaataaatca gacaataaga gcagcacaaa ctcattacga 13020
gacattgaaa ctaggataca taaaatttaa gagaatgatt atgactacta ctctagaaga 13080
tatagcacca tctattccaa ataatcagaa aacttataaa ctattctcgg acatttcagc 13140
catcggcaaa gcatcacgga atccaagtaa gatggtatat gctctgctgc tttacatgtt 13200
tcccaatttg tttggagatg accatagatt cattcgttat agaatgcatc caatgagtaa 13260

```
aatcaaacac aagatcttct ctcctttcaa acttaatctt attagaatat tagtggaaga  13320
aagattctat aataatgaat gcagatctaa taaatggaac acaagttgat aaaatgttga  13380
tagctgaatc tgataaatat acaatagatg caaggtataa cctaaaaccc atgtatagaa  13440
tcaagggaga atctgaagaa gataccctct tcatcaaaca gatggtagaa caatgtgtga  13500
catcccagga attggtggaa aaagtgttga agatactgtt tagagatttg ttcaagagtg  13560
gagaatacaa agcatacaga tacgatgatg atgtagaaaa tggatttatt ggattggata  13620
cactaaaatt aaacattgtt catgatatag ttgaaccatg tatgcctgtt cgtaggccag  13680
tggctaagat actgtgtaaa gaaatggtaa ataaatactt tgagaatccg ctacatatta  13740
ttggtaaaaa tcttcaagag tgcattgact ttgttagtga ataggcattt catctttctc  13800
caatactaat tcaaattgtt aaattaataa tggatagtat aaatagttat tagtgataaa  13860
atagtaaaaa taattattag aataagagtg tagtatcata gataactctc ttctataaaa  13920
atggatttta ttcgtagaaa gtatcttata tacacagtag aaaataatat agatttttta  13980
aaggatgata cattaagtaa agtaaacaat tttaccctca atcatgtact agctctcaag  14040
tatctagtta gcaattttcc tcaacacgtt attactaagg atgtattagc taataccaat  14100
tttttgttt tcatacatat ggtacgatgt tgtaaagtgt acgaagcggt tttacgacac  14160
gcatttgatg cacccacgtt gtacgttaaa gcattgacta agaattattt atcgtttagt  14220
aacgcaatac aatcgtacaa ggaaaccgtg cataaactaa cacaagatga aaaattttta  14280
gaggttgccg aatacatgga cgaattagga gaacttatag gcgtaaatta tgacttagtt  14340
cttaatccat tatttcacgg aggggaaccc atcaaagata tggaaatcat ttttttaaaa  14400
ctgtttaaga aaacagactt caaagttgtt aaaaaaattaa gtgttataag attacttatt  14460
tgggcttacc taagcaagaa agatacaggc atagagtttg cggataatga tagacaagat  14520
atatacactc tatttcaaca aactggtaga atagtccata gcaatctaac agaaacgttt  14580
agagattata tctttcccgg agataagact agctattggg tgtggttaaa cgaaagtata  14640
gctaatgatg cggatattgt tcttaataga cacgccatta ccatgtatga taaaattctt  14700
agttatatat actctgagat aaaacaagga cgcgttaata aaaacatgct taagttagtt  14760
tatatctttg agcctgaaaa agatatcaga gaacttctgc tagaaatcat atatgatatt  14820
cctggagata tcctatctat tattgatgca aaaaacgacg attggaaaaa atattttatt  14880
agtttttata aagctaattt tattaacggt aatacattta ttagtgataa aacgtttaac  14940
gaggacttat tcagagttgt tgttcaaata aatcccgaat atttcgataa tgaacgaatt  15000
atgtctttat tctctacgag tgctgcggac attaaacgat ttgatgagtt agatattaat  15060
aacagttata tatctaatat aatttatgag gtgaacgata tcacattaga tacaatggat  15120
gatatgaaga agtgtcaaat ctttaacgag gatacgtcgt attatgttaa ggaatacaat  15180
acatacctgt tttgcacgga gtcggatccc atggtcatag agaacggaat actaaagaaa  15240
ctgtcatcta taaaatccaa gagtagacgg ctgaacttgt ttagcaaaaa cattttaaaa  15300
tattatttag acggacaatt ggctcgtcta ggtcttgtgt tagatgatta taaaggagac  15360
ttgttagtta aaatgataaa ccatcttaag tctgtggagg atgtatccgc attcgttcga  15420
ttttctacag ataaaaaccc tagtattctt ccatcgctaa tcaaaactat tttagctagt  15480
tataatattt ccatcatcgt cttatttcaa aggtttttga gagataatct atatcatgta  15540
gaagaattct tggataaaag catccatcta accaagacgg ataagaaata tatacttcaa  15600
ttgataagac acggtagatc atagaacaga ccaaatatat tattaataat ttgtatatac  15660
```

```
atagatataa ttatcacata ttaaaaattc acacattttt gataaatggg aactgctgca  15720
acaattcaga ctcccaccaa attaatgaat aaagaaaatg cagaaatgat tttggaaaaa  15780
attgttgatc atatagttat gtatattagt gacgaatcaa gtgattcaga aaataatcct  15840
gaatatattg attttcgtaa cagatacgaa gactatagat ctctcattat aaaaagtgat  15900
cacgagtttg taaagctatg taaaaatcat gcggagaaaa gttctccaga aacgcaacaa  15960
atgattatca aacacatata cgaacaatat cttattccag tatctgaagt actattaaaa  16020
cctataatgt ccatgggtga cataattaca tataacggat gtaaagacaa tgaatggatg  16080
ctagaacaac tctctaccct aaactttaac aatctccgca catggaactc atgtagcata  16140
ggcaatgtaa cgcgtctgtt ttatacattt tttagttatc tgatgaaaga taaactaaat  16200
atataagtat aatcccattc taatacttta acctgatgta ttagcatctt attagaatat  16260
taacctaact aaaagacata acataaaaac tcattacata gttgataaaa agcggtagga  16320
tataaatatt atggctgcca ccgttccgcg ttttgacgac gtgtacaaaa atgcacaaag  16380
aagaattcta gatcaagaaa catttttag tagaggtcta agtagaccgt taatgaaaaa  16440
cacatatcta tttgataatt acgcgtatgg atggatacca gaaactgcaa tttggagtag  16500
tagatacgca aacctagatg ctagtgacta ttatcccatt tcgttgggat tacttaaaaa  16560
gtttgagttt ctcatgtctc tatataaagg tcctattccc gtatatgaag aaaaagtaaa  16620
tactgaattc attgctaatg gatctttctc cggtagatat gtatcatatc ttagaaagtt  16680
ttctgctctt ccaacaaacg agtttattag tttttgtta ctgacttcca ttccaatcta  16740
taatatcttg ttctggttta aaaatactca gtttgatatt actaaacaca cattattcag  16800
atacgtctat acagataatg ccaaacacct ggcgttggct aggtatatgc atcaaacagg  16860
agactataag cctttgttta gtcgtctcaa agagaattat atatttaccg gtcccgttcc  16920
aataggtatc aaagatatag atcaccctaa tcttagtaga gcaagaagtc catccgatta  16980
tgagacatta gctaatatta gtactatatt gtactttacc aagtatgatc cggtattaat  17040
gtttttattg ttttacgtac ctgggtattc aattactaca aaaattactc cagccgtaga  17100
atatctaatg gataaactga atctaacaaa gagcgacgta caactgttgt aaattatttt  17160
atgcttcgta aaatgtaggt tttgaaccaa acattctttc aaagaatgag atgcataaaa  17220
ctttattatc caatagattg actatttcgg acgtcaatcg tttaaagtaa acttcgtaaa  17280
atattctttg atcactgccg agtttaaaac ttctatcgat aattgtttca tatgttttaa  17340
tatttacaag ttttttggtc catggtccat taggacaaat atatgcaaaa taatatcgtt  17400
ctccaagttc tatagtctct ggattatttt tattatattc agtaaccaaa tacatattag  17460
ggttatctgc ggatttataa tttgagtgat gcattcgact caacataaat aattctagag  17520
gagacgatct actatcaaat tcggatcgta aatctgtttc taaagaacgg agaatatcta  17580
tacatacctg attagaattc atccgtcctt cagacaacat ctcagacagt ctggttttgt  17640
acatcttaat catattctta tgaaacttgg aaacatctct tctagtttca ctagtacctt  17700
tattaattct ctcaggtaca gattttgaat tcgacgatgc tgagtatttc atcgttgtat  17760
atttcttctt cgattgcata atcagattct tatataccgc ctcaaactct attttaaaat  17820
tattaaacaa tactctatta ttaatcagtc gttctaactc tttcgctatt tctatagact  17880
tatcgacatc ttgactgtct atctctgtaa acacggagtc ggtatctcca tacacgctac  17940
gaaaacgaaa tctgtaatct ataggcaacg atgttttcac aatcggatta atatctctat  18000
```

cgtccatata aaatggatta cttaatggat tggcaaaccg taacataccg ttagataact 18060
ctgctccatt tagtaccgat tctagataca agatcattct acgtcctatg gatgtgcaac 18120
tcttagccga agcgtatgag tatagagcac tatttctaaa tcccatcaga ccatatactg 18180
agttggctac tatcttgtac gtatattgca tggaatcata gatggccttt tcagttgaac 18240
tggtagcctg ttttaacatc tttttatatc tggctctctc tgccaaaaat gttcttaata 18300
gtctaggaat ggttccttct atcgatctat cgaaaattgc tatttcagag atgaggttcg 18360
gtagtctagg ttcacaatga accgtaatat atctaggagg tggatatttc tgaagcaata 18420
gctgattatt tatttcttct tccaatctat tggtactaac aacgacaccg actaatgttt 18480
ccggagatag atttccaaag atacacacat taggatacag actgttataa tcaaagatta 18540
atacattatt actaaacatt ttttgttttg gagcaaatac cttaccgcct tcataaggaa 18600
acttttgttt tgtttctgat ctaactaaga tagttttagt ttccaacaat agctttaaca 18660
gtggaccctt gatgactgta ctcgctctat attcgaatac catggattga ggaagcacat 18720
atgttgacgc acccgcgtct gtttttgttt ctactccata atactcccac aaatactgac 18780
acaaacaagc atcatgaata cagtatctag ccatatctaa agctatgttt agattataat 18840
ccttatacat ctgagctaaa tcaacgtcat cctttccgaa agataattta tatgtatcat 18900
taggtaaagt aggacataat agtacgactt taaatccatt ttcccaaata tctttacgaa 18960
ttactttaca tataatatcc tcatcaacag tcacataatt acctgtggtt aaaacctttg 19020
caaatgcagc ggctttgcct ttcgcgtctg tagtatcgtc accgatgaac gtcatttctc 19080
taactcctct atttaatact ttacccatgc aactgaacgc gttcttggat atagaatcca 19140
atttgtacga atccaatttt tcagattttt gaatgaatga atatagatcg aaaaatatag 19200
ttccattatt gttattaacg tgaaacgtag tattggccat gccgcctact cccttatgac 19260
tagactgatt tctctcataa atacagagat gtacagcttc ctttttgtcc ggagatctaa 19320
agataatctt ctctcctgtt aataactcta gacgattagt aatatatctc agatcaaagt 19380
tatgtccgtt aaaggtaacg acgtagtcga acgttagttc caacaattgt ttagctattc 19440
gtaacaaaac tatttcagaa catagaacta gttctcgttc gtaatccatt tccattagtg 19500
actgtatcct caaacatcct ctatcgacgg cttcttgtat ttcctgttcc gttaacatct 19560
cttcattaat gagcgtaaac aataatcgtt taccacttaa atcgatataa cagtaacttg 19620
tatgcgagat tgggttaata aatacagaag gaaacttctt atcgaagtga cactctatat 19680
ctagaaataa gtacgatctt gggatatcga atctaggtat ttttttagcg aaacagttac 19740
gtggatcgtc acaatgataa catccattgt taatctttgt caaatattgc tcgtccaacg 19800
agtaacatcc gtctggagat atcccgttag aaatataaaa ccaactaata ttgagaaatt 19860
catccatggt ggcattttgt atgctgcgtt tctttggctc ttctatcaac cacatatctg 19920
cgacggagca ttttctatct ttaatatcta gattataact tattgtctcg tcaatgtcta 19980
tagttctcat ctttcccaac ggcctcgcat taaatggagg aggagacaat gactgatata 20040
tttcgtccgt aactacgtaa taaaagtaat gaggaaatcg tataaataca gtctcaccat 20100
ttcgacatct ggatttcaga tataaaaatc tgttttcacc gtgactttca aaccaattaa 20160
tgcaccgaac atccatttct agaatttaga aatatatttt catttaaatg aatcccaaac 20220
attggggaag agccgtatgg accattattt ttatagtact ttcgcaagcg ggtttagacg 20280
gcaacataga agcgtgtaaa cgaaaactat atactatagt cagcactctt ccatgtcctg 20340
catgtagacg gcacgcgact atcgctatag aggacaataa tgtcatgtct agcgatgatc 20400

```
tgaattatat ttattatttt ttcatcagat tatttaacaa tttggcatct gatcccaaat  20460
acgcaatcaa tgtgtcaaag gttaaccctt tataaactta acccattata aaacttatga  20520
ttagtcacaa ctgaaataac cgcgtgatta ttttttggta taattctaca cggcatggtt  20580
tctgtgacta tgaattcaac ccccgttaca ttagtgaaat ctttaacaaa cagcaagggt  20640
tcgtcaaaga cataaaactc attgtttaca atcgaaatag acccccctatc acacttaaaa  20700
taaaaaatat ccttatcctt taccaccaaa taaaattctg attggtcaat gtgaatgtat  20760
tcacttaaca gttccacaaa tttatttatt aactccgagg cacatacatc gtcggtattt  20820
tttatggcaa actttactct tccagcatcc gtttctaaaa aaatattaac gagttccatt  20880
tatatcatcc aatattattg aaatgacgtt gatggacaga tgatacaaat aagaaggtac  20940
ggtacctttg tccaccatct cctccaattc atgctctatt ttgtcattaa ctttaatgta  21000
tgaaaacagt acgccacatg cttccatgac agtgtgtaac actttggata caaaatgttt  21060
gacattagta taattgtcca agactgtcaa tctataatag atagtagcta taatatattc  21120
tatgatggta ttgaagaaga tgacaacctt ggcatattga tcatttaaca cagacatggt  21180
atcaacagat agcttgaatg aaagagaatc agtaattgga ataagcgtct tctcgataga  21240
gtgtccgtat accaacatgt ctgatatttt gatgtattcc attaaattat ttagtttttt  21300
ctttttattt tcgttaaaca gcatttctgt caacggaccc caacatcgtt gaccgattaa  21360
gttttgattg atttttccgt gtaaggcgta tctagtcaga tcgtatagcc tatccaataa  21420
tccatcatct gtgcgtagat cacatcgtac actttttaat tctctataga agagcgacag  21480
acatctggag caattacaga cagcaatttc tttattctct acagatgtaa gatacttgaa  21540
gacattccta tgatgatgca gaattttgga taacacggta ttgatggtat ctgttaccat  21600
aattcctttg atggctgata gtgtcagagc acaagatttc caatctttga caatttttag  21660
caccattatc tttgttttga tatctatatc agacagcatg gtgcgtctga caacacaggg  21720
attaagacgg aaagatgaaa tgattctctc aacatcttca atggatacct tgctattttt  21780
tctggcatta tctatatgtg cgagaatatc ctctagagaa tcagtatcct ttttgatgat  21840
agtggatctc aatgacatgg gacgtctaaa ccttcttatt ctatcaccag attgcatggt  21900
gatttgtctt ctttctttta tcataatgta atctctaaat tcatcggcaa attgtctata  21960
tctaaaatca taatatgaga tgtttacctc tacaaatatc tgttcgtcca atgttagagt  22020
atctacatca gttttgtatt ccaaattaaa catggcaacg gatttaattt tatattcctc  22080
tattaagtcc tcgtcgataa taacagaatg tagataatca tttaatccat cgtacatggt  22140
tggaagatgc ttgttgacaa aatctttaat tgtcttgatg aaggtgggac tatatctaac  22200
atcttgatta ataaaattta taacattgtc cataggatac tttgtaacta gttttataca  22260
catctcttca tcggtaagtt tagacagaat atcgtgaaca ggtggtatat tatattcatc  22320
agatatacga agaacaatgt ccaaatctat attgtttaat atattatata gatgtagcgt  22380
agctcctaca ggaatatctt taactaagtc aatgatttca tcaaccgtta gatctatttt  22440
aaagttaatc atataggcat tgatttttaa aaggtatgta gccttgacta cattttcatt  22500
aattaaccat tccaagtcac tgtgtgtaag aagattatat tctatcataa gcttgactac  22560
atttggtccc aataccatta aagaattctt atgatataag gaaacagctt ttaggtactc  22620
atctactcta caagaatttt ggagagcctt aacgatatca gtgacgttta ttatttcagg  22680
aggaaagaat ctaacattga gaatatcgga attaatagct tccagataca gtgattttgg  22740
```

caatagtccg tgtaatccat aatccagtaa cacgagctgg tgcttgctag acaccttttc 22800
aatgtttaat tttttgaaa taagctttga taaagccttc ctcgcaaatt ccggatacat 22860
gaacatgtcg gcgacatgat taagtattgt tttttcatta ttttctcaac aagttctcaa 22920
taccccaata gatgatagaa tatcacccaa tgcgtccatg ttgtctattt ccaacaggtc 22980
gctatatcca ccaatagaag ttttcccaaa aaagattcta ggaacagttc taccaccagt 23040
aatttgttca aaataatccc gcaattcatt ttcgggttta aattctttaa tatcgacaat 23100
ttcatacgct cctcttttga aactaaactt atttagaata tccagtgcat ttctacaaaa 23160
aggacatgta tacttgacaa aaattgtcac tttgttattg gccaaccttt gttgtacaaa 23220
ttcctcggcc attttaatat ttaagtgata taaaactatc tcgacttatt taactcttta 23280
gtcgagatat atggacgcag atagctatat gatagtaggg ataacagggt aat 23333

<210> SEQ ID NO 4
<211> LENGTH: 26445
<212> TYPE: DNA
<213> ORGANISM: Vaccinia virus

<400> SEQUENCE: 4
tagggataac agggtaattt tctagaattt agaaatatat tttcatttaa atgaatccca 60
aacattgggg aagagccgta tggaccatta tttttatagt actttcgcaa gcgggtttag 120
acggcaacat agaagcgtgt aaacgaaaac tatatactat agtcagcact cttccatgtc 180
ctgcatgtag acggcacgcg actatcgcta tagaggacaa taatgtcatg tctagcgatg 240
atctgaatta tatttattat tttttcatca gattatttaa caatttggca tctgatccca 300
aatacgcaat caatgtgtca aaggttaacc ctttataaac ttaacccatt ataaaactta 360
tgattagtca caactgaaat aaccgcgtga ttattttttg gtataattct acacggcatg 420
gtttctgtga ctatgaattc aaccccccgtt acattagtga aatctttaac aaacagcaag 480
ggttcgtcaa agacataaaa ctcattgttt acaatcgaaa tagacccccct atcacactta 540 aaataaaaaa tatccttatc ctttaccacc aaataaaatt ctgattggtc aatgtgaatg 600
tattcactta acagttccac aaatttattt attaactccg aggcacatac atcgtcggta 660 tttttatgg caaactttac tcttccagca tccgtttcta aaaaaatatt aacgagttcc 720
atttatatca tccaatatta ttgaaatgac gttgatggac agatgataca aataagaagg 780
tacggtacct ttgtccacca tctcctccaa ttcatgctct attttgtcat taactttaat 840
gtatgaaaac agtacgccac atgcttccat gacagtgtgt aacactttgg atacaaaatg 900
tttgacatta gtataattgt ccaagactgt caatctataa tagatagtag ctataatata 960
ttctatgatg gtattgaaga agatgacaac cttggcatat tgatcattta acacagacat 1020
ggtatcaaca gatagcttga atgaaagaga atcagtaatt ggaataagcg tcttctcgat 1080
agagtgtccg tataccaaca tgtctgatat tttgatgtat tccattaaat tatttagttt 1140
tttcttttta ttttcgttaa acagcatttc tgtcaacgga ccccaacatc gttgaccgat 1200
taagttttga ttgatttttc cgtgtaaggc gtatctagtc agatcgtata gcctatccaa 1260
taatccatca tctgtgcgta gatcacatcg tacacttttt aattctctat agaagagcga 1320
cagacatctg gagcaattac agacagcaat ttctttattc tctacagatg taagatactt 1380
gaagacattc ctatgatgat gcagaatttt ggataacacg gtattgatgg tatctgttac 1440
cataattcct ttgatggctg atagtgtcag agcacaagat ttccaatctt tgacaatttt 1500
tagcaccatt atctttgttt tgatatctat atcagacagc atggtgcgtc tgacaacaca 1560

```
gggattaaga cggaaagatg aaatgattct ctcaacatct tcaatggata ccttgctatt   1620
ttttctggca ttatctatat gtgcgagaat atcctctaga gaatcagtat cctttttgat   1680
gatagtggat ctcaatgaca tgggacgtct aaaccttctt attctatcac cagattgcat   1740
ggtgatttgt cttctttctt ttatcataat gtaatctcta aattcatcgg caaattgtct   1800
atatctaaaa tcataatatg agatgtttac ctctacaaat atctgttcgt ccaatgttag   1860
agtatctaca tcagttttgt attccaaatt aaacatggca acggatttaa ttttatattc   1920
ctctattaag tcctcgtcga taataacaga atgtagataa tcatttaatc catcgtacat   1980
ggttggaaga tgcttgttga caaaatcttt aattgtcttg atgaaggtgg gactatatct   2040
aacatcttga ttaataaaat ttataacatt gtccatagga tactttgtaa ctagttttat   2100
acacatctct tcatcggtaa gtttagacag aatatcgtga acaggtggta tattatattc   2160
atcagatata cgaagaacaa tgtccaaatc tatattgttt aatatattat atagatgtag   2220
cgtagctcct acaggaatat ctttaactaa gtcaatgatt tcatcaaccg ttagatctat   2280
tttaaagtta atcatatagg cattgatttt taaaaggtat gtagccttga ctacattttc   2340
attaattaac cattccaagt cactgtgtgt aagaagatta tattctatca taagcttgac   2400
tacatttggt cccaatacca ttaaagaatt cttatgatat aaggaaacag cttttaggta   2460
ctcatctact ctacaagaat tttggagagc cttaacgata tcagtgacgt ttattatttc   2520
aggaggaaag aatctaacat tgagaatatc ggaattaata gcttccagat acagtgattt   2580
tggcaatagt ccgtgtaatc cataatccag taacacgagc tggtgcttgc tagacacctt   2640
ttcaatgttt aatttttttg aaataagctt tgataaagcc ttcctcgcaa attccggata   2700
catgaacatg tcggcgacat gattaagtat tgtttttttca ttattttctc aacaagttct   2760
caatacccca atagatgata gaatatcacc caatgcgtcc atgttgtcta tttccaacag   2820
gtcgctatat ccaccaatag aagttttccc aaaaaaagatt ctaggaacag ttctaccacc   2880
agtaatttgt tcaaaataat cccgcaattc attttcgggt ttaaattctt taatatcgac   2940
aatttcatac gctcctcttt tgaaactaaa cttatttaga atatccagtg catttctaca   3000
aaaaggacat gtatacttga caaaaattgt cactttgtta ttggccaacc tttgttgtac   3060
aaattcctcg gccattttaa tatttaagtg atataaaact atctcgactt atttaactct   3120
ttagtcgaga tatatggacg cagatagcta tatgatagcc aactacagaa ggcaaacgct   3180
ataaaaaaca taattacgac gagcatattt ataaatattt ttattcagca ttacttgata   3240
tagtaatatt aggcacagtc aaacattcaa ccactctcga tacattaact ctctcatttt   3300
ctttaacaaa ttctgcaata tcttcgtaaa aagattcttg aaacttttta gaatatctat   3360
cgactctaga tgaaatagcg ttcgtcaaca tactatgttt tgtatacata aaggcgccca   3420
ttttaacagt ttctagtgac aaaatgctag cgatcctagg atcctttaga atcacataga   3480
ttgacgattc gtctctctta gtaactctag taaaataatc atacaatcta gtacgcgaaa   3540
taatattatc cttgacttga ggagatctaa acaatctagt tttgagaaca tcgataagtt   3600
catcgggaat gacatacata ctatctttaa tagaactctt ttcatccagt tgaatggatt   3660
cgtccttaac caactgatta atgagatctt ctattttatc attttccaga tgatatgtat   3720
gtccattaaa gttaaattgt gtagcgcttc tttttagtct agcagccaat actttaacat   3780
cactaatatc gatatacaaa ggagatgatt tatcgatggc attaagaatt cgtttttcga   3840
catctgtcaa aaccaattcc tttttgcctg tatcatccag ttttccatcc tttgtaaaga   3900
```

-continued aattattttc tactagacta ttaataagac tgataaggat tcctccataa ttgcacaatc 3960
caaacttttt cacaaaacta gactttacaa gatctacagg aatgcgtact tcaggtttct 4020
tagcttgtga ttttttcttt tgtggacatt ttcttgtgac caactcatct accatttcat 4080
tgattttagc agtgaaataa gctttcaatg cacgggcact gatactattg aaaacgagtt 4140
gatcttcaaa ttccgccatt taagttcacc aaacaacttt taaatacaaa tatatcaata 4200
gtagtagaat aagaactata aaaaaaataa taattaacca ataccaaccc caacaaccgg 4260
tattattagt tgatgtggta gttttctcat cacttagaac agatttaaca atttctataa 4320
agtctgtcaa atcatctttc ggagaaccca tatatacacc aaatatagcg gcgtacaact 4380
tatccattta tacattgaat attggctttt ctttatcgct atcttcatca tattcatcat 4440
caatatcaac aagtcccaga ttacgagcca gatcttcttc tacattttca gtcattgata 4500
cacgttcact atctccagag agtccgataa cgttagccac cacttctcta tcaatgatta 4560
gtttcttgag tgcgaatgta atttttgttt ccgttccgga tctatagaaa actacaggtg 4620
tgataattgc cttggccaat tgtctttctc ttttactgag tgattctagt tcaccttcta 4680
tagatctgag aatggatgat tctccagtcg aaacatattc taccatggat ccgtttaatt 4740
tgttgatgaa gatggattca tccttaaatg ttttctctgt aatagtttcc accgaaagac 4800
tatgcaaaga atttggaatg cgttccttgt gcttaatgtt tccatagacg gcttctagaa 4860
gttgatacaa cataggacta gccgcggtaa cttttatttt tagaaagtat ccatcgcttc 4920
tatcttgttt agatttattt ttataaagtt tagtctctcc ttccaacata ataaaagtgg 4980
aagtcatttg actagataaa ctatcagtaa gttttataga gatagacgaa caattagcgt 5040
attgagaagc atttagtgta acgtattcga tacattttgc attagattta ctaatcgatt 5100
ttgcatactc tataacaccc gcacaagtct gtagagaatc gctagatgca gtaggtcttg 5160
gtgaagtttc aactctcttc ttgattacct tactcatgat taaacctaaa taattgtact 5220
ttgtaatata atgatatata ttttcacttt atctcatttg agaataaaaa tgtttttgtt 5280
taaccactgc atgatgtaca gatttcggaa tcgcaaacca ccagtggttt tattttatcc 5340
ttgtccaatg tgaattgaat gggagcggat gcgggtttcg tacgtagata gtacattccc 5400
gtttttagac cgagactcca tccgtaaaaa tgcatactcg ttagtttgga ataactcgga 5460
tctgctatat ggatattcat agattgactt tgatcgatga aggctcccct gtctgcagcc 5520
atttttatga tcgtcttttg tggaatttcc caaatagttt tataaactcg cttaatatct 5580
tctggaaggt ttgtattctg aatggatcca ccatctgcca taatcctatt cttgatctca 5640
tcattccata attttctctc ggttaaaact ctaaggagat gcggattaac tacttgaaat 5700
tctccagaca atactctccg agtgtaaata ttactggtat acggttccac cgactcatta 5760
tttcccaaaa tttgagcagt tgatgcagtc ggcataggtg ccaccaataa actatttcta 5820
agaccgtatg ttctgatttt atcttttaga ggttcccaat tccaaagatc cgacggtaca 5880
acattccaaa gatcatattg tagaataccg ttactggcgt acgatcctac atatgtatcg 5940
tatggtcctt ccttctcagc tagttcacaa ctcgcctcta atgcaccgta ataaatggtt 6000
tcgaagatct tcttatttag atcttgtgct tccaggctat caaatggata atttaagaga 6060
ataaacgcgt ccgctaatcc ttgaacacca ataccgatag gtctatgtct cttattagag 6120
atttcagctt ctggaatagg ataataatta atatctataa ttttattgag atttctgaca 6180
attactttga ccacatcctt cagtttgaga aaatcaaatc gcccatctat tacaaacatg 6240
ttcaaggcaa cagatgccag attacaaacg gctacctcat tagcatccgc atattgtatt 6300

```
atctcagtgc aaagattact acacttgata gttcctaaat tttgttgatt actctttttg   6360
ttacacgcat ccttataaag aatgaatgga gtaccagttt caatctgaga ttctataatc   6420
gctttccaga cgactcgagc ctttattata gatttgtatc tcctttctct ttcgtatagt   6480
gtatacaatc gttcgaactc gtctccccaa acattgtcca atccaggaca ttcatccgga   6540
cacatcaacg accactctcc gtcatccttc actcgtttca taaagagatc aggaatccaa   6600
agagctataa atagatctct ggttctatgt tcctcgtttc ctgtattctt tttaagatcg   6660
aggaacgcca taatatcaga atgccacggt tccaagtata tggccataac tccaggccgt   6720
ttgtttcctc cctgatctat gtatctagcg gtgttattat aaactctcaa cattggaata   6780
ataccgtttg atataccatt ggtaccggag atatagcttc cactggcacg aatattacta   6840
attgatagac ctattccccc tgccatttta gagattaatg cgcatcgttt taacgtgtca   6900
tagataccct ctatgctatc atcgatcatg ttaagtagaa aacagctaga catttggtga   6960
cgactagttc ccgcattaaa taaggtagga gaagcgtgcg taaaccattt ttcagaaagt   7020
agattgtacg tctcaatagc tgagtctata tcccattgat gaattcctac tgcgacacgc   7080
attaacatgt gctgaggtct ttcaacgatc ttgttgttta ttttcaacaa gtaggatttt   7140
tccaaagttt taaaaccaaa atagttgtat gaaaagtctc gttcgtaaat aataaccgag   7200
ttgagtttat ccttatattt gttaactata tccatggtga tacttgaaat aatcggagaa   7260
tgtttcccat ttttaggatt aacatagttg aataaatcct ccatcacttc actaaatagt   7320
tttttgttt ccttgtgtag atttgatacg gctattctgg cggctagaat ggcataatcc   7380
ggatgttgtg tagtacaagt ggctgctatt tcggctgcca gagtgtccaa ttctaccgtt   7440
gttactccat tatatattcc ttgaataacc ttcatagcta ttttaatagg atctatatga   7500
tccgtgttta agccataaca taattttcta atacgagacg tgattttatc aaacatgaca   7560
ttttccttgt atccatttcg tttaatgaca aacattttg ttggtgtaat aaaaaaatta   7620
tttaactttt cattaatagg gatttgacgt atgtagcgta caaaattatc gttcctggta   7680
tatagataaa gagtcctata tatttgaaaa tcgttacggc tcgattaaac tttaatgatt   7740
gcatagtgaa tatatcatta ggatttaact ccttgactat catggcggcg ccagaaatta   7800
ccatcaaaag cattaataca gttatgccga tcgcagttag aacggttata gcatccacca   7860
tttatatcta aaaattagat caaagaatat gtgacaaagt cctagttgta tactgagaat   7920
tgacgaaaca atgtttctta catatttttt tcttattagt aaccgactta atagtaggaa   7980
ctggaaaact agacttgatt attctataag tatagatacc cttccaaata atattctctt   8040
tgataaaagt tccagaaaat gtagaatttt ttaaaaagtt atcttttgct attaccaaga   8100
ttgtgtttag acgcttatta ttaatatgag tgatgaaatc cacaccgcct ctagatatcg   8160
cttttatttc cacattagat ggtaaatcca atagtgaaac tatcttttta ggaatgtatg   8220
gactcgcgtt tagaggagtg aacgtcttgg gcgtcggaaa ggatgattcg tcaaacgaat   8280
aaacaatttc acaaatggat gttaatgtat tagtaggaaa tttttgacg ctagtggaat   8340
tgaagattct aatggatgat gttctaccta tttcatccga taacatgtta atttccgaca   8400
ccaacggttt taatatttcg atgatatacg gtagtctctc tttcggactt atatagctta   8460
ttccacaata cgagtcatta tatactccaa aaaacaaaat aactagtata aaatctgtat   8520
cgaatgggaa aaacgaaatt atcgacatag gtatagaatc cggaacattg aacgtattaa   8580
tacttaattc tttttctgtg gtaagtaccg ataggttatt gacattgtat ggttttaaat   8640
```

-continued attctataac ttgagacttg atagatatta gtgatgaatt gaaaattatt tttatcacca 8700
cgtgtgtttc aggatcatcg tcgacgcccg tcaaccaacc gaatggagta aaataaatat 8760
cattaatata tgctctaaat attagtattt ttattaatcc tttgattatc atcttctcgt 8820
acgcgaatga ttccatgatc aagagtgatt tgagaacatc ctccggagta ttaatgggct 8880
tagtaaacag tacatcgttg caataataaa agttatccaa gttaaaggat attatgcatt 8940
cgtttaaaga tatcacctca tctgacggag acaatttttt ggtaggtttt agagactttg 9000
aagctacttg tttaacaaag ttattcatcg tcgtttacta ttctatttaa ttttgtagtt 9060
aatttatcac atatcacatt aattgacttt ttggtccact tttccatacg tttatattct 9120
tttaatcctg cgttatccgt ttccgttata tccagtgata gatcgtgcag gttaaataga 9180
atgctcttaa ataatgtcat tttcttatcc gctaaaaatt taaagaatgt ataaaccttt 9240
ttcagagatt tgaaactctt aggtggtgtc ctagtacaca atatcataaa caaactaata 9300
aacattccac attcagattc caacagctga ttaacttcta cattaataca gcctattttc 9360
gctccaaatg tacattcgaa aaatctgaat aaaacatcga tgtcacaatt tgtattatcc 9420
aatacagaat gtctgtgatt cgtgttaaaa ccatcggaga aggaatagaa ataaaaatta 9480
ttatagtggt ggaattcagt tggaatattg cctccggagt cataaaagga tactaaacat 9540
tgttttttat cataaattac acatttccaa tgagacaaat aacaaaatcc aaacattaca 9600
aatctagagg tagaactttt aattttgtct ttaagtatat acgataagat atgtttattc 9660
ataaacgcgt caaatttttc atgaatcgct aaggagttta agaatctcat gtcaaattgt 9720
cctatataat ccacttcgga tccataagca aactgagaga ctaagttctt aatacttcga 9780
ttgctcatcc aggctcctct ctcaggctct attttcatct tgacgacctt tggattttca 9840
ccagtatgta ttcctttacg tgataaatca tcgattttca aatccatttg tgagaagtct 9900
atcgccttag atactttttc ccgtagtcga ggtttaaaga aatacgctaa cggtatacta 9960
gtaggtaact caaagacatc atatatagaa tggtaacgcg tctttaactc gtcggttaac 10020
tctttctttt gatcgagttc gtcgctacta ttgggtctgc tcaggtgccc cgactctact 10080
agttccaaca tcataccgat aggaatacaa gacactttgc cggcggttgt agatttatca 10140
tatttttcca ctacatatcc gttacaattt gttaaaaatt tagatacatc tatattgcta 10200
cataatccag ctagtgaata tatatgacat aataaattgg taaatcctag ttctggtatt 10260
ttactaatta ctaaatctgt atatctttcc atttatcatg gaaaagaatt taccagatat 10320
cttctttttt ccaaactgcg ttaatgtatt ctcttacaaa tattcacaag atgaattcag 10380
taatatgagt aaaacggaac gtgatagttt ctcattggcc gtgtttccag ttataaaaca 10440
tagatggcat aacgcacacg ttgtaaaaca taaaggaata tacaaagtta gtacagaagc 10500
acgtggaaaa aaagtatctc ctccatcact aggaaaaccc gcacacataa acctaaccac 10560
gaaacaatat atatacagtg aacacacaat aagctttgaa tgttatagtt ttctaaaatg 10620
tataacaaat acagaaatca attcgttcga tgagtatata ttaagaggac tattagaagc 10680
tggtaatagt ttacagatat tttccaattc cgtaggtaaa cgaacagata ctataggtgt 10740
actagggaat aagtatccat ttagcaaaat tccattggcc tcattaactc ctaaagcaca 10800
acgagagata tttttagcgt ggatttctca tagacctgta gttttaactg gaggaactgg 10860
agtgggtaag acgtcacagg tacccaagtt attgctttgg tttaattatt tatttggtgg 10920
attctctact ctagataaaa tcactgactt tcacgaaaga ccagtcattc tatctcttcc 10980
taggatagct ttagttagat tgcatagcaa taccatttta aaatcattgg gatttaaggt 11040
actagatgga tctcctattt ctttacggta cggatctata ccggaagaat taataaacaa 11100
acaaccaaaa aaatatggaa ttgtattttc tacccataag ttatctctaa caaaactatt 11160
tagttatggc actcttatta tagacgaagt tcatgagcat gatcaaatag gagatattat 11220
tatagcagta gcgagaaagc atcatacgaa aatagattct atgtttttaa tgactgccac 11280
gttagaggat gacagggaac ggctaaaagt atttttacct aatcccgcat ttatacatat 11340
tcctggagat acactgttta aaattagcga ggtatttatt cataataaga taaatccatc 11400
ttccagaatg gcatacatag aagaagaaaa gagaaattta gttactgcta tacagatgta 11460
tactcctcct gatggatcat ccggtatagt ctttgtggca tccgttgcac agtgtcacga 11520
atataaatca tatttagaaa aaagattacc gtatgatatg tatattattc atggtaaggt 11580
tttagatata gacgaaatat tagaaaaagt gtattcatca cctaatgtat cgataattat 11640
ttctactcct tatttggaat ccagcgttac tatacacaat gttacacaca tttatgatat 11700
gggtagagtt tttgtccccg ctccttttgg aggatcgcaa caatttattt ctaaatctat 11760
gagagatcaa cgaaaaggaa gagtaggaag agttaatcct ggtacatacg tctatttcta 11820
tgatctgtct tatatgaagt ctatacagcg aatagattca gaatttctac ataattatat 11880
attgtacgct aataagttta atctaacact ccccgaagat ttgtttataa tccctacaaa 11940
tttggatatt ctatggcgta caaaggaata tatagactcg ttcgatatta gtacagaaac 12000
atggaataaa ttattatcca attattatat gaagatgata gagtatgcta aactttatgt 12060
actaagtcct attctcgctg aggagttgga taattttgag aggacgggag aattaactag 12120
tattgtacaa gaagccattt tatctctaaa tttacgaatt aagattttaa attttaaaca 12180
taaagatgat gatacgtata tacacttttg taaaatatta ttcggtgtct ataacggaac 12240
aaacgctact atatattatc atagacctct aacgggatat atgaatatga tttcagatac 12300
tatatttgtt cctgtagata ataactaaaa attaaactct aatgaccaca tcttttttta 12360
gagatgaaaa attttccaca tctccttttg tagacacgac taaacatttt gcagaaaaaa 12420
gtttattagt gtttagataa tcgtatactt catcagtgta gatagtaaat gtgaacagat 12480
aaaaggtatt cttgctcaat agattggtaa attccataga atatattaat cctttcttct 12540
tgagatccca catcatttca accagagacg ttttatccaa tgatttacct cgtactatac 12600
cacatacaaa actagatttt gcagtgacgt cgtacctggt attcctacca aacaaaattt 12660
tacttttagt tcttttagaa aattctaagg tagaatctct atttgccaat atgtcatcta 12720
tggaattacc actagcaaaa aatgatagaa atatatattg atacatcgca gctggttttg 12780
atctactata ctttaaaaac gaatcagatt ccataattgc ctgtatatca tcagctgaaa 12840
aactatgttt tacacgtatt ccttcggcat ttctttttaa tgatatatct tgtttagaca 12900
atgataaagt tatcatgtcc atgagagacg cgtctccgta tcgtataaat atttcattag 12960
atgttagacg cttcattagg ggtatacttc tataaggttt cttaatcagt ccatcattgg 13020
ttgcgtcaag aactactatc ggatgttgtt gggtatctct agtgttacac atggccttac 13080
taaagtttgg gtaaataact atgatatctc tattaattat agatgcatat atttcatttg 13140
tcaaggatat tagtatcgac ttgctatcgt cattaatacg tgtaatgtaa tcatataaat 13200
catgcgatag ccaaggaaaa tttaaataga tgttcatcat ataatcgtcg ctataattca 13260
tattaatacg ttgacattga ctaatttgta atatagcctc gccacgaaga aagctctcgt 13320
attcagtttc atcgataaag gataccgtta aatataactg gttgccgata gtctcatagt 13380

```
ctattaagtg gtaagtttcg tacaaataca gaatccctaa aatattatct aatgttggat  13440
taatctttac cataactgta taaaatggag acggagtcat aactatttta ccgtttgtac  13500
ttactggaat agatgaagga ataatctccg gacatgctgg taaagaccca aatgtctgtt  13560
tgaagaaatc caatgttcca ggtcctaatc tcttaacaaa aattacgata ttcgatcccg  13620
atatcctttg cattctattt accagcatat cacgaactat attaagatta tctatcatgt  13680
ctattctccc accgttatat aaatcgcctc cgctaagaaa cgttagtata tccatacaat  13740
ggaatacttc atttctaaaa tagtattcgt tttctaattc tttaatgtga aatcgtatac  13800
tagaaaggga aaaattatct ttgagttttc cgttagaaaa gaaccacgaa actaatgttc  13860
tgattgcgtc cgattccgtt gctgaattaa tggatttaca ccaaaaactc atataacttc  13920
tagatgtaga agcattcgct aaaaaattag tagaatcaaa ggatataagt agatgttcca  13980
acaagtgagc aattcccaag atttcatcta tatcattctc gaatccgaaa ttagaaattc  14040
ccaagtagat atcctttttc atccgatcgt tgatgaaaat acgaacttta ttcggtaaga  14100
caatcattta ctaaggagta aaataggaag taatgttcgt atgtcgttat catcgtataa  14160
attaaaggtg tgttttttac cattaagtga cattataatt ttaccaatat tggaattata  14220
atataggtgt atttgcgcac tcgcgacggt tgatgcatcg gtaaatatag ctgtatctaa  14280
tgttctagtc ggtatttcat catttcgctg tctaataata gcgttttctc tatctgtttc  14340
cattacagct gcctgaagtt tattggtcgg ataatatgta aaataataag aaatacatac  14400
gaataacaaa aataaaataa gatataataa agatgccatt tagagatcta attttgttca  14460
acttgtccaa attcctactt acagaagatg aggaatcgtt ggagatagtg tcttccttat  14520
gtagaggatt tgaaatatct tatgatgact tgataactta ctttccagat aggaaatacc  14580
ataaatatat ttataaagta tttgaacatg tagatttatc ggaggaatta agtatggaat  14640
tccatgatac aactctgaga gatttagtct atcttagatt gtacaagtat tccaagtgta  14700
tacggccgtg ttataaatta ggagataatc taaaaggcat agttgttata aaggacagga  14760
atatttatat tagggaagca aatgatgact tgatagaata tctcctcaag gaatacactc  14820
ctcagattta tacatattct aatgagcgag ttcccatagc tggttcaaaa ttaattcttt  14880
gtggatttc tcaagttaca tttatggcgt atacaacgtc gcatataaca acaaataaaa  14940
aggtagatgt tctcgtttcc aaaaaatgta tagatgaact agtcgatcca ataaattatc  15000
aaatacttca aaatttattt gataaaggaa gcggaacaat aaacaaaata ctcaggaaga  15060
tattttattc ggtaacaggt ggccaaactc cataggtagc tttttctatt tcggatttta  15120
gaatttccaa attcaccagc gatttatcgg ttttggtgaa atccaaggat ttattaatgt  15180
ccacaaatgc catttgtttt gtctgtggat tgtatttgaa aatggaaacg atgtagttag  15240
atagatgcgc tgcaaagttt cctattaggg ttccgcgctt tacgtcaccc agcatacttg  15300
aatcaccatc ctttaaaaaa aatgataaga tatcaacatg gagtatatca tactcggatt  15360
ttaattcttc tactgactca ctgacatttt cacaaatact acaatacggt ttaccgaaaa  15420
taatcaatac gttcttcatt tatgggtatc aaaaacttaa aatcgttact gctggaaaat  15480
aaatcactga cgatattaga tgataattta tacaaagtat acaatggaat atttgtggat  15540
acaatgagta tttatatagc cgtcgccaat tgtgtcagaa acttagaaga gttaactacg  15600
gtattcataa aatacgtaaa cggatgggta aaaaagggag ggcatgtaac cctttttatc  15660
gatagaggaa gtataaaaat taaacaagac gttagagaca agagacgtaa atattctaaa  15720
ttaaccaagg acagaaaaat gttagaatta gaaaagtgta catccgaaat acaaaatgtt  15780
```

```
accggattta tggaagaaga aataaaggca aaaatgcaat taaaaatcga taaacttaca  15840
tttcaaatat atttatctga ttctgataac ataaaaatat cattgaatga gatactaaca  15900
catttcaaca ataatgagaa tgttacatta ttttattgtg atgaacgaga cgcagaattc  15960
gttatgtgtc tcgaggctaa aacacatttc tctaccacag gagaatggcc gttgataata  16020
agtaccgatc aggatactat gctatttgca tctgctgata atcatcctaa gatgataaaa  16080
aacttaactc aactgtttaa atatgttcca tctgcagagg ataactattt agcaaaatta  16140
acggcgttag tgaatggatg tgatttcttt cctggactct atggggcatc tataacaccc  16200
aacaacttaa acaaaataca attgtttagt gattttacaa tcgataatat agtcactagt  16260
ttggcaatta aaaattatta tagaaagact aactctaccg tagacgtgcg taatattgtt  16320
acgtttataa acgattacgc taatttagac gatgtctact cgtatgttcc tccttgtcaa  16380
tgcactgttc aagaatttat attttccgca ttagatgaaa aatggaacaa ttttaaatca  16440
tcttatttag aaaccgttcc gttaccctgt caattaatgt acgcgttaga accacgtaag  16500
gagattgatg tttcagaagt taaaacttta tcatcttata tagatttcga aaatactaaa  16560
tcagatatcg atgttataaa atctatatcc tcgatttttg gatattctaa cgaaaactgt  16620
aacactatag tgttcggcat ctataaggat aatttactac tgagtataaa tagttcattt  16680
tactttaacg atagtctgtt aataaccaat actaaaagtg ataatataat aaatataggt  16740
tactagatta aaaatggtgt tccaactcgt gtgctctaca tgcggtaaag atatttctca  16800
cgaacgatat aaattgatta tacgaaaaaa atcattaaag gatgtactcg tcagtgtaaa  16860
gaacgaatgt tgtaggttaa aattatctac acaaatagaa cctcaacgta acttaacagt  16920
gcaacctcta ttggatataa actaatatgg atccggttaa ttttatcaag acatatgcgc  16980
ctagaggttc tattattttt attaattata ccatgtcatt aacaagtcat ttgaatccat  17040
cgatagaaaa acatgtgggt atttattatg gtacgttatt atcggaacac ttggtagttg  17100
aatctaccta tagaaaagga gttcgaatag tcccattgga tagttttttt gaaggatatc  17160
ttagtgcaaa agtatacatg ttagagaata ttcaagttat gaaaatagca gctaatacgt  17220
cattaacttt attgggtatt ccgtatggat ttggtcataa tagaatgtat tgttttaaat  17280
tggtagctga atgttataaa aatgccggta ttgatacatc gtctaaacga atattgggca  17340
aagatatttt tctgagccaa aacttcacag acgataatag atggataaag atatatgatt  17400
ctaataattt aacattttgg caaattgatt accttaaagg gtgagttaat atgcataact  17460
actcctccgt tgttttttcc ctcgttcttt ttcttaacgt tgtttgccat cactctcata  17520
atgtaaagat attctaaaat ggtaaacttt tgcatatcgg acgcagaaat tggtataaat  17580
gttgtaattg tattatttcc cgtcaatgga ctagtcacag ctccatcagt tttatatcct  17640
ttagagtatt tctcactcgt gtctaacatt ctagagcatt ccatgatctg tttatcgttg  17700
atattggccg gaaagataga ttttttattt tttattatat tactattggc aattgtagat  17760
ataacttctg gtaaatattt ttctaccttt tcaatctctt ctattttcaa gccggctata  17820
tattctgcta tattgttgct agtatcaata ccttttcttg ctaagaagtc atatgtggta  17880
ttcactatat cagttttaac tggtagttcc attagccttt ccacttctgc agaataatca  17940
gaaattggtt ctttaccaga aaatccagct actataatag gctcaccgat gatcattggc  18000
aaaatcctat attgtaccag attaatgaga gcatatttca tttccaataa ttctgctagt  18060
tcttgagaca ttgatttatt tgatgaatct agttggttct ctagatactc taccatttct  18120
```

gccgcataca ataacttgtt agataaaatc agggttatca aagtgtttag cgtggctaga 18180
atagtgggct tgcatgtatt aaagaatgcg gtagtatgag taaaccgttt taacgaatta 18240
tatagtctcc agaaatctgt ggcgttacat acatgagccg aatgacatcg aagattgtcc 18300
aatattttta atagctgctc tttgtccatt atttctatat ttgactcgca acaattgtaa 18360
ataccattaa tcactgattc ctttttcgat gccggacaat agcacaattg tttagctttg 18420
gactctatgt attcagaatt aatagatata tctcttaata cagattgcac tatacatttt 18480
gaaactatgt caaaaattgt agaacgacgc tgttctgcag ccatttaact ttaaataatt 18540
tacaaaaatt taaaatgagc atccgtataa aaatcgataa actgcgccaa attgtggcat 18600
atttttcaga gttcagtgaa gaagtgtcta taaatgtaga ctcgacggat gagttaatgt 18660
atatttttgc cgccttgggc ggatctgtaa acatttgggc cattatacct ctcagtgcat 18720
cagtgttcta ccgcggagcc gaaaatattg tgtttaatct tccggtgtcc aaggtaaaat 18780
cgtgtttgtg tagttttcac aatgatgcca tcatagatat agaacctgat ctgaaaaata 18840
atctagtaaa actttctagt tatcatgtag taagtgtcga ttgtaacaag gaactgatgc 18900
ctattaggac agatactact atttgtctaa gtatagatca aaagaaatct tatgtgttta 18960
attttcacaa gtatgaagaa aaatgttgtg gtagaaccgt cattcatcta gaatggttgt 19020
tgggctttat caagtgtatt agtcagcatc agcatctggc tattatgttt aaagatgaca 19080
atattattat gaagactcct ggtaatactg atgcattttc cagggaatat tctatgactg 19140
aatgttctca agaactacaa aagttttctt tcaaaatagc tatctcgtct ctcaacaaac 19200
tacgaggatt caaaaagaga gtcaatgttt ttgaaactag aatcgtaatg gataatgacg 19260
ataacatttt aggaatgttg ttttcggata gagttcaatc ctttaagatc aacatcttta 19320
tggcgttttt agattaatac tttcaatgag ataaatatgg gtggcggagt aagtgttgag 19380
ctccctaaac gggatccgcc tccgggagta cccactgatg agatgttatt aaacgtggat 19440
aaaatgcatg acgtgatagc tcccgctaag cttttagaat atgtgcatat aggaccacta 19500
gcaaaagata aagaggataa agtaaagaaa agatatccag agtttagatt agtcaacaca 19560
ggacccggtg gtctttcggc attgttaaga caatcgtata atggaaccgc acccaattgc 19620
tgtcgcactt ttaatcgtac tcattattgg aaaaaggatg gaaagatatc agataagtat 19680
gaagagggtg cagtattaga atcgtgttgg ccagacgttc acgacactgg aaaatgcgat 19740
gttgatttat tcgactggtg tcagggggat acgttcgata gaaacatatg ccatcagtgg 19800
atcggttcag cctttaatag gagtgataga actgtagagg gtcaacaatc gttaataaat 19860
ctgtataata agatgcaaac attatgtagt aaagatgcta gtgtaccaat atgtgaatca 19920
tttttgcatc atttacgcgc acacaataca gaagatagca aagagatgat cgattatatt 19980
ctaagacaac agtctgcgga ctttaaacag aaatatatga gatgtagtta tcccactaga 20040
gataagttag aagagtcatt aaaatatgcg gaacctcgag aatgttggga tccagagtgt 20100
tcgaatgcca atgttaattt cttgctaaca cgtaattata ataatttagg actttgcaat 20160
attgtacgat gtaataccag cgtgaacaac ttacagatgg ataaaacttc ctcattaaga 20220
ttgtcatgtg gattaagcaa tagtgataga ttttctactg ttcccgtcaa tagagcaaaa 20280
gtagttcaac ataatattaa acattcgttc gacctaaaat tgcatttgat cagtttatta 20340
tctctcttgg taatatggat actaattgta gctatttaaa tgggtgccgc ggcaagcata 20400
cagacgacgg tgaatacact cagcgaacgt atctcgtcta aattagaaca agaagcgaac 20460
gctagtgctc aaacaaaatg tgatatagaa atcggaaatt tttatatccg acaaaaccat 20520
ggatgtaacc tcactgttaa aaatatgtgc tctgcggacg cggatgctca gttggatgct 20580
gtgttatcag ccgctacaga aacatatagt ggattaacac cggaacaaaa agcatacgtg 20640
ccagctatgt ttactgctgc gttaaacatt cagacgagtg taaacactgt tgttagagat 20700
tttgaaaatt atgtgaaaca gacttgtaat tctagcgcgg tcgtcgataa caaattaaag 20760
atacaaaacg taatcataga tgaatgttac ggagccccag gatctccaac aaatttggaa 20820
tttattaata caggatctag caaaggaaat tgtgccatta aagcgttgat gcaattgacg 20880
actaaggcca ctactcaaat agcacctaga caagttgctg gtacaggagt tcagttttat 20940
atgattgtta tcggtgttat aatattggca gcgttgttta tgtactatgc caagcgtatg 21000
ttgttcacat ccaccaatga taaaatcaaa cttattttag ccaataagga aaacgtccat 21060
tggactactt acatggacac attctttaga acttctccga tggttattgc taccacggat 21120
atgcaaaact gaaaatatat tgataatatt ttaatagatt aacatggaag ttatcgctga 21180
tcgtctagac gatatagtga aacaaaatat agcggatgaa aaatttgtag attttgttat 21240
acacggtcta gagcatcaat gtcctgctat acttcgacca ttaattaggt tgtttattga 21300
tatactatta tttgttatag taatttatat ttttacggta cgtctagtaa gtagaaatta 21360
tcaaatgttg ttggtggtgc tagtcatcac attaactatt ttttattact ttatactata 21420
atagtactag actgacttct aacaaacatc tcacccgcca taaataaatg cttgatatta 21480
aagtcttcta tttctaacac tattccatct gtggaaaata atactctgac attatcgcta 21540
attgacacat cggtgagtga tatgcctata aagtaataat cttctttggg cacatatacc 21600
agtgtaccag gttctaacaa cctatttact ggtgctcctg tagcatactt tttctttacc 21660
ttgagaatat ccatcgtttg cttggtcaat agcgatatgt gatttttat caaccactcg 21720 aaaaagtaat tggagtgttc atatcctcta cgggctattg tctcatggcc gtgtatgaaa 21780
tttaagtaac acgactgtgg tagatttgtt ctatagagcc ggttgccgca aatagataga 21840
actaccaata tgtctgtaca aatgttaaac attaattgat taacagaaaa aacaatgttc 21900
gttctgggaa tagaaaccag attaaaacaa aattcgttag aatatatgcc acgtttatac 21960
atggaatata aaataactac agtttgaaaa ataacagtat catttaaaca tttaacttgc 22020
ggggttaatt tcacaacttt actgtttttg aactgttcaa aatatagcat cgatccatga 22080
gaaatacgtt tagccgcctt taatagagga aatcccaccg cctttctgga tctcaccaac 22140
gacgatagtt ctgaccagca actcatttct tcatcatcca cctgttttaa catataatag 22200
gcaggagata gatatccgtc attgcaatat tccttctcgt aggcacacaa tctaatattg 22260
ataaaatctc cattctcttc tctgcattta ttatcttgtt tcggtggctg attaggctgt 22320
agtcttggtt taggctttgg tatatcgttg ttgaatctat tttggtcatt aaatctttca 22380
tttcttcctg gtatatttct atcacctcgt ttggttggat ttttgtctat attatcgttt 22440
gtaacatcgg tacgggtatt catttatcac aaaaaaaact tctctaaatg agtctactgc 22500
tagaaaacct catcgaagaa gataccatat tttttgcagg aagtatatct gagtatgatg 22560
atttacaaat ggttattgcc ggcgcaaaat ccaaatttcc aagatctatg ctttctattt 22620
ttaatatagt acctagaacg atgtcaaaat atgagttgga gttgattcat aacgaaaata 22680
tcacaggagc aatgtttacc acaatgtata atataagaaa caatttgggt ctaggcgatg 22740
ataaactaac tattgaagcc attgaaaact atttcttgga tcctaacaat gaggttatgc 22800
ctcttatcat taataatacg gatatgactg ccgtcattcc taaaaaaagt ggtaggagaa 22860
agaataagaa catggttatt ttccgtcaag gatcatcacc tatcttgtgt attttcgaaa 22920
ctcgtaaaaa gattaatatt tataaagaaa atatggaatc cgcgtcgact gagtatacac 22980
ctatcggaga caacaaggct ttgatatcta aatatgcggg aattaatgtc ctgaatgtgt 23040
attctccttc cacatccatg agattgaatg ccatttacgg attcaccaat aaaaataaac 23100
tagagaaact tagtactaat aaggaactag aatcgtatag ttctagccct cttcaagaac 23160
ccattaggtt aaatgatttt ctgggactat tggaatgtgt taaaaagaat attcctctaa 23220
cagatattcc gacaaaggat tgattactat aaatggagaa tgttcctaat gtatacttta 23280
atcctgtgtt tatagagccc acgtttaaac attctttatt aagtgtttat aaacacagat 23340
taatagtttt atttgaagta ttcgttgtat tcattctaat atatgtattt tttagatctg 23400
aattaaatat gttcttcatg cctaaacgaa aaatacccga tcctattgat agattacgac 23460
gtgctaatct agcgtgtgaa gacgataaat taatgatcta tggattacca tggatgacaa 23520
ctcaaacatc tgcgttatca ataaatagta aaccgatagt gtataaagat tgtgcaaagc 23580
ttttgcgatc aataaatgga tcacaaccag tatctcttaa cgatgttctt cgcagatgat 23640
gattcatttt ttaagtattt ggctagtcaa gatgatgaat cttcattatc tgatatattg 23700
caaatcactc aatatctaga ctttctgtta ttattattga tccaatcaaa aaataaatta 23760
gaagccgtgg gtcattgtta tgaatctctt tcagaggaat acagacaatt gacaaaattc 23820
acagactctc aagattttaa aaaactgttt aacaaggtcc ctattgttac agatggaagg 23880
gtcaaactta ataaaggata tttgttcgac tttgtgatta gtttgatgcg attcaaaaaa 23940
gaatcagctc tagctaccac cgcaatagat cctgttagat acatagatcc tcgtcgcgat 24000
atcgcatttt ctaacgtgat ggatatatta aagtcgaata aagtgaacaa taattaattc 24060
tttattgtca tcaaaaattg aaattttatt tttttttttt ggaatataaa tatatctagc 24120
gctaccggtc gccaccatgg tgagcaaggg cgaggagctg ttcaccgggg tggtgcccat 24180
cctggtcgag ctggacggcg acgtaaacgg ccacaagttc agcgtgtccg gcgagggcga 24240
gggcgatgcc acctacggca agctgaccct gaagttcatc tgcaccaccg gcaagctgcc 24300
cgtgccctgg cccaccctcg tgaccacctt cggctacggc ctgcagtgct tcgcccgcta 24360
ccccgaccac atgaagcagc acgacttctt caagtccgcc atgcccgaag gctacgtcca 24420
ggagcgcacc atcttcttca aggacgacgg caactacaag acccgcgccg aggtgaagtt 24480
cgagggcgac accctggtga accgcatcga gctgaagggc atcgacttca aggaggacgg 24540
caacatcctg gggcacaagc tggagtacaa ctacaacagc cacaacgtct atatcatggc 24600
cgacaagcag aagaacggca tcaaggtgaa cttcaagatc cgccacaaca tcgaggacgg 24660
cagcgtgcag ctcgccgacc actaccagca gaacaccccc atcggcgacg gccccgtgct 24720
gctgcccgac aaccactacc tgagctacca gtccgccctg agcaaagacc ccaacgagaa 24780
gcgcgatcac atggtcctgc tggagttcgt gaccgccgcc gggatcactc tcggcatgga 24840
cgagctgtac aagtccggac tcaggtctag acggattcag atgacacttc acatgagcga 24900
aaaatacatc gtcacctggg acatgttgca gatccatgca cgtaaactcg caagccgact 24960
gatgccttct gaacaatgga aaggcattat tgccgtaagc cgtggcggtc tggtaccggg 25020
tgcgttactg gcgcgtgaac tgggtattcg tcatgtcgat accgtttgta tttccagcta 25080
cgatcacgac aaccagcgcg agcttaaagt gctgaaacgc gcagaaggcg atggcgaagg 25140
cttcatcgtt attgatgacc tggtggatac cggtggtact gcggttgcga ttcgtgaaat 25200
gtatccaaaa gcgcactttg tcaccatctt cgcaaaaccg gctggtcgtc cgctggttga 25260
tgactatgtt gttgatatcc cgcaagatac ctggattgaa cagccgtggg atatgggcgt 25320
cgtattcgtc ccgccaatct ccggtcgcta atgatagtat tatatttttt atctaaaaaa 25380
ctaaaaataa acattgatta aattttaata taatacttaa aaatggatgt tgtgtcgtta 25440
gataaaccgt ttatgtattt tgaggaaatt gataatgagt tagattacga accagaaagt 25500
gcaaatgagg tcgcaaaaaa actgccgtat caaggacagt taaaactatt actaggagaa 25560
ttattttttc ttagtaagtt acagcgacac ggtatattag atggtgccac cgtagtgtat 25620
ataggatctg ctcccggtac acatatacgt tatttgagag atcatttcta taatttagga 25680
gtgatcatca aatggatgct aattgacggc cgccatcatg atcctatttt aaatggattg 25740
cgtgatgtga ctctagtgac tcggttcgtt gatgaggaat atctacgatc catcaaaaaa 25800
caactgcatc cttctaagat tattttaatt tctgatgtga gatccaaacg aggaggaaat 25860
gaacctagta cggcggattt actaagtaat tacgctctac aaaatgtcat gattagtatt 25920
ttaaaccccg tggcatctag tcttaaatgg agatgcccgt ttccagatca atggatcaag 25980
gacttttata tcccacacgg taataaaatg ttacaacctt ttgctccttc atattcagct 26040
gaaatgagat tattaagtat ttataccggt gagaacatga gactgactcg agttaccaaa 26100
ttagacgctg taaattatga aaaaaagatg tactacctta ataagatcgt ccgtaacaaa 26160
gtagttgtta actttgatta tcctaatcag gaatatgact attttcacat gtactttatg 26220
ctgaggaccg tgtactgcaa taaaacattt cctactacta aagcaaaggt actatttcta 26280
caacaatcta tatttcgttt cttaaatatt ccaacaacat caactgaaaa agttagtcat 26340
gaaccaatac aacgtaaagt atctagcaaa gattttatgt ctaaaaacag aaatagcaag 26400
agatccgtac gcagtaataa atagaaatag ggataacagg gtaat 26445

<210> SEQ ID NO 5
<211> LENGTH: 26077
<212> TYPE: DNA
<213> ORGANISM: Vaccinia virus

<400> SEQUENCE: 5
tagggataac agggtaatta ttatattttt tatctaaaaa actaaaaata aacattgatt 60
aaattttaat ataatactta aaaatggatg ttgtgtcgtt agataaaccg tttatgtatt 120
ttgaggaaat tgataatgag ttagattacg aaccagaaag tgcaaatgag gtcgcaaaaa 180
aactgccgta tcaaggacag ttaaaactat tactaggaga attatttttt cttagtaagt 240
tacagcgaca cggtatatta gatggtgcca ccgtagtgta tataggatct gctcccggta 300
cacatatacg ttatttgaga gatcatttct ataatttagg agtgatcatc aaatggatgc 360
taattgacgg ccgccatcat gatcctattt taaatggatt gcgtgatgtg actctagtga 420
ctcggttcgt tgatgaggaa tatctacgat ccatcaaaaa acaactgcat ccttctaaga 480
ttattttaat ttctgatgtg agatccaaac gaggaggaaa tgaacctagt acggcggatt 540
tactaagtaa ttacgctcta caaaatgtca tgattagtat tttaaacccc gtggcatcta 600
gtcttaaatg gagatgcccg tttccagatc aatggatcaa ggacttttat atcccacacg 660
gtaataaaat gttacaacct tttgctcctt catattcagc tgaaatgaga ttattaagta 720
tttataccgg tgagaacatg agactgactc gagttaccaa attagacgct gtaaattatg 780
aaaaaaagat gtactacctt aataagatcg tccgtaacaa agtagttgtt aactttgatt 840
atcctaatca ggaatatgac tattttcaca tgtactttat gctgaggacc gtgtactgca 900
ataaaacatt tcctactact aaagcaaagg tactatttct acaacaatct atatttcgtt 960
tcttaaatat tccaacaaca tcaactgaaa aagttagtca tgaaccaata caacgtaaag 1020
tatctagcaa agattttatg tctaaaaaca gaaatagcaa gagatccgta cgcagtaata 1080
aatagaaacg tactactgag atatactacc gatatagagt ataatgattt agttacttta 1140
ataaccgtta gacataaaat tgattctatg aaaactgtgt ttcaggtatt taacgaatca 1200
tccataaatt atactccggt tgatgatgat tatggagaac caatcattat aacatcgtat 1260
cttcaaaaag gtcataacaa gtttcctgta aattttctat acatagatgt ggtaatatct 1320
gacttatttc ctagctttgt tagactagat actacagaaa ctaatatagt taatagtgta 1380
ctacaaacag gtgatggtaa aaagactctt cgtcttccca aaatgttaga gacggaaata 1440
gttgtcaaga ttctctatcg ccctaatata ccattaaaaa ttgttagatt tttccgcaat 1500
aacatggtaa ctggagtaga gatagccgat agatctgtta tttcagtcgc tgattaatca 1560
attagtagag atgagataag aacattataa taatcaataa tattatctta tatcttgttt 1620
agaaaaatgc taatattaaa atagctaacg ctagtaatcc aatcggaagc catttgatat 1680
ctataatagg gtatctaatt tcctgattca gatagcggac agctatattc tcggtagcta 1740
ctcgtttgga atcacaaaca ttatttacat ctaatttact atctgtaatg gaaacgtttc 1800
ccaatgaaat ggtacaatcc gatacattgc attttgttat attttttttt aaagaggctg 1860
gtaacaacgc atcgcttcgt ttacatggct cgtaccaaca ataatagggt aatcttgtat 1920
ctattcctat ccgtactatg cttttatcag gataaataca tttacatcgt atatcgtctt 1980
tgttagcatc acagaatgca taaatttgtt cgtccgtcat gataaaaatt taaagtgtaa 2040
atataactat tatttttata gttgtaataa aaagggaaat ttgattgtat actttcggtt 2100
ctttaaaaga aactgacttg ataaaaatgg ctgtaatctc taaggttacg tatagtctat 2160
atgatcaaaa agagattaat gctacagata ttatcattag tcatgttaaa aatgacgacg 2220
atatcggtac cgttaaagat ggtagactag gtgctatgga tggggcatta tgtaagactt 2280
gtgggaaaac ggaattggaa tgtttcggtc actggggtaa agtaagtatt tataaaactc 2340
atatagttaa gcctgaattt atttcagaaa ttattcgttt actgaatcat atatgtattc 2400
actgcggatt attgcgttca cgagaaccgt attccgacga tattaaccta aaagagttat 2460
cgggacacgc tcttaggaga ttaaaggata aaatattatc caagaaaaag tcatgttgga 2520
acagtgaatg tatgcaaccg tatcaaaaaa ttactttttc aaagaaaaag gtttgtttcg 2580
tcaacaagtt ggatgatatt aacgttccta attctctcat ctatcaaaag ttaatttcta 2640
ttcatgaaaa gttttggcca ttattagaaa ttcatcaata tccagctaac ttattttata 2700
cagactactt tcccatccct ccgttgatta ttagaccggc tattagtttt tggatagata 2760
gtatacccaa agaaaccaat gaattaactt acttattagg tatgatcgtt aagaattgta 2820
acttgaatgc tgatgaacag gttatccaga aggcggtaat agaatacgat gatattaaaa 2880
ttatttctaa taacactacc agtattaatt tatcatatat cacatccggc aaaaataata 2940
tgattagaag ttatatcgtc gcccggcgaa aagatcagac cgctagatct gtaattggtc 3000
ccagtacatc tatcaccgtt aatgaggtag gaatgcccgc atatattaga aatacactta 3060
cagaaaagat atttgttaat gcctttacag tggataaagt taaacaacta ttagcatcaa 3120
accaagttaa attttacttt aataaacgat taaaccaatt aacaagaata cgccaaggaa 3180
agtttattaa aaataaaata catttattgc ctggtgattg ggtagaagta gctgttcaag 3240
aatatacaag tattattttt ggaagacagc cgtctctaca tagatacaac gtcatcgctt 3300

```
catctatcag agctaccgaa ggagatacta tcaaaatatc tcccggaatt gccaactctc   3360
aaaatgctga tttcgacggg gatgaggaat ggatgatatt agaacaaaat cctaaagctg   3420
taattgaaca aagtattctt atgtatccga cgacgttact caaacacgat attcatggag   3480
cccctgttta tggatctatt caagatgaaa tcgtagcagc gtattcattg tttaggatac   3540
aagatctttg tttagatgaa gtattgaaca tcttggggaa atatggaaga gagttcgatc   3600
ctaaaggtaa atgtaaattc agcggtaaag atatctatac ttacttgata ggtgaaaaga   3660
ttaattatcc gggactctta aaggatggtg aaattattgc aaacgacgta gatagtaatt   3720
ttgttgtggc tatgaggcat ctgtcattgg ctggactctt atccgatcat aagtcgaacg   3780
tggaaggtat caactttatt atcaagtcat cttatgtttt taagagatat ctatctattt   3840
acggttttgg ggtgacattc aaagatctca gaccaaattc gacgttcact aataaattgg   3900
aggccatcaa cgtagaaaaa atagaactta tcaaagaagc atacgccaaa tatctcaacg   3960
atgtaagaga cgggaaaata gttccattat ctaaagcttt agaggcggac tatgtggaat   4020
ccatgttatc caacttgaca aatcttaata tccgagagat agaagaacat atgagacaaa   4080
cgctgataga tgatccagat aataacctcc tgaaaatggc caaagcgggt tataaagtaa   4140
atcccacaga actaatgtat attctaggta cttatggaca acagaggatt gatggtgaac   4200
cagcagagac tcgagtattg ggtagagttt taccttacta tcttccagac tctaaggatc   4260
cagaaggaag aggttatatt cttaattctt taacaaaagg attaacaggt tctcaatatt   4320
acttttcgat gctggttgca agatctcaat ctactgatat cgtctgtgaa acatcacgta   4380
ccggaacact ggctagaaaa atcattaaaa agatggagga tatggtggtc gacggatacg   4440
gacaagtagt tataggtaat acgctcatca agtacgccgc caattatacc aaaattctag   4500
gctcagtatg taaacctgta gatcttatct atccagatga gtccatgact tggtatttgg   4560
aaattagtgc tctgtggaat aaaataaaac agggattcgt ttactctcag aaacagaaac   4620
ttgcaaaaaa gacattggcg ccgtttaatt tcctagtatt cgtcaaaccc accactgagg   4680
ataatgctat taaggttaag gatctgtacg atatgattca taacgtcatt gatgatgtga   4740
gagagaaata cttctttacg gtatctaata tagattttat ggagtatata ttcttgacgc   4800
atcttaatcc ttctagaatt agaattacaa aagaaacggc tatcactatc tttgaaaagt   4860
tctatgaaaa actcaattat actctaggtg gtggaactcc tattggaatt atttctgcac   4920
aggtattgtc tgagaagttt acacaacaag ccctgtccag ttttcacact actgaaaaaa   4980
gtggtgccgt caaacaaaaa cttggtttca acgagtttaa taacttgact aatttgagta   5040
agaataagac cgaaattatc actctggtat ccgatgatat ctctaaactt caatctgtta   5100
agattaattt cgaatttgta tgtttgggag aattaaatcc aaacatcact cttcgaaaag   5160
aaacagataa atatgtagta gatataatag ttaatagatt atacatcaag agagcagaaa   5220
taaccgaatt agttgtcgaa tatatgattg aacgatttat ctcctttagc gtcattgtaa   5280
aggaatgggg tatggagaca ttcattgagg acgaggataa tattagattt actgtctatc   5340
taaatttcgt tgaaccagag gaattgaatc ttagtaagtt tatgatggtt cttccggggg   5400
cagccaacaa gggaaagatt agtaaattca agattcctat ctctgactat acgggatatg   5460
acgacttcaa tcaaacaaaa aagctcaata agatgactgt agaactcatg aatctaaaag   5520
aattgggttc tttcgatttg gaaaacgtca acgtgtatcc tggagtatgg aatacatacg   5580
atatcttcgg tatcgaggcc gctcgtgaat acttgtgcga agccatgtta aacacctatg   5640
```

-continued

```
gagaagggtt cgattatctg tatcagcctt gtgatcttct cgctagttta ctatgtgcta   5700
gttacgaacc agaatcagtg aataaattca agttcggcgc agctagtact cttaagagag   5760
ctacgttcgg agacaataaa gcattgttaa acgcggctct tcataaaaag tcagaaccta   5820
ttaacgataa tagtagctgc cactttttta gcaaggtccc taatatagga actggatatt   5880
acaaatactt tatcgacttg ggtcttctca tgagaatgga aaggaaacta tctgataaga   5940
tatcttctca aaagatcaag gaaatggaag aaacagaaga cttttaattc ttatcaataa   6000
catatttttc tatgatctgt cttttaaacg atggattttc cacaaatgcg cctctcaagt   6060
ccctcataga atgatacacg tataaaaaat atagcatagg caatgactcc ttatttttag   6120
acattagata tgccaaaatc atagccccgc ttctatttac tcccgcagca caatgaacca   6180
acacgggctc gtttcgttga tcacatttag ataaaaaggc ggttacgtcg tcaaaatatt   6240
tactaatatc ggtagttgta tcatctacca acggtatatg aataatatta atattagagt   6300
taggtaatgt atatttatcc atcgtcaaat ttaaaacata tttgaactta acttcagatg   6360
atggtgcatc catagcattt ttataatttc ccaaatacac attattggtt acccttgtca   6420
ttatagtggg agatttggct ctgtgcatat ctccagttga acgtagtagt aagtatttat   6480
acaaactttt cttatccatt tataacgtac aaatggataa aactacttta tcggtaaacg   6540
cgtgtaattt agaatacgtt agagaaaagg ctatagtagg cgtacaagca gccaaaacat   6600
caacacttat attctttgtt attatattgg caattagtgc gctattactc tggtttcaga   6660
cgtctgataa tccagtcttt aatgaattaa cgagatatat gcgaattaaa aatacggtta   6720
acgattggaa atcattaacg gatagcaaaa caaaattaga aagtgataga ggtagacttc   6780
tagccgctgg taaggatgat atattcgaat tcaaatgtgt ggatttcggc gcctatttta   6840
tagctatgcg attggataag aaaacatatc tgccgcaagc tattaggcga ggtactggag   6900
acgcgtggat ggttaaaaag gcggcaaagg tcgatccatc tgctcaacaa ttttgtcagt   6960
atttgataaa acacaagtct aataatgtta ttacttgtgg taatgagatg ttaaatgaat   7020
taggttatag cggttatttt atgtcaccgc attggtgttc cgattttagt aatatggaat   7080
agtgttagat aaatgcggta acgaatgttc ctgtaaggaa ccataacagc ttagatttaa   7140
cgttaaagat gagcataaac ataataaaca aaattacaat caaacctata acattaatat   7200
caaacaatcc aaaaaatgaa atcagtggag tagtaaacgc gtacataact cctggataac   7260
gtttagcagc tgccgttcct attctagacc aaaaattcgg tttcatgttt tcgaagcggt   7320
gttctgcaac aagtcgggga tcgtgttcta catatttggc ggcgttatcc agtatctgcc   7380
tattgatctt catttcgttt tcgattctgg ctatttcaaa ataaaatccc gatgatagac   7440
ctccagactt tataatttca tctacgatgt tcagcgccgt agtaactcta ataatatagg   7500
ctgataagct aacatcatac cctcctgtat atgtgaatat ggcatgattt ttgtccatta   7560
caagctcggt tttaacttta ttgcctgtaa taatttctct catctgtagg atatctattt   7620
ttttgtcatg cattgccttc aagacgggac gaagaaacgt aatatcctca ataacgttat   7680
cgttttctac aataactaca tattctacct ttttattttc taactcggta aaaaaattag   7740
aatcccatag ggctaaatgt ctagcgatat ttcttttcgt ttcctctgta cacatagtgt   7800
tacaaaaccc tgaaaagaag tgagtatact tgtcatcatt tctaatgttt cctccagtcc   7860
actgtataaa cgcataatcc ttgtaatgat ctggatcatc cttgactacc acaacatttc   7920
tttttctgg cataacttcg ttgtccttta catcatcgaa cttctgatca ttaatatgct   7980
catgaacatt aggaaatgtt tctgatggag gtctatcaat aactggcaca acaataacag   8040
```

```
gagttttcac cgccgccatt tagttattga aattaatcat atacaactct ttaatacgag   8100
ttatattttc gtctatccat tgtttcacat ttacatattt cgacaaaaag atataaaatg   8160
cgtattccaa tgcttctctg tttaatgaat tactaaaata tacaaacacg tcactgtctg   8220
gcaataaatg atatcttaga atattgtaac aatttatttt gtattgcaca tgttcgtgat   8280
ctatgagttc ttcttcgaat ggcataggat ctccgaatct gaaaacgtat aaataggagt   8340
tagaataata atatttgaga gtattggtaa tatataaact ctttagcggt ataattagtt   8400
tttttctctc aatttctatt tttagatgtg atggaaaaat gactaatttt gtagcattag   8460
tatcatgaac tctaatcaaa atcttaatat cttcgtcaca cgttagctct ttgaagtttt   8520
taagagatgc atcagttggt tctacagatg gagtaggtgc aacaattttt tgttctacac   8580
atgtatgtac tggagccatt gttttaacta taatggtgct tgtatcgaaa aactttaatg   8640
cagatagcgg aagctcttcg ccgcgacttt ctacatcgta attgggttct aacgccgatc   8700
tctgaatgga tactagtttt ctaagttcta atgtgattct ctgaaaatgt aaatccaatt   8760
cctccggcat tatagatgtg tatacatcgg taaataaaac tatagtatcc aacgatccct   8820
tctcgcaaat tctagtctta accaaaaaat cgtatataac cacggagatg gcgtatttaa   8880
gagtggattc ttctaccgtt ttgttcttgg atgtcatata ggaaactata aagtccgcac   8940
tactgttaag aatgattact aacgcaacta tatagttcaa attaagcatt ttggaaacat   9000
aaaataactc tgtagacgat acttgacttt cgaataagtt tgcagacaaa cgaagaaaga   9060
acagacctct cttaatttca gaagaaaact ttttttcgta ttcctgacgt ctagagttta   9120
tatcaataag aaagttaaga attagtcggt taatgttgta tttcattacc caagtttgag   9180
atttcataat attatcaaaa gacatgataa tattaaagat aaagcgctga ctatgaacga   9240
aatagctata tggttcgctc aagaatatag tcttgttaaa cgtggaaacg ataactgtat   9300
ttttaatcac gtcagcggca tctaaattaa atataggtat atttattcca cacactctac   9360
aatatgccac accatcttca taataaataa attcgttagc aaaattatta attttagtga   9420
aatagttagc gtcaactttc atagcttcct tcaatctaat ttgatgctca cacggtgcga   9480
attccactct aacatccctt ttccatgcct caggttcatc gatctctata atatctagtt   9540
ttttgcgttt cacaaacaca ggctcgtctc tcgcgatgag atctgtatag taactatgta   9600
aatgataact agatagaaag atgtagctat atagatgacg atcctttaag agaggtataa   9660
taactttacc ccaatcagat agactgttgt tatggtcttc ggaaaaagaa tttttataaa   9720
tttttccagt attttccaaa tatacgtact taacatctaa aaaatcctta atgataatag   9780
gaatggataa tccgtctatt ttataaagaa atacatatcg cacattatac ttttttttgg   9840
aaatgggaat accgatgtgt ctacataaat atgcaaagtc taaatatttt ttagagaatc   9900
ttagttggtc caaattcttt tccaagtacg gtaatagatt tttcatattg aacggtatct   9960
tcttaatctc tggttctagt tccgcattaa atgatgaaac taagtcacta tttttataac  10020
taacgattac atcacctcta acatcatcat ttaccagaat actgatcttc ttttgtcgta  10080
aatacatgtc taatgtgtta aaaaaaagat catacaagtt atacgtcatt tcatctgtgg  10140
tattcttgtc attgaaggat aaactcgtac taatctcttc tttaacagcc tgttcaaatt  10200
tatatcctat atacgaaaaa atagcaacca gtgtttgatc atccgcgtca atattctgtt  10260
ctatcgtagt gtataacaat cgtatatctt cttctgtgat agtcgatacg ttataaaggt  10320
tgataacgaa aatattttta tttcgtgaaa taaagtcatc gtaggatttt ggacttatat  10380
```

-continued tcgcgtctag tagatatgct tttatttttg gaatgatctc aattagaata gtctctttag 10440
agtccattta aagttacaaa caactaggaa attggtttat gatgtataat ttttttagtt 10500
tttatagatt ctttattcta tacttaaaaa atgaaaataa atacaaaggt tcttgagggt 10560
tgtgttaaat tgaaagcgag aaataatcat aaattatttc attatcgcga tatccgttaa 10620
gtttgtatcg taatggcgtg gtcaattaca aataaagcgg atactagtag cttcacaaag 10680
atggctgaaa tcagagctca tctaaaaaat agcgctgaaa ataaagataa aaacgaggat 10740
attttcccgg aagatgtaat aattccatct actaagccca aaaccaaacg agccactact 10800
cctcgtaaac cagcggctac taaaagatca accaaaaagg aggaagtgga agaagaagta 10860
gttatagagg aatatcatca aacaactgaa aaaaattctc catctcctgg agtcggcgac 10920
attgtagaaa gcgtggctgc tgtagagctc gatgatagcg acggggatga tgaacctatg 10980
gtacaagttg aagctggtaa agtaaatcat agtgctagaa gcgatctttc tgacctaaag 11040
gtggctaccg acaatatcgt taaagatctt aagaaaatta ttactagaat ctctgcagta 11100
tcgacggttc tagaggatgt tcaagcagct ggtatctcta gacaatttac ttctatgact 11160
aaagctatta caacactatc tgatctagtc accgagggaa aatctaaagt tgttcgtaaa 11220
aaagttaaaa cttgtaagaa gtaaatgcgt gcactttttt ataaagatgg taaactcttt 11280
accgataata attttttaaa tcctgtatta gatgataatc cagcgtatga ggttttgcaa 11340
catgttaaaa ttcctactca tttaacagat gtagtagtat atgaacaaac gtgggaagag 11400
gcattaacta gattaatttt tgtgggaagc gattcaaaag gacgtagaca atacttttac 11460
ggaaaaatgc atgtacagaa tcgcaacgct aaaagagatc gtatttttgt tagagtatat 11520
aacgttatga aacgaattaa ttgttttata aacaaaaata taaagaaatc gtccacagat 11580
tccaattatc agttggcggt ttttatgtta atggaaacta tgttttttat tagatttggt 11640
aaaatgaaat atcttaagga gaatgaaaca gtagggttat taacactaaa aaataaacac 11700
atagaaataa gtcccgatga aatagttatc aagtttgtag gaaaggacaa agtttcacat 11760
gaatttgttg ttcataagtc taatagacta tataaaccgc tattgaaact gacggatgat 11820
tctagtcccg aagaatttct gttcaacaaa ctaagtgaac gaaaggtata cgaatgtatc 11880
aaacagtttg gtattagaat caaggatctc cgaacgtatg gagtcaatta tacgttttta 11940
tataattttt ggacaaatgt aaagtccata tctcctcttc cgtcaccaaa aaagttaata 12000
gcattaacta tcaaacaaac tgctgaagtt gtaggtcata ctccatcaat ttcaaaaaga 12060
gcttatatgg caacgactat tttagaaatg gtaaaggata aaaatttttt agatgtagta 12120
tctaaaacta cgttcgatga attcctatct atagtcgtag atcacgttaa atcatctacg 12180
gatggatgat atagatcttt acacaaataa ttacaagacc gataaatgga aatggataag 12240
cgtataaaat ctctcgcaat gaccgctttc tttggggagc taagcacatt agatattatg 12300
gcattgataa tgtctatatt taaacgccat ccaaacaata ccatttttttc agtggataag 12360 gatggtcagt ttatgattga tttcgaatac gataattata aggcttctca atatttggat 12420
ctgaccctca ctccgatatt tggagatgaa tgcaagactc acgcatcgag tatagccgaa 12480
caattggcgt gtgcggatat tattaaagag gatattagcg aatacatcaa aactactccc 12540
cgtcttaaac gatttataaa aaaataccgc aatagatcag atactcgtat cagtcgagat 12600
acagaaaagc ttaaaatagc tctagctaaa ggcatagatt acgaatatat aaaagacgct 12660
tgttaataag taaatgaaaa aaaactagtc gtttataata aaacacgata tggatgccaa 12720
cgtagtatca tcttctacta ttgcaacgta tatagacgct ttagcgaaga atgcttcaga 12780

```
attagaacag aggtctaccg catacgaaat aaataatgaa ttggaactag tatttattaa  12840
gccgccatta attactttga caaatgtagt gaatatctct acgattcagg aatcgtttat  12900
tcgatttacc gttactaata aggaaggtgt caaaattaga actaagattc cattatctaa  12960
ggtacatggt ctagatgtaa aaaatgtaca gttagtagat gctatagata acatagtttg  13020
ggaaaagaaa tcattagtga cggaaaatcg tcttcacaaa gaatgcttgt tgagactatc  13080
gacagaggaa cgtcatatat ttttggatta caagaaatat ggatcctcta tccgactaga  13140
attagtcaat cttattcaag caaaaacaaa aaactttacg atagacttta agctaaaata  13200
ttttctagga tccggtgccc aatctaaaag ttctttgttg cacgctatta atcatccaaa  13260
gtcaaggcct aatacatctc tggaaataga attcacacct agagacaatg aaacagttcc  13320
atatgatgaa ctaataaagg aattgacgac tctctcgcgt catatattta tggcttctcc  13380
agagaatgta attctttctc cgcctattaa cgcgcctata aaaaccttta tgttgcctaa  13440
acaagatata gtaggtttgg atctggaaaa tctatatgcc gtaactaaga ctgacggcat  13500
tcctataact atcagagtta catcaaacgg gttgtattgt tattttacac atcttggtta  13560
tattattaga tatcctgtta agagaataat agattccgaa gtagtagtct ttggtgaggc  13620
agttaaggat aagaactgga ctgtatatct cattaagcta atagagcccg tgaatgctat  13680
cagtgataga ctagaagaaa gtaagtatgt tgaatctaaa ctagtggata tttgtgatcg  13740
gatagtattc aagtcaaaga aatacgaagg tccgtttact acaactagtg aagtcgtcga  13800
tatgttatct acatatttac caaagcaacc agaaggtgtt attctgttct attcaaaggg  13860
acctaaatct aacattgatt ttaaaattaa aaaggaaaat actatagacc aaactgcaaa  13920
tgtagtattt aggtacatgt ccagtgaacc aattatcttt ggagaatcgt ctatctttgt  13980
agagtataag aaatttagca acgataaagg ctttcctaaa gaatatggtt ctggtaagat  14040
tgtgttatat aacggcgtta attatctaaa taatatctat tgtttggaat atattaatac  14100
acataatgaa gtgggtatta agtccgtggt tgtacctatt aagtttatag cagaattctt  14160
agttaatgga gaaatactta aacctagaat tgataaaacc atgaaatata ttaactcaga  14220
agattattat ggaaatcaac ataatatcat agtcgaacat ttaagagatc aaagcatcaa  14280
aataggagat atctttaacg aggataaact atcggatgtg ggacatcaat acgccaataa  14340
tgataaattt agattaaatc cagaagttag ttattttacg aataaacgaa ctagaggacc  14400
gttgggaatt ttatcaaact acgtcaagac tcttcttatt tctatgtatt gttccaaaac  14460
atttttagac gattccaaca aacgaaaggt attggcgatt gattttggaa acggtgctga  14520
cctggaaaaa tacttttatg gagagattgc gttattggta gcgacggatc cggatgctga  14580
tgctatagct agaggaaatg aaagatacaa caaattaaac tctggaatta aaaccaagta  14640
ctacaaattt gactacattc aggaaactat tcgatccgat acatttgtct ctagtgtcag  14700
agaagtattc tattttggaa agtttaatat catcgactgg cagtttgcta tccattattc  14760
ttttcatccg agacattatg ctaccgtcat gaataactta tccgaactaa ctgcttctgg  14820
aggcaaggta ttaatcacta ccatggacgg agacaaatta tcaaaattaa cagataaaaa  14880
gacttttata attcataaga atttacctag tagcgaaaac tatatgtctg tagaaaaaat  14940
agctgatgat agaatagtgg tatataatcc atcaacaatg tctactccaa tgactgaata  15000
cattatcaaa aagaacgata tagtcagagt gtttaacgaa tacggatttg ttcttgtaga  15060
taacgttgat ttcgctacaa ttatagaacg aagtaaaaag tttattaatg gcgcatctac  15120
```

```
aatggaagat agaccgtcta caaaaaactt tttcgaacta aatagaggag ccattaaatg  15180
tgaaggttta gatgtcgaag acttacttag ttactatgtt gtttatgtct tttctaagcg  15240
gtaaataata atatggtatg ggttctgata tccccgttct aaatgcatta aataattcca  15300
atagagcgat ttttgttcct ataggacctt ccaactgtgg atactctgta ttgttaatag  15360
atatattaat acttttgtcg ggtaacagag gttctacgtc ttctaaaaat aaaagtttga  15420
taacatctgg cctgttcata aataaaaact tggcgattct atatatactc ttattatcaa  15480
atctagccat tgtcttatag atgtgagcta ctgtaggtgt accatttgat tttctttcta  15540
atactatata tttctctcga agaagttctt gcacatcatc tgggaataaa atactactgt  15600
tgagtaaatc agttattttt tttatatcga tattgatgga catttttata gttaaggata  15660
ataagtatcc caaagtcgat aacgacgata acgaagtatt tatactttta ggaaatcaca  15720
atgactttat cagattaaaa ttaacaaaat taaaggagca tgtatttttt tctgaatata  15780
ttgtgactcc agatacatat ggatctttat gcgtcgaatt aaatgggtct agttttcagc  15840
acggcggtag atatatagag gtggaggaat ttatagatgc tggaagacaa gttagatggt  15900
gttctacatc caatcatata tctaaagata tacccgaaga tatgcacact gataaatttg  15960
tcatttatga tatttatacg tttgattcgt tcaagaataa acgattggta ttcgtacagg  16020
tgcctccatc attaggagat gatagctatt tgactaatcc gttattgtct ccgtattatc  16080
gtaattcagt agccagacaa atggtcaatg atatgatttt taatcaagat tcatttttaa  16140
aatatttatt agaacatctg attagaagcc actatagagt ttctaaacat ataacaatag  16200
ttagatacaa ggataccgaa gaattaaatc taacgagaat atgttataat agagataagt  16260
ttaaggcgtt tgtattcgct tggtttaacg gcgtttcgga aaatgaaaag gtactagata  16320
cgtataaaaa ggtatctaat ttgatataat gaattcagtg actgtatcac acgcgccata  16380
tactattact tatcacgatg attgggaacc agtaatgagt caattggtag agttttataa  16440
cgaagtagcc agttggctgc tacgagacga gacgtcgcct attcctgata agttctttat  16500
acagttgaaa caaccgctta gaaataaacg agtatgtgtg tgcggtatag atccgtatcc  16560
gaaagatgga actggtgtac cgttcgaatc accaaatttt acaaaaaaat caattaagga  16620
gatagcttca tctatatcta gattaaccgg agtaattgat tataaaggtt ataaccttaa  16680
tataatagac ggggttatac cctggaatta ttacttaagt tgtaaattag gagaaacaaa  16740
aagtcacgcg atctactggg ataagatttc caagttactg ctgcagcata taactaaaca  16800
cgttagtgtt ctttattgtt tgggtaaaac agatttctcg aatatacggg ccaagttaga  16860
atccccggta actaccatag tcggatatca tccagcggct agggaccgcc aattcgagaa  16920
agatagatca tttgaaatta tcaacgtttt actggaatta gacaacaagg cacctataaa  16980
ttgggctcaa gggtttattt attaatgctt tagtgaaatt ttaacttgtg ttctaaatgg  17040
atgcaactat tagaggtaat gatgttattt ttgtccttaa gactataggt gtcccatcag  17100
catgtagaca aaatgaagat ccaagattcg tagaagcatt taaatgcgac gagttaaaaa  17160
gatatattga gaataatcca gaatgtacac tattcgaaag tcttagggat gaggaagcat  17220
actctatagt cagaattttc atggatgtag atttagacgc gtgtctagac gaaatagatt  17280
atttaacggc tattcaagat tttattatcg aggtgtcaaa ctgtgtagct agattcgcgt  17340
ttacagaatg cggtgccatt catgaaaatg taataaaatc catgagatct aatttttcat  17400
tgactaagtc tacaaataga gataaaacaa gttttcatat tatcttttta gacacgtata  17460
ccactatgga tacattgata gctatgaaac gaacactatt agaattaagt agatcatctg  17520
```

```
aaaatccact aacaagatcg atagacactg ccgtatatag gagaaaaaca actcttcggg  17580
ttgtaggtac taggaaaaat ccaaattgcg acactattca tgtaatgcaa ccaccgcatg  17640
ataaatataga agattaccta ttcacttacg tggatatgaa caacaatagt tattactttt  17700
ctctacaacg acgattggag gatttagttc ctgataagtt atgggaacca gggtttattt  17760
cattcgaaga cgctataaaa agagtttcaa aaatattcat taattctata ataaacttta  17820
atgatctcga tgaaaataat tttacaacgg taccactggt catagattac gtaacacctt  17880
gtgcattatg taaaaaacga tcgcataaac atccgcatca actatcgttg gaaaatggtg  17940
ctattagaat ttacaaaact ggtaatccac atagttgtaa agttaaaatt gttccgttgg  18000
atggtaataa actgtttaat attgcacaaa gaattttaga cactaactct gttttattaa  18060
ccgaacgagg tgaccatata gtttggatta ataattcatg gaaatttaac agcgaagaac  18120
ccttgataac aaaactaatt ttgtcaataa gacatcaact acctaaggaa tattcaagcg  18180
aattactctg tccaagaaaa cgaaagactg tagaagctaa catacgagac atgttagtag  18240
attcagtgga aaccgatacc tatccggata aacttccgtt taaaaatggt gtattggacc  18300
tggtagacgg aatgttttac tctggagata atgctaaaaa atatacgtgt actgtatcaa  18360
ccggatttaa atttgacgat acaaagttcg tcgaagacag tccagaaatg gaagagttaa  18420
tgaatatcat taacgatatc caaccattaa cggatgaaaa taagaaaaat agagagttgt  18480
acgaaaaaac tttatctagt tgtttatgcg gtgctaccaa aggatgttta acattctttt  18540
ttggagaaac tgcaactgga aagtcgacaa ccaaacgttt gttaaagtct gctatcggtg  18600
acctgtttgt tgagacgggt caaacaattt taacagatgt attggataaa ggacctaatc  18660
catttatcgc taacatgcat ttgaaaagat ctgtattctg tagcgaacta cctgattttg  18720
cctgtagtgg atcaaagaaa attagatctg acaatattaa aaagttgaca gaaccttgtg  18780
tcattggaag accgtgtttc tccaataaaa ttaataatag aaaccatgcg acaatcatta  18840
tcgatactaa ttacaaacct gtttttgata ggatagataa cgcattaatg agaagaattg  18900
ccgtcgtgcg attcagaaca cacttttctc aaccttctgg tagagaggct gctgaaaata  18960
atgacgcgta cgataaagtc aaactattag acgaggggtt agatggtaaa atacaaaata  19020
atagatatag attcgcattt ctatacttgt tggtgaaatg gtacagaaaa tatcatgttc  19080
ctattatgaa actatatcct acaccggaag agattccgga ctttgcattc tatctcaaaa  19140
taggtactct gttggtatct agctctgtaa agcatattcc attaatgacg gacctctcca  19200
aaaagggata tatattgtac gataatgtgg tcactcttcc gttgactact ttccaacaga  19260
aaatatccaa gtattttaat tctagactat ttggacacga tatagagagc ttcatcaata  19320
gacataagaa atttgccaat gttagtgatg aatatctgca atatatattc atagaggata  19380
tttcatctcc gtaaatatat gctcatatat ttatagaaga tatcacatat ctaaatgaat  19440
accggaatca tagatttatt tgataatcat gttgatagta taccaactat attacctcat  19500
cagttagcta ctctagatta tctagttaga actatcatag atgagaacag aagcgtgtta  19560
ttgttccata ttatgggatc aggtaaaaca ataatcgctt tgttgttcgc cttggtagct  19620
tccagattta aaaaggttta cattctagtg ccgaacatca acatcttaaa aattttcaat  19680
tataatatgg gtgtagctat gaacttgttt aatgacaaat tcatagctga gaatatcttt  19740
attcattcca caacaagttt ttattctctt aattataacg ataacgtcat taattataac  19800
ggattatctc gctacaataa ctctattttt atcgttgatg aggcacataa tatctttggg  19860
```

```
aataatactg gagaacttat gaccgtgata aaaaataaaa acaagattcc tttttacta  19920
ttgtctggat ctcccattac taacacacct aatactctgg gtcatattat agatttaatg  19980
tccgaagaga cgatagattt tggtgaaatt attagtcgtg gtaagaaagt aattcagaca  20040
cttcttaacg aacgcggtgt gaatgtactt aaggatttgc ttaaaggaag aatatcatat  20100
tacgaaatgc ctgataaaga tctaccaacg ataagatatc acggacgtaa gtttctagat  20160
actagagtag tatattgtca catgtctaaa cttcaagaga gagattatat gattactaga  20220
cgacagctat gttatcatga aatgtttgat aaaaatatgt ataacgtgtc aatggcagta  20280
ttgggacaac ttaatctgat gaataattta gatactttat ttcaggaaca ggataaggaa  20340
ttgtacccaa atctgaaaat aaataatggc gtgttatacg gagaagaatt ggtaacgtta  20400
aacattagtt ccaaatttaa atactttatc aatcggatac agacactcaa cggaaaacat  20460
tttatatact tttctaattc tacatatggc ggattggtaa ttaaatatat catgctcagt  20520
aatggatatt ctgaatataa tggttctcag ggaactaatc cacatatgat aaacggcaaa  20580
ccaaaaacat ttgctatcgt tactagtaaa atgaaatcgt ctttagagga tctattagat  20640
gtgtataatt ctcctgaaaa cgatgatggc agtcaattga tgtttttgtt ttcgtcaaac  20700
attatgtccg aatcctatac tctgaaagag gtaaggcata tttggtttat gactatccca  20760
gatactttt ctcaatacaa ccaaattctt ggacgatcta ttagaaaatt ctcttacgcc  20820
gatatttctg aaccagttaa tgtatatctt ttagccgccg tatattccga tttcaatgac  20880
gaagtgacgt cattaaacga ttacacacag gatgaattaa ttaatgtttt accatttgac  20940
atcaaaaagc tgttatatct aaaatttaag acgaaagaaa cgaatagaat atactctatt  21000
cttcaagaga tgtctgaaac gtattctctt ccaccacatc catcaattgt aaaagtttta  21060
ttgggagaat tggtcagaca attttttat aataattctc gtattaagta taacgactcc  21120
aagttactta aaatggttac atcagttata aaaaataaag aagacgctag gaattacata  21180
gatgatattg taaacggtca cttctttgta tcgaataaag tatttgataa atctctttta  21240
tacaaatacg aaaacgatat tattacagta ccgtttagac tttcctacga accatttgtt  21300
tggggagtta actttcgtaa agaatataac gtggtatctt ctccataaaa ctgatgagat  21360
atataaagaa ataaatgtcg agctttgtta ccaatggata ccttccagtt acattggaac  21420
ctcatgagct gacgttagac ataaaaaacta atattaggaa tgccgtatat aagacgtatc  21480
tccatagaga aattagtggt aaaatggcca agaaaataga aattcgtgaa gacgtggaat  21540
tacctctcgg cgaaatagtt aataattctg tagttataaa cgttccgtgt gtaataacct  21600
acgcgtatta tcacgttggg gatatagtca gaggaacatt aaacatcgaa gatgaatcaa  21660
atgtaactat tcaatgtgga gatttaatct gtaaactaag tagagattcg ggtactgtat  21720
catttagcga ttcaaagtac tgcttttttc gaaatggtaa tgcgtatgac aatggcagcg  21780
aagtcactgc cgttctaatg gaggctcaac aaggtatcga atctagtttt gtttttctcg  21840
cgaatatcgt cgactcataa aaaagagaat agcggtaagt ataaacacga atactatggc  21900
aataattgcg aatgttttat tcccttcgat atatttttga taatatgaaa aacatgtctc  21960
tctcaaatcg gacaaccatc tcataaaata gttctcgcgc gctggagagg tagttgctgc  22020
tcgtataatc tccccagaat aatatacttc tgtgtcatcg ttcaatttat acggatttct  22080
atagttctct gttatataat gcggtttgcc ctcatgatta gacaacgaca atagtgttct  22140
gaatttagat agttgatcag aatgaatgtt tattggcgtt ggaaaaatta tccatacagc  22200
gtctgcagag tggttgatag ttgttcctag atatgtaaaa taatccaact tactaggcag  22260
```

```
caaattgtct agataaaata ctgaatcaaa cggtgcagac gtattggcgg atctaatgga  22320
atccaattga ttaactatct tttgaaaata tacattttta tgatccaata cttgtaagaa  22380
tatagaaata atgataagtc catcatcgtg ttttttgcc tcttcataag aactatattt  22440
tttcttattc caatgaacaa gattaatctc tccagagtat ttgtacacat ctatcaagtg  22500
attggatcca taatcgtctt cctttcccca atatatatgt agtgatgata acacatattc  22560
attggggaga aaccctccac ttatatatcc tcctttaaaa ttaatcctta ctagttttcc  22620
agtgttctgg atagtggttg gtttcgactc attataatgt atgtctaacg gcttcaatcg  22680
cgcgttagaa attgcttttt tagtttctat attaatagga gatagttgtt gcggcatagt  22740
aaaaatgaaa tgataactgt ttaaaaatag ctcttagtat gggaattaca atggatgagg  22800
aagtgatatt tgaaactcct agagaattaa tatctattaa acgaataaaa gatattccaa  22860
gatcaaaaga cacgcatgtg tttgctgcgt gtataacaag tgacggatat ccgttaatag  22920
gagctagaag aacttcattc gcgttccagg cgatattatc tcaacaaaat tcagattcta  22980
tctttagagt atccactaaa ctattacggt ttatgtacta caatgaacta agagaaatct  23040
ttagacggtt gagaaaaggt tctatcaaca atatcgatcc tcactttgaa gagttaatat  23100
tattgggtgg taaactagat aaaaaggaat ctattaaaga ttgtttaaga agagaattaa  23160
aagaggaaag tgatgaacgt ataacagtaa aagaatttgg aaatgtaatt ctaaaactta  23220
caacacggga taaattattt aataaagtat atataagtta ttgcatggcg tgttttatta  23280
atcaatcgtt ggaggattta tcgcatacta gtatttacaa tgtagaaatt agaaagatta  23340
aatcattaaa tgattgtatt aacgacgata aatacgaata tctgtcttat atttataata  23400
tgctagttaa tagtaaatga acttttacag atctagtata attagtcaga ttattaagta  23460
taatagacga ctagctaagt ctattatttg caaggatgac tctcaaatta ttacactcac  23520
ggcattcgtt aaccaatgcc tatggtgtca taaacgagta tccgtgtccg ctattttatt  23580
aactactgat aacaaaatat tagtatgtaa cagacgagat agttttctct attctgaaat  23640
aattagaact agaaacatgt ttagaaagaa acgattattt ctgaattatt ccaattattt  23700
gtccaaacag gaaagaagta tactatcgtc atttttttct ctatatccag ctactgctga  23760
taatgataga atagacgcta tttatccggg tggcataccc aaaaggggtg agaatgttcc  23820
agagtgttta tccagggaaa ttaaagaaga agttaatata gacaattctt ttgtattcat  23880
agacactcgg ttttttattc atggcatcat agaagatacc attattaata aatttttga  23940
ggtaatcttc tttgtcggaa gaatatctct aacgagtgat caaatcattg atacatttaa  24000
aagtaatcat gaaatcaagg atctaatatt tttagatccg aattcaggta atggactaca  24060
atacgaaatt gcaaaatatg ctctagatac tgcaaaactt aaatgttacg gccatagagg  24120
atgttattac gaatcattaa aaaaattaac tgaggatgat tgattagaaa atataaatta  24180
atttaccatc gtgtattttt ataacgggat tgtccggcat atcatgtaga tagttaccgt  24240
ctacatcgta tactcgacca tctacgcctt taaatcctct atttattgac attaatctat  24300
tagaattgga ataccaaata ttagtaccct caattagttt attggtaata tttttttag  24360
acgatagatc gatggctctt gaaaccaagg ttttccaacc ggactcattg tcgatcggtg  24420
agaagtcttt ttcattagca tgaatccatt ctaatgatgt atgtttaaac actctaaaca  24480
attggacaaa ttcttttgat ttgctttgaa tgatttcaaa taggtcttcg tctacagtag  24540
gcataccatt agataatcta gccattataa agtgcacgtt tacatatcta cgttctggag  24600
```

gagtaagaac gtgactattg agacgaatgg ctcttcctac tatctgacga agagacgcct 24660
cgttccatgt catatctaaa atgaagatat cattaattga gaaaaaacta ataccctcgc 24720
ctccactaga agagaatacg catgttttaa tgcattctcc gttagtgttt gattcttggt 24780
taaactcagc caccgccttg attctagtat cttttgttct agatgagaac tctatattag 24840
agataccaaa gactttgaaa tatagtaata agatttctat tcctgactga ttaacaaatg 24900
gttcaaagac tagacattta ccatgggatg ctaatattcc caaacataca tctataaatt 24960
tgacgctttt ctcttttaat tcagtaaata gagagatatc agccgcacta gcatcccctt 25020
tcaatagttc tccctttta aaggtatcta atgcggattt agaaaactct ctatctctta 25080
atgaattttt aaaatcatta tatagtgttg ctatctcttg cgcgtattcg cccggatcac 25140
gattttgtct ttcaggaaag ctatcgaacg taaacgtagt agccatacgt ctcagaattc 25200
taaatgatga tatacctgtt tttatttcag cgagtttagc cttttgataa atttcttctt 25260
gctttttcga catattaacg tatcgcatta atactgtttt cttagcgaat gatgcagacc 25320
cttctacgtc atcaaaaata gaaaactcgt tattaactat atacgaacat agtcctccta 25380
gtttggagac taattctttt tcatcgacta gacgtttatt ctcaaatagt gattggtgtt 25440
gtaaggatcc tggtcgtagt aagttaacca acatggtgaa ttcttgcaca ctattgacga 25500
taggtgtagc cgataaacaa atcatcttat ggtttttaa tgcgatggtc ttggataaaa 25560
aattatatac tgaacgagta ggacggatct taccatcttc tttgattaat gatttagaaa 25620
tgaagttatg acattcatca ataatgacgc atattctact cttggaatta atagttttga 25680
tattagtaaa aaatttattt ctaaaatttt gatcatcgta attaataaaa atacaatcct 25740
tcgttatctc tggagcgtat ctgagtatag tgttcatcca aggatcttct atcaaagcct 25800
ttttcaccaa taagataata gcccaattcg tataaatatc cttaagatgt ttgagaatat 25860
atacagtagt cattgtttta ccgacacccg tttcatggaa caataaaaga gaatgcatac 25920
tgtctaatcc taagaaaact cttgctacaa aatgttgata atccttgagg cgtactacgt 25980
ctgttcccat catttcaaca ggcatattag tagttctgcg caatgcataa tcgatatagg 26040
ccgcgtgtga tttactcatt agggataaca gggtaat 26077

<210> SEQ ID NO 6
<211> LENGTH: 24671
<212> TYPE: DNA
<213> ORGANISM: Vaccinia virus

<400> SEQUENCE: 6
tagggataac agggtaattt agaaaatata aattaattta ccatcgtgta tttttataac 60
gggattgtcc ggcatatcat gtagatagtt accgtctaca tcgtatactc gaccatctac 120
gcctttaaat cctctattta ttgacattaa tctattagaa ttggaatacc aaatattagt 180
accctcaatt agtttattgg taatattttt tttagacgat agatcgatgg ctcttgaaac 240
caaggttttc caaccggact cattgtcgat cggtgagaag tctttttcat tagcatgaat 300
ccattctaat gatgtatgtt taaacactct aaacaattgg acaaattctt ttgatttgct 360
ttgaatgatt tcaaataggt cttcgtctac agtaggcata ccattagata atctagccat 420
tataaagtgc acgtttacat atctacgttc tggaggagta agaacgtgac tattgagacg 480
aatggctctt cctactatct gacgaagaga cgcctcgttc catgtcatat ctaaaatgaa 540
gatatcatta attgagaaaa aactaatacc ctcgcctcca ctagaagaga atacgcatgt 600
tttaatgcat tctccgttag tgtttgattc ttggttaaac tcagccaccg ccttgattct 660

```
agtatctttt gttctagatg agaactctat attagagata ccaaagactt tgaaatatag    720
taataagatt tctattcctg actgattaac aaatggttca aagactagac atttaccatg    780
ggatgctaat attcccaaac atacatctat aaatttgacg cttttctctt ttaattcagt    840
aaatagagag atatcagccg cactagcatc ccctttcaat agttctccct ttttaaaggt    900
atctaatgcg gatttagaaa actctctatc tcttaatgaa tttttaaaat cattatatag    960
tgttgctatc tcttgcgcgt attcgcccgg atcacgattt tgtctttcag gaaagctatc   1020
gaacgtaaac gtagtagcca tacgtctcag aattctaaat gatgatatac ctgtttttat   1080
ttcagcgagt ttagcctttt gataaatttc ttcttgcttt ttcgacatat taacgtatcg   1140
cattaatact gttttcttag cgaatgatgc agacccttct acgtcatcaa aaatagaaaa   1200
ctcgttatta actatatacg aacatagtcc tcctagtttg gagactaatt ctttttcatc   1260
gactagacgt ttattctcaa atagtgattg gtgttgtaag gatcctggtc gtagtaagtt   1320
aaccaacatg gtgaattctt gcacactatt gacgataggt gtagccgata aacaaatcat   1380
cttatggttt tttaatgcga tggtcttgga taaaaaatta tatactgaac gagtaggacg   1440
gatcttacca tcttctttga ttaatgattt agaaatgaag ttatgacatt catcaataat   1500
gacgcatatt ctactcttgg aattaatagt tttgatatta gtaaaaaatt tatttctaaa   1560
attttgatca tcgtaattaa taaaaataca atccttcgtt atctctggag cgtatctgag   1620
tatagtgttc atccaaggat cttctatcaa agcctttttc accaataaga taatagccca   1680
attcgtataa atatccttaa gatgtttgag aatatataca gtagtcattg ttttaccgac   1740
acccgtttca tggaacaata aaagagaatg catactgtct aatcctaaga aaactcttgc   1800
tacaaaatgt tgataatcct tgaggcgtac tacgtctgtt cccatcattt caacaggcat   1860
attagtagtt ctgcgcaatg cataatcgat ataggccgcg tgtgatttac tcatttatga   1920
gtgataagta ataactatgt tttaaaaatc acagcagtag tttaactagt cttctctgat   1980
gtttgttttc gatacttttt gaatcagaag tcatactaga ataaagcaac gagtgaacgt   2040
aatagagagc ttcgtatact ctattcgaaa actctaagaa cttattaatg aattccgtat   2100
ccactggatt gtttaaaata ctaaattgaa cactgttcac atccttccaa gaagaagact   2160
tagtgacgga cttaacatga gacataaata aatccaaatt ttttttacaa acatcactag   2220
ccaccataat ggcgctatct ttcaaccagc tatcgcttac gcattttagc agtctaacat   2280
ttttaaagag actacaatat attctcatag tatcgattac acctctaccg aataaagttg   2340
gaagtttaat aatacaatat ttttcgttta caaaatcaaa taatggtcga aacacgtcga   2400
aggttaacat cttataatcg ctaatgtata gattgttttc agtgagatga ttattagatt   2460
taatagcatc tcgttcacgt ttgaacagtt tattgcgtgc gctgaggtcg gcaactacgg   2520
cgtccgcttt agtactcctc ccataatact ttacgctatt aatctttaaa atttcataga   2580
ctttatctag atcgctttct ggtaacatga tatcatgtgt aaaaagtttt aacatgtcgg   2640
tcggcattct atttagatca ttaactctag aaatctgaag aaagtaatta gctccgtatt   2700
ccagactagg taatgggctt ttacctagag acagattaag ttctggcaat gtttcataaa   2760
atggaagaag gacatgcgtt ccctcccgga tattttttac aatttcatcc atttacaact   2820
ctatagtttg ttttcattat tattagttat tatctcccat aatcttggta atacttaccc   2880
cttgatcgta agatacctta tacaggtcat tacatacaac taccaattgt ttttgtacat   2940
aatagattgg atggttgaca tccatggtgg aataaactac tcgaacagat agtttatctt   3000
```

-continued

```
tccccctaga tacattagcc gtaatagttg tcggcctaaa gaatatcttt ggtgtaaagt   3060
taaaagttag ggttcttgtt ccattattgc tttttgtcag tagttcatta taaattctcg   3120
agatgggtcc gttctctgaa tatagaacat catttccaaa tctaacttct agtctagaaa   3180
taatatcggt cttattctta aaatctattc ccttgatgaa gggatcgtta atgaacaaat   3240
ccttggcctt tgattcggct gatctattat ctccgttata gacgttacgt tgactagtcc   3300
aaagacttac aggaatagat gtatcgatga tgttgatact atgtgatatg tgagcaaaga   3360
ttgttctctt agtggcatca ctatatgttc cagtaatggc ggaaaacttt ttagaaatgt   3420
tatatataaa agaatttttt cgtgttccaa acattagcag attagtatga agataaacac   3480
tcatattatc aggaacatta tcaattttta catacacatc agcatcttga atagaaacga   3540
taccatcttc tggaacctca acaatctcgg cagactccgg ataaccagtc ggtgggccat   3600
cactaacaat aactagatca tccaacaatc tactcacata tgcatctata taatcttttt   3660
catcttgtga gtaccctgga tacgaaataa atttattatc cgtatttcca taataaggtt   3720
tagtataaac agagagcgat gttgccgcat gaacttcagt tacagtcgcc gttggttggt   3780
ttatttgacc tattactctc ctaggtttct ctataaacga tggtttaatt tgtacattct   3840
taaccatata tccaataaag ctcaattcag gaacataaac aaattctttg ttgaacgttt   3900
caaagtcgaa cgaagagtca cgaataacga tatcggatac tggattgaag gttaccgtta   3960
cggtaatttt tgaatcggat agtttaagac tgctgaatgt atcttccaca tcaaacggag   4020
ttttaatata aacgtatact gtagatggtt ctttaatagt gtcattagga gttaggccaa   4080
tagaaatatc attaagttca ctagaatatc cagagtgttt caaagcaatt gtattattga   4140
tacaattatt atataattct tcgccctcaa tttcccaaat aacaccgtta cacgaagaca   4200
ccgatacgta attaatacat ttatatccaa catatggtac gtaaccgaat cttcccatac   4260
ctttaacttc tggaagttcc aaactcagaa ccaaatgatt aagcgcagta atatactgat   4320
ccctaatttc gaagctagcg atagcctgat tgtctggacc atcgtttgtc ataactccgg   4380
atagagaaat atattgcggc atatataaag ttggaatttg actatcgact gcgaagacat   4440
tagaccgttt aatagagtca tccccaccga tcaaagaatt aatgatagta ttattcattt   4500
tctatttaaa atggaaaaag cttacaataa actccgtaga gaaatatcta taatttgtga   4560
gttttcctta aagtaacagc ttccgtaaac gccgtcttta tctcttagta agtttattgt   4620
atttataacc ttttccttat cttcatagaa tactaaaggc aacaaagaaa tttttggttc   4680
ttctctaaga gctacgtgag acttaaccat agacgccaac gaatccctac atattttaga   4740
acagaaatac ccaacttcac cacccttgaa tgtctcaata ctaataggtt taaaaaccaa   4800
atcttgatta caaaaccaac acttatcaat tacactattt gtcttaatag acacatctgc   4860
catagattta taatactttg gtagtataca agcgagtgct tcttctttag cgggcttaaa   4920
gactgcttta ggtgctgaaa taaccacatc tggaaggctt actcgcttag ccatttaatt   4980
acggaactat ttttttatac ttctaatgag caagtagaaa acctctcatc tacaaaaaca   5040
tactcgtgtc cataatcctc taccatagtt acacgttttt tagatctcat atgtgctaaa   5100
aagttttccc atactaattg gttactatta tttttcgtat aatttttaac agtttgaggt   5160
tttagatttt tagttacaga agtgatatcg aatattttat ccaaaaagaa tgaataatta   5220
attgtcttag aaggagtgtt ttcttggcaa aagaatacca agtgcttaaa tatttctact   5280
acttcattaa tcttttctgt actcagattc agtttctcat cttttacttg attgattatt   5340
tcaaagacta acttataatc ctttttattt attctctcgt tagccttaag aaaactagat   5400
```

```
acaaaatttg catctacatc atccgtggat atttgatttt tttccatgat atccaagagt   5460
tccgagataa tttctccaga acattgatga gacaataatc tccgcaatac atttctcaaa   5520
tgaataagtt tattagacac gtggaagttt gactttttt gtacctttgt acatttttga   5580
aataccgact cgcaaaaaat acaatattca tatccttgtt cagatactat accgttgtgt   5640
ctacaaccgc tacataatcg tagattcatg ttaacactct acgtatctcg tcgtccaata   5700
ttttatataa aaacatttta tttctagacg ttgccagaaa atcctgtaat atttttagtt   5760
ttttgggctg tgaataaagt atcgccctaa tatggttacc gtcctccgcc aatatagtag   5820
ttaaattatc cgcacatgca gaagaacacc gcttaggcgg attcagtaca atgttatatt   5880
tttcgtacca actcatttaa atatcataat ctaaaatagt tctgtaatat gtctagcgct   5940
aatatattga tcataatcct gtgcataaat taagatacaa caatgtctcg aaatcatcga   6000
catggcttct tccatagtta gaagatcgtc gtcaaagtta gcaacgtgat tcatcaacat   6060
ttgctgtttt gaggcagcaa atactgaacc gtcgccattc aaccattcat aaaaaccatc   6120
gtctgaatcc attgataatt tcttgtactg gtttttgaga gctcgcatca atctagcatt   6180
tctagctccc ggattgaaaa cagaaagagg atcgtacatc cagggtccat tttctgtaaa   6240
tagaatcgta taatgtccct tcaagaagat atcagacgat ccacaatcaa agaattgatc   6300
tccgagtttg taacaaactg cggactttaa cctatacatg ataccgttta gcatgatttc   6360
tggtgatacg tcaatcggag tatcatctat tagagatcta aagccggtgt aacattctcc   6420
accaaacata ttcttattct gacgtcgttc tacataaaac atcattgctc cattaacgat   6480
aacaggggaa tgaacagcac tacccatcac attagttccc aatggatcaa tgtgtgtaac   6540
tccagaacat cttccatagc ctatgttagg aggagcgaac accactcttc cactattgcc   6600
atcgaatgcc atagaataaa tatccttgga attgatagaa atcggactgt cggatgttgt   6660
gatcatcttc ataggattaa caactatgta tggtgccgcc tgaagtttca tatcgtaact   6720
gatgccgttt ataggtctag ccacagaaac caacgtaggt ctaaatccaa ctatagacaa   6780
aatagaagcc aatatctgtt cctcatctgt cataacttga gagcatccag tatgaataat   6840
cttcattaga tggggatcta ccgcatcatc atcgttacaa taaaaaattc ccattctaat   6900
gttcataatt gcttttctaa tcatggtatg catgtttgct ctctgaatct ctgtggaaat   6960
tagatctgat acacctgtaa tcactatcgg attatcctcc gtaagacgat taaccaacaa   7020
catataatta taagacttta cttttctaaa ttcataaagt tgctggatta ggctataggt   7080
gtctccatgt acatacgcgt tctcgagcgc aggaagttta ataccgaata gtgccatcag   7140
aataggatga atatagtaat tagtttctgg ttttctataa ataaaagaca aatcttgtga   7200
actagacata tcggtaaaat gcatggattg gaatcgtgta gtcgacagaa gaatatgatg   7260
attagatgga gagtatattt tatctaactc tttgagttgg tcaccgattc taggactagc   7320
tcgagaatga ataagtacta aaggatgagt acatttcaca gaaacactag cattgttcaa   7380
tgtgctcttt acatgggtaa ggagttgaaa tagctcgttt ctatttgttc tgacaatatt   7440
tagtttattc ataatgttaa gcatatcctg aatagtaaag ttagatgtgt catacttgtt   7500
agtagttaga tatttagcaa ttgcattccc atcatttctc aatctcgtac tccaatcatg   7560
cgtggatgct acttcgtcga tggaaaccat acaatccttt ttgataggct gttgagattg   7620
attatttcct gcacgtttag gtttggtacg ttgatttcta gcccctgcgg atataaagtc   7680
atcgtctaca attttggata atgaattgca tacactacaa gacaaagatt tatcagaagt   7740
```

```
gtgaatatga tcttcatcta ccaaagaaag agtttgatta gtataactag attttagtcc   7800
tgcgttagat gttaaaaaaa catcgctatt gaccacggct tccattattt atattcgtag   7860
tttttactcg aaagcgtgat tttaatatcc aatcttatta cttttggaat cgttcaaaac   7920
ctttgactaa ttgtagaatt tgatctattg ccctacgcgt atactccctt gcatcatata   7980
cgttcgtcac cagatcgttt gtttcggcct gaagttggtg catatctctt tcaacattcg   8040
acatgagatc cttaagggcc atatcgtcta gattttgttg agatgttgct cctggatttt   8100
gttgtgctgt tgtacatact gtaccaccag taggtgtagg agtacataca gtggccacaa   8160
taggaggttg aggaggtgta accgttggag tagtacaaga aatatttcca tccgattgtt   8220
gtgtacatgt agttgttggt aacgtctgag aaggttgggt agatggcggt gtcgtcgtct   8280
tttgatcttt attaaattta gagataatat cctgaacagc attgctcggc gtcaacgctg   8340
gaaggagtga actcgccggc gcatcagtat ctgcagacag ccaatcaaaa agattagaca   8400
tatcagatga tgtattagtt tgttgtcgtg gttttggtgt aggagcagta ctactaggta   8460
gaagaatagg agccgatgta ggtgtcggaa ccggaaccgg ctgtggagtt atatgaatag   8520
ttggttgtag cggttggata ggctgtctgc tggcggccat catattatct ctagctagtt   8580
gttctcgcaa ctgtctttga taatacgact cttgagactt tagtcctatt tcaatcgctt   8640
catccttttt cgtatccgga tccttttctt cagaataata gattgacgac tttggtgtag   8700
aggattctgc cagcccctgt gagaacttgt taaagaagtc catttaaggc tttaaaattg   8760
aattgcgatt ataagattaa atggcagaca cagacgatat tatcgactat gaatccgatg   8820
atctcactga atacgaggat gatgaagaag aggaagaaga tggagagtca ctagaaacta   8880
gtgatataga tcccaaatct tcttataaga ttgtagaatc agcatccact catatagaag   8940
atgcgcattc caatcttaaa catataggga atcatatatc tgctcttaaa cgacgctata   9000
ctagacgtat aagtctattt gaaatagcgg gtataatagc agaaagctat aacttgcttc   9060
aacgaggaag attacctcta gtttcagaat tttctgacga aacgatgaag caaaatatgc   9120
tacatgtaat tatacaagag atagaggagg gttcttgtcc tatagtcatc gaaaagaacg   9180
gagaattgtt gtcggtaaac gattttgaca aagatggtct aaaattccat ctagactata   9240
ttatcaaaat ttggaaactt caaaaacgat attagaattt atacgaatat cgttctctaa   9300
atgtcacaat caagtctcgc atgttcagca atttattgtc gtactttata tcgtgttcat   9360
taacgatatc ttgcaaaata gtaatgattc tatcttcctt cgatagatat tcttcagaga   9420
ttattgtctt atattctttc ttgttatcag atatgaattt gataagactt tgaacattat   9480
tgatacccgt ctgtttaatt ttttctacag atattttagt tttggcagat tctatcgtat   9540
ctgtcaatag acatccaaca tcgacattcg acgtcaattg tctataaatc aacgtataaa   9600
ttttagaaat aacattagcg aattgttgtg cattgatgtc gttattctga aacagtatga   9660
ttttaggtag cattttctta acaaagagaa cgtatttatt gttactcagt tgaacagatg   9720
atatatccag attactaacg catctgattc cgtataccaa actttcagaa gaaatggtgt   9780
acaattgttt gtattcattc aatgtctcct tttcagaaat tagtttagag tcgaatactg   9840
caataatttt caagagatag ttttcatcag ataagatttt atttagtgta gatatgataa   9900
aactattgtt ttgttggaga acttgatacg ccgcgttctc tgtagtcgac gctctcaaat   9960
gggaaacgat ctccattatt tttttggaat cggatacaat atcttcggta tcttgacgca  10020
atctagtata catagagtta agagaaatta gagtttgtac attgagcaac atgtctctaa  10080
atgtggctac aaacttttcc tttttcacat catctagttt attatatacc gatttcacaa  10140
```

```
cggcaccaga tttaaggaac cagaatgaaa aactctgata actacaatat ttcatcatag  10200
ttacgatttt atcatcttct atagttggtg taatagcgca tacctttttc tccaagactg  10260
gaaccaacgt cataaaaatg tttaaatcaa aatccatatc aacatctgat gcgctaagac  10320
cagtctcgcg ttcaagatta tctttactaa tggtgacgaa ctcatcgtat agaactctaa  10380
gtttgtccat tatttattta cagatttagt tgtttaattt atttgtgctc ttccagagtt  10440
gggatagtat ttttctaacg tcggtattat attattagga tctacgttca tatgtatcat  10500
aatattaatc atccacgttt tgataaatct atctttagct tctgaaataa cgtatttaaa  10560
caaaggagaa aaatatttag ctacggcatc agacgcaata acatttttttg taaatgtaac  10620
gtatttagac gacagatctt cgttaaaaag ttttccatct atgtagaatc catcggttgt  10680
taacaccatt cccgcgtcag attgaatagg agtttgaata gtttgttttg gaaatagatc  10740
cttcaataac ttatagttgg gtgggaaaaa atcgatttta tcactagact ctttcttttt  10800
tactatcatt acctcatgaa ctatttcttg aatgagtata tgtattttct ttcctatatc  10860
ggacgcgttc attggaaaat ataccatgtc gttaactata agaatatttt tatcctcgtt  10920
tacaaactga ataatatcag atgtagttcg taaacgaact atatcatcac cagcacaaca  10980
tctaactata tgatatccac tagtttcctt tagtcgttta ttatcttgtt ccatattagc  11040
agtcattcca tcatttaaga aggcgtcaaa gataataggg agaaatgaca ttttggattc  11100
tgttacaact ttaccaaaat taaggatata cggacttact atcttttttt caacgtcaat  11160
ttgatgaaca cacgatgaaa atgtacttcg atgagattga tcatgtagaa aacaacaagg  11220
gatacaatat ttccgcatat catgaaatat attaagaaat cccaccttat tatatttccc  11280
caaaggatcc atgcacgtaa acattatgcc gttatcatta ataaagactt ctttctcatc  11340
ggatctgtaa aagttgttac tgattttttt cattccagga tctagataat taataatgat  11400
gggttttcta ttcttattct ttgtattttg gcatatccta gaccagtaaa cagtttccac  11460
tttggtaaaa tcagcagact tttgaacgct attaaacatg gcattaatgg caataactaa  11520
aaatgtaaaa tatttttcta tgttaggaat atggttttc actttaatag atatatggtt  11580
tttggccaaa atgatagata tttttttatc cgaggatagt aaaatattat tagtcgccgt  11640
ctctataaaa atgaagctag tctcgatatc caattttatt ctagaattga taggagtcgc  11700
caaatgtacc ttatacgtta tatctccctt gatgcgttcc atttgtgtat ctatatcgga  11760
cacaagatct gtaaatagtt ttacgttatt aatcatcacg gtatcgccgt cgctagataa  11820
cgctaatgta ccatccaagt cccaaatgga gagatttaac tgttcatcgt ttagaataaa  11880
atgattaccg gtcatattaa taaagtgttc atcgtatcta gataacaacg acttataatt  11940
aatgtccaag tcttgaactc gctgaatgat cttttttaac ccagttagtt ttagattggt  12000
acgaaatata ttgttaaact ttgattctac agtaatgtcc aaatctagtt gtggaaatac  12060
ttccatcaac attgtttcaa acttgataat attattatct acatcttcgt acgatccaaa  12120
ttccggaata gatgtatcgc acgctctagc cacccagata accaaaaagt cacacgctcc  12180
aggatataca ttgtataaaa agctatcgtt ttttagtagt gttttttttct gagtatatac  12240
gaagggatta aaaatagtat tatcaacgta actatattcc aaattattct tatgagaata  12300
gataataata tcgtccttaa tatctaacaa atttcctaaa tatcccttta attgagtcat  12360
tcgaagcgtc aatagaatat gtctcttaac tatttccggc tgttgtatat ttaaatgact  12420
tcgtaaaaaa taatatatgg gcgacttctc atctatgtaa tcatatggag tgagatatag  12480
```

```
ggctcgttct acctcctgcc ccttacccac ctgtaatacc aattgcggac ttactatata  12540
tcgcatattt atatcgtggg gtaaagtgaa aatctactac cgatgatgta agtcttacaa  12600
tgttcgaacc agtaccagat cttaatttgg aggcctccgt agaactaggg gaggtaaata  12660
tagatcaaac aacacctatg ataaaggaaa atagcggttt tatatcccgt agtagacgtc  12720
tattcgccca tagatctaag gatgatgaga gaaaactagc actacgattc tttttacaaa  12780
gactttattt tttagatcat agagagattc attatttgtt cagatgcgtt gacgctgtaa  12840
aagacgtcac tattaccaaa aaaaataaca ttatcgtggc gccttatata gcacttttaa  12900
ctatcgcatc aaaaggatgc aaacttacag aaacaatgat tgaagcattc tttccagaac  12960
tatataatga acatagtaag aaatttaaat tcaactctca agtatccatc atccaagaaa  13020
aactcggata ccagtttgga aactatcacg tttatgattt tgaaccgtat tactctacag  13080
tagctctggc tattcgagat gaacattcat ctggcatttt taatatccgt caagagagtt  13140
atctggtaag ttcattatct gaaataacat atagatttta tctaattaat ctaaaatctg  13200
atcttgttca atggagtgct agtacgggcg ctgtaattaa tcaaatggta aatactgtat  13260
tgattacagt gtatgaaaag ttacaactgg tcatagaaaa tgattcacaa tttacatgtt  13320
cattggctgt ggaatcagaa cttccaataa aattacttaa agatagaaat gaattattta  13380
caaaattcat caacgagtta aaaaagacca gttcattcaa gataagcaaa cgcgataagg  13440
atacgctact aaaatatttt acttaggact ggagttagaa tttatagacg actcatttcg  13500
tttatcattg ttactattat tactattact atcattatta gtgttggcat tattagtatt  13560
cttcttgtca tcttgttcag aaatatacag caatgctata cctaatacta aatacattat  13620
catgctcgca atggctctaa caacgacgaa ccaaaatgaa tttggtcgta gcttttgttc  13680
acaaaaatac ataaagaaat gtctacataa atctatggcg ccattggcta cttgaaatag  13740
cgccagtcct cctacagatt ttaatatagc tgtataacat gacatttatt catcatcaaa  13800
agagacagag tcaccatctg tcatatttag atttttttc atgtgttcaa agtatcctct  13860
actcatttca ttataatagt ttatcatact tagaatttta ggacggatca atgagtaaga  13920
cttgactaga tcgtcagtag taatttgtgc atcgtctatt ctgcatccgc ttcgtcgaat  13980
aatgtatagc atcgctttga gattctccat agctatcaag tctttataca atgacatgga  14040
aatatctgtg aatactttat acttctccaa catcgatgcc ttaacatcat cgcctacttt  14100
agcattgaaa atacgttcta ttgtgtagat ggatgtaaca agatttttaa acaacaatgc  14160
cattttacac gatgattgtc tcaagtctcc aatcgtttgt ttagaacgat tagctacaga  14220
gtccaatgct tggctgacta gcatattatt atctttagaa attgtattct tcaatgaggc  14280
gtttatcata tctgtgattt cgttagtcat attacagtct gactgggttg taatgttatc  14340
caacatatca cctatggata cggtacacgt accagcattt gtaataatcc tatctaagat  14400
gttgtatggc attgcgcaga aaatatcttc tcctgtaata tctccactct cgataaatct  14460
actcagatta ttcttaaatg ccttattctc tggagaaaag atatcagtgt ccatcatttc  14520
attaatagta tacgcagaaa agataccacg agtatcaatt ctatccaaga tacttatcgg  14580
ttccgagtca cagataatgg tttcctctcc ttcgggagat cctgcataga aatatctagg  14640
acaatagttt ctatactgtc tgtaactctg ataatctcta aagtcactaa ctgataccat  14700
gaaattgaga agatcaaacg ctgaagtaat taatttttct gcctcgtttt tactacaact  14760
agttttcatc aatgtagtga cgatgtattg tttagttact cttggtctaa tactgatgat  14820
agagatatta ttacttccca taatggatct tctagtagtc accttaaagc ccattgatgc  14880
```

```
aaatagcaga tagataaagt cttggtatga ctcctttcta atatagtacg gactaccttt  14940
gtcacccaac tttataccca cataagccat aacaacctct ttaatagccg tttcatgagg  15000
tttatcagcc atgagcctga gtagttggaa gaatctcatg aatcccgtct cagaaagtcc  15060
tatatgcatg atagatttat ctttcctggg aaactctcgt atagtcatag atgaaatact  15120
cttcaaagtt tctgaaataa gattagtaac agtcttacct ccgactactc taggtaacaa  15180
acaaactcta ataggtgttt tctctgcgga gataatatca gaaaggatag agcaataagt  15240
agtattattg tgattataaa gaccgaatac ataacaggta gaatttataa acatcatgtc  15300
ctgaaggttt ttagacttgt attcctcgta atccataccg tcccaaaaca tggatttggt  15360
aactttgata gccgtagatc tttgttcctt cgccaacagg ttaaagaaat taataaagaa  15420
tttgtggttt ctacctatgt ctacaaattg cacgtttgga agcgtaactg ttacgttcac  15480
tgcagcattt tgaggatttc gagtatgaag tacgatgtta ttgtttactg gtatatctgg  15540
aaagaattct accagtctag gaataagaga ttgatatcgc atagaaatac aaaagttcat  15600
aatctcatca tcgaagagca ttttgttacc attgtaataa atatccactc tgtcatatgt  15660
ataaatgaag tactgttcaa acatgatgag atgtttatat gttggcatag tagtgagatc  15720
gacgtttggt aatggcaatg tattaagatt aactccataa tgtctagcag catctgcgat  15780
gttataagcg tcgtcaaagc ggggtcgatc ttgtgctgtt atatattgtc taacacctat  15840
aagattatca aaatcttgtc tgcttaatac accgttaaca atttttgcct tgaattcttt  15900
tattggtgca ttaataacat ccttatagag gatgttaaac aaataagtat tatcaaagtt  15960
aagatctggg tatttctttt ctgctagaac atccattgag tcggagccat ctggtttaat  16020
ataaccaccg ataaatctag ctctgtattc tgtatccgtc aatctaatat taagaaggtg  16080
ttgagtgaaa ggtggaagat cgtaaaagct gtgagtatta ataatagggt tagtttccga  16140
actaatgtta attggggtat taataatatc tatatttcca gcgttaagtg taacattaaa  16200
cagttttaat tcacgtgacg tggtatcaat taaataatta atgcccaatt tggatatagc  16260
agcctgaagc tcatcttgtt tagttacgga tcctaatgag ttattaagca atatatcgaa  16320
cggatgaacg aaggttgttt taagttggtc acatactttg taatctagac atagatgcgg  16380
aagaacggta gaaactatac gaaataaata ttcagagtcc tctaattgat caagagtaac  16440
tattgactta ataggcatca tttatttagt attaaatgac gaccgtacca gtgacggata  16500
tacaaaacga tttaattaca gagttttcag aagataatta tccatctaac aaaaattatg  16560
aaataactct tcgtcaaatg tctattctaa ctcacgttaa caacgtggta gatagagaac  16620
ataatgccgc cgtagtgtca tctccagagg aaatatcctc acaacttaat gaagatctat  16680
ttccagatga tgattcaccg gccactatta tcgaacgagt acaacctcat actactatta  16740
ttgacgatac tccacctcct acgtttcgta gagagttatt gatatcggaa caacgtcaac  16800
aacgagaaaa aagatttaat attacagtat cgaaaaatgc tgaagcaata atggaatcta  16860
gatctatgat aacttctatg ccaacacaaa caccatcctt gggagtagtt tatgataaag  16920
ataaaagaat tcagatgtta gaggatgaag tggttaatct tagaaatcaa cgatctaata  16980
caaaatcatc tgataattta gataatttta ccaaaatact atttggtaag actccgtaca  17040
aatcaacaga agttaataag cgtatagcca tcgttaatta tgcaaatttg aacggctctc  17100
ccttatcagt cgaggacttg gatgtttgtt cagaggatga aatagataga atctataaaa  17160
cgattaaaca atatcacgaa agtagaaaac gaaaaattat cgtcactaac gtgattatta  17220
```

ttgtcataaa cattatcgag caggcattgc taaaactcgg atttgaagaa atcaaaggac 17280
tgagtaccga tatcacttca gaaattatcg atgtggagat cggagatgac tgcgatgctg 17340
tagcatctaa actaggaatc ggtaacagtc cggttcttaa tattgtattg tttatactca 17400
agatattcgt taaacgaatt aaaattattt aatttaatac attcccatat ccagacaaca 17460
atcgtctgga ttaatctgtt cctgtcgtct cataccggac gacatattaa tctttttatt 17520
agtgggcatc tttttagatg gtttcttttt cccagcatta actgattcga tacctagaag 17580
atcgtgattg atctctccga ccattccacg aacttctaat tggccgtctc tgacggtacc 17640
ataaactatt ttaccagcat tagtaacagc ttggacaatc tgaccatcca tcgcattgta 17700
cgatgtagta gtaactgttg ttctacgttt aggagcacca gaagtatttt tggagccctt 17760
ggatgttgat gtagaagaag acgaggattt tgattttggt ttacatgtaa tacattttga 17820
actctttgat tttgtatcac atgcgccggc agtcacatct gtttgagaat taagattatt 17880
gttgcctcct ttgacggctg catctccacc gatttgcgct agtagatttt taagctgtgg 17940
tgtaatctta ttaactgttt cgatataatc atcgtaactg cttctaacgg ctaaattttt 18000
tttatccgcc atttagaagc taaaaatatt tttatttatg cagaagattt aactagatta 18060
tacaatgaac taatatgatc cttttccaga ttatttacaa acttggtatt tcttggttct 18120
ggaggaggcg aatttaaatt cggacttgga ttcggatttt gtgggttctt gatcttatta 18180
tacagcgcat ataggatggc gacggtaact gctacgcaaa taccgatcaa caaaagaata 18240
ccaatcattt attgacaata acttcactat tgatcaagta tgcaatatat catcttttca 18300
ctaaataagt agtaataatg attcaacaat gtcgagatat atggacgata ataacttagt 18360
tcacggaaat atcgctatga ttggtgtgaa tgactccgct aactctgtgg ggcgcgcagt 18420
gctttcccca catagaataa attagcattc cgactgtgat aataatacca agtataaacg 18480
ccataatact caatactttc catgtacgag tgggactggt agacttacta aagtcaataa 18540
aggcgaagat acacgaaaga atcaaaagaa tgattccagc gattagcacg ccggaaaaat 18600
aatttccaat cataagcatc atgtccattt aactaataaa aattttaaat cgccgaatga 18660
acaaagtgga atataaacca tataaaaaca atagtttgta ctgcaaaaat aatatctatt 18720
tttgttttcg aagatatggt aaaattaaat agtagtacac agcatgttat aactaacagc 18780
agcaacggct cgtaattact tatcatttac tagacgaaaa ggtggtggga tattttcttg 18840
ctcaaataat acgaatatat cacccatcca ttttatgcga tgtttatata ctctaatctt 18900
taatagatct atagacgacg ggtttaccaa caatatagat tttatcgatt catctaattt 18960
aaacccttcc ttaaacgtga atgatctatt atctggcata acgatgactc tacctgatga 19020
atcggacaat gtactgggcc atgtagaata aattatcaac gaattatcgt ctacgaacat 19080
ttatatcatt tgttttaatt ttaggacgcg aataaatgga tataaaatag aaaataacag 19140
atattacaac cagtgttatg gccgcgccca accaggtagg cagttttatt ttatctttta 19200
ctacaggttc tcctggatga tgtacgttac caactgcaga cgtagttcta gtacaattag 19260
acgtaagttc cgcttgggaa ttttttaacg ctaaagagtt aacgttaatc gtgcacccaa 19320
cgtatttaca tctagttctt tgaacatctt gattataata taaccatttt ctatctctag 19380
attcgtcggt gcactcatgt aaccaacata ccctaggtcc taaatattta tctccggaat 19440
tagattttgg ataattcgcg caccaacaat ttctatttcc tttatgatcg ttacaaaaga 19500
cgtataatgc cgtatcccca aaagtaaaat aatcaggacg aataattcta ataaactcag 19560
aacaatatct cgcatccata tgtttggagc aaatatcgga ataagtagac atagccggtt 19620

```
tccgttttgc acgtaaccat tctaaacaat tggggtttcc aggatcgttt ctacaaaatc  19680
cagtcatgaa atcatcacaa tgttctgtct tgtaattatt attaaatatt tttggacagt  19740
gtttggtatt tgtcttagaa caacattttg ccacgctatc actatcgccc aggagataat  19800
cctttttat aaaatgacat cgttgcccgg atgctatata atcagtagcg tgttttaaat  19860
ccttaatata ttcaggagtt acctcgttct gataatagat taatgatcca ggacgaaatt  19920
tgaaagaact acatggttct ccatgaatta atacatattg tttagcaaat tcaggaacta  19980
taaaactact acaatgatct atcgacatac catctatcaa acaaaatttg ggtttaattt  20040
ctcctggaga cgtttcataa taatacatat aactttcttc ggcaaactta acagctctat  20100
tatattcagg ataattaaaa cctaattcca tatatttgtc tcgtatatct gctattcctg  20160
gtgctatttt aattctatta agagtaacgg ctgcccccat ttttaataat cgtcagtatt  20220
taaactgtta aatgttggta tatcaacatt taccttattt cccgcagtat aaggtttgtt  20280
gcaggtatac tgttcaggaa tggttacatt tatacttctt ctatagtcct gtctttcgat  20340
gttcatcaca tatgcaaaga acagaataaa caaaataatg taagaaataa tattaaatat  20400
ctgtgaattc gtaaatacat tgattgccat aataattaca gcagctacaa tacatacaat  20460
agacattccc acagtgttgc cattacctcc acgatacatt tgagttacta agcaataggt  20520
aataactaag ctagtaagag gcaatagaaa agatgagata aatatcatca atatagagat  20580
tagaggaggg ctatatagag ccaagacgaa caaaatcaaa ccgagtaacg ttctaacatc  20640
attatttttg aagattccca aataatcatt cattcctcca taatcgtttt gcatcatacc  20700
tccatcttta ggcataaacg attgctgctg ttcctctgta aataaatctt tatcaagcac  20760
tccagcaccc gcagagaagt cgtcaagcat attgtaatat cttaaataac tcatttatat  20820
attaaaaaat gtcactatta aagatggagt ataatcttta tgccgaacta aaaaaaatga  20880
cttgtggtca accccctaagt ctttttaacg aagacgggga ttttgtagaa gttgaaccgg  20940
gatcatcctt taagtttctg atacctaagg gattttacgc ctctccttcc gtaaagacga  21000
gtctagtatt tgaaacatta acaacgaccg ataataaaat cactagtatc aatccaacaa  21060
atgcgccaaa gttatatcct cttcaacgca aagtcgtatc tgaagtagtt tctaatatga  21120
ggaaaatgat cgaatcaaaa cgtcctctat acattactct tcacttggcg tgtggatttg  21180
gtaagactat taccacgtgt tatcttatgg ctacacacgg tagaaaaacc gtcatttgcg  21240
tacccaataa aatgttaata catcaatgga agacacaggt agaggcagtc ggattggaac  21300
ataagatatc catagatgga gtaagtagtc tattaaagga actaaagact caaagtccgg  21360
atgtattaat agtagtcagt agacatctga caaacgatgc cttttgtaaa tatatcaata  21420
agcattatga tttgttcatc ttggatgaat cacatacgta taatctgatg aacaatacag  21480
cagttacaag atttttagcg tattatcctc cgatgatgtg ttattttta actgctacac  21540
ctagaccatc taacagaatt tattgtaaca gtattattaa tattgccaag ttatccgatc  21600
taaaaaaaac tatctatgcg gtagatagtt tttttgagcc atattccaca gacaatatta  21660
gacatatggt aaaacgacta gatggaccat ctaataaata tcatatatat accgagaagt  21720
tattatctgt agacgagcct agaaatcaac ttattcttaa taccctggta gaagaattca  21780
agtcaggaac tattaatcgc attttagtta ttactaaact acgtgaacat atggtattat  21840
tctacaaacg attattagat cttttcggac cagaggttgt atttatagga gacgcccaaa  21900
atagacgtac tccagatatg gtcaaatcaa tcaaggaact aaatagattt atattcgtat  21960
```

```
ccaccttatt ttattccggt actggtttag atattcctag tttggattct ttgttcattt  22020
gctcggcagt aatcaacaat atgcaaatag agcaattact agggaggata tgtcgagaaa  22080
cagaactatt agataggacg gtatatgtat ttcctagcac atccatcaaa gaaataaagt  22140
acatgatagg aaatttcgtt caacgaatta ttagtctgtc tgtagataaa ctaggattta  22200
aacaaaaaag ttatcggaaa catcaagaat ccgatcccac ttctgcatgt acaacatcat  22260
ccagagaaga acgtgtatta aatagaatat ttaactcgca aaatcgttaa gaagtttaag  22320
cgacgatccg catgctgcgc aggccagtgt attacccctc atagtattaa tataatccaa  22380
tgatactttt gtgatgtcgg aaatcttaac caatttagac tgacaggcag aacacgtcat  22440
gcaatcatca tcgtcatcga taactgtagt cttgggcttc tttttgcgac tcttcattcc  22500
ggaacgcaca ttggtgctat ccatttaggt agtaaaaaat aagtcagaat atgccctata  22560
gcacgatcgt gcaaaacctg gtatatcgtc tctatcttta tcacaatata gtgtatcgac  22620
atttttatta ttattgacct cgtttatctt ggaacatgga atggaaacat ttttgttatc  22680
aacggccacc tttgccttaa ttccagatgt tgtaaaatta taactaaaca gtctatcatc  22740
gacacaaatg aaattcttgt ttagacgttt gtagtttacg tatgcggctc gttcgcgtct  22800
catttttca gatattgcag gtactataat attaaaaata agaatgaaat aacataggat  22860
taaaaataaa gttatcatga cttctagcgc tgatttaact aacttaaaag aattacttag  22920
tctgtacaaa agtttgagat tttcagattc tgcggctata gaaaagtata attctttggt  22980
agaatgggga acatctactt actggaaaat aggcgtgcaa aaggtagcta atgtcgagac  23040
gtcaatatct gattattatg atgaggtaaa aaataaaccg tttaatattg atccgggcta  23100
ttacattttc ttaccggtat attttgggag cgtctttatt tattcgaagg gtaaaaatat  23160
ggtagaactt ggatctggaa actcttttca aataccagat aatatgcgaa gtgcgtgtaa  23220
caaagtatta gatagtgata acggaataga ctttctgaga tttgttttgt taaacaatag  23280
atggataatg gaagatgcta tatcaaaata tcagtctcca gttaatatat ttaaactagc  23340
tagtgagtac ggattaaaca tacccaaata tttagaaatt gaaatagagg aagacacatt  23400
atttgacgac gagttatact ctattataga acgctctttt gatgataaat ttccaaaaat  23460
atccatatcg tatattaagt tgggagaact taggcggcaa gttgtagact ttttcaaatt  23520
ctcattcatg tatattgagt ccatcaaggt agatcgtata ggagataata tttttattcc  23580
tagcgttata acaaaatcag gaaaaaagat attagtaaaa gatgtagacc atttaatacg  23640
atccaaggtt agagaacata catttgtaaa agtaaaaaag aaaaacacat tttccatttt  23700
atacgactat gatggaaacg gaacagaaac tagaggagaa gtaataaaac gaattataga  23760
cactatagga cgagactatt atgttaacgg aaagtatttc tctaaggttg gtagtgcagg  23820
cttaaagcaa ttgactaata aattagatat taatgagtgc gcaactgtcg atgagttagt  23880
tgatgagatt aataaatccg gaactgtaaa acgaaaaata aaaaaccaat cagcatttga  23940
tttaagcaga gaatgtttgg gatatccaga agcggatttt ataacgttag ttaataacat  24000
gcggttcaaa atagaaaatt gtaaggttgt aaatttcaat attgaaaata ctaattgttt  24060
aaataacccg agtattgaaa ctatatatgg aaactttaac cagttcgtct caatctttaa  24120
tgtcgtcacc gatgtcaaaa aaagattatt cgagtgaaat aatatgcgcc tttgatatag  24180
gtgcaaaaaa tcctgccaga actgttttag aagtcaagga taactccgtt agggtattgg  24240
atatatcaaa attagactgg agttctgatt gggaaaggcg catagctaaa gatttgtcac  24300
aatatgaata cactacagtt cttctagaac gtcagcctag aaggtcgccg tatgttaaat  24360
```

```
ttatctattt tattaaaggc tttttatatc atacatcggc tgccaaagtt atttgcgtct  24420

cgcctgtcat gtctggtaat tcatatagag atcgaaaaaa gagatcggtc gaagcatttc  24480

ttgattggat ggacacattc ggattgcgag actccgttcc ggatagacgc aaattagacg  24540

atgtagcgga tagtttcaat ttggctatga gatacgtatt agataaatgg aatactaatt  24600

atacacctta taataggtgt aaatctagaa attacataaa aaaaatgtaa taatagggat  24660

aacagggtaa t                                                       24671
```

<210> SEQ ID NO 7
<211> LENGTH: 25970
<212> TYPE: DNA
<213> ORGANISM: Vaccinia virus

<400> SEQUENCE: 7

```
tagggataac agggtaattt aggtagtaaa aaataagtca gaatatgccc tatagcacga     60

tcgtgcaaaa cctggtatat cgtctctatc tttatcacaa tatagtgtat cgacattttt    120

attattattg acctcgttta tcttggaaca tggaatggaa acatttttgt tatcaacggc    180

cacctttgcc ttaattccag atgttgtaaa attataacta aacagtctat catcgacaca    240

aatgaaattc ttgtttagac gtttgtagtt tacgtatgcg gctcgttcgc gtctcatttt    300

ttcagatatt gcaggtacta taatattaaa aataagaatg aaataacata ggattaaaaa    360

taaagttatc atgacttcta gcgctgattt aactaactta aaagaattac ttagtctgta    420

caaaagtttg agattttcag attctgcggc tatagaaaag tataattctt tggtagaatg    480

gggaacatct acttactgga aaataggcgt gcaaaaggta gctaatgtcg agacgtcaat    540

atctgattat tatgatgagg taaaaaataa accgtttaat attgatccgg gctattacat    600

tttcttaccg gtatattttg ggagcgtctt tatttattcg aagggtaaaa atatggtaga    660

acttggatct ggaaactctt ttcaaatacc agataaatatg cgaagtgcgt gtaacaaagt    720

attagatagt gataacggaa tagactttct gagatttgtt ttgttaaaca atagatggat    780

aatggaagat gctatatcaa aatatcagtc tccagttaat atatttaaac tagctagtga    840

gtacggatta aacataccca aatatttaga aattgaaata gaggaagaca cattatttga    900

cgacgagtta tactctatta tagaacgctc ttttgatgat aaatttccaa aaatatccat    960

atcgtatatt aagttgggag aacttaggcg gcaagttgta gactttttca aattctcatt   1020

catgtatatt gagtccatca aggtagatcg tataggagat aatattttta ttcctagcgt   1080

tataacaaaa tcaggaaaaa agatattagt aaaagatgta gaccatttaa tacgatccaa   1140

ggttagagaa catacatttg taaaagtaaa aaagaaaaac acattttcca ttttatacga   1200

ctatgatgga aacggaacag aaactagagg agaagtaata aaacgaatta tagacactat   1260

aggacgagac tattatgtta acggaaagta tttctctaag gttggtagtg caggcttaaa   1320

gcaattgact aataaattag atattaatga gtgcgcaact gtcgatgagt tagttgatga   1380

gattaataaa tccggaactg taaaacgaaa aataaaaaac caatcagcat ttgatttaag   1440

cagagaatgt ttgggatatc cagaagcgga ttttataacg ttagttaata acatgcggtt   1500

caaaatagaa aattgtaagg ttgtaaattt caatattgaa aatactaatt gtttaaataa   1560

cccgagtatt gaaactatat atggaaactt taaccagttc gtctcaatct ttaatgtcgt   1620

caccgatgtc aaaaaaagat tattcgagtg aaataatatg cgcctttgat ataggtgcaa   1680

aaaatcctgc cagaactgtt ttagaagtca aggataactc cgttagggta ttggatatat   1740
```

```
caaaattaga ctggagttct gattgggaaa ggcgcatagc taaagatttg tcacaatatg   1800
aatacactac agttcttcta gaacgtcagc ctagaaggtc gccgtatgtt aaatttatct   1860
attttattaa aggcttttta tatcatacat cggctgccaa agttatttgc gtctcgcctg   1920
tcatgtctgg taattcatat agagatcgaa aaaagagatc ggtcgaagca tttcttgatt   1980
ggatggacac attcggattg cgagactccg ttccggatag acgcaaatta gacgatgtag   2040
cggatagttt caatttggct atgagatacg tattagataa atggaatact aattatacac   2100
cttataatag gtgtaaatct agaaattaca taaaaaaaat gtaataacgt tagtaacgcc   2160
attatggata atctatttac ctttctacat gaaatagaag atagatatgc cagaactatt   2220
tttaactttc atctaataag ttgcgatgaa ataggagata tatatggtct tatgaaagaa   2280
cgcatttcct cagaggatat gtttgataat atagtgtata ataaagatat acatcatgcc   2340
attaagaaac tagtgtattg cgacatccaa cttactaaac acattattaa tcagaatacg   2400
tatccggtat ttaacgattc ttcacaagtg aaatgttgtc attatttcga tataaactca   2460
gataatagca atattagctc tcgtacagta gagatatttg agagggaaaa gtcatctctt   2520
gtatcatata ttaaaactac caataagaag agaaaggtca attatgggga aataaagaaa   2580
actgtacatg gaggcactaa tgcaaattac ttttccggta aaaagtctga tgagtatctg   2640
agcactacag tcaggtccaa cattaatcaa ccttggatca aaaccatttc taagagaatg   2700
agagtagata tcattaatca ctctatagta acgcgtggaa aagctctat attacaaact   2760
atagaaatta tttttactaa tagaacatgt gtgaaaatat tcaaggattc tactatgcac   2820
attattctat ccaaggacaa ggatgaaaag ggtgtatac acatgattga caaattattc   2880
tatgtctatt ataatttatt tctgttgttc gaagatatca tccaaaacga gtactttaaa   2940
gaagtagcta atgttgtaaa ccacgtactc acggctacgg cattagatga gaaattattc   3000
ctaattaaga aaatggctga acacgatgtt tatggagtta gcaatttcaa aatagggatg   3060
tttaacctga catttattaa gtcgttggat cataccgttt tcccctctct gttagatgag   3120
gatagcaaaa taaagttttt taaggggaaa aagctcaata ttgtagcatt acgatctctg   3180
gaggattgta taaattacgt gactaaatcc gagaatatga tagaaatgat gaaggaaaga   3240
tcgactattt taaatagcat agatatagaa acggaatcgg tagatcgtct aaaagaattg   3300
cttctaaaat gaaaaaaaac actgattcag aaatggatca acgactaggg tataagtttt   3360
tggtgcctga tcctaaagcc ggagtttttt atagaccgtt acatttccaa tatgtatcgt   3420
attctaattt tatattgcat cgattgcatg aaatcttgac cgtcaagcgg ccactcttat   3480
cgtttaagaa taatacagaa cgaattatga tagaaattag caatgttaaa gtgactcctc   3540
cagattactc acctataatc gcgagtatta aaggtaagag ttatgacgca ttagccacgt   3600
tcactgtaaa tatctttaaa gaggtaatga ccaaagaggg tatatccatc actaaaataa   3660
gtagttatga gggaaaagat tctcatttga taaaaattcc gctactaata ggatacggga   3720
ataaaaatcc acttgataca gccaagtatc ttgttcctaa tgtcataggt ggagtcttta   3780
tcaataaaca atctgtcgaa aaagtaggaa ttaatctagt agaaaagatt acaacatggc   3840
caaaatttag ggttgttaag ccaaactcat tcactttctc gttttcctcc gtatcccctc   3900
ctaatgtatt accgacaaga tatcgccatt acaagatatc tctggatata tcacaattgg   3960
aagcgttgaa tatatcatcg acaaagacat ttataacggt caatattgtt ttgctgtctc   4020
aatatttatc tagagtgagt ctagaattca ttagacgtag tttatcatac gatatgcctc   4080
cagaagttgt ctatctagta aacgcgataa tagatagtgc taaacgaatt actgaatcta   4140
```

```
ttactgactt taatattgat acatacatta atgacctggt ggaagctgaa cacattaaac   4200
aaaaatctca gttaacgatt aacgagttca aatatgaaat gctgcataac tttttacctc   4260
atatgaacta tacacccgat caactaaagg gattttatat gatatcttta ctaagaaagt   4320
ttctctactg tatctaccac acttctagat atccagatag agattcgatg gtttgtcatc   4380
gtatactaac atacggcaaa tattttgaga cgttggcaca tgatgaatta gagaattaca   4440
taggcaacat ccgaaacgat atcatgaaca atcacaagaa cagaggcact tacgcggtaa   4500
acattcatgt actaacaact cctggactta atcatgcgtt ttctagctta ttgagtggaa   4560
agttcaaaaa gtcagacggt agttatcgaa cacatcctca ctattcatgg atgcagaata   4620
tttctattcc taggagtgtt ggattttatc cggatcaagt aaagatttca aagatgtttt   4680
ctgtcagaaa ataccatcca agtcaatatc tttacttttg ttcatcggac gttccggaaa   4740
gaggtcctca ggtaggttta gtatctcaat tgtctgtctt gagttccatt acaaatatac   4800
taacgtctga gtatttggat ttggaaaaga aaatttgtga gtatatcaga tcatattata   4860
aagatgatat aagttacttt gaaacaggat ttccaatcac tatagaaaat gctctagtcg   4920
catctcttaa tccaaatatg atatgtgatt ttgtaactga ctttagacgt agaaaacgga   4980
tgggattctt cggtaacttg gaggtaggta ttactttagt tagggatcac atgaatgaaa   5040
ttcgcattaa tattggagcg ggaagattag tcagaccatt cttggttgtg gataacggag   5100
agctcatgat ggatgtgtgt ccggagttag aaagcagatt agacgatatg acattctctg   5160
acattcagaa agagtttcca catgtcatcg aaatggtaga tatagaacaa tttactttta   5220
gtaacgtatg tgaatcggtt caaaaattta gaatgatgtc aaaggatgaa agaaagcaat   5280
acgatttatg tgactttcct gccgaattta gagatggata tgtagcatct tcactagtgg   5340
gaatcaatca caattctgga cccagagcta ttcttggatg tgctcaagct aaacaagcta   5400
tctcttgtct gagttcggat atacgaaata aaatagacaa tggaattcat ttgatgtatc   5460
cagagaggcc aattgtcatt agtaaggctt tagaaacttc aaagattgcg gctaattgct   5520
tcggccaaca tgttactata gcattaatgt cgtacaaagg tatcaatcaa gaggatggaa   5580
ttatcatcaa aaaacaattt attcagagag gcggtctgga tatagttacc gcaaagaaac   5640
atcaagtaga aattccgttg gaaaacttta ataacaaaga aagagatagg tctaacgcct   5700
attcaaaatt agaaagtaat ggattagtta gactgaatgc tttcttggaa tccggagacg   5760
ctatggcacg aaatatctca tcaagaactc ttgaagatga ttttgctaga gataatcaga   5820
ttagcttcga tgtttccgag aaatataccg atatgtacaa atctcgcgtt gaacgagtac   5880
aagtagaact tactgacaaa gttaaggtac gagtattaac catgaaagaa agaagaccca   5940
ttctaggaga caaatttacc actagaacga gtcaaaaggg aacagtcgcg tatgtcgcgg   6000
atgaaacgga acttccatac gacgaaaatg gtatcacacc agatgtcatt attaattcta   6060
catccatctt ctctagaaaa actatatcta tgttgataga agttatttta acagccgcat   6120
attctgctaa gccgtacaac aataagggag aaaaccgacc tgtctgtttt cctagtagta   6180
acgaaacatc catcgataca tatatgcaat tcgctaaaca atgttatgag cattcaaatc   6240
cgaaattgtc tgatgaagaa ttatcggata aaatcttttg tgaaaagatt ctctatgatc   6300
ctgaaacgga taagccttat gcatccaaag tatttttgg accaatttat tacttgcgtc    6360
tgagacattt aactcaggac aaggcaaccg ttagatgtag aggtaaaaag acgaagctca   6420
ttagacaagc gaatgaggga cgaaaacgtg gaggaggtat taagtttgga gaaatggaga   6480
```

```
gagactgttt aatagcgcat ggcgcagcca atactattac agaagttttg aaagattcgg   6540
aagaagatta tcaagatgtg tatgtttgtg aaaattgtgg agacatagca gcacaaatca   6600
agggtattaa tacatgtctt agatgttcaa aacttaatct ctctcctctc ttaacaaaaa   6660
ttgataccac gcacgtatct aaagtatttc ttactcaaat gaacgccaga ggcgtaaaag   6720
ttaaattaga tttcgaacga aggcctcctt cgttttataa accattagat aaagttgatc   6780
tcaagccgtc ttttctggtg taatattcta gtttggtagt agatacatat caatatcatc   6840
aaattcgaga tccgaattat aaaatgggcg tggattgtta actatagaat cggacgtctg   6900
atattcgaaa atctgtggag tttcaggttt tggtggaggt gtaactgcta cttgggatac   6960
tgaagtctga tattcagaaa gctgggggat gttctggttc gacatccacc gatggtgtca   7020
catcactaat cggttcggta acgtctgtgg atggaggtgc tacttctaca gaacctgtag   7080
cctcagttgt caacggagat acatttttaa tgcgaggaaa tgtataattt ggtaatggtt   7140
tctcatgtgg atctgaagaa gaggtaagat atctactaga aagataccga tcacgttcta   7200
gttctctttt gtagaactta actttttctt tctcagcatc tagttgatat tccaacctct   7260
tcacgttact acgttcagat ttcaattcac gttcgcatgg gttacctccg cagtttttac   7320
gagcgatttc acgttcagcc ttcatgcgtc tttccctctc tctatcgagt ttatcagagc   7380
agtctttctg aaggcgatcg aactccataa atttctccaa cgctttgatt gtttccatag   7440
atttccgaag ttcagctttt aggactgtga ttctttttct ttcgaattca cagctggatg   7500
tacaaccgtt tccattaccg ccatctctaa gtttcttttc tagatcggca acatttcatc   7560
cccatgcctt ttacattcct cgagtctact gtcgtcgaaa tatcgttcca gctccttttc   7620
gacatcaata actttagcac gttgtctctc aagctctctt ttgtagttat ctgattccct   7680
ggcacgttta agatcttcat gcaattgagt cagctcttaa cacaatctct tgcttcttcg   7740
tcatagtact tacaatcact atgggatcca ttgttaccac gtctacactc ggcgagctcg   7800
cgtttaagag attcaatttc ccgtttgtat tggtccatgt ttccattgct accaccatta   7860
gatttacagg ctgctagttg tcgttcgaga tcagaaatac gggttttctt ggaattgatt   7920
tcgtcgatgt acttggcatc gaaacactta ttaagttctt tttccaattc tacgatttta   7980
tttctttcgc gagtcaattc cctcctgtag taactatctg ttttgtcaga ttcacgctct   8040
ctacgtagac tttcttgcaa gttactaatt tgttccctag cacgtccgag tttagtttta   8100
tatgccgaat agagttctga ttcatccttt gagcagatct ctagagatcg ttcaagatcc   8160
ctgattctag tctttagcct atttacctcc tcggaagatg ctccgttacc gttgcgttta   8220
cactcgttaa gctgtctatc aagatccatg attctatctc taagacgttg catctctctt   8280
tccatatcag cattgctttc attattacgt ctgcagtcac tcaactgtct ttcaatatct   8340
gagattctat ctctaagacg tcgcatctct ctctgtttcg gcattggttt cattattacg   8400
tctacagtcg ttcaactgtc tttcaagatc tgatattcta gattggagtc tgctaatctc   8460
tgtagcattt tcacggcatt cactcagttg tctttcaaga tctgagattt tagattggag   8520
tctgctaatc tctgtaagat ttcctcctcc gctctcgatg cagtcggtca acttattctc   8580
tagttctcta atacgcgaac gcagtgcatc aacttcttgc gtgtcttcct ggttgcgtgt   8640
acattcatcg agatctctaa cgcgtcgtcg ttcttcctca agttctctgc gtactacaga   8700
aagcgtgtcc ctatcttgtt gatatttagc aatttctgat tctagagtac tgattttgct   8760
tacgtagtta ctaatatttg tcttggcctt atcaagatcc tccttgtatt tgtcgcattc   8820
cttgatatcc ctacgaagtc tggacagttc ccattcgaca ttacgacgtt tatcgatttc   8880
```

```
agctcggaga tcgtcatcgc gttgttttag ccacatacga ctgagttcaa gttctcgttg   8940
acaagatcca tctacttttc cattcctaat agtatccagt tccttttcta gttctgaacg   9000
catttctcgt tccctatcaa gcgattctct caattctcgg atagtcttct tatcaatttc   9060
taataaatct gaaccatcat ctgtcccatt ttgaatatcc ctgtgttctt tgatctcttt   9120
tgtaagtcgg tcgattcttt cggttttata aacagaatcc ctttccaaag tcctaatctt   9180
actgagttta tcactaagtt ctgcattcaa ttcggtgagt tttctcttgg cttcttccaa   9240
ctctgtttta aactctccac tatttccgca ttcttcctcg catttatcta accattcaat   9300
tagtttatta ataactagtt ggtaatcagc gattcctata gccgttcttg taattgtggg   9360
aacataatta ggatcttcta atggattgta tggcttgata gcatcatctt tatcattatt   9420
agggggatgg acaaccttaa ttggttggtc ctcatctcct ccagtagcgt gtggttcttc   9480
aataccagtg ttagtaatag gcttaggcaa atgcttgtcg tacgcgggca cttcctcatc   9540
catcaagtat ttataatcgg gttctacttc agaatattct tttctaagag acgcgacttc   9600
gggagttagt agaagaactc tgtttctgta tctatcaacg ctggaatcaa tactcaagtt   9660
aaggatagcg aatacctcat cgtcatcatc cgtatcttct gaaacaccat catatgacat   9720
ttcatgaagt ctaacgtatt gataaacaga atcagattta gtattaaaca gatccttaac   9780
ctttttagta aacgcatatg tatattttag atctccagat ttcataatat gatcacatgc   9840
cttaaatgtc agtgcttcca tgatataatc tggaacacta atgggtgacg aaaaagatac   9900
agcaccatat gctacgttga taaataaatc tgaaccacta agtagataat gattaatgtt   9960
aaggaaaaga aaatattcag tgtataggta tgtcttggcg tcatatcttg tactaaacac  10020
gctaaacagt ttattgatgt gatcaatttc caacagaata attagagcag caggaatacc  10080
aacaaacata ttaccacatc cgtattttct atgaatatca catatcatgt taaaaaatct  10140
tgatagaaga gcgaatatct cgtctgactt aatgagtcgt agttcagcag caacataagt  10200
cataactgta aatagaacat actttcctgt agtgttgatt ctagactcca catcaacacc  10260
attattaaaa atagttttat atacatcttt aatctgctct ccgttaatcg tcgaacgttc  10320
tagtatacgg aaacactttg atttcttatc tgtagttaat gacttagtga tatcacgaag  10380
aatattacga attacatttc ttgtttttct tgacagacct gattcagaac tcaactcatc  10440
gttccatagt ttttctacct cagtggcgaa atctttggag tgcttggtac atttttcaat  10500
aaggttcgtg acctccattt attataaaaa attttattca aaacttaact acaatcgggt  10560
aattataaaa tcgtagatct cccatgtggt ggaatactac catctatcgc atgtggatgg  10620
acagtaggta atggccatgg gaacagtaat gtttgcatat ttatctttct tgccagtatt  10680
actgcatatt gtcccaatgt ttcgatgtga tgttctaacc tatcaactgc cgctgtatca  10740
caacaatagt gtccgatgaa attaagatta tgatccaatg tgtttaatat atgattatca  10800
agtcttatac gatccgcgtc tttttgaca ggatcaggtt cttctacagg aagaagtttc  10860
ggcctcttat gatattcatg tctgggaaac ggtggtctag ggtgaggctc cggtatcgga  10920
gtgggttttg gattataatc atcatcgtct atgacatcat cttcgacttc gatatttatt  10980
ttgctatctt gatgatgtcc tgtatcagtt gcattttcag cactcgactg aatattagcg  11040
cattcattgt ctattattac catatttcta aatccaaaat gtatatgttg aacatcacta  11100
ctatcgttga tgagtcttat agcatgaatt cgcttatcgt tatcgggttt agcttctgtc  11160
accttagcaa ttcctttttt attaaactct acataatcat atccatttct attgtttgtt  11220
```

```
ctaatataaa cgagtatagc atcattgcta aatttttcaa tagtatcgaa aacagaatat  11280
cctaaaccat ataatatata ttcaggaaca ctcaaactaa atgtccagga ttctcctaaa  11340
tacgtaaact ttaatagtgc gaaatcattc aaaaatctac cacttataga tagatagtac  11400
ataaatgcgt atagtagtct acctatctct ttattatgaa aaccggcatt acgatcatat  11460
atatcatgat atacctgtga cccgtttacg ttaaaccata aatacatggg tgatcctata  11520
aacatgaatt tatttctaat tctcagagct atagttaatt gaccgtgtaa tatttgctta  11580
catgcatact tgatacgctc attaataaga tttttatcat tgctcgttat ctcagaatcg  11640
tatatataag gagtaccatc gtgattctta ccagatatta tacaaaatac tatatataaa  11700
atatattgac caacgttagt aatcatataa atgtttaacg ttttaaattt tgtattcaat  11760
gatccattat catacgctag catggtctta tgatattcat tctttaaaat ataatattgt  11820
gttagccatt gcattggggc tcctaatgga gatttttat tctcatccat tttaggatag  11880
gctttcataa agtccctaat aacttcgtga ataatgtttc tatgttttct actgatgcat  11940
gtatttgctt cgattttttt atcccatgtt tcatctatca tagatttaaa cgcagtaatg  12000
ctcgcaacat taacatcttg aaccgttggt acaattccgt tccataaatt tataatgttc  12060
gccatttata taactcattt tttgaatata cttttaatta acaaaagagt taagttactc  12120
atatggacgc cgtccagtct gaacatcaat ctttttagcc agagatatca tagccgctct  12180
tagagtttca gcgtgatttt ccaacctaaa tagaacttca tcgttgcgtt tacaacactt  12240
ttctatttgt tcaaactttg ttgttacatt agtaatcttt ttttccaaat tagttagccg  12300
ttgtttgaga gtttcctcat tgtcgtcttc atcggcttta acaattgctt cgcgtttagc  12360
ctctggcttt ttagcagcct ttgtagaaaa aaattcagtt gctggaattg caagatcgtc  12420
atctccgggg aaaagagttc cgtccattta aagtacagat tttagaaact gacactctgc  12480
gttatttata tttggtacaa cacatggatt ataaatatcg atgttaataa catcagaaaa  12540
tgtaaagtct atacattgtt gcatcgtgtt aaattttcta atggatctag tattattggg  12600
tccaacttct gcctgaaatc caaatatgga agcggataca aaaccgtttc ctggataaac  12660
cacacatctc cacttttgct ttacatcaga aattgtgtcg ttgacatctt gaactctcct  12720
atctaatgcc ggtgttccac ctatagattt tgaatattcg aatgctgcat gagtagcatt  12780
aaattcctta atattgccat aattttcata tattgagtaa ccctggataa aaagtaaaca  12840
caccgcagcc gtcgctacca caataaaaaa aattgataga gagttcattt ataatctatt  12900
agaagctgac aaaatttttt tacacgcatc agacaatgct ttaataaata gttcaacatc  12960
tacttttgtc atatcgaacc gatggtatga ttctaaccta gaattacatc cgaaaaagtt  13020
gactatgttc atagtcatta agtcattaac aaacaacatt ccagactctg gattataaga  13080
cgatactgtt tcgtcacaat tacctacctt aatcatgtga ttatgaatat tggctattag  13140
agcaccttct aagaaatcta taatatcttt gaaacacgat ttaaaatcaa accacgaata  13200
tacttctacg aagaaagtta gtttacccat aggagagata actataaatg gagatctaga  13260
tacaaaatcc ggatctatga tagttttaac attattatat tctctattaa atacctccac  13320
atctaaaaat gttaattttg aaactatgtc ttcgtttatt accgtacctg aactaaacgc  13380
tataagctct attgtttgag aactctttaa acgatattct tgaaatacat gtaacaaagt  13440
ttcctttaac tcggtcggtt tatctaccat agttacagaa tttgtatcct tatctataat  13500
ataataatca aaatcgtata aagttatata attatcgcgt tcagattggg atcttttcaa  13560
atagactaaa aaccccattt ctctagtaag tatcttatgt atatgtttgt aaaatatctt  13620
```

```
catggtggga atatgctcta ccgcagttat ccattcctca ttgacagcgg tagatgtatt  13680
agacaaaact attccaatgt ttaacaaggg ccattttacg agattattaa atccttgttt  13740
gataaatgta gccaatgagg gttcgagttc aacgacgatt gaattctctt cccgcggatg  13800
ctgcatgatg aacgacggga tgttgttcga ttgatttgga attctttttc gactttttgt  13860
ttatattaaa tattttaaaa tttatagcgg atagcaattc atgtaccacg gataatgtag  13920
acgcgtattg cgcatcgata tctttattat tagataaatt tatcaataaa tgtgagaagt  13980
ttgcctcgtt aaggtcttcc atttaaatat tatataaaca tttgtgtttg tatcttattc  14040
gtcttttatg gaatagtttt ttactagtaa agctgcaatt acacactttg tccgtaaaac  14100
ataaatataa acaccagctt ttatcaatcg ttccaaaaag tcgacggcgg acatttttaa  14160
catggcatct attttaaata cacttaggtt tttggaaaaa acatcatttt ataattgtaa  14220
cgattcaata actaaagaaa agattaagat taaacataag ggaatgtcat ttgtatttta  14280
taagccaaag cattctaccg ttgttaaata cttgtctgga ggaggtatat atcatgatga  14340
tttggttgta ttggggaagg taacaattaa tgatctaaag atgatgctat tttacatgga  14400
tttatcatat catggagtga caagtagtgg agcaatttac aaattgggat cgtctatcga  14460
tagactttct ctaaatagga ctattgttac aaaagttaat aattatgatg atacattttt  14520
tgacgacgat gattgatcgc tattgcacaa ttttgttttt gtactttcta atatagtgtt  14580
taggttcttt ttcatatgag aatattgatt tactaaaata tctatgttta acttttgttc  14640
tataacgtcc ttatcggcgg tatcggtaca tatacgtaat tcaccttcac aaaatacgga  14700
gtcttcgata ataatagcca atcgattatt ggatctagct gtctgtatca tattcaacat  14760
gtttaatata tcctttcgtt tcccctttac aggcatcgat cgtagcatat tttccgcgtc  14820
tgagatggaa atgttaaaac tacaaaaatg cgtaatgtta gcccgtccta atattggtac  14880
gtgtctataa gtttggcata gtagaataat agacgtgttt aaatgccttc caaagtttaa  14940
gaattctatt agagtattgc attttgatag tttatcgcct acatcatcaa aaataagtaa  15000
aaagtgtgct gattttttat gattttgtgc gacagcaata catttttcta tgttactttt  15060
agttcgtatc agattatatt ctagagcttc ctgactacta acgaaattaa tatgatttgg  15120
ccaaatgtat ccatcataat ctgggttata aacgggtgta aacaagaata tatgtttata  15180
tttttaact agtgtagaaa acagagatag taaatagata gtttttccag atccagatcc  15240
tcccgttaaa accattctaa acggcatttt taataaattt tctcttgaaa attgtttttc  15300
ttggaaacaa ttcataatta tatttacagt tactaaatta atttgataat aaatcaaaat  15360
atggaaaact aaggtcgtta gtagggagga gaacaaagaa ggcacatcgt gacataaata  15420
acatttatta tcatgatgac accagaaaac gacgaagagc agacatctgt gttctccgct  15480
actgtttacg gagacaaaat tcagggaaag aataaacgca aacgcgtgat tggtctatgt  15540
attagaatat ctatggttat ttcactacta tctatgatta ccatgtccgc gtttctcata  15600
gtgcgcctaa atcaatgcat gtctgctaac gaggctgcta ttactgacgc cgctgttgcc  15660
gttgctgctg catcatctac tcatagaaag gttgcgtcta gcactacaca atatgatcac  15720
aaagaaagct gtaatggttt atattaccag ggttcttgtt atatattaca ttcagactac  15780
cagttattct cggatgctaa agcaaattgc actgcggaat catcaacact acccaataaa  15840
tccgatgtct tgattacctg gctcattgat tatgttgagg atacatgggg atctgatggt  15900
aatccaatta caaaaactac atccgattat caagattctg atgtatcaca agaagttaga  15960
```

aagtattttt gtgttaaaac aatgaactaa tatttatttt tgtacattaa taaatgaaat 16020
cgcttaatag acaaactgta agtaggttta agaagttgtc ggtgccggcc gctataatga 16080
tgatactctc aaccattatt agtggcatag gaacatttct gcattacaaa gaagaactga 16140
tgcctagtgc ttgcgccaat ggatggatac aatacgataa acattgttat ttagatacta 16200
acattaaaat gtctacagat aatgcggttt atcagtgtcg taaattacga gccagattgc 16260
ctagaccgga tactagacat ctgagagtat tgtttagtat tttttataaa gattattggg 16320
taagtttaaa aaagaccaat aataaatggt tagatattaa taatgataaa gatatagata 16380
ttagtaaatt aacaaatttt aaacaactaa acagtacgac ggatgctgaa gcgtgttata 16440
tatacaagtc tggaaaactg gttaaaacag tatgtaaaag tactcaatct gtactatgtg 16500
ttaaaaaatt ctacaagtga caacaaaaaa tgaattaata ataagtcgtt aacgtacgcc 16560
gccatggacg ccgcgtttgt tattactcca atgggtgtgt tgactataac agatacattg 16620
tatgatgatc tcgatatctc aatcatggac tttataggac catacattat aggtaacata 16680
aaaactgtcc aaatagatgt acgggatata aaatattccg acatgcaaaa atgctacttt 16740
agctataagg gtaaaatagt tcctcaggat tctaatgatt tggctagatt caacatttat 16800
agcatttgtg ccgcatacag atcaaaaaat accatcatca tagcatgcga ctatgatatc 16860
atgttagata tagaagataa acatcagcca ttttatctat tcccatctat tgatgttttt 16920
aacgctacaa tcatagaagc gtataacctg tatacagctg gagattatca tctaatcatc 16980
aatccttcag ataatctgaa aatgaaattg tcgtttaatt cttcattctg catatcagac 17040
ggcaatggat ggattataat tgatgggaaa tgcaatagta attttttatc ataaaagttg 17100
taaagtaaat aataaaacaa taaatattga actagtagta cgtatattga gcaatcagaa 17160
atgatgctgg tacctcttat cacggtgacc gtagttgcgg gaacaatatt agtatgttat 17220
atattatata tttgtaggaa aaagatacgt actgtctata atgacaataa aattatcatg 17280
acaaaattaa aaaagataaa gagttctaat tccagcaaat ctagtaaatc aactgatagc 17340
gaatcagact gggaggatca ctgtagtgct atggaacaaa acaatgacgt agataatatt 17400
tctaggaatg agatattgga cgatgatagc ttcgctggta gtttaatatg ggataacgaa 17460
tccaatgtta tggcgcctag cacagaacac atttacgata gtgttgctgg aagcacgctg 17520
ctaataaata atgatcgtaa tgaacagact atttatcaga acactacagt agtaattaat 17580
gaaacggaga ctgttaaagt acttaatgaa gataccaaac agaatcctaa ctattcatcc 17640
aatcctttcg taaattataa taaaaccagt atttgtagca agtcaaatcc gtttattaca 17700
gaacttaaca ataaatttag tgagaataat ccgtttagac gagcacatag cgatgattat 17760
cttaataagc aagaacaaga tcatgaacac gatgatatag aatcatcggt cgtatcattg 17820
gtgtgattag tttccttttt ataaaattga agtaatattt agtattattg ctgccgtcac 17880
gttgtacaaa tggagatatt ccctgtattc ggcatttcta aaattagcaa ttttattgct 17940
aataatgact gtagatatta tatagataca gaacatcaaa aaattatatc tgatgagatc 18000
aatagacaga tggatgaaac ggtacttctt accaacatct taagcgtaga agttgtaaat 18060
gacaatgaga tgtaccatct tattcctcat agattatcga cgattatact ctgtattagt 18120
tctgtcggag gatgtgttat ctctatagat aatgacgtca atggcaaaaa tattctaacc 18180
tttcccattg atcatgctgt aatcatatcc ccactgagta aatgtgtcgt agttagcaag 18240
ggtcctacaa ccatattggt tgttaaagcg gatataccca gcaaacgatt ggtaacatcg 18300
tttacaaacg acatactata tgtaaacaat ctgtcactga ttaattattt gccgttgtct 18360
gtattcatta ttagacgagt taccgactat ttggatagac acatatgcga tcagatattt 18420
gcgaataata agtggtattc cattataacc atcgacaata agcagtttcc tattccatca 18480
aactgtatag gtatgtcctc tgccaagtac ataaattcta gcatcgagca agatacttta 18540
atacatgttt gtaacctcga gcatccattc gacttagtat acaaaaaaat gcagtcgtac 18600
aattctgtac ctatcaagga acaaatattg tacggtagaa ttgataatat aaatatgagc 18660
attagtattt ctgtgtatta atagatttct agtatgggga tcattaatca tctctaatct 18720
ctaaatacct cataaaacga aaaaaaagct attatcaaat actgtacgga atggattcat 18780
tctcttctct ttttatgaaa ctctgttgta tatctactga taaaactgga agcaaaaaat 18840
ctgataaaaa gaataagaat aagatcaagg attatatgga acacgattat tataaaataa 18900
caatagttcc tggttcctct tccacgtcta ctagctcgtg gtattataca catgcctagt 18960
aatagtctct ttgcgttgat ggaaagcaga ctagaaataa caggctaaaa tgttcagaca 19020
ccataatagt tcccaaccca gataataaca gagttccatc aacacattcc tttaaactca 19080
atcccaaacc caaaaccgtt aaaatgtatc cggccaattg atagtagata atgaggtgta 19140
cagcacatga taatttacac agtaaccaaa atgaaaacac tttagtaatt ataagaaata 19200
tagacggtaa tgtcatcatc aacaatccga taatatgcct gagagtaaac attgacggat 19260
aaaacaaaaa tgctccgcat aactctatca tggcaataac acaaccaaat acttgtaaga 19320
ttcctaaatt agtagaaaat acaacggata tcgatgtata agtgatctcg agaaataata 19380
agaataaagt aatgcccgta aagataaaca tcaacattgt ttggtaatca ttaaaccaat 19440
tagtatgaag ttgaactaat ttcacagtag attttattcc agtattatcc ccgcatgtat 19500
acgtacctgg taagatatct ttatattcta taatcaatga gacatcacta tccgataacg 19560
aatgaagtct agcactagta tgccatttac ttaatatggt cgtcttggaa gttttattat 19620
aagttaaaat atcatggtta tccaatttcc atctaatata ctttgtcgga ttatctatag 19680
tacacggaat aatgatggta tcattacatg ctgtatactc tatggtcttt gtagttgtta 19740
taacaaccaa cgtatagagg tatatcaacg atattctaac tcttgacatt ttttatttat 19800
ttaaaatgat acctttgtta tttattttat tctattttgc taacggtatt gaatggcata 19860
agtttgaaac gagtgaagaa ataatttcta cttacttatt agacgacgta ttatacacgg 19920
gtgttaatgg ggcggtatac acattttcaa ataataaact aaacaaaact ggtttaacta 19980
ataataatta tataacaaca tctataaaag tagaggatgc ggataaggat acattagtat 20040
gcggaaccaa taacggaaat cccaaatgtt ggaaaataga cggttcagac gacccaaaac 20100
atagaggtag aggatacgct ccttatagca aagtaacgat aatcagttac aacgaatgtg 20160
tactatctga cataaacata tcaaaagaag gaattaaacg atagagaaga tttgacggac 20220
catgtggtta tgatttattc acggcggata acgtaattcc aaaagatggt ttacgaggag 20280
cattcgtcga taaagacggt acttatgaca aagtttacat tcttttcact gatactatcg 20340
gctcaaagag aattgttaaa attccgtata taacacaaat gtgcttaaac gacgaaggtg 20400
gtccatcatc gttgtctagt catagatggt cgacgtttct caaagtcgaa ttagaatgtg 20460
acatcgacgg aagaagttat agataaatta ttcattctaa aactataaaa acagataatg 20520
atacgatact atatgtattc ttcgatagtc cgcattatgt acctattcta tgaataccat 20580
taaacaatct ttttctacgt caaaattgga aggatataca aagcaattgc cgtctccagc 20640
tcctggtata tgtctaccag ctggaaaagt tgttccacat accacgtttg aagtcataga 20700

-continued

```
aaaatataat gtactagatg atattataaa gcctttatct aaccaaccta tcttcgaagg  20760
accgtctggc gttaaatggt tcgatataaa ggagaaggaa aatgaacatc gggaatatag  20820
aatatacttc ataaaagaaa attctatata ttcattcgat acaaaaacta aacaaactcg  20880
cagtgcacaa gtcaatgcac aactattttc agtaatggta actgcgaaac cgttatttat  20940
agcagatata gggataggag taggaatgcc acaaatgaaa aaaatactta aaatgtaatc  21000
ttaatcgagt acaccacacg acaatgaaca aacataagac agattatgct ggttatgctt  21060
gctgcgtaat atgcggtcta attgttggaa ttatttttac agcgacacta ttaaaagttg  21120
tagaacgtaa attagttcat acaccatcaa tagataaaac gataaaagat gcatatatta  21180
gagaagattg tcctactgac tggataagct ataataataa atgtatccat ttatctactg  21240
atcgaaaaac ctgggaggaa ggacgtaata catgcaaagc tctaaatcca aattcggatc  21300
taattaagat agagactcca aacgagttaa gtttttaag aagcattaga cgcggatatt  21360
gggtaggaga atccgaaata ttaaaccaga caaccccata taattttata gctaagaatg  21420
ccacgaagaa tggaaatata tttgtagtac aacgaatact cccaaactgc attcgtgtta  21480
cactatataa caattacact acatttttat cataccacta cttcggttag atgttttaga  21540
aaaaaataaa tatcgccgta ccgttcttgt ttttataaaa ataacaatta acaattatca  21600
aatttttct ttaatatttt acgtggttga ccattcttgg tggtaaaata atctcttagt  21660
gttggaatgg aatgctgttt aatgtttccg cactcatcgt atattttgac gtatgcagtc  21720
acatcgttta cgcaatagtc agactgtagt tctatcatgc ttcctacatc agaaggagga  21780
acagttttaa agtctcttgg ttttaatcta ttgccattag ttttcatgaa atcctttgtt  21840
ttatccactt cacattttaa ataaatgtcc actatacatt cttttgttaa ttttactaga  21900
tcgtcatggg tcatagaatt tataggttcc gtagtccatg gatccaaact agcaaacttc  21960
gcgtatacgg tatcgcgatt agtgtataca ccaactgtat gaaaattaag aaaacagttt  22020
aataaatcaa cagaaatatt taatcctccg tttgatacag atgcaccata tttatggatt  22080
tcggattcac acgttgtttg tctgaggtgt tcgtctagtg ttgcttctac ataaacttcg  22140
attcccatat attctttatt gtcagaatcg cataccgatt tatcatcata cactgtttga  22200
aaactaaatg gtatacacat caaaataata aataataacg agtacattct gcaatattgt  22260
tatcgtaatt ggaaaaatag tgttcgagtg agttggatta tgtgagtatt ggattgtata  22320
ttttatttta tattttgtaa taagaataga atgctaatgt caagtttatt ccaatagatg  22380
tcttattaaa aaacatatat aataaataac aatggctgaa tggcataaaa ttatcgagga  22440
tatctcaaaa aataataagt tcgaggatgc cgccatcgtt gattacaaga ctacaaagaa  22500
tgttctagct gctattccta acagaacatt tgccaagatt aatccgggtg aaattattcc  22560
tctcatcact aatcgtaata ttctaaaacc tcttattggt cagaaatatt gtattgtata  22620
tactaactct ctaatggacg agaacacgta tgctatggag ttgcttactg ggtacgcccc  22680
tgtatctccg atcgttatag cgagaactca taccgcactt atatttttga tgggtaagcc  22740
aacaacatcc agacgtgacg tgtatagaac gtgtagagat cacgctaccc gtgtacgtgc  22800
aactggtaat taaaataaaa agtaatattc atatgtagtg tcaattttaa atgatgatga  22860
tgaaatggat aatatccata ttgacgatgt caataatgcc ggtattggca tacagctcat  22920
cgatttttag atttcattca gaggatgtgg aattatgtta tgggcatttg tattttgata  22980
ggatctataa tgtagtaaat ataaaatata atccgcatat tccatataga tataatttta  23040
ttaatcgcac gttaaccgta gatgaactag acgataatgt ctttttaca catggttatt  23100
```

ttttaaaaca caaatatggt tcacttaatc ctagtttgat tgtctcatta tcaggaaact 23160
taaaatataa tgatatacaa tgctcagtaa atgtatcgtg tctcattaaa aatttggcaa 23220
cgagtacatc tactatatta acatctaaac ataagactta ttctctacat cggtccaagt 23280
gtattattat aataggatat gattctatta tatggtataa agatataaat gacaagtata 23340
atggcatcta tgattttact gcaatatgta tgctaatagc gtctacattg atagtgacca 23400
tatacgtgtt taaaaaaata aaaatgaact cttaattatg ctatgctatt agaaatggat 23460
aaaatcaaaa ttacggttga ttcaaaaatt ggtaatgttg ttaccatatc gtataacttg 23520
gaaaagataa ctattgatgt tacaccaaaa aagaaaagga tgtattatta gcgcaatcag 23580
ttgctgtcga agaggcaaaa gatgtcaagg tagaagaaaa aaatattatc gatattgaag 23640
atgacgatga tatggatgta gaaagcgcat aatacgatct ataaaaataa gtatataaat 23700
actttttatt tactgtactc ttactgtgta gtggtgatac cctactcgat tattttttta 23760
aaaaaaaaat acttattctg attcttctaa ccatttccgt gttcgttcga atgccacatc 23820
gacgtcaaag ataggggagt agttgaaatc tagttctgca ttgttggtac gcacctcaaa 23880
tgtagtgttg gatatcttca acgtatagtt gttgagtagt gatggttttc taaatagaat 23940
tctcttcata tcattcttgc acgcgtacat ttttagcatc catcttggaa tcctagatcc 24000
ttgttctatt cccaatggtt tcatcaatag aagattaaac atatcgtacg aacacgatgg 24060
agagtaatcg tagcaaaagt aagcatttcc tttaatctta gatcccggat actggatata 24120
ttttgcagcc aacacgtgca tccatgcagc atttcctaca tatacccggc tatgtaccgc 24180
gttatcatcg actgtacgat acataatgtt accgtgttgc ttacattgct cgtaaaagac 24240
tttcgtcaat ttgtctcctt ctccgtaaat tccagtgggt cttaggcaac aagtatacaa 24300
ttttgctcca ttcatgatta cggaattatt ggctttcata accagttgct cggccatacg 24360
tttacttttt gcgtatacat gtcctggtga tatatcataa agggtatgct catggccgat 24420
gaatggatca ccgtgtttat tgggtcctat tgcttccatg ctactagtat agatcaaata 24480
cttgattcct aggtccacac aagctgccaa aatagtctgt gttccataat agtttacttt 24540
catgatttca ttatcggtgt attttccaaa tacatccact agagcagctg tatgaataat 24600
cagatttacc ccatttagcg cttctctcac cttatcaaag tcgtttatat cacattgtat 24660
atagtttata accttaactt tcgaggttat tggttgtgga tcttctacaa tatctatgac 24720
tctgatttct tgaacatcat ctgcactaat taacagtttt actatatacc tgcctagaaa 24780
tccggcacca ccagtaaccg cgtacacggc cattgctgcc acttataata tcaaactact 24840
tattctattt tactaaataa tggctgtttg tataataaac cacgataata tcagaggagt 24900
tatttacttt gaaccagttc atggaaaaga taaagtttta ggatcagtta ttggattaaa 24960
atccggaacg tatagtttga taattcatcg ttacggagat attagtcaag gatgtgattc 25020
cataggcagt ccagaaatat ttatcggtaa catctttgta aacagatatg gtgtagcata 25080
tgtttattta gatacagatg taaatatatt tacaattatt ggaaaggcgt tatctatttc 25140
aaaaaatgat cagagattag cgtgtggagt tattggtatt tcttacataa atgaaaagat 25200
aatacatttt cttacaatta acgagaatgg cgtttgatat atcagttaat gcgtctaaaa 25260
caataaatgc attagtttac ttttctactc agcaaaataa attagtcata cgtaatgaag 25320
ttaatgatac acactacact gtcgaatttg atagggacaa agtagttgac acgtttattt 25380
catataatag acataatgac tccatagaga taagaggggt gcttccagag gaaactaata 25440
ttggttgcgc ggttaatacg ccggttagta tgacttactt gtataataag tatagtttta 25500
aactgatttt agcagaatat ataagacaca gaaatactat atccggcaat atttattcgg 25560
cattgatgac actagatgat ttggctatta aacagtatgg agacattgat ctattattta 25620
atgagaaact taaagtagac tccgattcgg gactatttga ctttgtcaac tttgtaaagg 25680
atatgatatg ttgtgattct agaatagtag tagctctatc tagtctagta tctaaacatt 25740
gggaattgac aaataaaaag tataggtgta tggcattagc cgaacatata tctgatagta 25800
ttccaatatc tgagctatct agactacgat acaatctatg taagtatcta cgcgggcaca 25860
ctgagagcat agaggataaa tttgattatt ttgaagacga tgattcgtct acatgttctg 25920
ccgtaaccga cagggaaacg gatgtataat tttagggata acagggtaat 25970

<210> SEQ ID NO 8
<211> LENGTH: 28837
<212> TYPE: DNA
<213> ORGANISM: Vaccinia virus

<400> SEQUENCE: 8
tagggataac agggtaatta cttattctga ttcttctaac catttccgtg ttcgttcgaa 60
tgccacatcg acgtcaaaga taggggagta gttgaaatct agttctgcat tgttggtacg 120
cacctcaaat gtagtgttgg atatcttcaa cgtatagttg ttgagtagtg atggttttct 180
aaatagaatt ctcttcatat cattcttgca cgcgtacatt tttagcatcc atcttggaat 240
cctagatcct tgttctattc ccaatggttt catcaataga agattaaaca tatcgtacga 300
acacgatgga gagtaatcgt agcaaaagta agcatttcct ttaatcttag atcccggata 360
ctggatatat tttgcagcca acacgtgcat ccatgcagca tttcctacat atacccggct 420
atgtaccgcg ttatcatcga ctgtacgata cataatgtta ccgtgttgct tacattgctc 480
gtaaaagact ttcgtcaatt tgtctccttc tccgtaaatt ccagtgggtc ttaggcaaca 540
agtatacaat tttgctccat tcatgattac ggaattattg gctttcataa ccagttgctc 600
ggccatacgt ttactttttg cgtatacatg tcctggtgat atatcataaa gggtatgctc 660
atggccgatg aatggatcac cgtgtttatt gggtcctatt gcttccatgc tactagtata 720
gatcaaatac ttgattccta ggtccacaca agctgccaaa atagtctgtg ttccataata 780
gtttactttc atgatttcat tatcggtgta ttttccaaat acatccacta gagcagctgt 840
atgaataatc agatttaccc catttagcgc ttctctcacc ttatcaaagt cgtttatatc 900
acattgtata tagtttataa ccttaacttt cgaggttatt ggttgtggat cttctacaat 960
atctatgact ctgatttctt gaacatcatc tgcactaatt aacagtttta ctatatacct 1020
gcctagaaat ccggcaccac cagtaaccgc gtacacggcc attgctgcca cttataaatat 1080 caaactactt attctatttt actaaataat ggctgtttgt ataataaacc acgataaatat 1140 cagaggagtt atttactttg aaccagttca tggaaaagat aaagttttag gatcagttat 1200
tggattaaaa tccggaacgt atagtttgat aattcatcgt tacggagata ttagtcaagg 1260
atgtgattcc ataggcagtc cagaaatatt tatcggtaac atctttgtaa acagatatgg 1320
tgtagcatat gtttatttag atacagatgt aaatatattt acaattattg gaaaggcgtt 1380
atctatttca aaaaatgatc agagattagc gtgtggagtt attggtattt cttacataaa 1440
tgaaaagata atacattttc ttacaattaa cgagaatggc gtttgatata tcagttaatg 1500
cgtctaaaac aataaatgca ttagtttact tttctactca gcaaaataaa ttagtcatac 1560
gtaatgaagt taatgataca cactacactg tcgaatttga tagggacaaa gtagttgaca 1620
cgtttatttc atataataga cataatgact ccatagagat aagaggggtg cttccagagg 1680
aaactaatat tggttgcgcg gttaatacgc cggttagtat gacttacttg tataataagt 1740
atagttttaa actgatttta gcagaatata taagacacag aaatactata tccggcaata 1800
tttattcggc attgatgaca ctagatgatt tggctattaa acagtatgga gacattgatc 1860
tattatttaa tgagaaactt aaagtagact ccgattcggg actatttgac tttgtcaact 1920
ttgtaaagga tatgatatgt tgtgattcta gaatagtagt agctctatct agtctagtat 1980
ctaaacattg ggaattgaca aataaaaagt ataggtgtat ggcattagcc gaacatatat 2040
ctgatagtat tccaatatct gagctatcta gactacgata caatctatgt aagtatctac 2100
gcgggcacac tgagagcata gaggataaat ttgattattt tgaagacgat gattcgtcta 2160
catgttctgc cgtaaccgac agggaaacgg atgtataatt ttttttatag cgtgaaggat 2220
atgataaaaa atataattgt tgtatttatc ccattccaat caccttatat gattctgtaa 2280
aaaaattata ctgtaacaca ataaaggagt cttatagatg tatagaggtc agatactggt 2340
ttgataaact gtttattcca cataagtatg tttgacttta tggttagacc cgcatacttt 2400
aacaaatcac tgaaaattgg agttaggtat tgacctctca gaatcagttg ccgttctgga 2460
acattaaatg tattttttat gatatactcc aacgcattta tgtgggcata caacaagtca 2520
ttactaatgg agtattccaa gagttttagt tgtctagtat ttaacaagag aagagatttc 2580
aacagactgt ttatgaactc gaatgccgcc tcattgtcgc ttatattgat gatgtcgaat 2640
tctcccaata tcatcaccga tgagtagctc atcttgttat cgggatccaa gttttctaaa 2700
gatgtcatta aaccctcgat catgaatgga tttatcatca tcgtttttat gttggacatg 2760
agcttagtcc gtttgtccac atctatagaa gatgatttct gaattatttc atatatctct 2820
ctctttaact ccaggaactt gtcaggatgg tctactttaa tatgttctcg tctaagagat 2880
gaaaatcttt ggatggttgc acgcgacttt tctctaaagg atgacgttgc ccaagatcct 2940
ctcttaaatg aatccatctt atccttggac aagatggaca gtctattttc cttagatggt 3000
ttaatatttt tgttacccat gatctataaa ggtagaccta atcgtctcgg atgaccatat 3060
atttattttc agttttatta tacgcataaa ttgtaaaaaa tatgttaggt ttacgaaaat 3120
gtctcgtggg gcattaatcg tttttgaagg attggacaaa tctggaaaaa caacacaatg 3180
tatgaacatc atggaatcta taccggcaaa cacgataaaa tatcttaact ttcctcagag 3240
atccactgtc actggaaaga tgatagatga ctatctaact cgtaaaaaaa cctataatga 3300
tcatatagtt aatctattat tttgtgcaaa tagatgggag tttgcatctt ttatacaaga 3360
acaactagaa cagggaatta ctttaatagt tgatagatac gcattctctg gagtagcgta 3420
tgccgccgct aaaggcgcgt caatgactct cagtaagagt tatgaatctg gattgcctaa 3480
acccgactta gttatattct tggaatctgg tagcaaagaa attaatagaa acgtcggcga 3540
ggaaatttat gaagatgtta cattccaaca aaaggtatta caagaatata aaaaaatgat 3600
tgaagaagga gatattcatt ggcaaattat ttcttctgaa ttcgaggaag atgtaaagaa 3660
ggagttgatt aagaatatag ttatagaggc tatacacacg gttactggac cagtggggca 3720
actgtggatg taatagtgaa attacatttt ttataaatag atgttagtac agtgttataa 3780
atggatgaag catattactc tggcaacttg gaatcagtac tcggatacgt gtccgatatg 3840
cataccgaac tcgcatcaat atctcaatta gttattgcca agatagaaac tatagataat 3900
gatatattaa acaaggacat tgtaaatttt atcatgtgta gatcaaactt ggataatcca 3960

```
tttatctctt tcctagatac tgtatatact attatagatc aagagatcta tcagaccgaa   4020
ttgattaatt cattagacga caatgaaatt atcgattgta tagttaataa gtttatgagc   4080
ttttataagg ataacctaga aaatatagta gatgctatca ttactctaaa atatataatg   4140
aataatccag attttaaaac tacgtatgca gaagtactcg gttccagaat agcggatata   4200
gatattaaac aagtgatacg tgagaatata ctacaattgt ctaataatat ccgcgaacga   4260
tatttgtgaa aatattaaaa aaaaatactt tttttattaa atgacgtctt ttcgtgaatt   4320
tagaaaatta tgctgtgcta tatatcacgc atcaggatat aaagaaaaat ctaaattaat   4380
tagagacttt ataacagata gggatgataa atatttgatc attaagctat tgcttcccgg   4440
attagacgat agaatttata acatgaacga taaacaaatt ataaaattat atagtataat   4500
atttaaacaa tctcaggaag atatgctaca agatttagga tacggatata taggagacac   4560
tattagtaca ttcttcaaag aaaacacaga aatccgtcca agagataaaa gcattttaac   4620
tttagaagac gtggatagtt tcttaactac gttatcatcc gtaactaaag aattgcatca   4680
aataaaatta ttgactgatg tagcatctgt ttgtacatgt aatgatttaa aatgtgtagt   4740
catgcttatt gataaagatc taaaaattaa agcgggccct cggtacgtac ttaacgctat   4800
tagtcctcat gcctatgatg tttttagaaa atctaataac ttgaaagaga taatagaaaa   4860
tgcatctaaa caaaatctag actctatatc tatttctgtt atgactccaa ttaatcccat   4920
gttagcggaa tcgtgtgatt ctgtcaataa ggcgtttaaa aaatttccat caggaatgtt   4980
tgcggaagtt aaatacgatg gtgaaagagt acaagttcat aaaaataata acgagtttgc   5040
cttctttagt agaaacatga aaccagtact ctctcataaa gtggattatc tcaaagaata   5100
cataccgaaa gcatttaaaa aagctacgtc tatcgtattg gattctgaaa ttgttcttgt   5160
agacgaacat aatgtaccgc tcccgtttgg aagtttaggt atacacaaaa agaaagaata   5220
taaaaactct aacatgtgtt tgttcgtgtt tgactgtttg tactttgatg gattcgatat   5280
gacggacatt ccattgtacg aacgaagatc ttttctcaaa gatgttatgg ttgaaatacc   5340
caatagaata gtattctcag agttgacgaa tattagtaac gagtctcagt taactgacgt   5400
attggatgat gcactaacga gaaaattaga aggattggtc ttaaaagata ttaatggagt   5460
atacgaaccg ggaaagagaa gatggttaaa aataaagcga gactatttga acgagggttc   5520
catggcagat tctgccgatt tagtagtact aggtgcttac tatggtaaag gagcaaaggg   5580
tggtatcatg gcagtctttc taatgggttg ttacgacgat aaatccggta aatggaagac   5640
ggttaccaag tgttcaggac acgatgataa tacgttaagg gagttgcaag accaattaaa   5700
gatgattaaa attaacaagg atcccaaaaa aattccagag tggttggtag ttaataaaat   5760
ctatattccc gattttgtag tagaggatcc aaaacaatct cagatatggg aaatttcagg   5820
agcagagttt acatcttcca agtcacatac agcgaatgga atatcgatta gatttcctag   5880
atttactagg ataagagagg ataaaacgtg gaaagaatct actcatctaa acgatttagt   5940
aaacttgact aaatcttaat agttacatac aaactgaaaa ttaaaataac accatttagt   6000
tggtggtcgc catggatggt gttattgtat actgtctaaa cgcgttagta aaacatggcg   6060
aggaaataaa tcatataaaa aatgatttca tgattaaacc atgttgtgaa aaagttaaga   6120
acgttcacat cgacggacaa tctaaaaaca atacagtgat tgcagatttg ccatatctgg   6180
ataatgctgt atcggatgta tgcaaatcga tatatatata gtatcaagaa tatccagatt   6240
tgctaatttg ataaagatag atgacgatga caagactcct actggtgtat ataattattt   6300
taaacctaaa gatgccattc ctgttattat atccatagga aaggatagag atgtttgtga   6360
```

```
actattaatc tcatctgata aagcgtgtgc gtgtatagag ttaaattcat ataaagtagc   6420
cattcttccc atggatgttt cctttttac caaaggaaat gcatcattga ttattctcct   6480
gtttgatttc tctatcgatg cggcacctct cttaagaagt gtaaccgata ataatgttat   6540
tatatctaga caccagcgtc tacatgacga gcttccgagt tccaattggt tcaagtttta   6600
cataagtata aagtccgact attgttctat attatatatg gttgttgatg gatctgtgat   6660
gcatgcgata gctgataata gaacttacgc aaatattagc aaaaatatat tagacaatac   6720
tacaattaac gatgagtgta gatgctgtta ttttgaacca cagattagga ttcttgatag   6780
agatgagatg ctcaatggat catcgtgtga tatgaacaga cattgtatta tgatgaattt   6840
acctgatgta ggcaaatttg gatctagtat gttggggaaa tatgaacctg acatgattaa   6900
gattgctctt ttggtggctg gtaatttaat aagaaatcga gactacattc ccgggagacg   6960
aggatatagc tactacgttt acggtatagc ctctagataa ttttttaag cacgaaataa   7020
aaaacataat tttaaaccaa tctatttcat actattttgt gtgatcacca tggacataaa   7080
gatagatatt agtattttg gtgataaatt tacggtgact actaggaggg aaaatgaaga   7140
aaaaaaaaaa tatctacctc tccaaaaaga aaaaactact gatgttatca aacctgatta   7200
tcttgagtac gatgacttgt tagatagaga tgagatgttt actattctag aggaatattt   7260
tatgtacaga ggtctattag gcctcagaat aaaatatgga cgactcttta acgaaattaa   7320
aaaattcgac aatgatgcgg aagaacaatt cggtactata gaagaactca agcagaaact   7380
tagattaaat tctgaagagg gagcagataa ctttatagat tatataaagg tacaaaaaca   7440
ggatatcgtc aaacttactg tatacgattg catatctatg ataggattgt gtgcatgcgt   7500
ggtagatgtt tggagaaatg agaaactgtt ttctagatgg aaatattgtt tacgagcgat   7560
taaactgttt attaatgatc acatgcttga taagataaaa tctatactgc agaatagact   7620
agtgtatgtg gaaatgtcat agaaagttaa aagttaatga gagcaaaaat atataaggtt   7680
gtattccata tttgttattt tttctgtaat agttaaaaaa tacattcgat ggtctatcta   7740
tcagattatt atgtgttata aggtactttt tctcataata aactagagta tgagtaagat   7800
agtgtttttc aaaacatata aatctaaaat tgatggatga gatatacagc tattaatttc   7860
gaaaatatat tttaatctga taactttaaa catggatttt tgatggtggt ttaaagttta   7920
aaaaaaagat tttgttattg tagtatatga taatatcaaa aagatggata taaagaattt   7980
gctgactgta tgtactattt tttacattac tacattggct acggcagata tacctacttc   8040
gtcactgcca cacgctccgg taaacggggc atgtgacgag ggagaatatc ttgataagag   8100
gcataatcaa tgttgtaatc agtgtccacc tggagaattt gccaaggtca gatgtagtgg   8160
tagtgataac acaaaatgtg aacgctgccc acctcataca tataccgcaa tccccaatta   8220
ctctaatgga tgtcatcaat gtagaaaatg cccaacagga tcatttgata aggtaaagtg   8280
taccggaaca cagaacagta aatgttcgtg tcttcctggt tggtattgcg ctactgattc   8340
ttcacagact gaagattgtt gaaattgtgt accaaaaagg agatgtccat gcggatactt   8400
tggtggaata gatgaacaag gaaatcctat ttgtaaatcg tgctgtattg gtgaatattg   8460
caactaccta cgtaattata gacttgatcc attttctcca tgcaaactat ctaaatgtaa   8520
ttaattatga ttttgatgat aatgttacca tacattatat cgctacttgg ttagtgtatt   8580
attcagtatg aagacctatt aataattact tatcttttga cgatcttgtt ataattataa   8640
tataaaaact tatggcatag taacttataa ttgctaacac gataaattcg taataatctg   8700
```

ttttgttcaa atttttataa ggaatctaca ggcataaaaa taaaaatata atttataata 8760
tactcttaca acgccatcat gaatagcagc agtaaattaa ttgctgttat taatggattt 8820
agaaatagtg gacgattttg tgatattaat atagttatta atgatgaaag gataaacgct 8880
cataaactca tcctatctgg agcctccgaa tatttttcca ttctgttttc caataatttt 8940
atcgattcta atgaatacga agttaatcta agtcatttag attatcaaag cgtaaacgat 9000
ttgatcgatt atatttatgg gataccttg agcctaacta acgataacgt gaaatatatt 9060
ctttcaaccg ctgatttttt acaaattgga tctgctatta cggagtgtga aaattacata 9120
cttaaaaatc tttgttctaa aaactgtatc gatttctaca tatacgctga taaatataat 9180
aacaagaaaa tagaatcagc gtcgtttaac acaatattac aaaatatttt gagactcatc 9240
aacgatgaaa actttaaata cttaacagag gaatcaatga taaaaatttt aagcgatgat 9300
atgttaaata taaaaaatga ggatttcgcc ccactaattc tcattaaatg gttagagagt 9360
actcaacaat catgcaccgt cgagttactt aaatgcctca gaatatcatt gctttcccca 9420
caagttataa aatcacttta tagtcatcaa ctggttagtt caatctacga atgtataaca 9480
ttcttaaaca atatagcatt cttggatgaa tcatttccta gataccatag catcgagttg 9540
atatctatcg gtataagtaa ttcgcgtgat aaaatttcca taaactgcta caatcataaa 9600
aaaaatacat gggaaatgat atcttcacgt agatataggt gtagtttcgc agtggccgtc 9660
ctggataata ttatctatat gatgggtgga tatgatcagt ccccgtatag aagttcaaag 9720
gttatagcgt acaatacatg tacaaattct tggatatatg atataccaga gctaaaatat 9780
cctcgttcta attgtggggg actggctgat gacgaataca tttattgtat aggcggcata 9840
cgcgatcagg attcatcgtt gacatctagt attgatagat ggaagccatc aaaaccatat 9900
tggcagaagt atgctaaaat gcgcgaacca aaatgtgata tgggggttgc gatgttaaac 9960
ggattaatat atgtcatggg tggaatcgtt aaaggtgaca cgtgtaccga cgcactagag 10020
agtttatcag aagatggatg gatgaagcat caacgtcttc caataaaaat gtccaatatg 10080
tcgacgattg ttcatgatgg caagatttat atatctggag gttacaacaa tagtagtgta 10140
gttaatgtaa tatcgaatct agtccttagc tataattcga tatatgatga atggaccaaa 10200
ttatcatcat taaatattcc tagaattaat cccgctctat ggtcagcgca taataaatta 10260
tatgtaggag gaggaatatc tgatgatgtt caaactaata catctgaaac atacgataaa 10320
gaaaaagatt gttggacatt ggataatggt cacgtgttac cacgcaatta tataatgtat 10380
aaatgcgaac cgattaaaca taaatatcca ttggaaaaaa cacagtacac gaatgatttt 10440
ctaaagtatt tggaaagttt tataggtagt tgatagaaca aaatacataa ttttgtaaaa 10500
ataaatcact ttttatacta atatgacacg attaccaata cttttgttac taatatcatt 10560
agtatacgct acaccttttc ctcagacatc taaaaaaata ggtgatgatg caactctatc 10620
atgtaatcga aataatacaa atgactacgt tgttatgagt gcttggtata aggagcccaa 10680
ttctattatt cttttagctg ctaaaagcga cgtcttgtat tttgataatt ataccaagga 10740
taaaatatct tacgactctc catacgatga tctagttaca actatcacaa ttaaatcatt 10800
gactgctaga gatgccggta cttatgtatg tgcattcttt atgacatcaa ctacaaatga 10860
cactgataaa gtagattatg aagaatactc cacagagttg attgtaaata cagatagtga 10920
atcgactata gacataatac tatctggatc tacacattca ccggaaacta gttctgagaa 10980
acctgattat atagataatt ctaattgctc gtcggtattc gaaatcgcga ctccggaacc 11040
aattactgat aatgtagaag atcatacaga caccgtcaca tacactagtg atagcattaa 11100
tacagtaagt gcaacatctg gagaatccac aacagacgag actccggaac caattactga 11160
taaagaagat catacagtta cagacactgt ctcatacact acagtaagta catcatctgg 11220
aattgtcact actaaatcaa ccaccgatga tacgtacaat gataatgata cagtaccacc 11280
aactactgta ggcggtagta caacctctat tagcaattat aaaaccaagg actttgtaga 11340
aatatttggt attaccgcat taattatatt gtcggccgtg gcaatattct gtattacgta 11400
ttatatatgt aataaacgtt cacgtaaata caaaacagag aacaaagtct agatttttga 11460
cttacataaa tgtctgggat agtaaaatct atcatattga gcggaccatc tggttcagga 11520
aagacagcca tagccaaaag actatgggaa tatatttgga tttgtggtgt cccataccac 11580
tagatttcct cgtcctatgg aacgagaagg tgtcgattac cattacgtta acagagaggc 11640
catctggaag ggaatagccg ccggaaactt tctagaacat actgagtttt taggaaatat 11700
ttacggaact tctaaaacag ctgtgaatac agcggctatt aataatcgta tttgtgtgat 11760
ggatctaaac atcgatggcg ttagaagtct taaaaatacg tacctaatgc cttactcggt 11820
gtatataaga cctacctctc ttaaaatggt tgaaaccaag cttcgttgta gaaacactga 11880
agctaacgat gagattcatc gtcgcgtgat attggcaaaa acggatatgg atgaggccaa 11940
cgaagcaggt ctattcgaca ctattattat tgaagatgat gtgaatttag catatagtaa 12000
gttaattcag atactacagg accgtattag aatgtatttt aacactaatt aaagacttaa 12060
gacttaaaac ttgataatta ataatataac tcgtttttat atgtgtctat ttcaacgtct 12120
aatgtattag ttaaatatta aaacttacca cgtaaaactt aaaatttaaa atggtatttc 12180
attgacagat agatcacaca ttatgaactt tcaaggactt gtgttaactg acaattgcaa 12240
aaatcaatgg gtcgttggac cattaatagg aaaaggtgga tttggtagta tttatactac 12300
taatgacaat aattatgtag taaaaataga gcccaaagct aacggatcat tatttaccga 12360
acaggcattt tatactagag tacttaaacc atccgttatc gaagaatgga aaaaatctca 12420
caatataaag cacgtaggtc ttatcacgtg caaggcattt ggtctataca aatccattaa 12480
tgtggaatat cgattcttgg taattaatag attaggtgca gatctagatg cggtgatcag 12540
agccaataat aatagattac caaaaaggtc ggtgatgttg atcggaatcg aaatcttaaa 12600
taccatacaa tttatgcacg agcaaggata ttctcacgga gatattaaag cgagtaatat 12660
agtcttagat caaatagata agaataaatt atatctagtg gattacggat tggtttctaa 12720
attcatgtct aatggcgaac atgttccatt tataagaaat ccaaataaaa tggataacgg 12780
tactctagaa tttacaccta tagattcgca taaaggatac gttgtatcta gacgtggaga 12840
tctagaaaca cttggatatt gtatgattag atggttggga ggtatcttgc catggactaa 12900
gatatctgaa acaaagaatt gtgcattagt aagtgccaca aaacagaaat atgttaacaa 12960
tactgcgact ttgttaatga ccagtttgca atatgcacct agagaattgc tgcaatatat 13020
taccatggta aactctttga catattttga ggaacccaat tacgacgagt ttcggcacat 13080
attaatgcag ggtgtatatt attaagtgtg gtgtttggtc gatgtaaaat ttttgtcgat 13140
aaaaattaaa aaataactta atttattatt gatctcgtgt gtacaaccga aatcatggcg 13200
atgttttacg cacacgctct cggtgggtac gacgagaatc ttcatgcctt tcctggaata 13260
tcatcgactg ttgccaatga tgtcaggaaa tattctgttg tgtcagttta taataacaag 13320
tatgacattg taaaagacaa atatatgtgg tgttacagtc aggtgaacaa gagatatatt 13380
ggagcactgc tgcctatgtt tgagtgcaat gaatatctac aaattggaga tccgatccat 13440
gatcaagaag gaaatcaaat ctctatcatc acatatcgcc acaaaaacta ctatgctcta 13500
agcggaatcg ggtacgagag tctagacttg tgtttggaag gagtagggat tcatcatcac 13560
gtacttgaag caggaaacgc tgtatatgga aaagttcaac atgattattc tactatcaaa 13620
gagaaggcca aagaaatgag tacacttagt ccaggaccta taattgatta ccacgtctgg 13680
ataggagatt gtatctgtca agttactgct gtggacgtac atggaaagga aattatgaaa 13740
atgagattca aaaagggtgc ggtgcttccg atcccaaatc tggtaaaagt taaacttggg 13800
gagaatgata cagaaaatct ttcttctact atatcggcgg caccatcgag gtaaccacct 13860
ctctggaaga cagcgtgaat aatgtactca tgaaacgttt ggaaactata cgccatatgt 13920
ggtctgttgt atatgatcat tttaatattg tgaatggtaa agaatgctgt tatgtgcata 13980
cgcatttgtc taatcaaaat cttataccga gtactgtaaa aacaaatttg tacatgaaga 14040
ctatgggatc atgcattcaa atggattcca tggaagctct agagtatctt agcgaactga 14100
aggaatcagg tggatggagt cccagaccag aaatgcagga atttgaatat ccagatggag 14160
tggaagacac tgaatcaatt gagagattgg cagaggagtt cttcaataga tcagaacttc 14220
aggctggtaa atcagttaaa tttggtaatt ctattaattg ttaaacatat acatctgttt 14280
cagctaagca actaagaaca cgtatacggc agcagcttcc ttctatactc tcatctttta 14340
ccaagggtgg atatttgttc attggagttg ataataatac acacaaagta attggattca 14400
cggtgggtta cgactacctc agactggtag agaatgatat agaaaagcat atcaaaagac 14460
tttgtgttgt gtatttctgt gagaagaaag aggacatcaa gtacacgtgt cgattcatca 14520
aggtatataa acctggggat gagactacct cgacatacgt gtgcgctatc aaagtggaaa 14580
gatgctgttg tgctgtgttt gcagattggc cagaatcatg gtatatggat actaatggta 14640
tcaataagta ttctccagat gaatgggtgt cacatataaa attttaatta atgtaataga 14700
gaacaaataa taaggttgta atatcatata gacaataact aacaattaat tagtaactgt 14760
tatctctttt ttaactaacc aactaactat atacctatta atacatcgta attatagttc 14820
ttaacatcta ttaatcatta attcgcttct ttaatttttt ataaactaac attgttaatt 14880
gaaaagggat aacatgttac agaatataaa ttatatatgg attttttaa aaaggaaata 14940
cttgactgga gtatatattt atctcttcat tatatagcac gcgtgttttc caatttttcc 15000
acatcccata taatacagga ttataatctc gttcgaacat acgagaaagt ggataaaaca 15060
atagttgatt ttttatctag gttgccaaat ttattccata ttttagaata tggggaaaat 15120
attctacata tttattctat ggatgatgct aatacgaata ttataatttt ttttctagat 15180
agagtattaa atattaataa gaacgggtca tttatacaca atctcgggtt atcatcatcc 15240
attaatataa aagaatatgt atatcaatta gttaataatg atcatccaga taataggata 15300
agactaatgc ttgaaaatgg acgtagaaca agacattttt tgtcctatat atcagataca 15360
gttaatatct atatatgtat tttaataaat catggatttt atatagatgc cgaagacagt 15420
tacggttgta cattattaca tagatgtata tatcactata agaaatcaga atcagaatca 15480
tacaatgaat taattaagat attgttaaat aatggatccg atgtagataa aaaagatacg 15540
tacggaaaca cacctttat cctattatgt aaacacgata tcaacaacgt ggaattgttt 15600
gagatatgtt tagagaatgc taatatagac tctgtagact ttaatagata tacacctctt 15660
cattatgtct catgtcgtaa taaatatgat tttgtaaagt tattaatttc taaaggagca 15720
aatgttaatg cgcgtaataa attcggaact actccatttt attgtggaat tatacacggt 15780
atctcgctta taaaactata tttggaatca gacacagagt tagaaataga taatgaacat 15840
atagttcgtc atttaataat ttttgatgct gttgaatctt tagattatct attatccaga 15900
ggagttattg atattaacta tcgtactata tacaacgaaa catctattta cgacgctgtc 15960
agttataatg cgtataatac gttggtctat ctattaaaca gaaatggtga ttttgagacg 16020
attactacta gtggatgtac atgtatttcg gaagcagtcg caaacaacaa caaaataata 16080
atggaagtac tattgtctaa acgaccatct ttgaaaatta tgatacagtc tatgatagca 16140
attactaaac ataaacagca taatgcagat ttattgaaaa tgtgtataaa atatactgcg 16200
tgtatgaccg attatgatac tcttatagat gtacagtcgc tacagcaata taaatggtat 16260
attttaagat gtttcgatga aatagatatc atgaagagat gttatataaa aaataaaact 16320
gtattccaat tagtttttg tatcaaagac attaatactt taatgagata cggtaaacat 16380
ccttctttcg tgaaatgcac tagtctcgac gtatacggaa gtcgtgtacg taatatcata 16440
gcatctatta gatatcgtca gagattaatt agtctattat ccaagaagct ggatgcggga 16500
gataaatggt cgtgttttcc taacgaaata aaatataaaa tattggaaaa ctttaacgat 16560
aacgaactgt ccacatatct aaaaatctta taaacattat taaaatataa aatctaagta 16620
ggataaaatc acactacatc attgtttcct tttagtgctc gacagtgtat actattttta 16680
acactcataa ataaaaatga aaacgatttc cgttgttacg ttgttatgcg tactacctgc 16740
tgttgtttat tcaacatgta ctgtacccac tatgaataac gctaaattaa cgtctaccga 16800
aacatcgttt aataataacc agaaagttac atttacatgt gatcagggat atcattcttt 16860
ggatccaaat gctgtctgcg aaacagataa atggaaatac gaaaatccat gcaagaaaat 16920
gtgcacagtt tctgattatg tctctgaact atataataaa ccgctatacg aagtgaattc 16980
caccatgaca ctaagttgca acggcgaaac aaaatatttt cgttgcgaag aaaaaaatgg 17040
aaatacttct tggaatgata ctgttacgtg tcctaatgcg gaatgtcaac ctcttcaatt 17100
agaacacgga tcgtgtcaac cagttaaaga aaaatactca tttggggaat atataactat 17160
caactgtgat gttggatatg aggttattgg tgcttcgtac ataagttgta cagctaattc 17220
ttggaatgtt attccatcat gtcaacaaaa atgtgatata ccgtctctat ctaatggatt 17280
aatttccgga tctacatttt ctatcggtgg cgttatacat cttagttgta aaagtggttt 17340
tatactaacg ggatctccat catccacatg tatcgacggt aaatggaatc ccatactccc 17400
aacatgtgta cgatctaacg aaaaatttga tccagtggat gatggtcccg acgatgagac 17460
agatttgagc aaactctcga aagacgttgt acaatatgaa caagaaatag aatcgttaga 17520
agcaacttat catataatca tagtggcgtt aacaattatg ggcgtcatat ttttaatctc 17580
cgttatagta ttagtttgtt cctgtgacaa aaataatgac caatataagt tccataaatt 17640
gctaccgtaa atataaatcc gttaaaataa ttaataatta ataacgaaca agtatcaaaa 17700
gattaaagaa ttatagctag aatcaattga gatgtcttct tcagtggatg ttgatatcta 17760
cgatgccgtt agagcatttt tactcaggca ctattataac aagagattta ttgtgtatgg 17820
aagaagtaac gccatattac ataatatata caggctattt acaagatgcg ccgttatacc 17880
gttcgatgat atagtacgta ctatgccaaa tgaatcacgt gttaaacaat gggtgatgga 17940
tacacttaat ggtataatga tgaatgaacg cgatattact gtatgtgtgg gcaccggaat 18000
actattcatg gaaatgtttt tcgattacaa taaaaatagt atcaacaatc aactaatgta 18060
tgatataatt aatagcgtat ctataattct agctaatgag agatatagaa gcgcttttaa 18120
cgacgatggt atatacatcc gtagaaatat gattaacaag ttgtacggat acgcatctct 18180
aactactatt ggcacgatcg ctggaggtgt ttgttattat ctgttgatgc atctagttag 18240
tttgtataaa taattatttc aatatactag ttaaaatttt aagattttaa atgtataaaa 18300
aactaataac gtttttattt gtaataggtg cagtagcatc ctattcgaat aatgagtaca 18360
ctccgtttaa taaactgagt gtaaaactct atatagatgg agtagataat atagaaaatt 18420
catatactga tgataataat gaattggtgt taaattttaa agagtacaca atttctatta 18480
ttacagagtc atgcgacgtc ggatttgatt ccatagatat agatgttata aacgactata 18540
aaattattga tatgtatacc attgactcgt ctactattca acgcagaggt cacacgtgta 18600
gaatatctac caaattatca tgccattatg ataagtaccc ttatattcac aaatatgatg 18660
gtgatgagcg acaatattct attactgcag agggaaaatg ctataaagga ataaaatatg 18720
aaataagtat gatcaacgat gatactctat tgagaaaaca tactcttaaa attggatcta 18780
cttatatatt tgatcgtcat ggacatagta atacatatta ttcaaaatat gatttttaaa 18840
aatttaaaat atattatcac ttcagtgaca gtagtcaaat aacaaacaac accatgagat 18900
atattataat tctcgcagtt ttgttcatta atagtataca tgctaaaata actagttata 18960
agtttgaatc cgtcaatttt gattccaaaa ttgaatggac tggggatggt ctatacaata 19020
tatcccttaa aaattatggc atcaagacgt ggcaaacaat gtatacaaat gtaccagaag 19080
gaacatacga catatccgca tttccaaaga atgatttcgt atctttctgg gttaaatttg 19140
aacaaggcga ttataaagtg gaagagtatt gtacgggact atgcgtcgaa gtaaaaattg 19200
gaccaccgac tgtaacatta actgaatacg acgaccatat caatttgtac atcgagcatc 19260
cgtatgctac tagaggtagc aaaaagattc ctatttacaa acgcggtgac atgtgtgata 19320
tctacttgtt gtatacggct aacttcacat tcggagattc taaagaacca gtaccatatg 19380
atatcgatga ctacgattgc acgtctacag gttgcagcat agactttgtc acaacagaaa 19440
aagtgtgcgt gacagcacag ggagccacag aagggtttct cgaaaaaatt actccatgga 19500
gttcggaagt atgtctgaca cctaaaaaga gtgtatatac atgcgcaatt agatccaaag 19560
aagatgttcc caatttcaag gacaaaatgg ccagagttat caagagaaaa tttaataaac 19620
agtctcaatc ttatttaact aaatttctcg gtagcacatc aaatgatgtt accacttttc 19680
ttagcatgct taacttgact aaatattcat aactaatttt tattaatgat acaaaaacga 19740
aataaaactg catattatac actggttaac gcccttatag gctctaacca ttttcaagat 19800
gaggtccctg attatagtcc ttctgttccc ctctatcatc tactccatgt ctattagacg 19860
atgtgagaag actgaagagg aaacatgggg attgaaaata gggttgtgta taattgccaa 19920
agatttttat cccgaaagaa ctgattgcag tgttcatctc ccaactgcaa gtgaaggatt 19980
gataactgaa ggcaatggat tcagggatat acgaaacacc gataaattat aaaaaaagca 20040
atgtgtccgc tgtttccgtt aataatacta ttttcgtaac tggcggatta ttcataaata 20100
actctaatag cacgatcgtg gttaacaata tggaaaaact tgacatttat aaagacaaac 20160
aatggtcgat tatagaaatg cctatggcta gggtatatca cggcatcgac tcgacatttg 20220
gaatgttata ttttgccgga ggtctatccg ttaccgaaca atatggtaat ttagagaaaa 20280
acaacgagat atcttgttac aatcctagaa cgaataagtg gtttgatatt tcatatacta 20340
tttataagat atccatatca tcattgtgta aactaaataa cgtcttctat gtatttagta 20400
aggacattgg atatgtggaa aagtatgatg gtgcatggaa gttagtacat gatcgtctcc 20460
ccgctataaa ggcattatca acttctcctt attgattgaa aatgaaaata taaatagttt 20520
ttatgtatag cagtattacc ctatagtttt attgcttact actaacatgg atacagatgt 20580

```
tacaaatgta gaagatatca taaatgaaat agatagagag aaagaagaaa tactaaaaaa  20640
tgtagaaatt gaaaataata aaaacattaa caagaatcat cccaatgaat atattagaga  20700
agcactcgtt attaatacca gtagtaatag tgattccatt gataaagaag ttatagaatg  20760
tatctgtcac gatgtaggaa tatagatcat atctactaat ttttataatc gatacaaaac  20820
ataaaaaaca actcgttatt acatagcagg catggaatcc ttcaagtatt gttttgataa  20880
cgatggcaag aaatggatta tcggaaatac tttatattct ggtaattcaa tactatataa  20940
ggtcagaaaa aatttcacta gttcgttcta caattacgta atgaagatag atcacaaatc  21000
acacaagcca ttgttgtctg aaatacgatt ctatatatct gtattggatc ctttgactat  21060
cgacaactgg acacgggaac gtggtataaa gtatttggct attccagatc tgtatggaat  21120
tggagaaacc gatgattata tgttcttcgt tataaaaaat tcgggaagag tattcgcccc  21180
aaaggatact gaatcagtct tcgaagcatg tgtcactatg ataaacacgt tagagtttat  21240
acactctcga ggatttaccc atggaaaaat agaaccgagg aatatactga ttagaaataa  21300
acgtctttca ctaattgact attctagaac taacaaacta tacaagagtg gaaactcaca  21360
tatagattac aacgaggaca tgataacttc aggaaatatc aattatatgt gtgtagacaa  21420
tcatcttgga gcaacagttt caaaacgagg agatttagaa atgttgggat attgcatgat  21480
agaatggttc ggtggcaaac ttccatggaa aaacgaaagt agtataaaag taataaaaca  21540
aaaaaaagaa tataaaaaat ttatagctac tttctttgag gactgttttc ctgaaggaaa  21600
tgaacctctg gaattagtta gatatataga attagtatac acgttagatt attctcaaac  21660
tcctaattat gacagactac gtaaactgtt tatacaagat tgaaattata ttcttttttt  21720
atagagtgtg gtagtgttac ggatatctaa tattaatatt agactatctc tatcgcgcta  21780
cacgaccaat atcgattact atggatatct tcagggaaat cgcatcttct atgaaaggag  21840
agaatgtatt tatttctcca gcgtcaatct cgtcagtatt gacaatactg tattatggag  21900
ctaatggatc cactgctgaa cagctatcaa aatatgtaga aacggaggag aacacggata  21960
aggttagcgc tcagaatatc tcattcaaat ccatgaataa agtatatggg cgatattctg  22020
ccgtgtttaa agattccttt ttgagaaaaa ttggcgataa gtttcaaact gttgacttca  22080
ctgattgtcg cactatagat gcaatcaaca agtgtgtaga tatctttact gaggggaaaa  22140
tcaatccact attggatgaa ccattgtctc ctagcaatta gtgccgtata ctttaaagca  22200
aaatggttga cgccattcga aaaggaattt accagtgatt atccctttta cgtatctccg  22260
acggaaatgg tagatgtaag tatgatgtct atgtacggca aggcatttaa tcacgcatct  22320
gtaaaggaat cattcggcaa cttttcaatc atagaactgc catatgttgg agatactagt  22380
atgatggtca ttcttccaga caagattgat ggattagaat ccatagaaca aaatctaaca  22440
gatacaaatt ttaagaaatg gtgtgacttt atggatgcta tgtttataga tgttcacatt  22500
cccaagttta aggtaacagg ctcgtataat ctggtggata ctctagtaaa gtcaggactg  22560
acagaggtgt tcggttcaac tggagattat agcaatatgt gtaattcaga tgtgagtgtc  22620
gacgctatga tccacaaaac gtatatagat gtcaatgaag agtatacaga agcagctgca  22680
gcaacttgtg cactggtgtc agactgtgca tcaacaatta caaatgagtt ctgtgtagat  22740
catccgttca tctatgtgat taggcatgtt gatggcaaaa ttcttttcgt tggtagatat  22800
tgctctccaa caactaattg ttaaccattt tttttaaaaa aatagaaaaa acatgtggta  22860
ttagtgcagg tcgttattct tccaattgca attggtaaga tgacggccaa ctttagtacc  22920
```

cacgtctttt caccacagca ctgtggatgt gacagactga ccagtattga tgacgtcaaa 22980
caatgtttga ctgaatatat ttattggtcg tcctatgcat accgcaacag gcaatgcgct 23040
ggacagttgt attccacact cctctctttt agagatgatg cggaattagt gttcatcgac 23100
attcgcgagc tggtaaaaca tatgccgtgg gatgatgtca aagattgtgc agaaatcatc 23160
cgttgttata taccggatga gcaaaaaacc atcagagaga tttcggccat catcggactt 23220
tgtgcatatg ctgctactta ctggggaggt gaagaccatc ccactagtaa cagtctgaac 23280
gcattgtttg tgatgcttga gatgctaaat tacgtggatt ataacatcat attccggcgt 23340
atgaattgat gagttgtaca tcttgacatt ttcttctttc ttctcttctc cctttcccag 23400
aaacaaactt tttttaccca ctataaaata aaatgagtat actacctatt atatttcttt 23460
ctatattttt ttattcttca ttcgttcaga cttttaacgc gtctgaatgt atcgacaaag 23520
ggcaatattt tgcatcattc atggagttag aaaacgagcc agtaatctta ccatgtcctc 23580
aaataaatac gctatcatcc ggatataata tattagatat tttatgggaa aaacgaggag 23640
cggataatga tagaattata ccgatagata atggtagcaa tatgctaatt ctgaacccga 23700
cacaatcaga ctctggtatt tatatatgca ttaccacgaa cgaaacctac tgtgacatga 23760
tgtcgttaaa tttgacaatc gtgtctgtct cagaatcaaa tatagatctt atctcgtatc 23820
cacaaatagt aaatgagaga tctactggcg aaatggtatg tcccaatatt aatgcattta 23880
ttgctagtaa cgtaaacgca gatattatat ggagcggaca tcgacgcctt agaaataaga 23940
gacttaaaca acggacacct ggaattatta ccatagaaga tgttagaaaa aatgatgctg 24000
gttattatac atgtgtttta gaatatatat acggtggcaa aacatataac gtaaccagaa 24060
ttgtaaaatt agaggtacgg gataaaataa taccttctac tatgcaatta ccagatggca 24120
ttgtaacttc aataggtagt aatttgacta ttgcgtgtag agtatcgttg aggcctccca 24180
caacggacac cgacgtcttt tggataagta atggtatgta ttacgaagaa gatgatgggg 24240
acggaaacgg tagaataagt gtagcaaata aaatctatat gaccgataag agacgtgtta 24300
ttacatcccg gttaaacatt aatcctgtta aggaagaaga tgctacaacg tttacgtgta 24360
tggcgtttac tattcctagc atcagtaaaa cagttactgt tagtataacg tgaatgtatg 24420
ttgttacatt tccatgtcaa ttgagtttat aagaattttt atacattatc ttccaacaag 24480
caattgacga acgtattgct atgattaact cccacgatac tatgcatatt attaatcatt 24540
aacttgcaga ctatacctag agctattttg acatactcgt gttcttgtgt aattgcagta 24600
tctatattat taaagtacgt aaatctagct atagttttat tatttaattt tagataatat 24660
accgtctcct tatttttaaa aattgccaca tcctttatta aatcatgaat gggaatttct 24720
atgtcatcgt tagtatattg tgaacaacaa gagcagatat ctataggaaa gggtggaatg 24780
cgatacattg atctatgtag ttttaaaaca cacgcgaact ttgaagaatt tatataaatc 24840
attccatcga tacatccttc tatgttgaca tgtatatatc caggaattcg tttattaata 24900
tcgggaaatg tataaactaa aacattgccc ggaagcggtg cctctatctg cgttatatcc 24960
gttcttaact tacaaaatgt aaccaatacc tttgcatgac ttgttttgtt cggcaacgtt 25020
agtttaaact tgacgaatgg attaattaca atagcatgat ccgcgcatct attaagtttt 25080
tttactttaa cgcccttgta tgtttttaca gagactttat ctaaatttct agtgcttgta 25140
tgtgttataa atataacggg atatagaact gaatcaccta ccttagatac ccaattacat 25200
tttatcagat ccagataata aacaaatttt gtcgccctaa ctaattctat attgttatat 25260
attttacaat tggttatgat atcatgtaat aacttggagt ctaacgcgca tcgtcgtacg 25320

```
tttatacaat tgtgatttag tgtagtatat ctacacatgt atttttccgc actatagtat  25380
tctggactag tgataaaact atcgttatat ctgtcttcga tgaactcatc gagatattgc  25440
tctctgtcat attcatagac ctgcataaac tttctagaca tcttacaatc cgtgttattt  25500
taggatcata tttacatatt tacgggtata tcaaagatgt tagattagtt aatgggaatc  25560
gtctataata atgaatatta aacaattata tgaggacttt taccacaaag catcataaaa  25620
atgagtcgtc gtctgattta tgttttaaat atcaaccgcg aatcaactca taaaatacaa  25680
gagaatgaaa tatatacata ttttagtcat tgcaatatag accatacttc tacagaactt  25740
gattttgtag ttaaaaacta tgatctaaac agacgacaac ctgtaactgg gtatactgca  25800
ctacactgct atttgtataa taattacttt acaaacgatg tactgaagat attattaaat  25860
catggagtgg atgtaacgat gaaaaccagt agcggacgta tgcctgttta tatattgctt  25920
actagatgtt gtaatatttc acatgatgta gtgatagata tgatagacaa agataaaaac  25980
cacttatcgc atagagacta ttccaaccta ctactagagt atataaaatc tcgttacatg  26040
ttattgaagg aagaggatat cgatgagaac atagtatcaa ctttattaga taagggaatc  26100
gatcctaact ttaaacaaga cggatataca gcgttacatt attattattt gtgtctcgca  26160
cacgtttata aaccaggtga gtgtagaaaa ccgataacga taaaaaaggc caagcgaatt  26220
atttctttgt ttatacaaca tggagctaat ctaaacgcgt tagataattg tggtaataca  26280
ccattccatt tgtatcttag tattgaaatg tgtaataata ttcatatgac taaaatgctg  26340
ttgactttta atccgaattt caaaatatgt aataatcatg gattaacgcc tatactatgt  26400
tatataactt ccgactacat acaacacgat attcttgtta tgttaataca tcactatgaa  26460
acaaatgttg gagaaatgcc gatagatgag cgtcgtataa tcgtattcga gtttatcaaa  26520
acatattcta cacgtccggc agattcgata acttatttga tgaataggtt taaaaatata  26580
aatatttata cccgctatga aggaaagaca ttattacacg tagcatgtga atataataat  26640
acacaagtaa tagattatct tatacgtatc aacggagata taaatgcgtt aaccgacaat  26700
aacaaacacg ctatccaact cattatagat aacaaagaaa attccccgta taccatcgat  26760
tgtttattgt atatacttag atatattgta gataagaatg tgataagatc gttggtggat  26820
caacttccat ctctacctat cttcaatata aaatcatttg agaaattcat atcctactgt  26880
atacttttag atgacacatt ttacaatagg cacgttagga atcgcaattc taaaacgtat  26940
cgatacgcat tttcaaaata catgtcgttt gataaatacg atggtataat aactaaatgt  27000
cataaagaaa caatattgct caaactatcc actgttctag acactacact atatgcagtt  27060
ttaagatgcc ataattcgaa aaagttaaga agatacctca acgagttaaa aaaatataat  27120
aacgataagt cctttaaaat atattctaat attatgaatg agagatacct taatgtatat  27180
tataaagata tgtacgtgtc aaaggtatat gataaactat ttcctgtttt cacagataaa  27240
aattgtctac taacattact accttcagaa attatatacg aaatattata catgctgaca  27300
attaacgatc tttataatat atcgtatcca cctaccaaag tatagttgta tttttctcat  27360
gcgatgtgtg taaaaaaact gatattatat aaatatttta gtgccgtata ataaagatga  27420
cgatgaaaat gatggtacat atatatttcg tatcattatc attattgtta ttgctattcc  27480
acagttacgc catagacatc gaaaatgaaa tcacagaatt cttcaataaa atgagagata  27540
ctctaccagc taaagactct aaatggttga atccagcatg tatgttcgga ggcacaatga  27600
atgatatggc cactctagga gagccattca gcgcaaagtg tcctcctatt gaagacagtc  27660
```

```
ttttatcgca cagatataaa gactatgtgg ttaaatggga aaggctagaa aagaatagac  27720
ggcgacaggt ttctaataaa cgtgttaaac atggtgattt atggatagcc aactatacat  27780
ctaaattcag taaccgtagg tatttgtgta ccgtaactac aaagaatggt gactgtgttc  27840
agggtatagt tagatctcat attagaaaac ctccttcatg cattccaaaa acatatgaac  27900
taggtactca tgataagtat ggcatagact tatactgtgg aattctttac gcaaaacatt  27960
ataataatat aacttggtat aaagataata aggaaattaa tatcgacgat attaagtatt  28020
cacaaacggg aaagaaatta attattcata atccagagtt agaagatagc ggaagatacg  28080
actgttacgt tcattacgac gacgttagaa tcaagaatga tatcgtagta tcaagatgta  28140
aaatacttac ggttataccg tcacaagacc acaggtttaa actaaaaaga aattgcggat  28200
atgcgtcaaa ttaaaataaa tggtacggac atgcttacag tgatgtacat gttaaataaa  28260
cctacaaaga aacgatatgt taataatccg atatttacag attgggctaa taagcaatat  28320
aagttttata atcaaataat atataatgct aataagttaa tagaacaaag taagaaaata  28380
gacgacatga tagaggaggt atccattgac gataatcgtt tatcaacact accgttagaa  28440
attagacatt tgattttctc gtacgcgttc ctataaaaat agaaactata atcatataat  28500
agtgtaggtt ggtagtattg ctcttgtgac tagagacttt agttaaggta ctgtaaaaat  28560
agaaactata atcatataat agtgtaggtt ggtagtaggg tactcgtgat taattttatt  28620
gttaaacttg tccttaagtc ttattaatat gtcttctaaa gggggtagtg gcggcatgtg  28680
gagtgtcttt atccatggac atgatggtag taataaagga tctaaaactt atacatctgg  28740
tggcggtgga atgtggggag gaggatcgtc cagtggggtt aacggaggtg taaaatctgg  28800
aactggtaaa atttaaacat agggataaca gggtaat                           28837
```

```
<210> SEQ ID NO 9
<211> LENGTH: 17641
<212> TYPE: DNA
<213> ORGANISM: Vaccinia virus

<400> SEQUENCE: 9

tagggataac agggtaatat gacgatgaaa atgatggtac atatatattt cgtatcatta     60
tcattattgt tattgctatt ccacagttac gccatagaca tcgaaaatga aatcacagaa    120
ttcttcaata aaatgagaga tactctacca gctaaagact ctaaatggtt gaatccagca    180
tgtatgttcg gaggcacaat gaatgatatg gccactctag gagagccatt cagcgcaaag    240
tgtcctccta ttgaagacag tcttttatcg cacagatata aagactatgt ggttaaatgg    300
gaaaggctag aaaagaatag acggcgacag gtttctaata aacgtgttaa acatggtgat    360
ttatggatag ccaactatac atctaaattc agtaaccgta ggtatttgtg taccgtaact    420
acaaagaatg gtgactgtgt tcagggtata gttagatctc atattagaaa acctccttca    480
tgcattccaa aaacatatga actaggtact catgataagt atggcataga cttatactgt    540
ggaattcttt acgcaaaaca ttataataat ataacttggt ataaagataa taaggaaatt    600
aatatcgacg atattaagta ttcacaaacg ggaaagaaat taattattca taatccagag    660
ttagaagata gcggaagata cgactgttac gttcattacg acgacgttag aatcaagaat    720
gatatcgtag tatcaagatg taaaatactt acggttatac cgtcacaaga ccacaggttt    780
aaactaaaaa gaaattgcgg atatgcgtca aattaaaata aatggtacgg acatgcttac    840
agtgatgtac atgttaaata aacctacaaa gaaacgatat gttaataatc cgatatttac    900
agattgggct aataagcaat ataagtttta taatcaaata atatataatg ctaataagtt    960
```

```
aatagaacaa agtaagaaaa tagacgacat gatagaggag gtatccattg acgataatcg   1020
tttatcaaca ctaccgttag aaattagaca tttgattttc tcgtacgcgt tcctataaaa   1080
atagaaacta taatcatata atagtgtagg ttggtagtat tgctcttgtg actagagact   1140
ttagttaagg tactgtaaaa atagaaacta taatcatata atagtgtagg ttggtagtag   1200
ggtactcgtg attaatttta ttgttaaact tgtccttaag tcttattaat atgtcttcta   1260
aagggggtag tggcggcatg tggagtgtct ttatccatgg acatgatggt agtaataaag   1320
gatctaaaac ttatacatct ggtggcggtg gaatgtgggg aggaggatcg tccagtgggg   1380
ttaacggagg tgtaaaatct ggaactggta aaatttaaac actaaattat ttttattaat   1440
aattgtacaa gtttttgaca tgatatttaa tgacattagt tgtgtgggtg tatagagttc   1500
acagtagctc attcagtcaa aatgtttgac tatttggaaa atgaggaggt ggctctcgat   1560
gaacttaaac agatgttgag agacagagat cctaatgata ccaggaacca attcaagaat   1620
aatgctttac acgcatacct ttttaatgag cattgtaata atgtcgaggt cgtcaaacta   1680
ctactagaca gtggcactaa tccattacgc aaaaattgga gacagctacc ccattagaag   1740
aatacacaaa tagtagacat gttaaagtta aaggatatag cgatggctct actagaagcc   1800
actggattta gcaacataaa tgactttaat atattcagct atatgaaatc caaaaatgta   1860
gacgttgact tgataaaggt gttggtagaa catggatttg acttgagtgt taaatgtgaa   1920
aaccatcgtt cagttataga aaattatgta atgacaatga tcctgttcct aaaattattg   1980
atttgttcat agaaaatggc tgcagtgttc tttatgagga cgagtactga tacgcgtatg   2040
atgattatca actacgaaat tgcggtaccg tattgcatct gtattcaaag tcggatacga   2100
gagcatatgt gcgtccggaa gttgttaaat gtctaattaa tcacggaatc aagccgtctt   2160
ttatagataa aaactattgt acaggtcttc aatattatat taagtcatct catatagata   2220
tagacatcgt taaattgtta atgaaaggaa tagataacac tgcttattca tatatagacg   2280
atctaacatg ttgcactcga ggaattatgg ctgattatct aaatagtgat tatagataca   2340
ataaagatgt agatttggtc aaattgtttt tggagaatgg aaagcctcac ggaataaatgt   2400
gtagtattgt accactatgg agaaatgata aggaaaccat ctttttgata ttgaaaacaa   2460
tgaactcgga tgtcctccaa catatactaa ttgagtatat gacattcggc gatatccctc   2520
tagtggaata tggaactgtg gtaaataaag aggctataca cggatacttt agaaatatta   2580
atattgattc ttacacgatg aaatatctac taaaaaagga agggagatgc catcaattat   2640
ctcgatgatg gagagatccc gattggacac ctatgtaaat ccaactatga atgttataat   2700
ttttacactt atacatacaa aaagggtctt tgtgacatgt cttatgcttg cccaattctt   2760
agtactataa acatttgcct accttatctt aaagacatta acatgattga caaacgagga   2820
gaaacacttc ttcacaaggc tgttagatat aataaacaat ctctagtatc tttactgcta   2880
gaatccggtt cagatgtcaa cattagatca aataacggat atacatgtat agccattgcc   2940
atcaacgaat ctaaaaacat tgaactgctg aaaatgctat tatgtcataa acctacatta   3000
gattatgtga ttgattcatt gagagaaata tctaacatcg tagataacta ctatgctata   3060
aaacaatgta ttaaatatgc catgattata gatgactgta catcgtctaa gattccagag   3120
tccataagtc aacgctataa tgattatata gatctttgca attaagaatt gaatgagatg   3180
aaaaaaataa tggtaggtgg taatactatg ttctcattaa tatttactga tcatggagct   3240
aaaattattc atagatatgc caataatcca gaattacgtg agtattatga gttaaaacaa   3300
```

aataaaatat atgtggaagc atatgatatt atttccaacg caatagtgaa acatgataga 3360
atacataaaa ccatagaatc agttgatgat aatacctaca tttctaatct tccgtatacc 3420
atcaaataca aaatattcga gcaacaataa gtatttttta tacctttaaa attgataaat 3480
aaattttttc tagtgatatt ttggcaagat gagaatccta tttctcatcg ccttcatgta 3540
tgggtgtgtt cacccatatg ttaatgccga cgaaatcaaa tgtcctaacc taaacatcgt 3600
aacatcttct ggagaatttc gttgcactgg atgtgtgaaa tttatgccta attttagcta 3660
catgtattgg ttggcaaagg atatgagatc ggacgaggat accaagttta tagaacatct 3720
gggtgatggc atcaaagaag atgaaaccgt tcgtaccata gatggtagaa tcgtcactct 3780
acagaaagtc cttcatgtaa ccgatactaa taaatttgct cattataggt tcacttgtgt 3840
cctcactacg atagatggca tttataaaaa gaatgtttgc tgaagtagtt gtgtgctact 3900
atttttattt atgatataat ctaaatgcaa ttgtcttgag aatccatcca atacggcaga 3960
ttatattaga aacaacgaat tgaattgaat ttaatctttc atacgagaaa aataacgaca 4020
tacgtcgtca acaaattaaa ctttttattt attagttaac tagcttatag aacttgctca 4080
ttgttatgtt tctaaaacgg gtacgacata taggacaatt atccgacgca ccggtttctc 4140
ttcgtgtttt atgccatata ttgatacatg ttatgcaaaa tatatgatta cacgaatcca 4200
ataaaccaaa gtatctatcg ttttgagtaa acaacttcat agcaaattcc acattctttt 4260
tctttactta ctctatacac gtcctcgtat ttatccagta ttttgatgat atccaactca 4320
gaaatggttg ttgtattatt gggtgtatag gtattattag ctatgtacca atttaccaac 4380
cttcttaata ttgattgata atcacatcgg ttatccaatt aataactaaa ttgtagtgta 4440
tatatagacc atatatgttt ctattttttt gacagttacg tatagtttca gtaagttttg 4500
attgttgtat tcctgtatct ctagataagt tagtcatata gtcccttccg gcgatacgtt 4560
ttttccaagc ccgaaattga ttagccaaat gtggatttat ttttgtgata ttgatataat 4620
atttcggata atgcatactg ttagtcttat atcatttggt tcatctatgt attgtaatat 4680
tgttacatga tctatagatg atgtattgat tttggcagga tcgaattcca tatccgcgac 4740
taaacagtga aaaaaatgta aatacttttt aaattttaaa ttagtaaaac ttttttttat 4800
tttttatgat tccaaaaata ctgaatacaa agtcctaaat tataaatatg gagatcatac 4860
taccacaact tattattatg tatacaaggc cggtgtaata gatagatata tataattcta 4920
ttacaccggc agacaattac cgatcggtat ttgtcgttac caacataccg tataatatgt 4980
aatatacaat tccataaccc attgacagtt gttatacatc aaaattgcaa ttcttttgat 5040
tacgatgtta taagaatgta gttaattgat gtatgatgtt aatgtgtcct ctttcctctt 5100
ataacatcgt aatcaaaaac ttttttataa tatataccta ataatgtgtc ttaatagttc 5160
tcgtgattcg tcaaacaatc attcttataa aatataataa atcaacgtaa aaacacataa 5220
aaataagcgt aactaataag acaatggata tttacgacga taaaggtcta cagactatta 5280
aactgtttaa taatgaattt gattgtataa ggaatgacat cagagaatta tttaaacatg 5340
taactgattc cgatagtata caacttccga tggaagacaa ttctgatatt atagaaaata 5400
tcagaaaaat actatataga cgattaaaaa atgtagaatg tgttgacatc gataacacaa 5460
taacttttat gaaatacgat ccaaatgatg ataataagcg tacgtgttct aattgggtac 5520
ccttaactaa taactatatg gaatattgtc tagtaatata tttggaaaca ccgatatgtg 5580
gaggcaaaat aaaattatac caccctacag gaaatataaa gtcggataag gatattatgt 5640
ttgcaaagac tctagacttt aaatcaaaga aagtgttaac tggacgtaag acaattgccg 5700

```
ttctagacat atccgtttca tataatagat caataactac tattcactac aacgacgacg   5760
ttgatataga tatacatact gataaaaatg gaaaagagtt atgttattgt tatataacaa   5820
tagatgatca ttacttggtt gatgtggaaa ctataggagt tatagtcaat agatctggaa   5880
aatgtctgtt agtaaataac catctaggta taggtatcgt taaagataaa cgtataagcg   5940
atagttttgg agatgtatgt atggatacaa tatttgactt ttctgaagca cgagagttat   6000
tttcattaac taatgatgat aacagaaata tagcatggga cactgataaa ctagacgatg   6060
atacagatat atggactccc gtcacagaag atgattacaa atttctttct agactagtat   6120
tgtatgcaaa atctcaatcg gatactgtat tcgactatta tgttcttact ggtgatacgg   6180
aaccacccac tgtattcatt ttcaaggtaa ctagatttta ctttaatatg ctgaaataaa   6240
aaatttttgt ataatatcta gaggtagagg tattgtttag ataaatacaa ataacataga   6300
tacatcgcat atttagcatt tttataaata tacataagac atacacttta tacatttttg   6360
taaaaatact cataaaaaaa atttataaaa attatggcac aaccatatct tgtagaggta   6420
gtttagttcg tcgagtgaac ctataaacag ataatagaca acacataata ataatgccta   6480
ctaatacaag cataataccg ggagatggga tatatgacgt tgtagtgttt ggtttttctg   6540
aacgttgata gtctactaat actacatgct gacatctaat gcctgtataa ccatgagagc   6600
atctacaata cataccgtcg atatctctag cgtggataca gtcaccgtgt aaacaatatc   6660
catctccctc tggaccgcat aatctgatag ctggaatatc tgttgtagcg tttgtaattt   6720
ctggcaatgt cgtttcgata gcgttaccac tatcggcgaa tgatctgatt atcatagcag   6780
cgaacaacaa catcagatat ttcatcgaca tttttgatgg attctgtgtt tatgctgttt   6840
ctcagtgtgt gtttatgaca agattgggaa ttttatatta ttaattcagt aatataaact   6900
aataatatat tgttaattgt gtaaataata taaaaataac aatacaatat tgaatgtgtt   6960
gctgttaaaa atgtatgtgt taatataata gaataaaata aatgagtatg atcattttag   7020
ataacgattg attttatcat tacccttcat tcttatattc tttgcttacg gaacctatat   7080
ttagaaacat ctactaacga ttttttatgc ttgcattatt aatggtatgt aataccaatt   7140
tgttaagtat gaatacgggg tacaaacata aactgaaatt taacattatt tatttatgat   7200
atatatcgtt atcgttattg tttggtctat accatggata tctttaaaga actaatcgta   7260
aaacaccctg atgaaaatgt tttgatttct ccagtttcca ttttatctac tttatctatt   7320
ctaaatcatg gagcagctgg ttctacagct gaacaactat caaaatatat agagaatatg   7380
aatgagaata cacccgatga taagaaggat gacaataatg acatggacgt agatattccg   7440
tattgtgcga cactagctac cgcaaataaa atatacggta gcgatagtat cgagttccat   7500
gcctccttcc tacaaaaaat aaaagacgat tttcaaactg taaactttaa taatgctaac   7560
caaacaaagg aactaatcaa cgaatgggtt aagacaatga caaatggtaa aattaattcc   7620
ttattgacta gtccgctatc cattaatact cgtatgacag ttgttagcgc cgtccatttt   7680
aaagcaatgt ggaaatatcc attttctaaa catcttacat atacagacaa gttttatatt   7740
tctaagaata tagttaccag cgttgatatg atggtgggta ccgagaataa cttgcaatat   7800
gtacatatta atgaattatt cggaggattc tctattatcg atattccata cgagggaaac   7860
tctagtatgg tgattatact accggacgac atagaaggta tatataacat agaaaaaaat   7920
ataacagatg aaaaatttaa aaaatggtgt ggtatgttat ctactaaaag tatagacttg   7980
tatatgccaa agtttaaagt ggaaatgaca gaaccgtata atctggtacc tattctagaa   8040
```

aatttaggac ttactaatat attcggatat tatgcagatt ttagcaagat gtgtaatgaa 8100
actatcactg tagaaaaatt tctacatacg acgtttatag atgttaatga ggagtataca 8160
gaagcatcgg ccgttacagg agtatttatg actaactttt cgatggtata tcgtacgaag 8220
gtctacataa accatccatt catgtacatg attaaagaca acacaggacg tatacttttt 8280
atagggaaat actgctatcc gcaataaata taaacaaata gacttttatc acgtttatct 8340
atgtctaaat attacaaata gtataaacta aagctgataa tacttaaaaa aataataata 8400
tcatttacaa ttaatagtat aaactaaaaa ttaaacaaat cgttattata agtaatatca 8460
aaatgatgat atacggatta atagcgtgtc ttatattcgt gacttcatcc atcgctagtc 8520
cactttatat tcccgttatt ccacccatta cggaagataa atcgttcaat agtgtagagg 8580
tattagtttc cttgtttaga gatgaccaaa aagactatac ggtaacttct cagttcaata 8640
actacactat cgataccaaa gactggacta tcggcgtact atccacacct gatggtttgg 8700
atataccatt gactaatata acttattggt cacggtttac tataggtcgt gcattgttca 8760
aatcagagtc tgaggatatt ttccaaaaga aaatgagtat tctaggtgtt tctatagaat 8820
gtaagaagtc gtcgacatta cttacttttt tgaccgtgcg taaaatgact cgagtattta 8880
ataaatttcc agatatggct tattatcgag gagactgttt aaaagccgtt tatgtaacaa 8940
tgacttataa aaatactaaa actggagaga ctgattacac gtacctctct aatggggggt 9000
tgcctgcata ctatcgtaat ggggtcgatg gttgattatt gattagtata ttccttattc 9060
acacaaaaag aacattttta taaacatgaa accactgtct aaatgtaatt atgatcttga 9120
tttatagatg aagatcagcc tttagaggat tttaaccagt atgtttaata tgaaaaaaat 9180
aaacataaca tattttgaga ttaagcgcta ttgtgcttaa ttattttgct ctataaactg 9240
aatatatagc cacaattatt gacgggcttg tttatgaccg gcaatcatga atttacagaa 9300
attatctctg gctatatatc ttactgcgac atgttcgtgg tgttatgaaa catgcataag 9360
aaaaactgcg ttgtatcatg acattcaatt ggagcatgta gaagacaata aagatagtgt 9420
agcgtcgcta ccgtacaagt agtcaatcaa agagaacgta gtagattgtt ggctacattt 9480
aattggacag atatagctga gggtgttaga aatgagttca ttaaaatatg tgatatcaac 9540
ggaacatatt tatataatta tactattgct gttagtataa ttattgattc cacggaagaa 9600
ctaccaacag ttactccaat tacaacaaca tatgaacctt ctacatataa ttatactatc 9660
gatgatagca ctgttattac tactgaagaa ctacaagtga ctcctcatat ggatctccat 9720
cgatgataca tgtattaaaa tactttccga ataagtcttt taaatattgt attaattatg 9780
aaaaactatg ctatgcgagt atgatgcaaa gatgtttaat gatacgatac tagattttat 9840
ctctagcgag agatgtcgtt agaatcattt atcataacta cgtttaataa taattcatca 9900
acgaatatcg ataacatgtg tcatttatac gttaaagtct gtccgtcttc tctattgttt 9960
agactgtttg tagaatgctg tgatataaac aaactagtag aaggtacgac tccgttacac 10020
tgttatctaa tgaatgaagg atttgaatca tctgttttaa aaaacctatt aaaggagtat 10080
gtcatgacag tgatggtcac attccattac acaaatattt aactcatgat gaagttgaga 10140
atgatatgct ttctgatagt atagatagct ttagctaata taaaaatata ttaatccact 10200
atatattcta gacttgattt aaaaccgata aactactacg tactgtataa gttgttaaga 10260
aaaggagcag accctaatta tgcagatgat agaggtaata cttttcttca ttacttctgc 10320
atctatatgt ccacttatga gaaaacgtca tttaataaga tgcatcgtga aaagaaattt 10380
attaaagagt tggtaaaata tgaaaccgaa agtaaataat ataggaaata cacctctaca 10440
taactacgta tctcaatatg atatcactct cattcctcat ccacaaccca ttaaaaaaat 10500
ggaaattaaa gccctctatt agcataaacg gctacaggtc tacctttaca atggcctttc 10560
cttgtgccca gttcagaccc tgtcattgcc acgctactaa ggactccctg aataccgtgg 10620
ccgacgtcag acattgtctg actgaataca tcctgtgggt ttctcataga tggacccata 10680
gagaaactgc agggcctctc tacaggcttc tcatctcttt cagaactgat gcaacggagc 10740
tctttggtgg tgagttgaag gattcacttc cgtgggacaa tatcgacaat tgcgtggaga 10800
tcattaaatg tttcatcaga aatgactcca tgaaaaccgc cgaagaactt cgtgcaatca 10860
ttggactttg tactcaatca gctatcgtct ctggaagagt cttcaacgat aagtatatcg 10920
acatactact tatgctgcga aagattctga acgagaacga ctatctcacc ctcttggatc 10980
atatccgcac tgctaaatac taaatctcct tcatgctctc tcactacact ttttatcatc 11040
ttatgaggaa tgattgcctt catcattttt cgtgaaatag gaataattag caccagaata 11100
gctatggatt gcacatgtat tctatgtcgt ctactggatg aagatgtgac gtacaaaaaa 11160
ataaaactag aaattgaaac gtgtcacaac ttatcaaaac atatagatag acgaggaaac 11220
aatgcgctac attgttacgt cttcaataaa tgcgatacag acattaagat tgttcgactg 11280
ttactctctc gcggagtcga gagactttgt agaaacaacg aaggattaac tccgctagga 11340
gtatacagta agcatagata cgtcaaatct caaattgtgc atctactgat atccagctat 11400
tcgaattcct ctaacgaact caagtcgaat ataaatgatt tcgatctgta ttcggataat 11460
atcgacttac gtctgctaaa atacctaatt gtggataaac ggatacgtcc gtccaagaat 11520
acgaattatg caatcaatgg tctcggattg gtggatatat acgtaacgac gcctaatccg 11580
agaccagaag tattgctatg gcttcttaaa tcagaatgtt acagcaccgg ttacgtattt 11640
cgtacctgta tgtacaacag tgatatgtgt aagaactctc ttcattacta tatatcgtct 11700
catagagaat ctcaatctct atccaaggat gtaattaaat gtttgatcaa taacaatgtt 11760
tccatccatg gcagagacga aggaggatct ttacccatcc aatactactg gtctttctca 11820
accatagata tagagattgt taaattatta ttaataaagg atgtggacac gtgtagagta 11880
tacgacgtca gccctatatt agaggcgtat tatctaaaca agcgatttag agtaacccca 11940
tataatgtag acatggaaat cgttaatctt cttattgaga gacgtcatac tcttgtcgac 12000
gtaatgcgta gtattacttc gtacgattcc agagaatata accactacat catcgataac 12060
attctaaaga gatttagaca acaggatgaa tccatcgtac aagccatgtt gataaactac 12120
ttacattacg gcgatatggt cgttcgatgc atgttagata acggacaaca actatcctct 12180
gcacgactac tttgttaata ataatctcgt cgatgtaaac gtcgtaaggt ttatcgtgga 12240
aaatatggac acgcggctgt aaatcacata tctaacaatg gccgtctatg tatgtacggt 12300
ctgatattat cgagatttaa taattgcggg tatcactgtt atgaaaccat actaatagat 12360
gtatttgata tactaagcaa gtacatggat aatatagata tgatcgataa tgagaataaa 12420
actctactat attacgcggt cgatgtcaat aatatacaat ttgcaaagcg gttattggaa 12480
tatggagcga gtgttacaac atcacgctcg ataatcaata cggccatcca gaaaagtagt 12540
tacagaagag aaaacaaaac gaagctagtt gatttattac ttagctacca tcccactcta 12600
gagactatga ttgacgcatt taatagagat atacgctatc tatatcctga accattattc 12660
gcctgtatca gatacgcctt aatcatagat gatgattttc cttctaaagt aaagtatgat 12720
atcgccggtc gtcataagga actaaagcgc tatagagtag acattaatag aatgaagaat 12780

```
gcctacatat caggcgtctc catgtttgat atattattta aacgaagcaa acgccacaga  12840
ttgagatacg caaagaatcc gacatcaaat ggtacaaaaa agaactaacg tccatcatta  12900
cagaaactgt aaagaacaat gagaggatcg actccatagt ggacaacatt aatacagacg  12960
ataacttgat ttcgaaatta cccatggaga tactttatta ctccattaaa taatttatca  13020
tggagcgata atgtcctgtt tcatttgttt ccatgacata ttacaaaatc gattccgtcc  13080
aagatgataa aaacatttac cggcatcata aacacggagt ttattttata tgtctcgcat  13140
aaacattact aaaaaaatat attgttcggt tttctttcac atctttaatt atgaaaaagt  13200
aaatcattat gagatggacg agattgtacg catcgttcgc gacagtatgt ggtacatacc  13260
taacgtattt atggacgacg gtaagaatga aggtcacgtt tctgtcaaca atgtttgtca  13320
tatgtatttt acgttctttg atgtggatac atcgtctcat ctgtttaagc tagttattaa  13380
acactgcgat ctgaataaac gaggtaactc tccattacat tgctatacga tgaatacacg  13440
atttaatcca tctgtattaa agatattgtt acaccacggc atgcgtaact ttgatagcaa  13500
ggatgaccac tatcaatcga taacaagatc tttgatatac taacggacac cattgatgac  13560
tttagtaaat catccgatct attgctgtgt tatcttagat ataaattcaa tgggagctta  13620
aactattacg ttctgtacaa aggatccgac cctaattgcg ccgacgagga tgaactcact  13680
tctcttcatt actactgtaa acacatatcc acgttctaca aaagcaatta ttacaagtca  13740
agtcacacta agatgcgagc cgagaagcga ttcatctacg cgataataga ttatggagca  13800
aacattaacg ccgttacaca cttaccttca acagtatacc aaacatagtc ctcgtgtggt  13860
gtatgctctt ttatctcgag gatacgtaat aatcttgatt gtacacccat catggaacga  13920
ttgtgcaaca ggtcatattc tcataatgtt actcaattgg cacgaacaaa aggaagaagg  13980
acaacatcta ctttatctat tcataaaaca taatcaagga tacactctca atatactacg  14040
gtatctacta gataggttcg acattcagaa agacgaatat tataataccg cctttcaaaa  14100
ttgtaacaac aatgttgcct catacatcgg atacgacatc aaccttccga ctaaagacgg  14160
tattcgactt ggtgtttgaa aacagaaaca tcatatacaa ggcggatgtt gtgaatgaca  14220
tcatccacca cagactgaaa gtacctatga ttaaatcgtt gttctacaag atgtcagaat  14280
tctctcccta cgacgattac tacgtaaaaa agatactagc ctactgccta ttaagggacg  14340
agtcattcgc ggaactacat agtaaattct gtttaaacga ggactataaa agtgtattta  14400
tgaaaaatat atcattcgat aagatagatt ccatcatcgt gacataagtc gccttaaaga  14460
gattcgaatc tccgacaccg acctgtatac ggtatcacag ctatcttaaa gccatacatt  14520
cagacagtca catttcattt cccatgtacg acgatctcat agaacagtgc catctatcga  14580
tggagcgtaa aagtaaactc gtcgacaaag cactcaataa attagagtct accatcgatg  14640
gccaatctag actatcgtat ttgcctccgg aaattatgcg caatatcatc taaacagtat  14700
gttgtacgga aagaaccatt acaaatatta tccatgatag aaagaaaata tctatatgat  14760
tggagaagta ggaaacagga acaagacaac gattactaca ttattaaatt atgaagtccg  14820
tattatactc gtatatattg tttctctcat gtataataat aaacggaaga gatatagcac  14880
cgcatgcacc atccgatgga aagtgtaaag acaacgaata caaacgccat aatttgtgtc  14940
cgggaacata cgcttccaga ttatgcgata gcaagactaa cacacaatgt acgccgtgtg  15000
gttcgggtac cttcacatct cgcaataatc atttacccgc ttgtctaagt tgtaacggaa  15060
gatgcgatcg tgtaacacta ctcacaatag aatctgtgaa tgctctcccg gatattattg  15120
tcttctcaaa ggatcatccg gatgcaaggc atgtgtttcc caaacaaaat gtggaatagg  15180
```

atacggagta tccggagacg tcatctgttc tccgtgtggt ctcggaacat attctcacac 15240
cgtctcttcc gcagataaat gcgaacccgt acccagaaat acgtttaact atatcgatgt 15300
ggaaattaac ctgtatccag ttaacgacac atcgtgtact cggacgacca ctaccggtct 15360
cagcgaatcc atctcaacgt cggaactaac tattactatg aatcataaag actgcgatcc 15420
cgtctttcgt gatggatact tctctgtcct taataaggta gcaacttcag gtttctttac 15480
aggagaaagg tgtgcactct gaatttcgag attaaatgca ataacaaaga ttcttcctcc 15540
aaacagttaa cgaaagcaaa gaatgatact atcatgccgc attcggagac tgtctatcta 15600
gcgtcgacat ctatatacta tatagtaata ccaatactca agactacgaa actgatacaa 15660
tctcttatca tgtgggtaat gttctcgatg tcgatagcca tatgcccggt agttgcgata 15720
tacataaact gatcactaat tccaaaccca cccgcttttt atagtaagtt tttcacccat 15780
aaatacaata attaatttct cgtaaaagta gaaaatatat tctaatttat tgcacggtaa 15840
ggaagtagaa tcataaagaa cagtaatcaa tcaatagcaa tcatgaaaca atatatcgtc 15900
ctggcatgca tgtgcctgcc agtcttcagc aatcctcctc ctcgtgtacg gaagaagaaa 15960
acaaacatca tatgggaatc gatgttatta tcaaagtcac aaagcaagac caaacaccga 16020
ccaatgataa gatttgccaa tccgtaacgg aaattacaga gtccgagtca gatccagatc 16080
ccgaggtgga atcagaagat gattccacat cagtcgagga tgtagatcct cctaccactt 16140
attactccat catcggtgga ggtctgagaa tgaactttgg attcaccaaa tgtcctcaga 16200
ttaaatccat ctcagaatcc gctgatggaa acacagtgaa tgctagattg tccagcgtgt 16260
ccccaggaca aggtaaggac tctcccgcga tcactcatga agaagctctt gctatgatca 16320
aagactgtga ggtgtctatc gacatcagat gtagcgaaga agagaaagac agcgacatca 16380
agacccatcc agtactcggg tctaacatct ctcataagaa agtgagttac gaagatatca 16440
tcggttcaac gatcgtcgat acaaaatgcg tcaagaatct agagtttagc gttcgtatcg 16500
gagacatgtg caaggaatca tctgaacttg aggtcaagga tggattcaag tatgtcgacg 16560
gatcggcatc tgaaggtgca accgatgata cttcactcat cgattcaaca aaactcaaag 16620
cgtgtgtctg aatcgataac tctattcatc tgaaattgga tgagtagggt taatcgaacg 16680
attcaggcac accacgaatt aaaaaagtgt accggacact atattccggt ttgcaaaaca 16740
aaaatgttct taactacatt cacaaaaagt tacctctcgc gacttcttct ttttctgtct 16800
caatagtgtg atacgattat gacactattc ctattcctat tcctatttcc tttcagggta 16860
tcacaaaaat attaaacctc tttctgatgg tctcataaaa aaagttttac aaaaatattt 16920
ttattctctt tctctctttg atggtctcat aaaaaaagtt ttacaaaaat atttttattc 16980
tctttctctc tttgatggtc tcataaaaaa agttttacaa aaatattttt attctctttc 17040
tctctttgat ggtctcataa aaaaagtttt acaaaaatat ttttattctc tttctctctt 17100
tgatggtctc ataaaaaaag ttttacaaaa atatttttat tctctttctc tctttgatgg 17160
tctcataaaa aaagttttac aaaaatattt ttattctctt tctctctttg atggtctcat 17220
aaaaaaagtt ttacaaaaat atttttattc tctttctctc tttgatggtc tcataaaaaa 17280
agttttacaa aaatattttt attctctttc tctctttgat ggtctcataa aaaatattaa 17340
acctctttct gatggtgtca ctaaaatatt tttattctca ttctcatttt ctctttctct 17400
cttcaatgga gtcataaaat atttttattc tctttctctc ttcgatggtc tcacaaaaat 17460
attaaacctc tttctgatgg tgtcactaaa atatttttat tctcattctc atttctctt 17520

```
tctctcttca atggagtcat aaaatatttt tattctcttt ctctcttcga tggtctcaca  17580

aaaatattaa acctcttgct agcttctggc gaagagcttc ttctagggat aacagggtaa  17640

t                                                                  17641


<210> SEQ ID NO 10
<211> LENGTH: 2540
<212> TYPE: DNA
<213> ORGANISM: Vaccinia virus

<400> SEQUENCE: 10

tagggataac agggtaatga agaagctctt cgccatcaga aagaggttta atatttttgt     60

gagaccatcg aagagagaaa gagataaaac ttttttacga ctccatcaga aagaggttta    120

atatttttgt gagaccatcg aagagagaaa gagataaaac ttttttacga ctccatcaga    180

aagaggttta atatttttgt gagaccatcg aaggagaaag agataaaact tttttacgac    240

tccatcagaa agaggtttaa tatttttgtg agaccatcga aggagaaaga gataaaactt    300

ttttacgact ccatcagaaa gaggtttaat atttttgtga gaccatcgaa gagagaaaga    360

gataaaactt ttttacgact ccatcagaaa gaggtttaat atttttgtga gaccatcgaa    420

gagagaaaga gataaaactt ttttacgact ccatcagaaa gaggtttaat atttttgtga    480

gaccatcgaa ggagaaagag ataaaacttt tttacgactc catcagaaag aggtttaata    540

tttttgtgag accatcgaag agagaaagag ataaaacttt tttacgactc catcagaaag    600

aggtttaata tttttgtgag accatcgaag agagaaagag ataaaacttt tttacgactc    660

catcagaaag aggtttaata tttttgtgag accatcgaag agagaaagag ataaaacttt    720

tttacgactc catcagaaag aggtttaata tttttgtgag accatcgaag agagaaagag    780

ataaaacttt tttacgactc catcagaaag aggtttaata tttttgtgag accatcgaag    840

agagaaagag ataaaacttt tttacgactc catcagaaag aggtttaata tttttgtgag    900

accatcgaag agagaaagag aaagagatag ttgatctaga tatttttctt agtacaaaag    960

tcaatgtttt aaaatatatg gacaagaatt tgtctgtata aaaacttgtg tgaaattttg   1020

taccaaagaa aaaatgtgag cagtatcccc tacatggatt ttactagatc atttatatac   1080

caaaaaatat tatacgatct acgttttatt atatgatttt aacgtgtaaa ttataaacat   1140

tattttatga tatacaattg tctggtaacc tagatgggca taggggatgt tgataagctc   1200

gacgagtata tgttgttgga cgttattgtt taagaaatag ttgatgcatc agaaagagaa   1260

taaaaaatat tttagtgaga ccatcgaaga gagaaagaga taaaactttt ttacgactcc   1320

atcagaaaga ggtttaatat ttttgtgaga ccatcgaaga gagaaagaga taaaactttt   1380

ttacgactcc atcagaaaga ggtttaatat ttttgtgaga ccatcgaaga gagaaagaga   1440

taaaactttt ttacgactcc atcagaaaga ggtttaatat ttttgtgaga ccatcgaaga   1500

gagaaagaga taaaactttt ttacgactcc atcagaaaga ggtttaatat ttttgtgaga   1560

ccatcgaaga gagaaagaga taaaactttt ttacgactcc atcagaaaga ggtttaatat   1620

ttttgtgaga ccatcgaaga gagaaagaga taaaactttt ttacgactcc atcagaaaga   1680

ggtttaatat ttttgtgaga ccatcgaaga gagaaagaga taaaactttt ttacgactcc   1740

atcagaaaga ggtttaatat ttttgtgaga ccatcgaaga gagaaagaga taaaactttt   1800

ttacgactcc atcagaaaga ggtttaatat ttttgtgaga ccatcgaaga gagaaagaga   1860

taaaactttt ttacgactcc atcagaaaga ggtttaatat ttttgtgaga ccatcgaaga   1920

gagaaagaga taaaactttt ttacgactcc atcagaaaga ggtttaatat ttttgtgaga   1980
```

```
ccatcgaaga gagaaagaga taaaactttt ttacgactcc atcagaaaga ggtttaatat   2040

ttttgtgaga ccatcgaaga gagaaagaga taaaactttt ttacgactcc atcagaaaga   2100

ggtttaatat ttttgtgaga ccatcgaaga gagaaagaga taaaactttt ttacgactcc   2160

atcagaaaga ggtttaatat ttttgtgaga ccatcgaaga gagaaagaga taaaactttt   2220

ttacgactcc atcagaaaga ggtttaatat ttttgtgaga ccatcgaaga gagaaagaga   2280

taaaactttt ttacgactcc atcagaaaga ggtttaatat ttttgtgaga ccatcgaaga   2340

gagaaagaga taaaactttt ttacgactcc atcagaaaga ggtttaatat ttttgtgaga   2400

ccatcgaaga gagaaagaga taaaactttt ttacgactcc atcagaaaga ggtttaatat   2460

ttttgtgaga ccatcgaaga gagaaagaga taaaactttt ttacgactcc gctagcgaag   2520

aatagggata acagggtaat                                               2540
```

<210> SEQ ID NO 11
<211> LENGTH: 61
<212> TYPE: DNA
<213> ORGANISM: Vaccinia virus

<400> SEQUENCE: 11

```
tgtgtgaccc atgactgtag gaaactctag agtgtaagaa agatcgatcg ctttatagag     60

a                                                                     61
```

<210> SEQ ID NO 12
<211> LENGTH: 61
<212> TYPE: DNA
<213> ORGANISM: Vaccinia virus

<400> SEQUENCE: 12

```
tggtctctat aaagcgatcg atctttctta cactctagag tttcctacag tcatgggtca     60

c                                                                     61
```

<210> SEQ ID NO 13
<211> LENGTH: 157
<212> TYPE: DNA
<213> ORGANISM: Vaccinia virus

<400> SEQUENCE: 13

```
acattttttt ctagacacta aataaaatat ttaaaatata atattaatgt actaaaactt     60

atatattatt aatttatcta actaaagtta gtaaattata tatataattt tataattaat    120

ttaattttac taattttatt tagtgtctag aaaaaaa                             157
```

<210> SEQ ID NO 14
<211> LENGTH: 157
<212> TYPE: DNA
<213> ORGANISM: Vaccinia virus

<400> SEQUENCE: 14

```
acattttttt ctagacacta aataaaatta gtaaaattaa attaattata aaattatata     60

tataatttac taactttagt tagataaatt aataatatat aagttttagt acattaatat    120

tatattttaa atattttatt tagtgtctag aaaaaaa                             157
```

<210> SEQ ID NO 15
<211> LENGTH: 58
<212> TYPE: DNA
<213> ORGANISM: Vaccinia virus

<400> SEQUENCE: 15
gtgacccatg actgtaggaa actctagagt gtaagaaaga tcgatcgctt tatagaga 58

<210> SEQ ID NO 16
<211> LENGTH: 58
<212> TYPE: DNA
<213> ORGANISM: Vaccinia virus

<400> SEQUENCE: 16
gtgaccaacg accgtaggaa actctagagg gtaagaaaaa tcaatcgctt tatagaga 58

<210> SEQ ID NO 17
<211> LENGTH: 58
<212> TYPE: DNA
<213> ORGANISM: Vaccinia virus

<400> SEQUENCE: 17
gtgaccaacg accgtaggaa actctagagg gtaagaaaaa tcaatcgctt tatagaga 58

<210> SEQ ID NO 18
<211> LENGTH: 58
<212> TYPE: DNA
<213> ORGANISM: Vaccinia virus

<400> SEQUENCE: 18
gtgaccaacg accgtaggaa actctagagg gtaagaaaaa tcaatcgctt tatagaga 58

<210> SEQ ID NO 19
<211> LENGTH: 154
<212> TYPE: DNA
<213> ORGANISM: Vaccinia virus

<400> SEQUENCE: 19
acattttttt ctagacacta aataaatatt taaaatataa tattaatata ctaaaattta 60
tgtattatta atttatctaa ctaaagttag taaattatat acataatttt ataattaatt 120
taattttact atttatttag tgtctagaaa aaaa 154

<210> SEQ ID NO 20
<211> LENGTH: 154
<212> TYPE: DNA
<213> ORGANISM: Vaccinia virus

<400> SEQUENCE: 20
acattttttt ctagacacta aataaatagt aaaattaaat taattataaa attatgtata 60
taatttacta actttagtta gataaattaa taatacataa attttagtat attaatatta 120
tattttaaat atttatttag tgtctagaaa aaaa 154

<210> SEQ ID NO 21
<211> LENGTH: 61
<212> TYPE: DNA
<213> ORGANISM: Vaccinia virus

<400> SEQUENCE: 21
tgtgtgacca acgaccgtag gaaactctag agggtaagaa aaatcaatcg ctttatagag 60
a 61

<210> SEQ ID NO 22
<211> LENGTH: 61
<212> TYPE: DNA
<213> ORGANISM: Vaccinia virus -continued

```
<400> SEQUENCE: 22

tggtctctat aaagcgattg atttttctta ccctctagag tttcctacgg tcgttggtca     60

c                                                                      61
```

SYNTHETIC CHIMERIC VACCINIA VIRUS

This application is a national stage application under 35 U.S.C. § 371 of International Application PCT/US2019/030486, filed May 2, 2019, which claims the benefit of priority to U.S. Provisional Patent Application Ser. No. 62/665,973, filed May 2, 2018, the disclosures of which are hereby incorporated by reference in their entireties.

BACKGROUND OF THE DISCLOSURE

A Sequence Listing associated with this application is being submitted electronically via EFS-Web in text format and is hereby incorporated by reference in its entirety into the specification. The name of the text file containing the Sequence Listing is 104545-0031-301-SL. The text file, created on Oct. 27, 2020, is 288,697 bytes in size.

Poxviruses (members of the Poxviridae family) are double-stranded DNA viruses that can infect both humans and animals. Poxviruses are divided into two subfamilies based on host range. The Chordopoxviridae subfamily, which infects vertebrate hosts, consists of eight genera, of which four genera (Orthopoxvirus, Parapoxvirus, Molluscipoxvirus, and Yatapoxvirus) are known to infect humans. Smallpox is caused by infection with variola virus (VARV), a member of the genus Orthopoxvirus (OPV). The OPV genus comprises a number of genetically related and morphologically identical viruses, including camelpox virus (CMLV), cowpox virus (CPXV), ectromelia virus (ECTV, "mousepox agent"), horsepox virus (HPXV), monkeypox virus (MPXV), rabbitpox virus (RPXV), raccoonpox virus, skunkpox virus, Taterapox virus, Uasin Gishu disease virus, vaccinia virus (VACV), variola virus (VARV) and volepox virus (VPV). Other than VARV, at least three other OPVs, including VACV, MPXV and CPXV, are known to infect humans. So far, vaccination with "live" VACV is the only proven protection against smallpox. An aggressive program of vaccination led to the eradication of smallpox in 1980 and routine smallpox vaccination of the public was stopped. However, a need remains to find new safe and effective means of vaccinating individuals against VARV and other OPVs.

A variety of preparations of VACV have been used as smallpox vaccines. Most of these comprised of a number of related viruses (e.g., Dryvax), and one comprises a single molecular clone, ACAM2000. However, like Dryvax and other VACV vaccines, even ACAM2000 is associated with serious side effects including cardiomyopathy and pericarditis. To reduce risks, the ACAM2000 vaccine, like other live vaccines, has numerous contraindications that preclude individuals with cancer, immunodeficiencies, organ transplant recipients, patients with atopic dermatitis, eczema, psoriasis, heart conditions, and patients on immunosuppressants. It is estimated that 15-50% of the US population would fall under one of these categories, confirming the need for the development of a safer vaccine or vaccination protocol (Kennedy et al., 2007 Kennedy R, Poland GA. 2007. T-Cell epitope discovery for variola and vaccinia viruses. Rev Med Viroll7: 93-113). Therefore, there is a need for the development of a vaccine that is similar in efficacy to Dryvax or ACAM2000™, but that is safer.

The production of safe, pure, potent and efficacious vaccines requires quality assurance procedures to ensure the uniformity and consistency of the vaccine production process. In the past, embryonated hens' eggs or primary chick embryo fibroblast cultures have been used to grow viruses to manufacture vaccines against yellow fever, influenza, measles, and mumps. These substrates were considered acceptable, since it was believed that adventitious agents that could infect chickens would not infect and be pathogenic for humans (FDA Briefing Document Vaccines and Related Biological Products Advisory Committee Meeting. Sep. 19, 2012). However, safety could be compromised should the virus tropism change.

Other substrates have been used for growth of virus for production of vaccines, such as calf lymph for smallpox vaccines. After calves had been inoculated with smallpox, the lymph containing white blood cells are extracted and preserved in capillary tubes. This is then used to vaccinate people against smallpox. However, there's a risk of contamination with bovine spongiform encephalopathy or scrapie prions. Even though regulations and guidelines for modern vaccines state that all materials used must come from BSE-free regions, there is nothing about scrapie-free regional status. Of particular concern is the fact that the Dryvax vaccine produced in 1980-1982 has never been scrutinized by modern methods. Specifically, these stocks have never been subjected to testing for adventitious agents (Murphy and Osburn. Emerging Infectious Diseases. www.cdc.gov/eid. Vol. 11, No. 7, July 2005).

Therefore, there is a need for the development of a vaccine that is similar in efficacy to the existent Dryvax or ACAM2000™ vaccines, but that is safer, reproducible and free of residual cells, residual DNA, prions and adventitious agents.

The present application provides chimeric vaccinia viruses assembled and replicated from chemically synthesized DNA which are safe, reproducible and free of contaminants. Because chemical genome synthesis is not dependent on a natural template, a plethora of structural and functional modifications of the viral genome are possible. Chemical genome synthesis is particularly useful when a natural template is not available for genetic replication or modification by conventional molecular biology methods.

SUMMARY OF THE DISCLOSURE

An aspect of the present invention provides synthetic chimeric vaccinia viruses, methods for producing such viruses and the use of such viruses, for example, as immunogens, in immunogenic formulations, in in vitro assays, as vehicles for heterologous gene expression, or as oncolytic agents for the treatment of cancer. The synthetic chimeric vaccinia viruses of the application are characterized by one or more modifications relative to a wildtype vaccinia virus.

The disclosure, in one aspect, is based on the finding that a synthetic chimeric vaccinia virus (e.g., scVACV) can be produced from chemically synthesized overlapping fragments of the vaccinia virus genome.

Therefore, in one aspect, the invention relates to a synthetic chimeric vaccinia virus (e.g., scVACV) that is replicated and reactivated from DNA derived from synthetic DNA, the viral genome of said virus differing from a wild type genome of said virus in that it is characterized by one or more modifications, the modifications being derived from a group comprising chemically-synthesized DNA, cDNA or genomic DNA.

In another aspect, the invention relates to a method of producing a synthetic chimeric vaccinia virus (scVACV) comprising the steps of: (i) chemically synthesizing overlapping DNA fragments that correspond to substantially all of the viral genome of the vaccinia virus; (ii) transfecting the overlapping DNA fragments into helper virus-infected cells; (iii) culturing said cells to produce a mixture of helper virus and synthetic chimeric vaccinia particles in said cells; and (iv) plating the mixture on host cells specific to the scVACV to recover the scVACV.

In another aspect, the invention relates to a synthetic chimeric vaccinia virus (scVACV) generated by the method of the disclosure.

In another aspect, the invention relates to a pharmaceutical composition comprising the synthetic chimeric vaccinia virus (scVACV) of the disclosure and a pharmaceutically acceptable carrier.

In another aspect, the invention relates to a method for inducing an oncolytic response in a subject comprising administering to the subject a composition comprising the scVACV of the disclosure.

In another aspect, the invention relates to a method for expressing a heterologous protein in a host cell, comprising introducing the heterologous nucleic acid sequence into the scVACV of the disclosure, infecting the host cell with the scVACV and culturing the host cells under conditions for expression of the heterologous protein.

In another aspect, the invention relates to a method of triggering or boosting an immune response against vaccinia virus, comprising administering to a subject in need thereof a composition comprising the scVACV of the disclosure.

In another aspect, the invention relates to a method of triggering or boosting an immune response against variola virus infection, comprising administering to said subject a composition comprising the sc VACV of the disclosure.

In another aspect, the invention relates to a method of triggering or boosting an immune response against monkeypox virus infection, comprising administering to said subject a composition comprising the scVACV of the disclosure.

In another aspect, the invention relates to a method of immunizing a human subject to protect said subject from variola virus infection, comprising administering to said subject a composition comprising the scVACV of the disclosure.

In another aspect, the invention relates to a method of treating a variola virus infection, comprising administering to said subject a composition comprising the scVACV of the disclosure.

In another aspect, the invention relates to a method of treating cancer in a subject, comprising administering to the subject in need thereof a composition comprising the scVACV of the disclosure.

BRIEF DESCRIPTION OF THE DRAWINGS

This Patent application contains at least one drawing executed in color. Copies of this patent application with color drawings will be provided by the Office upon request and payment of the necessary fee.

The foregoing summary, as well as the following detailed description of the disclosure, will be better understood when read in conjunction with the appended drawings. For the purpose of illustrating the disclosure there are shown in the drawings embodiment(s) which are presently preferred. It should be understood, however, that the disclosure is not limited to the precise arrangements and instrumentalities shown.

FIG. 1A illustrates the unmodified genome sequence of VACV ACAM2000 genome with naturally occurring AarI and BsaI restriction sites indicated. FIG. 1B depicts the modified VACV ACAM2000 genome that was used to chemically synthesize large ds DNA fragments. The overlapping scVACV ACAM2000 genomic fragments are depicted in blue. The engineered BsaI restriction sites that were not silently mutated in the Left Inverted Terminal Repeat (LITR) and the Right Inverted Terminal Repeat (RITR), are also shown.

FIGS. 3A and 3B. Assembly of vaccinia virus terminal hairpin loop with duplex DNA to the first 70 bp repeat sequence. (A) The phosphorylated oligonucleotide sequences ordered to create the WR duplex DNA are depicted. (B) Gel electrophoresis of WR strain duplex DNA (lane 2) and hairpin DNA alone (lane 3) and following ligation (lane 4) are depicted. The ligated product (arrow) was subsequently excised from the gel and purified, so that it could be ligated to a 70 bp repeat sequence to mimic the sequence of the wtVACV ACAM2000 sequence.

FIG. 9. Nucleotide sequence variations between VACV strain sequences. FIG. 9A depicts the VACV nucleotide sequence variations within the duplex regions in the ITRs (SEQ ID NOS: 15-18). FIG. 9B depicts the VACV ACAM2000 secondary hairpin loops that are covalently attached to the terminal ends of the linear dsDNA genomes of ACAM2000 (S form SEQ ID NO: 19 and F form SEQ ID NO: 20). The terminal loop sequence is highlighted in green.

DETAILED DESCRIPTION OF THE DISCLOSURE

General Techniques

Figure 1A:
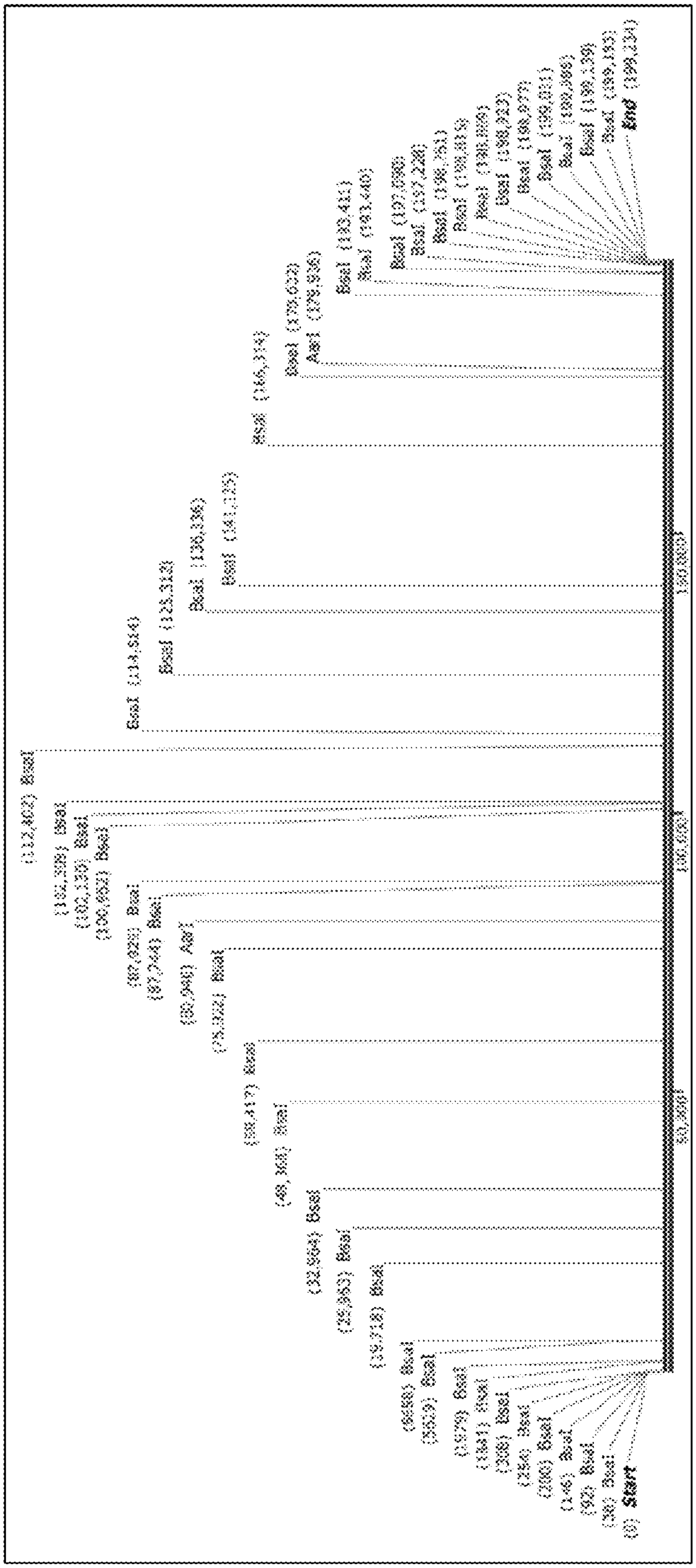
FIGS. 1A and 1B. Schematic representation of the linear dsDNA VACV genome strain ACAM2000; Genbank Accession AY313847.

Unless otherwise defined herein, scientific and technical terms used in this application shall have the meanings that are commonly understood by those of ordinary skill in the art. Generally, nomenclature used in connection with, and techniques of, pharmacology, cell and tissue culture, molecular biology, cell and cancer biology, neurobiology, neurochemistry, virology, immunology, microbiology, genetics and protein and nucleic acid chemistry, described herein, are those well-known and commonly used in the art. In case of conflict, the present specification, including definitions, will control.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Sambrook and Russell, Molecular Cloning: A Laboratory Manual, 3rd. ed., Cold Spring Harbor Laboratory Press, Cold Spring Harbor, NY (2001); Ausubel et al., Current Protocols in Molecular Biology, John Wiley & Sons, NY (2002); Harlow and Lane Using Antibodies: A Laboratory Manual, Cold Spring Harbor Laboratory Press, Cold Spring Harbor, NY (1998); Coligan et al., Short Protocols in Protein Science, John Wiley & Sons, NY (2003); Short Protocols in Molecular Biology (Wiley and Sons, 1999).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well-known and commonly used in the art. Standard techniques are used for chemical syntheses, and chemical analyses.

Throughout this specification and embodiments, the word "comprise," or variations such as "comprises" or "comprising," will be understood to imply the inclusion of a stated integer or group of integers but not the exclusion of any other integer or group of integers.

It is understood that wherever embodiments are described herein with the language "comprising," otherwise analogous embodiments described in terms of "consisting of" and/or "consisting essentially of" are also provided.

The term "including" is used to mean "including but not limited to." "Including" and "including but not limited to" are used interchangeably.

Any example(s) following the term "e.g." or "for example" is not meant to be exhaustive or limiting.

Unless otherwise required by context, singular terms shall include pluralities and plural terms shall include the singular.

The articles "a", "an" and "the" are used herein to refer to one or to more than one (i.e., to at least one) of the grammatical object of the article. By way of example, "an element" means one element or more than one element. Reference to "about" a value or parameter herein includes (and describes) embodiments that are directed to that value or parameter per se. For example, description referring to "about X" includes description of "X." Numeric ranges are inclusive of the numbers defining the range.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g., 1 to 6.1, and ending with a maximum value of 10 or less, e.g., 5.5 to 10.

Exemplary methods and materials are described herein, although methods and materials similar or equivalent to those described herein can also be used in the practice or testing of the present application. The materials, methods, and examples are illustrative only and not intended to be limiting.

Definitions

The following terms, unless otherwise indicated, shall be understood to have the following meanings:

As used herein, the terms “wild type virus”, “wild type genome”, “wild type protein,” or “wild type nucleic acid” refer to a sequence of amino or nucleic acids that occurs naturally within a certain population (e.g., a particular viral species, etc.).

The terms “chimeric” or “engineered” or “modified” (e.g., chimeric vacinia, engineered polypeptide, modified polypeptide, engineered nucleic acid, modified nucleic acid) or grammatical variations thereof are used interchangeably herein to refer to a non-native sequence that has been manipulated to have one or more changes relative a native sequence.

As used herein, “synthetic virus” refers to a virus initially derived from synthetic DNA (e.g., chemically synthesized DNA, PCR amplified DNA, engineered DNA, polynucleotides comprising nucleoside analogs, etc., or combinations thereof) and includes its progeny, and the progeny may not necessarily be completely identical (in morphology or in genomic DNA complement) to the original parent synthetic virus due to natural, accidental, or deliberate mutation. In some embodiments, the synthetic virus refers to a virus where substantially all of the viral genome is initially derived from synthetic DNA (e.g., chemically synthesized DNA, PCR amplified DNA, engineered DNA, polynucleotides comprising nucleoside analogs, etc., or combinations thereof). In a preferred embodiment, the synthetic virus is derived from chemically synthesized DNA.

As outlined elsewhere herein, certain positions of the viral genome can be altered. By “position” as used herein is meant a location in the genome sequence. Corresponding positions are generally determined through alignment with other parent sequences.

As used herein, the term “residue” in the context of a polypeptide refers to an amino-acid unit in the linear polypeptide chain. It is what remains of each amino acid, i.e —NH—CHR—C—, after water is removed in the formation of the polypeptide from α-amino-acids, i.e. NH2-CHR—COOH.

As known in the art, “polynucleotide,” or “nucleic acid,” as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, “caps”, substitution of one or more of the naturally occurring nucleotides with an analog; internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.); those containing pendant moieties, such as, for example, proteins (e.g., nucleases, toxins, antibodies, signal peptides, poly-L-lysine, etc.); those with intercalators (e.g., acridine, psoralen, etc.); those containing chelators (e.g., metals, radioactive metals, boron, oxidative metals, etc.); those containing alkylators; those with modified linkages (e.g., alpha anomeric nucleic acids, etc.); as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O) S (“thioate”), P(S) S (“dithioate”), (O)$NR_2$ (“amidate”), P(O)R, P(O) OR', CO or $CH_2$ (“formacetal”), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The terms “polypeptide”, “oligopeptide”, “peptide” and “protein” are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

“Homologous,” in all its grammatical forms and spelling variations, refers to the relationship between two proteins that possess a “common evolutionary origin,” including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. “Homologous” may also refer to a nucleic acid which is native to the virus.

However, in common usage and in the instant application, the term “homologous,” when modified with an adverb such as “highly,” may refer to sequence similarity and may or may not relate to a common evolutionary origin.

“Heterologous,” in all its grammatical forms and spelling variations, may refer to a nucleic acid which is non-native to the virus. It means derived from a different species or a different strain than the nucleic acid of the organism to which the nucleic acid is described as heterologous relative to. In a non-limiting example, the viral genome of the scVACV comprises heterologous terminal hairpin loops. Said heterologous terminal hairpin loops can be derived from a different virus species or from a different VACV strain.

The term "sequence similarity," in all its grammatical forms, refers to the degree of identity or correspondence between nucleic acid or amino acid sequences that may or may not share a common evolutionary origin.

"Percent (%) sequence identity" or "sequence % identical to" with respect to a reference polypeptide (or nucleotide) sequence is defined as the percentage of amino acid residues (or nucleic acids) in a candidate sequence that are identical with the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, a "host cell" includes an individual cell or cell culture that can be or has been a recipient for the virus of the disclosure. Host cells include progeny of a single host cell, and the progeny may not necessarily be completely identical (in morphology or in genomic DNA complement) to the original parent cell due to natural, accidental, or deliberate mutation. A host cell includes cells transfected and/or transformed in vivo with a poxvirus of this disclosure.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "isolated molecule" (where the molecule is, for example, a polypeptide, a polynucleotide, or fragment thereof) is a molecule that by virtue of its origin or source of derivation (1) is not associated with one or more naturally associated components that accompany it in its native state, (2) is substantially free of one or more other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, the term "isolated", in the context of viruses, refers to a virus that is derived from a single parental virus. A virus can be isolated using routine methods known to one of skill in the art including, but not limited to, those based on plaque purification and limiting dilution.

As used herein, the phrase "multiplicity of infection" or "MOI" is the average number of viruses per infected cell. The MOI is determined by dividing the number of virus added (ml added×plaque forming units (PFU)) by the number of cells added (ml added× cells/ml).

As used herein, "purify," and grammatical variations thereof, refers to the removal, whether completely or partially, of at least one impurity from a mixture containing the polypeptide and one or more impurities, which thereby improves the level of purity of the polypeptide in the composition (i.e., by decreasing the amount (ppm) of impurity(ies) in the composition). As used herein "purified" in the context of viruses refers to a virus which is substantially free of cellular material and culture media from the cell or tissue source from which the virus is derived. The language "substantially free of cellular material" includes preparations of virus in which the virus is separated from cellular components of the cells from which it is isolated or recombinantly produced. Thus, a virus that is substantially free of cellular material includes preparations of protein having less than about 30%, 20%, 10%, or 5% (by dry weight) of cellular protein (also referred to herein as a "contaminating protein"). The virus is also substantially free of culture medium, i.e., culture medium represents less than about 20%, 10%, or 5% of the volume of the virus preparation. A virus can be purified using routine methods known to one of skill in the art including, but not limited to, chromatography and centrifugation.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

The terms "patient", "subject", or "individual" are used interchangeably herein and refer to either a human or a non-human animal. These terms include mammals, such as humans, primates, livestock animals (including bovines, porcines, camels, etc.), companion animals (e.g., canines, felines, etc.) and rodents (e.g., mice and rats).

As used herein, the terms "prevent", "preventing" and "prevention" refer to the delay of the recurrence or onset of, or a reduction in one or more symptoms of a disease (e.g., a poxviral infection) in a subject as a result of the administration of a therapy (e.g., a prophylactic or therapeutic agent). For example, in the context of the administration of a therapy to a subject for an infection, "prevent", "preventing" and "prevention" refer to the inhibition or a reduction in the development or onset of an infection (e.g., a poxviral infection or a condition associated therewith), or the prevention of the recurrence, onset, or development of one or more symptoms of an infection (e.g., a poxviral infection or a condition associated therewith), in a subject resulting from the administration of a therapy (e.g., a prophylactic or therapeutic agent), or the administration of a combination of therapies (e.g., a combination of prophylactic or therapeutic agents).

As used herein, the terms "treat", "treating" or "treatment" refer to treating a condition or patient and refers to taking steps to obtain beneficial or desired results, including clinical results. With respect to infections (e.g., a poxviral infection or a variola virus infection), treatment refers to the eradication or control of the replication of an infectious agent (e.g., the poxvirus or the variola virus), the reduction in the numbers of an infectious agent (e.g., the reduction in the titer of the virus), the reduction or amelioration of the progression, severity, and/or duration of an infection (e.g., a poxviral/variola infection or a condition or symptoms associated therewith), or the amelioration of one or more symptoms resulting from the administration of one or more therapies (including, but not limited to, the administration of one or more prophylactic or therapeutic agents). With respect to cancer, treatment refers to the eradication, removal, modification, or control of primary, regional, or metastatic cancer tissue that results from the administration of one or more therapeutic agents of the disclosure. In certain embodiments, such terms refer to minimizing or delaying the spread of cancer resulting from the administration of one or more therapeutic agents of the disclosure to a subject with such a disease. In other embodiments, such terms refer to elimination of disease-causing cells.

"Administering" or "administration of" a substance, a compound or an agent to a subject can be carried out using one of a variety of methods known to those skilled in the art. For example, a compound or an agent can be administered sublingually or intranasally, by inhalation into the lung or rectally. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Each embodiment described herein may be used individually or in combination with any other embodiment described herein.

Overview

Poxviruses are large (~200 kbp) DNA viruses that replicate in the cytoplasm of infected cells. The Orthopoxvirus (OPV) genus comprises a number of poxviruses that vary greatly in their ability to infect different hosts. Vaccinia virus (VACV), for example, can infect a broad group of hosts, whereas variola virus (VARV), the causative agent of smallpox, only infects humans. A feature common to many, if not all poxviruses, is their ability to non-genetically "reactivate" within a host. Non-genetic reactivation refers to a process wherein cells infected by one poxvirus can promote the recovery of a second "dead" virus (for example one inactivated by heat) that would be non-infectious on its own.

Purified poxvirus DNA is not infectious because the virus life cycle requires transcription of early genes via the virus-encoded RNA polymerases that are packaged in virions. However, this deficiency can be overcome if virus DNA is transfected into cells previously infected with a helper poxvirus, providing the necessary factors needed to transcribe, replicate, and package the transfected genome in trans (Sam C K, Dumbell K R. Expression of poxvirus DNA in coinfected cells and marker rescue of thermosensitive mutants by subgenomic fragments of DNA. Ann Virol (Inst Past). 1981; 132:135-50). Although this produces mixed viral progeny, the problem can be overcome by performing the reactivation reaction in a cell line that supports the propagation of both viruses, and then eliminating the helper virus by plating the mixture of viruses on cells that do not support the helper virus' growth (Scheiflinger F, Dorner F, Falkner F G. Construction of chimeric vaccinia viruses by molecular cloning and packaging. Proceedings of the National Academy of Sciences of the United States of America. 1992; 89 (21): 9977-81).

Previously, Yao and Evans described a method in which the high-frequency recombination and replication reactions catalyzed by a Leporipoxvirus, Shope fibroma virus (SFV), can be coupled with an SFV-catalyzed reactivation reaction, to rapidly assemble recombinant vaccinia strains using multiple overlapping fragments of viral DNA (Yao X D, Evans D H. High-frequency genetic recombination and reactivation of orthopoxviruses from DNA fragments transfected into leporipoxvirus-infected cells. Journal of Virology. 2003; 77 (13): 7281-90). For the first time, the reactivation and characterization of a functional synthetic chimeric vaccinia virus [scVACV] using chemically synthesized, overlapping double-stranded DNA fragments is described.

Synthetic Chimeric Vaccinia Viruses of the Disclosure

In one aspect, the invention provides functional synthetic chimeric vaccinia viruses (scVACV) that are initially replicated and assembled from chemically synthesized DNA. The viruses that may be produced in accordance with the methods of the disclosure can be any vaccinia virus whose genome has been sequenced or can be sequenced in large part or for which a natural isolate is available. An scVACV of the various embodiments may be based on the genome sequences of naturally occurring strains, variants or mutants, mutagenized viruses or genetically engineered viruses. In some embodiments, the viral genome of an scVACV comprises one or more modifications relative to the wild type genome or base genome sequence of said virus. The modifications may include one or more deletions, insertions, substitutions, or combinations thereof. In one embodiment, the modification may include the insertion or one or more multiple cloning sites, so that exogenous DNA can be inserted. It is understood that the modifications may be introduced in any number of ways commonly known in the art. The modified portions of the genome may be derived from chemically synthesized DNA, cDNA or genomic DNA. In another embodiment, the viral genome of the scVACV of the disclosure comprises one or more modifications to add or repair one or more unique restriction site. The modifications to add or repair one or more restriction sites can be performed on the restriction sites that were eliminated to facilitate clone selection.

Chemical genome synthesis is particularly useful when a natural template is not available for genetic modification, amplification, or replication by conventional molecular biology methods. The genome sequence for wtVACV (strain NYCBH, clone ACAM2000) has been described and published, though it was not complete. The sequence of the terminal hairpin loops was not determined, only four 54 bp repeat sequences were identified. The presence of the 70 bp, 125 bp, and 54 bp tandem repeat sequences was confirmed in a wild-type isolate of VACV ACAM2000 after sequencing, indicating that the current published sequence of ACAM2000 was incomplete. The inventors generated a functional synthetic chimeric VACV (scVACV). Specifically, the inventors successfully generated a functional scVACV strain NYCBH, clone ACAM2000, by using terminal hairpin loops based on wtVACV telomeres of a different strain in lieu of the VACV own terminal hairpin loop sequences. In some embodiments, the viral genome of the VACV virus is a strain selected from the group of: Western Reserve, Clone 3, Tian Tan, Tian Tan clone TP5, Tian Tan clone TP3, NYCBH, NYCBH clone Acambis 2000, Wyeth, Copenhagen, Lister, Lister 107, Lister-LO, Lister GL-ONC1, Lister GL-ONC2, Lister GL-ONC3, Lister GL-ONC4, Lister CTC1, Lister IMG2 (Turbo FP635), IHD-W, LC16m18, Lederle, Tashkent clone TKT3, Tashkent clone TKT4, USSR, Evans, Praha, L-IVP, V—VET1 or LIVP 6.1.1, Ikeda, EM-63, Malbran, Duke, 3737, CV-1, Connaught Laboratories, Serro 2, CM-01, NYCBH Dryvax clone DPP13, NYCBH Dryvax clone DPP15, NYCBH Dryvax clone DPP20, NYCBH Dryvax clone DPP17, NYCBH Dryvax clone DPP21, VACV-IOC, Chorioallantois Vaccinia virus Ankara (CVA), Modified vaccinia Ankara (MVA), and MVA-BN. In a preferred embodiment, the viral genome is based on the NYCBH strain. More preferably, the viral genome is derived from NYCBH strain, clone Acambis 2000 or ACAM2000. New VACV strains are still being constantly discovered. It is understood that an scVACV of the disclosure may be based on such a newly discovered VACV strains.

Dryvax® is derived from the New York City Board of Health strain of vaccinia virus (Wyeth Laboratories, Marietta, PA) and was grown on the skin of calves and then essentially freeze-dried for storage.

VACV ACAM2000 strain, Smallpox (Vaccinia) Vaccine, Live, is a live vaccinia virus derived from plaque purification cloning from Dryvax® and grown in African Green Monkey kidney (Vero) cells and tested to be free of adventitious agents (Osborne J D et al. Vaccine. 2007; (52): 8807-32).

V-VET1 or LIVP 6.1.1 was developed by Genelux. It was isolated from a wild type stock of Lister strain of vaccinia virus (Lister strain, Institute of Viral Preparations (LIVP), Moscow, Russia) and represents a "native" virus (no genetic manipulations were conducted). The thymidine kinase (tk) gene of LIVP 6.1.1 virus is inactive (Shvalov A N et al. Genome Announc. 2016 May-June; 4 (3): e00372-16).

GLV-1 h68 (named GL-ONC1 as produced for clinical investigation) was developed by Genelux from the Lister strain by inserting three expression cassettes encoding *Renilla* luciferase-*Aequorea* green fluorescent protein fusion (Ruc-GFP), LacZ, and β-glucuronidase into the F14.5L, J2R (thymidine kinase) and A56R (hemagglutinin) loci of the viral genome, respectively (Zhang Q et al. Cancer Res. 2007; 67 (20): 10038-46).

Chemical viral genome synthesis also opens up the possibility of introducing a large number of useful modifications to the resulting genome or to specific parts of it. The modifications may improve ease of cloning to generate the virus, provide sites for introduction of recombinant gene products, improve ease of identifying reactivated viral clones and/or confer a plethora of other useful features (e.g., introducing a desired antigen, producing an oncolytic virus, etc.). In some embodiments, the modifications may include the attenuation or deletion of one or more virulence factors. In some embodiments, the modifications may include the addition or insertion of one or more virulence regulatory genes or gene-encoding regulatory factors.

Traditionally, the terminal hairpins of poxviruses have been difficult to clone and sequence, hence, it is not surprising that some of the published genome sequences (e.g., VACV, ACAM2000 and HPXV MNR-76) are incomplete. Specifically, the genome sequence for wtVACV, strain NYCBH, clone ACAM2000, has been described and published, though it is not complete. The sequence of the terminal hairpin loops was not determined, only four 54 bp repeat sequences were identified. Since the published sequence of the wtVACV strain NYCBH, clone ACAM2000 genome is incomplete, the hairpins cannot be precisely replicated and prior to this application, it was not known whether VACV could be replicated and assembled from polynucleotides based on only the known portion of the wtVACV genome. Nor was it known that hairpins from one strain virus would be operable in another strain. The inventors generated a functional synthetic chimeric VACV (scVACV) ACAM2000 by using terminal hairpin loops based on wtVACV telomeres of a different strain in lieu of the VACV own terminal hairpin loop sequences. In an exemplary embodiment, ssDNA fragments were chemically synthesized using the published sequence of the VACV WR strain telomeres as a guide and ligated onto dsDNA fragments comprising left and right ends of the VACV strain NYCBH. In some embodiments, the terminal hairpins are based on the terminal hairpins of any VACV strain whose genome has been completely sequenced or a natural isolate of which is available for genome sequencing. In some embodiments, the terminal hairpin loops are based on a strain selected from the group of: Western Reserve, Clone 3, Tian Tan, Tian Tan clone TP5, Tian Tan clone TP3, NYCBH, NYCBH clone Acambis 2000, Wyeth, Copenhagen, Lister, Lister 107, Lister-LO, Lister GL-ONC1, Lister GL-ONC2, Lister GL-ONC3, Lister GL-ONC4, Lister CTC1, Lister IMG2 (Turbo FP635), IHD-W, LC16m18, Lederle, Tashkent clone TKT3, Tashkent clone TKT4, USSR, Evans, Praha, L-IVP, V—VET1 or LIVP 6.1.1, Ikeda, EM-63, Malbran, Duke, 3737, CV-1, Connaught Laboratories, Serro 2, CM-01, NYCBH Dryvax clone DPP13, NYCBH Dryvax clone DPP15, NYCBH Dryvax clone DPP20, NYCBH Dryvax clone DPP17, NYCBH Dryvax clone DPP21, VACV-IOC, Chorioallantois Vaccinia virus Ankara (CVA), Modified vaccinia Ankara (MVA), and MVA-BN. In a preferred embodiment, the terminal hairpin loops are based on the Western Reserve strain (WR strain) of VACV. New VACV strains are still being constantly discovered. It is understood that an scVACV of the disclosure may be based on such a newly discovered VACV strains.

In another embodiment, the viral genome of the scVACV of the present disclosure comprises homologous or heterologous terminal hairpin loops and the tandem repeat regions (the 70 bp, the 125 bp and the 54 bp tandem repeats) located downstream of the hairpin loops, wherein the tandem repeat regions comprise a different number of repeats than the wtVACV (i.e. the virus present in nature). The number of repeats of the 70 bp, the 125 bp and the 54 bp tandem repeats found in the VACV virus, strain WR were 22, 2 and 8, respectively. In another embodiment, the number of tandem repeat regions are variable in different poxviruses, in different vaccinia viruses and in different vaccinia virus strains. The term homologous terminal hairpin loops means that said terminal hairpin loops are coming from the same virus species/the same strain, while the term heterologous terminal hairpin loops means that said terminal hairpin loops are coming from a different virus species/different strain.

In some embodiments, the modifications may include the deletion of one or more restriction sites. In some embodiments, the modifications may include the introduction of one or more restriction sites. In some embodiments, the restriction sites to be deleted from the genome or added to the genome may be selected from one or more of restriction sites such as, but not limited to, AanI, AarI, AasI, AatI, AatII, AbaSI, AbsI, Acc65I, AccI, AccII, AccIII, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI BanI, BanII, BbsI, BbvCI, BbvI, BccI, BceAI, BcgI, BciVI, BclI, BcoDI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFaI, BsrGI, BsrI, BssHII, BssSaI, BstAPI, BstBI, BstEII, BstNI, BstUI, BstXI, BstYI, BstZ17I, Bsu36I, BtgI, BtgZI, BtsaI, BtsCI, BtsIMutI, Cac8I, ClaI, CspCI, CviAII, CviKI-1, CviQI, DdeI, DpnI, DpnII, DraI, DrdI, EaeI, EagI, EarI, EciI, Eco53kI, EcoNI, EcoO109I, EcoP15I, EcoRI, EcoRV, FatI, FauI, Fnu4HI, FokI, FseI, FspEI, FspI, HaeII, HaeIII, HgaI, HhaI, HincII, HindIII, HinfI, HinPII, HpaI, HpaII, HphI, Hpyl66II, Hpyl88I, Hpy188III, Hpy991, HpyAV, HpyCH4III, HpyCH4IV, HpyCH4V, I-Ceul, I-SceI, KasI, KpnI, LpnPI, MboI, MboII, MfeI, MluCI, MluI, MlyI, MmeI, MnlI, MscI, MseI, MslI, MspAII, MspI, MspJI, Mwol, NaeI, NarI, NciI, NcoI, NdeI, NgoMIV, NheI, NlaIII, NlaIV, NmeAIII, NotI, NruI, NsiI, NspI, PacI, PaeR7I, PciI, PflFI, PflMI, PleI, PluTI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScrFI, SexAI, SfaNI, SfcI, SfiI, SfoI, SgrAI, SmaI, SmlI, SnaBI, SpeI, SphI, SrfI, SspI, StuI, StyD4I, StyI, SwaI, TagaI, TfiI, TseI, Tsp45I, TspMI, TspRI, Tth111I, XbaI, XcmI, XhoI, XmaI, XmnI, or ZraI. It is understood that any desired restriction site(s) or combination of restriction sites may be inserted into the genome or mutated and/or eliminated from the genome. In some embodiments, one or more AarI sites are deleted from the viral genome. In some embodiments, one or more BsaI sites are deleted from the viral genome. In some embodiments, one or more restriction sites are completely eliminated from the genome (e.g., all the AarI sites in the viral genome may be eliminated). In some embodiments, one or more AvaI restriction sites are introduced into the viral genome. In some embodiments, one or more StuI sites are introduced into the viral genome. In some embodiments, the one or more modifications may include the incorporation of recombineering targets including, but not limited to, loxP or FRT sites.

In some embodiments, the modifications may include the introduction of fluorescence markers such as, but not limited to, green fluorescent protein (GFP), enhanced GFP, yellow fluorescent protein (YFP), cyan/blue fluorescent protein (BFP), red fluorescent protein (RFP), or variants thereof, etc.; selectable markers such as but not limited to drug resistance markers (e.g., *E. coli* xanthine-guanine phosphoribosyl transferase gene (gpt), *Streptomyces alboniger* puromycin acetyltransferase gene (pac), neomycin phosphotransferase I gene (nptl), neomycin phosphotransferase gene II (nptII), hygromycin phosphotransferase (hpt), sh ble gene, etc.; protein or peptide tags such as but not limited to MBP (maltose-binding protein), CBD (cellulose-binding domain), GST (glutathione-S-transferase), poly(His), FLAG, V5, c-Myc, HA (hemagglutinin), NE-tag, CAT (chloramphenicol acetyl transferase), DHFR (dihydrofolate reductase), HSV (Herpes simplex virus), VSV-G (Vesicular stomatitis virus glycoprotein), luciferase, protein A, protein G, streptavidin, T7, thioredoxin, Yeast 2-hybrid tags such as B42, GAL4, LexA, or VP16; localization tags such as an NLS-tag, SNAP-tag, Myr-tag, etc. It is understood that other selectable markers and/or tags known in the art may be used. In some embodiments, the modifications include one or more selectable markers to aid in the selection of reactivated clones (e.g., a fluorescence marker such as YFP, a drug selection marker such as gpt, etc.) to aid in the selection of reactivated viral clones. In some embodiments, the one or more selectable markers are deleted from the reactivated clones after the selection step.

In one aspect, the scVACVs of the invention can be used as vaccines to protect against pathogenic poxviral infections (e.g., VARV, MPXV, MCV, ORFV, Ausdyk virus, BPSV, sealpox virus etc.), as therapeutic agents to treat or prevent pathogenic poxviral infections (e.g., VARV, MPXV, MCV, ORFV, Ausdyk virus, BPSV, sealpox virus etc.), as vehicles for heterologous gene expression, or as oncolytic agents. In some embodiments, the scVACVs can be used as vaccines to protect against VARV infection. In some embodiments, the scVACVs can be used to treat or prevent VARV infection.

Methods of Producing Synthetic Chimeric VACV

In one aspect, the invention provides systems and methods for synthesizing, reactivating and isolating functional synthetic chimeric VACVs (scVACVs) from chemically synthesized overlapping double-stranded DNA fragments of the viral genome. Recombination of overlapping DNA fragments of the viral genome and reactivation of the functional scVACVs are carried out in cells previously infected with a helper virus. Briefly, overlapping DNA fragments that encompass all or substantially all of the viral genome of the scVACVs are chemically synthesized and transfected into helper virus-infected cells. The transfected cells are cultured to produce mixed viral progeny comprising the helper virus and reactivated scVACVs. Next, the mixed viral progeny is plated on host cells that do not support the growth of the helper virus but allow the synthetic chimeric vaccinia virus to grow, in order to eliminate the helper virus and recover the synthetic chimeric vaccinia virus. In some embodiments, the helper virus does not infect the host cells. In some embodiments, the helper virus can infect the host cells but grows poorly in the host cells. In some embodiments, the helper virus grows more slowly in the host cells compared to the sc VACVs.

In some embodiments, substantially all of the synthetic chimeric vaccinia virus genome is derived from chemically synthesized DNA. In some embodiments, about 40%, about 50%, about 60%, about 70%, about 75%, about 80%, about 85%, about 90%, about 95%, about 96%, about 97%, about 98%, about 99%, over 99%, or 100% of the synthetic chimeric vaccinia virus genome is derived from chemically synthesized DNA. In some embodiments, the vaccinia virus genome is derived from a combination of chemically synthesized DNA and naturally occurring DNA. In some embodiments, all of the fragments encompassing the vaccinia virus genome are chemically synthesized. In some embodiments, one or more of the fragments are chemically synthesized and one or more of the fragments are derived from naturally occurring DNA (e.g., by PCR amplification or by well-established recombinant DNA techniques).

The number of overlapping DNA fragments used in the methods of the present disclosure will depend on the size of the vaccinia virus genome. Practical considerations such as reduction in recombination efficiency as the number of fragments increases on the one hand, and difficulties in synthesizing very large DNA fragments as the number of fragments decreases on the other hand, will also inform the number of overlapping fragments used in the methods of the disclosure. In some embodiments, the synthetic chimeric vaccinia virus genome may be synthesized as a single fragment. In some embodiments, the synthetic chimeric vaccinia virus genome is assembled from 2-14 overlapping DNA fragments. In some embodiments, the synthetic chimeric vaccinia virus genome is assembled from 4-12 overlapping DNA fragments. In some embodiments, the synthetic chimeric vaccinia virus genome is assembled from 6-12 overlapping DNA fragments. In some embodiments, the synthetic chimeric vaccinia virus genome is assembled from 8-11 overlapping DNA fragments. In some embodiments, the synthetic chimeric vaccinia virus genome is assembled from 8-10, 10-12, or 10-14 overlapping DNA fragments. In some embodiments, the synthetic chimeric vaccinia virus genome is assembled from 2, 3, 4, 5, 6, 7, 8, 9, 10, 11, 12, 13, 14, or 15 overlapping DNA fragments. In a preferred embodiment, the synthetic chimeric vaccinia virus genome is assembled from 9 overlapping DNA fragments. In an exemplary embodiment of the disclosure, a synthetic vaccinia virus (scVACV) is reactivated from 9 chemically synthesized overlapping double-stranded DNA fragments. In some embodiments, terminal hairpin loops are synthesized separately and ligated onto the fragments comprising the left and right ends of the vaccinia virus genome. In some embodiments, terminal hairpin loops may be derived from a naturally occurring template. In some embodiments, the terminal hairpins of the scVACV are derived from wtVACV. In some embodiments, the terminal hairpins are derived from wtVACV terminal hairpins of a different strain in lieu of the VACV own terminal hairpin loop sequences. In some embodiments, the terminal hairpins are based on the terminal hairpins of any wtVACV whose genome has been completely sequenced or a natural isolate of which is available for genome sequencing.

The size of the overlapping fragments used in the various aspects of the methods of the invention will depend on the size of the vaccinia virus genome. It is understood that there can be wide variations in fragment sizes and various practical considerations, such as the ability to chemically synthesize very large DNA fragments, will inform the choice of fragment sizes. In some embodiments, the fragments range in size from about 2,000 bp to about 50,000 bp. In some embodiments, the fragments range in size from about 3,000 bp to about 45,000 bp. In some embodiments, the fragments range in size from about 4,000 bp to 40,000 bp. In some embodiments, the fragments range in size from about 5,000 bp to 35,000 bp. In some embodiments, the largest fragments are about 18,000 bp, 20,000 bp, 21,000 bp, 22,000 bp, 23,000 bp, 24,000 bp, 25,000 bp, 26,000 bp, 27,000 bp, 28,000 bp, 29,000 bp, 30,000 bp, 31,000 bp, 32,000 bp, 33,000 bp, 34,000 bp, 35,000 bp, 36,000 bp, 37,000 bp, 38,000 bp, 39,000 bp, 40,000 bp, 41,000 bp, 42,000 bp, 43,000 bp, 44,000 bp, 45,000 bp, 46,000 bp, 47,000 bp, 48,000 bp, 49,000 bp, or 50,000 bp. In an exemplary embodiment of the disclosure, an scVACV is reactivated from 9 chemically synthesized overlapping double-stranded DNA fragments ranging in size from about 10,000 bp to about 32,000 bp (Table 1).

The helper virus may be any poxvirus that can provide the trans-acting enzymatic machinery needed to reactivate a poxvirus from transfected DNA. The helper virus may have a different or narrower host cell range than an scVACV to be produced (e.g., Shope fibroma virus (SFV) has a very narrow host range compared to Orthopoxviruses such as vaccinia virus (VACV) or HPXV). The helper virus may have a different plaque phenotype compared to the scVACV to be produced. In some embodiments, the helper virus is a Leporipoxvirus. In some embodiments, the Leporipoxvirus is an SFV, hare fibroma virus, rabbit fibroma virus, squirrel fibroma virus, or myxoma virus. In a preferred embodiment, the helper virus is an SFV. In some embodiments, the helper virus is an Orthopoxvirus. In some embodiments, the Orthopoxvirus is a camelpox virus (CMLV), cowpox virus (CPXV), ectromelia virus (ECTV, “mousepox agent”), HPXV, monkeypox virus (MPXV), rabbitpox virus (RPXV), raccoonpox virus, skunkpox virus, Taterapox virus, Uasin Gishu disease virus, VACV and volepox virus (VPV). In some embodiments, the helper virus is an Avipoxvirus, Capripoxvirus, Cervidpoxvirus, Crocodylipoxvirus, Molluscipoxvirus, Parapoxvirus, Suipoxvirus, or Yatapoxvirus. In some embodiments, the helper virus is a fowlpox virus. In some embodiments, the helper virus is an Alphaentomopoxvirus, Betaentomopoxvirus, or Gammaentomopoxvirus. In some embodiments, the helper virus is a psoralen-inactivated helper virus. In an exemplary embodiment of the disclosure, an scVACV is reactivated from overlapping DNA fragments transfected into SFV-infected BGMK cells. The SFV is then eliminated by plating the mixed viral progeny on BSC-40 cells.

The skilled worker will understand that appropriate host cells will be used for the reactivation of the scVACV and the selection and/or isolation of the scVACV will depend on the particular combination of helper virus and chimeric poxvirus being produced by the various aspects of the methods of the disclosure. Any host cell that supports the growth of both the helper virus and the sc VACV may be used for the reactivation step and any host cell that does not support the growth of the helper virus may be used to eliminate the helper virus and select and/or isolate the scVACV. In some embodiments, the helper virus is a Leporipoxvirus and the host cells used for the reactivation step may be selected from rabbit kidney cells (e.g., LLC-RK1, RK13, etc.), rabbit lung cells (e.g., R9ab), rabbit skin cells (e.g., SF1Ep, DRS, RAB-9), rabbit cornea cells (e.g., SIRC), rabbit carcinoma cells (e.g., Oc4T/cc), rabbit skin/carcinoma cells (e.g., CTPS), monkey cells (e.g., Vero, BGMK, etc.) or hamster cells (e.g., BHK-21, etc.). In a preferred embodiment, the host cells are BGMK cells.

In some embodiments, the scVACVs can be propagated in any substrate that allows the virus to grow to titers that permit the uses of the scVACVs described herein. In one embodiment, the substrate allows the scVACVs to grow to titers comparable to those determined for the corresponding wild-type viruses. In some embodiments, the scVACVs may be grown in cells (e.g., avian cells, bat cells, bovine cells, camel cells, canary cells, cat cells, deer cells, equine cells, fowl cells, gerbil cells, goat cells, human cells, monkey cells, pig cells, rabbit cells, raccoon cells, seal cells, sheep cells, skunk cells, vole cells, etc.) that are susceptible to infection by the VACV. Such methods are well-known to those skilled in the art. Representative mammalian cells include, but are not limited to, BHK, BGMK, BRL3A, BSC-40, CEF, CEK, CHO, COS, CVI, HaCaT, HEL, HeLa cells, HEK293, human bone osteosarcoma cell line 143B, MDCK, NIH/3T3 and Vero cells. For virus isolation, the scVACV is removed from cell culture and separated from cellular components, typically by well-known clarification procedures, e.g., such as gradient centrifugation and column chromatography, and may be further purified as desired using procedures well known to those skilled in the art, such as plaque assays.

In another aspect of the present invention, the method of producing a synthetic chimeric vaccinia virus (scVACV) comprises a step of (i) chemically synthesizing overlapping DNA fragments that correspond to substantially all of the viral genome of the vaccinia virus and chemically synthesizing the terminal hairpin loops from another strain of vaccinia virus; (ii) transfecting the overlapping DNA fragments into helper virus-infected cells; (iii) culturing said cells to produce a mixture of helper virus and synthetic chimeric vaccinia virus particles in said cells; and (iv) plating the mixture on host cells specific to the scVACV to recover the scVACV. In some embodiments, the scVACV of the present method derives from strain NYCBH strain, clone Acambis 2000 and the terminal hairpin loops derive from the Western Reserve strain of the vaccinia virus.

Polynucleotides of the Disclosure

In one aspect, the invention provides polynucleotides (e.g., double-stranded DNA fragments) for producing functional synthetic chimeric poxviruses (scVACVs). In some embodiments, the invention provides methods for producing functional scVACVs from synthetic DNA (e.g., chemically synthesized DNA, PCR amplified DNA, engineered DNA, polynucleotides comprising nucleoside analogs, etc.). In some embodiments, the invention provides methods for producing functional scVACVs from chemically synthesized overlapping double-stranded DNA fragments of the viral genome. The polynucleotides of the various aspects of the invention may be designed based on publicly available genome sequences. Where natural isolates of a vaccinia virus are readily available, the viral genome may be sequenced prior to selecting and designing the polynucleotides of the disclosure. Alternatively, where partial DNA sequences of a vaccinia virus are available, for example, from a clinical isolate, from a forensic sample or from PCR amplified DNA from material associated with an infected person, the partial viral genome may be sequenced prior to selecting and designing the polynucleotides of the disclosure. In one aspect, an scVACV of the invention, and thus, the polynucleotides of the present disclosure, may be based on the genome sequences of naturally occurring strains, variants or mutants, mutagenized viruses or genetically engineered viruses.

In one aspect, the invention provides isolated polynucleotides including a nucleotide sequence that is at least 90% identical (e.g., at least 91%, 92%, 93%, or 94% identical), at least 95% identical (e.g., at least 96%, 97%, 98%, or 99% identical), or 100% identical to all or a portion of a reference VACV genome sequence or its complement. The isolated polynucleotides of the disclosure may include at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35000, 40000, 45000 bp or more contiguous or non-contiguous nucleotides of a reference polynucleotide molecule (e.g., a reference VACV genome or a fragment thereof). One of ordinary skill in the art will appreciate that nucleic acid sequences complementary to the nucleic acids, and variants of the nucleic acids are also within the scope of this application. In further embodiments, the nucleic acid sequences of the disclosure can be isolated, recombinant, and/or fused with a heterologous nucleotide sequence, or in a DNA library.

In some aspects, the invention provides polynucleotides for producing scVACVs, wherein the VACV is selected from the following strains: Western Reserve, Clone 3, Tian Tan, Tian Tan clone TP5, Tian Tan clone TP3, NYCBH, NYCBH clone Acambis 2000, Wyeth, Copenhagen, Lister, Lister 107, Lister-LO, Lister GL-ONC1, Lister GL-ONC2, Lister GL-ONC3, Lister GL-ONC4, Lister CTC1, Lister IMG2 (Turbo FP635), IHD-W, LC16m18, Lederle, Tashkent clone TKT3, Tashkent clone TKT4, USSR, Evans, Praha, L-IVP, V—VET1 or LIVP 6.1.1, Ikeda, EM-63, Malbran, Duke, 3737, CV-1, Connaught Laboratories, Serro 2, CM-01, NYCBH Dryvax clone DPP13, NYCBH Dryvax clone DPP15, NYCBH Dryvax clone DPP20, NYCBH Dryvax clone DPP17, NYCBH Dryvax clone DPP21, VACV-IOC, Chorioallantois Vaccinia virus Ankara (CVA), Modified vaccinia Ankara (MVA), and MVA-BN. In a preferred embodiment, the sc VACV is derived from strain NYCBH clone Acambis 2000 or ACAM2000.

In one aspect, the invention provides polynucleotides for producing a synthetic chimeric vaccinia virus (scVACV). In a specific embodiment, the scVACV genome may be based on the published genome sequence described for VACV strain NYCBH clone ACAM2000 (GenBank accession AY313847; Osborne J D et al. Vaccine. 2007; 25 (52): 8807-32). It is shown in the various aspects of the present invention that terminal hairpin loops from vaccinia virus (VACV) strain WR can be ligated onto the ends of the VACV genome strain NYCBH clone ACAM2000 to produce functional scVACV particles using the methods of the disclosure. In some embodiments, the terminal hairpin loops from vaccinia virus (VACV) strain ACAM2000 can be ligated onto the ends of the VACV genome strain NYCBH clone ACAM2000 to produce functional scVACV particles using the methods of the disclosure. The scVACV genome may be divided into 9 overlapping fragments as described in the working examples of the disclosure and shown in Table 1. In some embodiments, the VACV genome may be divided into 2, 3, 4, 5, 6, 7, 8, 9, 10, 11, 12, 13, 14, or 15 overlapping fragments. In some embodiments, the entire genome may be provided as one fragment. The fragment sizes are shown in Table 1. In some embodiments, the VACV genome may be divided into 2, 3, 4, 5, 6, 7, 8, 9, 10, 11, 12, 13, 14, or overlapping fragments. In some embodiments, the entire genome may be provided as one fragment. The fragment sizes are shown in Table 1. The polynucleotides of the various aspects of the invention comprise nucleic acids sequences that are at least 65%, 70%, 75%, 80%, 85%, 90%, 91%, 92%, 93%, 94%, 95%, 96%, 97%, 98%, 99%, or 100% identical to SEQ ID NOs: 1-9. In some embodiments, an isolated polynucleotide of the invention comprises a variant of these sequences, wherein such variants can include missense mutations, nonsense mutations, duplications, deletions, and/or additions. SEQ ID NO: 13 and SEQ ID NO: 14 depict the nucleotide sequences of VACV (WR strain) terminal hairpin loops. SEQ ID NO: 19 and SEQ ID NO: 20 depict the nucleotide sequences of VACV (ACAM2000 strain) terminal hairpin loops. In some embodiments, the terminal hairpin loops comprise nucleic acid sequences that are at least 70%, 75%, 80%, 85%, 90%, 91%, 92%, 93%, 94%, 95%, 96%, 97%, 98%, 99%, or 100% identical to SEQ ID NO: 13 or to SEQ ID NO: 14. In some embodiments, the terminal hairpin loops comprise nucleic acid sequences that are at least 70%, 75%, 80%, 85%, 90%, 91%, 92%, 93%, 94%, 95%, 96%, 97%, 98%, 99%, or 100% identical to SEQ ID NO: 19 or to SEQ ID NO: 20.

In other embodiments, the scVACV genome is based on a strain selected a VACV strain selected from Western Reserve (Genbank Accession NC 006998; Genbank Accession AY243312), CL3 (Genbank Accession AY313848), Tian Tan (Genbank Accession AF095689.1), Tian Tan clones TP5 (JX489136), TP3 (Genbank Accession KC207810) and TP5 (Genbank Accession KC207811), NYCBH, Wyeth, Copenhagen (Genbank Accession M35027), NYCBH clone Acambis 2000 (Genbank Accession AY313847), Lister 107 (Genbank Accession DQ121394) Lister-LO (Genbank Accession AY678276), Modified Vaccinia virus Ankara (MVA) (Genbank Acccession U94848; Genbank Accession AY603355), MVA-BN (Genbank Accession DQ983238), Lederle, Tashkent clones TKT3 (Genbank Accession KM044309) and TKT4 (KM044310), USSR, Evans, Praha, LIVP, Ikeda, IHD-W (Genbank Accession KJ125439), LC16m8 (AY678275), EM-63, IC, Malbran, Duke (Genbank Accession DQ439815), 3737 (Genbank Accession DQ377945), VACV-IOC (Genbank Accession KT184690 and KT184691), CV-1, Connaught Laboratories, CVA (Genbank Accession AM501482), Serro 2 virus (Genbank Accession KF179385), Cantaglo virus isolate CM-01 (Genbank Accession KT013210), Dryvax clones DPP15 (Genbank Accession JN654981), DPP20 (Genbank Accession JN654985), DPP13 (Genbank Accession JN654980), DPP17 (Genbank Accession JN654983), DPP21 (Genbank Accession JN654986).

In one aspect, the invention provides isolated polynucleotides including a nucleotide sequence that is at least 90% identical (e.g., at least 91%, 92%, 93%, or 94% identical), at least 95% identical (e.g., at least 96%, 97%, 98%, or 99% identical), or 100% identical to all or a portion of a reference wtVACV genome sequence. In some embodiments, an isolated polynucleotide of the disclosure comprises a variant of the reference sequences, wherein such variants can include missense mutations, nonsense mutations, duplications, deletions, and/or additions. In some embodiments, the isolated polynucleotides of the invention may include at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35000, 40000, 45000 bp or more contiguous or non-contiguous nucleotides of a reference polynucleotide molecule (e.g., a reference wtVACV genome).

Polynucleotides complementary to any of the polynucleotide sequences disclosed herein are also encompassed by the present application. Polynucleotides may be single-stranded (coding or antisense) or double-stranded, and may be DNA (genomic or synthetic) or RNA molecules. RNA molecules include mRNA molecules. Additional coding or non-coding sequences may, but need not, be present within a polynucleotide of the present disclosure, and a polynucleotide may, but need not, be linked to other molecules and/or support materials.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about contiguous positions, usually 30 to about 75, or 40 to about 50, in which a sequence may be compared to a reference sequence of the same number of contiguous positions after the two sequences are optimally aligned. Polynucleotides or variants may also, or alternatively, be substantially homologous to a polynucleotide provided herein. Such polynucleotide variants are capable of hybridizing under moderately stringent conditions to a polynucleotide of the disclosure (or its complement).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer provider to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

In other embodiments, nucleic acids of the invention also include nucleotide sequences that hybridize under highly stringent conditions to the nucleotide sequences set forth in SEQ ID NOs: 1-9, or sequences complementary thereto. One of ordinary skill in the art will readily understand that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ due to degeneracy in the genetic code are also within the scope of some aspects of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. One skilled in the art will appreciate that these variations in one or more nucleotides (up to about 3-5% of the nucleotides) of the nucleic acids encoding a particular protein may exist among members of a given species due to natural allelic variation. Any and all such nucleotide variations and resulting amino acid polymorphisms are within the scope of this application.

One aspect of the present invention further provides recombinant cloning vectors and expression vectors that are useful in cloning a polynucleotide of the present disclosure. One aspect of the present invention further provides transformed host cells comprising a polynucleotide molecule or a recombinant vector, and novel strains or cell lines derived therefrom.

A host cell may be a bacterial cell, a yeast cell, a filamentous fungal cell, an algal cell, an insect cell, or a mammalian cell. In some embodiments, the host cell is *E. coli*. A variety of different vectors have been developed for specific use in each of these host cells, including phage, high copy number plasmids, low copy number plasmids, and shuttle vectors, among others, and any of these can be used to practice the present disclosure.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pBAD18, pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

To aid in the selection of host cells transformed or transfected with cloning vectors of the present disclosure, the vector can be engineered to further comprise a coding sequence for a reporter gene product or other selectable marker. Such a coding sequence is preferably in operative association with the regulatory element coding sequences, as described above. Reporter genes that are useful in some aspects of the present invention are well-known in the art and include those encoding green fluorescent protein, luciferase, xylE, and tyrosinase, among others. Nucleotide sequences encoding selectable markers are well known in the art, and include those that encode gene products conferring resistance to antibiotics or anti-metabolites, or that supply an auxotrophic requirement. Examples of such sequences include those that encode resistance to ampicillin, erythromycin, thiostrepton or kanamycin, among many others.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

One aspect of the present invention further provides transformed host cells comprising a polynucleotide molecule or a recombinant vector, and novel strains or cell lines derived therefrom. In some embodiments, host cells useful in the practice of the invention are *E. coli* cells. A strain of *E. coli* can typically be used, such as e.g., *E. coli* TOP10, or *E. coli* BL21 (DE3), DH5a, etc., available from the American Type Culture Collection (ATCC), 10801 University Blvd., Manassas, Va. 20110, USA and from commercial sources. In some embodiments, other prokaryotic cells or eukaryotic cells may be used. In some embodiments, the host cell is a member of a genus selected from: *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluyveromyces, Yarrowia, Pichia, Candida, Pichia*, or *Saccharomyces*. Such transformed host cells typically include but are not limited to microorganisms, such as bacteria transformed with recombinant bacteriophage DNA, plasmid DNA or cosmid DNA vectors, or yeast transformed with recombinant vectors, among others. Preferred eukaryotic host cells include yeast cells, although mammalian cells or insect cells can also be utilized effectively. Suitable host cells include prokaryotes (such as *E. coli, B. subtillis, S. lividans*, or *C. glutamicum*) and yeast (such as *S. cerevisae, S. pombe, P. pastoris*, or *K. lactis*).

In one aspect, the invention also includes the genome of the scVACV, its recombinants, or functional parts thereof. A functional part of the viral genome may be a portion of the genome that encodes a protein or portion thereof (e.g., domain, epitope, etc.), a portion that comprises regulatory elements or components of regulatory elements such as a promoter, enhancer, cis- or trans-acting elements, etc. Such viral sequences can be used to identify or isolate the virus or its recombinants, e.g., by using PCR, hybridization technologies, or by establishing ELISA assays.

Pharmaceutical Composition of the Disclosure

In one aspect, the invention relates to a pharmaceutical composition comprising the scVACV of the disclosure and a pharmaceutically acceptable carrier.

The term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In some embodiments, the pharmaceutical composition of the invention may be administered by standard routes of administration. Many methods may be used to introduce the formulations into a subject, these include, but are not limited to, intranasal, intratracheal, oral, intradermal, intramuscular, intraperitoneal, intravenous, conjunctival and subcutaneous routes.

Exemplary Uses

Prevention or Treatment of Pathogenic Poxviral Infections

In some embodiments, the synthetic chimeric vaccinia viruses (scVACVs) of the invention can be used in immunization or to trigger or to boost an immune response of a subject against a pathogenic poxviral infection. In another embodiment, the scVACVs can be used to trigger or boosting an immune response against a vaccinia virus. In another embodiment, the sc VACVs can be used to trigger or boosting an immune response against a variola virus. In another embodiment, the scVACVs can be used to trigger or boosting an immune response against a monkepox virus. In another embodiment, the scVACVs can be used to prevent, manage, or treat one or more pathogenic poxviral infections in a subject, such as for to treat a variola virus infection. In some embodiments, the scVACVs is selected from the following strains of vaccinia virus: Western Reserve, Clone 3, Tian Tan, Tian Tan clone TP5, Tian Tan clone TP3, NYCBH, NYCBH clone Acambis 2000, Wyeth, Copenhagen, Lister, Lister 107, Lister-LO, Lister GL-ONC1, Lister GL-ONC2, Lister GL-ONC3, Lister GL-ONC4, Lister CTC1, Lister IMG2 (Turbo FP635), IHD-W, LC16m18, Lederle, Tashkent clone TKT3, Tashkent clone TKT4, USSR, Evans, Praha, L-IVP, V—VET1 or LIVP 6.1.1, Ikeda, EM-63, Malbran, Duke, 3737, CV-1, Connaught Laboratories, Serro 2, CM-01, NYCBH Dryvax clone DPP13, NYCBH Dryvax clone DPP15, NYCBH Dryvax clone DPP20, NYCBH Dryvax clone DPP17, NYCBH Dryvax clone DPP21, VACV-IOC, Chorioallantois Vaccinia virus Ankara (CVA), Modified vaccinia Ankara (MVA), and MVA-BN. In a preferred embodiment, the scVACV is derived from strain NYCBH clone Acambis 2000 or ACAM2000.

In one aspect, the scVACVs of the invention can be used in immunogenic formulations, e.g., vaccine formulations. The formulations may be used to prevent, manage, neutralize, treat and/or ameliorate a pathogenic poxviral infection. The immunogenic formulations may comprise either a live or inactivated scVACVs. The scVACVs can be inactivated by methods well known to those of skill in the art. Common methods use formalin and heat for inactivation. In some embodiments, the immunogenic formulation comprises a live vaccine. Production of such live immunogenic formulations may be accomplished using conventional methods involving propagation of the scVACVs in cell culture followed by purification. For example, the scVACVs can be cultured in BHK, BGMK, BRL3A, BSC-40, CEF, CEK, CHO, COS, CVI, HaCaT, HEL, HeLa cells, HEK293, human bone osteosarcoma cell line 143B, MDCK, NIH/3T3, Vero cells, etc., as can be determined by the skilled worker.

In one aspect, the scVACVs of the invention can be used to prevent, manage, or treat smallpox. In another aspect, the scVACVs of the invention can be used as a vaccine for the prevention of smallpox in individuals or populations that have been exposed, potentially exposed, or are at risk of exposure to smallpox. The scVACVs of the various aspects of the invention can be used to create a new national stockpile of smallpox vaccine. In some embodiments, the scVACVs of the invention can be prophylactically administered to defense personnel, first responders, etc.

In one embodiment, a composition comprising a scVACV of the invention is used as a smallpox vaccine. In one aspect, the scVACV of the invention produced according to the methods of the disclosure will have a small plaque phenotype. In general, a small plaque phenotype is considered to reflect attenuation. Accordingly, a scVACV produced according to the various methods of the invention provides a safe alternative to the existing smallpox vaccines. In some embodiments, the vaccine may be safe for administration to immunosuppressed subjects (e.g., HIV patients, patients undergoing chemotherapy, patients undergoing treatment for cancer, rheumatologic disorders, or autoimmune disorders, patients who are undergoing or have received an organ or tissue transplant, patients with immune deficiencies, children, pregnant women, patients with atopic dermatitis, eczema, psoriasis, heart conditions, and patients on immunosuppressants etc.), who may suffer from severe complications from an existing smallpox vaccine and are thus contraindicated for an existing smallpox vaccine. In some embodiments the vaccine may be used in combination with one or more anti-viral treatments to suppress viral replication. In some embodiments the vaccine may be used in combination with brincidofovir treatment to suppress viral replication. In some embodiments the vaccine may be used in combination with tecovirimat/SIGA-246 treatment to suppress viral replication. In some embodiments, the vaccine may be used in combination with acyclic nucleoside phosphonates (cidofovir), oral alkoxyalkyl prodrugs of acyclic nucleoside or phosphonates (brincidofovir or CMX001). In some embodiments, the vaccine may be used in combination with Vaccinia Immune Globulin (VIG). In some embodiments, the vaccine may be used in subjects who have been previously immunized with peptides or protein antigens derived from VACV, VARV or HPXV. In some embodiments the vaccine may be used in subjects who have been previously immunized with killed or inactivated VACV. In some embodiments the vaccine may be used in subjects who have been previously immunized with the replication-deficient/defective VACV virus strain, MVA (modified virus Ankara). In some embodiments, a vaccine formulation comprising a scVACV of the invention may comprise either a live or inactivated scVACV.

In one embodiment, a composition comprising a scVACV of the disclosure is used as a smallpox vaccine. The scVACV may be based on a VACV strain selected from ACAM2000 (Genbank Accession AY313847), Western Reserve (Genbank Accession NC 006998; Genbank Accession AY243312), CL3 (Genbank Accession AY313848), Tian Tan (Genbank Accession AF095689.1), Tian Tan clones TP5 (JX489136), TP3 (Genbank Accession KC207810) and TP5 (Genbank Accession KC207811), NYCBH, Wyeth, Copenhagen (Genbank Accession M35027), NYCBH clone Acambis 2000 (Genbank Accession AY313847), Lister 107 (Genbank Accession DQ121394) Lister-LO (Genbank Accession AY678276), Modified Vaccinia virus Ankara (MVA) (Genbank Acccession U94848; Genbank Accession AY603355), MVA-BN (Genbank Accession DQ983238), Lederle, Tashkent clones TKT3 (Genbank Accession KM044309) and TKT4 (KM044310), USSR, Evans, Praha, LIVP, Ikeda, IHD-W (Genbank Accession KJ125439), LC16m8 (AY678275), EM-63, IC, Malbran, Duke (Genbank Accession DQ439815), 3737 (Genbank Accession DQ377945), CV-1, Connaught Laboratories, CVA (Genbank Accession AM501482), Serro 2 virus (Genbank Accession KF179385), Cantaglo virus isolate CM-01 (Genbank Accession KT013210), Dryvax clones DPP15 (Genbank Accession JN654981), DPP20 (Genbank Accession JN654985), DPP13 (Genbank Accession JN654980), DPP17 (Genbank Accession JN654983), DPP21 (Genbank Accession JN654986) and IOC (Genbank Accession KT184690 and KT184691). In one embodiment, the scVACV to be used as a smallpox vaccine is based on strain ACAM2000 (Genbank Accession AY313847). In one embodiment, the scVACV to be used as a smallpox vaccine is based on strain VACV-IOC (Genbank Accession KT184690 and KT184691). In one embodiment, the scVACV to be used as a smallpox vaccine is based on strain MVA (Genbank Acccession U94848; Genbank Accession AY603355). In one embodiment, the scVACV to be used as a smallpox vaccine is based on strain MVA-BN (Genbank Accession DQ983238). In some embodiments, a vaccine formulation comprising a scVACV of the disclosure may comprise either a live or inactivated scVACV.

In some embodiments, a composition comprising a scVACV of the invention is used as a vaccine against a VACV infection, a MPXV infection or a CPXV infection.

In some embodiments, a scVACV of the invention may be designed to express heterologous antigens or epitopes and can be used as vaccines against the source organisms of such antigens and/or epitopes.

The immunogenic formulations of the present disclosure (e.g., vaccines) comprise an effective amount of the scVACV, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration. The particular formulation may also depend on whether the scVACV is live or inactivated. In some embodiments, the purified scVACVs of the invention may be lyophilized for later use or can be immediately prepared in a pharmaceutical solution. The scVACVs may also be diluted in a physiologically acceptable solution such as sterile saline, with or without an adjuvant or carrier.

In one aspect, the immunogenic formulations (e.g., vaccines) of the invention may be administered to patients by scarification. The vaccines may also be administered by any other standard route of administration. Many methods may be used to introduce the immunogenic formulations (e.g., vaccines), these include, but are not limited to, intranasal, intratracheal, oral, intradermal, intramuscular, intraperitoneal, intravenous, conjunctival and subcutaneous routes. In birds, the methods may further include choanal inoculation. As an alternative to parenteral administration, an aspect of the invention also encompasses routes of mass administration for agricultural purposes such as via drinking water or in a spray. Alternatively, it may be preferable to introduce an scVACV of the disclosure via its natural route of infection. In some embodiments, the immunogenic formulations of the invention are administered as an injectable liquid, a consumable transgenic plant that expresses the vaccine, a sustained release gel or an implantable encapsulated composition, a solid implant or a nucleic acid. The immunogenic formulation may also be administered in a cream, lotion, ointment, skin patch, lozenge, or oral liquid such as a suspension, solution and emulsion (oil in water or water in oil). The accepted route of administration for live replicating smallpox vaccine is dermal scarification, which generates a virus-shedding lesion that persists for several days at the vaccination site. The lesion is a potential source of contact transmission of vaccine to individuals who may be contraindicated for receipt of the live vaccine. Therefore, the intramuscular administration of the immunogenic formulation may provide an advantage. In a preferred embodiment, the administration of the scVACV ACAM2000 is intramuscular. In another preferred embodiment, the administration is by dermal scarification. The intramuscular administration can also be used for other synthetic chimeric orthopoxviruses, such as the synthetic chimeric horsepox virus (scHPXV). In the case of intramuscular administration, it is important to use a needle with the correct length to reach the muscle mass and not seep into subcutaneous tissue. When administering intramuscular injections, the needle should be inserted at a 90° angle.

In certain embodiments, an immunogenic formulation of the disclosure (e.g., vaccine) does not result in complete protection from an infection, but results in a lower titer or reduced number of the pathogen (e.g., pathogenic poxvirus) compared to an untreated subject. In certain embodiments, administration of the immunogenic formulations of the disclosure results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of the pathogen relative to an untreated subject. Benefits of a reduction in the titer, number or total burden of pathogen include, but are not limited to, less severity of symptoms of the infection and a reduction in the length of the disease or condition associated with the infection.

In certain embodiments, an immunogenic formulation of the disclosure (e.g., vaccine) does not result in complete protection from an infection, but results in a lower number of symptoms or a decreased intensity of symptoms, or a decreased morbidity or a decreased mortality compared to an untreated subject.

In various embodiments, the immunogenic formulations of the invention (e.g., vaccines) or antibodies generated by the scVACVs of the disclosure are administered to a subject in combination with one or more other therapies (e.g., antiviral or immunomodulatory therapies) for the prevention of an infection (e.g., a pathogenic poxviral infection). In other embodiments, the immunogenic formulations or antibodies generated by the scVACVs of the invention are administered to a subject in combination with one or more other therapies (e.g., antiviral or immunomodulatory therapies) for the treatment of an infection (e.g., a pathogenic poxviral infection). In yet other embodiments, the immunogenic formulations or antibodies generated by the scVACVs of the invention are administered to a subject in combination with one or more other therapies (e.g., antiviral or immunomodulatory therapies) for the management and/or amelioration of an infection (e.g., a pathogenic poxviral infection). In a specific embodiment, the immunogenic formulations or antibodies generated by the scVACVs of the invention are administered to a subject in combination with one or more other therapies (e.g., antiviral or immunomodulatory therapies) for the prevention of smallpox. In another specific embodiment, the immunogenic formulations or antibodies generated by the scVACVs of the invention are administered to a subject in combination with one or more other therapies (e.g., antiviral or immunomodulatory therapies) for the treatment of smallpox. In some embodiments the vaccine may be used in combination with one or more anti-viral treatments to suppress viral replication. In some embodiments the vaccine may be used in combination with brincidofovir treatment to suppress viral replication. In some embodiments the vaccine may be used in combination with tecovirimat/SIGA-246 treatment to suppress viral replication. In some embodiments, the vaccine may be used in combination with acyclic nucleoside phosphonates (cidofovir), oral alkoxyalkyl prodrugs of acyclic nucleoside or phosphonates (brincidofovir or CMX001). In some embodiments, the vaccine may be used in combination with Vaccinia Immune Globulin (VIG). In some embodiments the vaccine may be used in subjects who have been previously immunized with peptide or protein antigens derived from VACV, VARV or HPXV. In some embodiments the vaccine may be used in subjects who have been previously immunized with killed or inactivated VACV. In some embodiments the vaccine may be used in subjects who have been previously immunized with the replication-deficient/defective VACV virus strain, MVA (modified virus Ankara).

Any anti-viral agent well-known to one of skill in the art can be used in the formulations (e.g., vaccine formulations) and the methods of the various aspects of the invention. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include but are not limited to antivirals that block extracellular virus maturation (tecovirimat/SIGA-246), acyclic nucleoside phosphonates (cidofovir), oral alkoxyalkyl prodrugs of acyclic nucleoside phosphonates (brincidofovir or CMX001) or Vaccinia Immune Globulin (VIG). In some embodiments, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, and AZT.

Doses and dosing regimens can be determined by one of skill in the art according to the needs of a subject to be treated. The skilled worker may take into consideration factors such as the age or weight of the subject, the severity of the disease or condition being treated, and the response of the subject to treatment. In some embodiments, a composition of the invention can be administered, for example, as needed or on a daily basis. Dosing may take place over varying time periods. For example, a dosing regimen may last for 1 week, 2 weeks, 3 weeks, 4 weeks, 5 weeks, 6 weeks, 7 weeks, 8 weeks, 9 weeks, 10 weeks, 11 weeks, 12 weeks, or longer. In some embodiments, a dosing regimen will last 1 month, 2 months, 3 months, 4 months, 5 months, 6 months, 7 months, 8 months, 9 months, 10 months, 11 months, 12 months, or longer.

In some aspects, the scVACVs of the invention can also be used to produce antibodies useful for passive immunotherapy, diagnostic or prognostic immunoassays, etc. Methods of producing antibodies are well-known in the art. The antibodies may be further modified (e.g., chimerization, humanization, etc.) prior to use in immunotherapy.

Oncolytic Agents

An "oncolytic virus" or "oncolytic agent" as used in the present disclosure is considered any virus which typically is able to kill a tumor cell (non-resistant) by infecting said tumor cell.

In one aspect, the synthetic chimeric poxviruses (scVACVs) of the invention can be used as oncolytic agents that selectively replicate in and kill cancer cells. In another aspect, the invention relates to a method for inducing an oncolytic response in a subject comprising administering to the subject a composition comprising the scVACV of the disclosure. Cells that are dividing rapidly, such as cancer cells, are generally more permissive for poxviral infection than non-dividing cells. Many features of poxviruses, such as safety in humans, ease of production of high-titer stocks, stability of viral preparations, and capacity to induce anti-tumor immunity following replication in tumor cells make poxviruses desirable oncolytic agents. The scVACVs produced according to the various methods of the invention may comprise one or modifications that render them suitable for the treatment of cancer. Accordingly, in one aspect, the disclosure provides a method of inducing death in cancer cells, the method comprising contacting the cells with an isolated scVACV or pharmaceutical composition comprising an scVACV of the disclosure. In one aspect, the disclosure provides a method of treating cancer, the method comprising administering to a patient in need thereof, a therapeutically effective amount of an scVACV of the disclosure. Another aspect includes the scVACV or a composition described herein for use in the treatment of cancer or in inducing death in a neoplastic disorder. Another aspect includes the use of an scVACV or a composition described herein to induce death in a neoplastic disorder cell such as a cancer cell or to treat a neoplastic disorder such as cancer. In some embodiments, the poxvirus oncolytic therapy is administered in combination with one or more conventional cancer therapies (e.g., surgery, chemotherapy, radiotherapy, thermotherapy, and biological/immunological therapy). In specific embodiments, the oncolytic virus is a scVACV NYCBH strain, clone Acambis 2000 or ACAM2000.

Using the methods of this application, one or more desirable genes can be easily introduced and one or more undesirable genes can be easily deleted from the scVACV genome. In some embodiments, the scVACVs of the invention for use as oncolytic agents are designed to express transgenes to enhance their immunoreactivity, antitumor targeting and/or potency, cell-to-cell spread and/or cancer specificity. In some embodiments, an scVACV of the invention is designed or engineered to express an immunomodulatory gene (e.g., GM-CSF, or a viral gene that blocks TNF function). In some embodiments, an scVACV of the invention is designed to include a gene that expresses a factor that attenuates virulence. In some embodiments, an scVACV of the invention is designed or engineered to express a therapeutic agent (e.g., hEPO, BMP-4, antibodies to specific tumor antigens or portions thereof, etc.). In some embodiments, the scVACVs of the invention has been designed or engineered to comprise the gmCSF gene. In some embodiments, the scVACVs of the invention have been modified for attenuation. In some embodiments, the sc VACV of the invention is designed or engineered to lack the viral thymidine kinase (TK) gene. In some embodiments, the scVACV of the invention is designed or engineered to lack the ribonucleotide reductase gene. In some embodiments, an scVACV of the invention is designed or engineered to lack vaccinia growth factor gene. In some embodiments, an scVACV of the invention is designed or engineered to lack the hemagglutinin gene.

In one aspect, the scVACVs of the invention are useful for treating a variety of neoplastic disorders and/or cancers. In some embodiments, the type of cancer includes, but is not limited to bone cancer, breast cancer, bladder cancer, cervical cancer, colorectal cancer, esophageal cancer, gliomas, gastric cancer, gastrointestinal cancer, head and neck cancer, hepatic cancer such as hepatocellular carcinoma, leukemia, lung cancer, lymphomas, ovarian cancer, pancreatic cancer, prostate cancer, renal cancer, skin cancer such as melanoma, testicular cancer, etc. or any other tumors or pre-neoplastic lesions that may be treated.

In another embodiment, the method further comprises detecting the presence of the administered scVACV, in the neoplastic disorder or cancer cell and/or in a sample from a subject administered an isolated or recombinant virus or composition described herein. For example, the subject can be tested prior to administration and/or following administration of the scVACV or composition described herein to assess for example the progression of the infection. In some embodiments, an scVACV of the disclosure comprises a detection cassette and detecting the presence of the administered chimeric VACV comprises detecting the detection cassette encoded protein. For example, wherein the detection cassette encodes a fluorescent protein, the subject or sample is imaged using a method for visualizing fluorescence.

In one aspect, the oncolytic formulations of the present invention comprise an effective amount of an scVACV of the disclosure, and a pharmaceutically acceptable carrier. The term "pharmaceutically acceptable" has been already explained above in the previous section.

In some embodiments, the composition of the invention is administered in a poxvirus treatment facility. In certain aspects, a poxvirus treatment facility is a facility wherein subjects in need of immunization or treatment with a composition or method of the disclosure may be immunized or treated in an environment such that they are sequestered from other subjects not intended to be immunized or treated or who might be potentially infected by the treated subject (e.g., caregivers and household members). In some embodiments, the subjects not intended to be immunized or potentially infected by the treated subject, include HIV patients, patients undergoing chemotherapy, patients undergoing treatment for cancer, rheumatologic disorders, or autoimmune disorders, patients who are undergoing or have received an organ or tissue transplant, patients with immune deficiencies, children, pregnant women, patients with atopic dermatitis, eczema, psoriasis, heart conditions, and patients on immunosuppressants, etc. In some embodiments, the poxvirus treatment facility is an orthopoxvirus treatment facility. In some embodiments, the poxvirus treatment facility is a smallpox treatment facility.

In some embodiments, the composition of the invention comprising scVACV is administered by a specialist in smallpox adverse events. In some embodiments, the smallpox adverse events include, but are not limited to, eczema vaccinatum, progressive vaccinia, postvaccinal encephalitis, myocarditis, and dilated cardiomyopathy.

Viral Vectors for Recombinant Gene Expression

In one aspect, the synthetic chimeric poxviruses (scVACVs) of the invention may be engineered to carry heterologous sequences. The heterologous sequences may be from a different poxvirus species or from any non-poxviral source. In one aspect, the heterologous sequences are antigenic epitopes that are selected from any non-poxviral source. A non-poxviral source, as used in the present application, refers to different organism than the poxvirus. In some embodiments, the recombinant virus may express one or more antigenic epitopes from a non-poxviral source including, but not limited to, *Plasmodium falciparum*, mycobacteria, *Bacillus anthracis, Vibrio cholerae*, MRSA, rhabdovirus, influenza virus, viruses of the family of flaviviruses, paramyxoviruses, hepatitis viruses, human immunodeficiency viruses, or from viruses causing hemorrhagic fever, such as hantaviruses or filoviruses, i.e., Ebola or Marburg virus. In another aspect, the heterologous sequences are antigenic epitopes from a different poxvirus species. These viral sequences can be used to modify the host spectrum or the immunogenicity of the scVACV.

In some embodiments, an scVACV of the invention may code for a heterologous gene/nucleic acid expressing a therapeutic nucleic acid (e.g., antisense nucleic acid) or a therapeutic peptide (e.g., peptide or protein with a desired biological activity).

In some embodiments, the expression of a heterologous nucleic acid sequence is preferably, but not exclusively, under the transcriptional control of a poxvirus promoter. In some embodiments, the heterologous nucleic acid sequence is preferably inserted into a non-essential region of the virus genome. Methods for inserting heterologous sequences into the poxviral genome are known to a person skilled in the art. In some embodiments, the heterologous nucleic acid is introduced by chemical synthesis. In an exemplary embodiment, a heterologous nucleic acid may be cloned into the VACV105/J2R locus of the scVACV of the disclosure.

An scVACV of one aspect of the present invention may be used for the introduction of a heterologous nucleic acid sequence into a target cell, the sequence being either homologous or heterologous to the target cell. The introduction of a heterologous nucleic acid sequence into a target cell may be used to produce in vitro heterologous peptides or polypeptides, and/or complete viruses encoded by the sequence. In one embodiment, this method comprises the infection of a host cell with the scVACV of the invention; cultivation of the infected host cell under suitable conditions; and isolation and/or enrichment of the peptide, protein and/or virus produced by the host cell. Suitable conditions for the culture of the scVACV-infected host cells, in order to express the heterologous peptide or polypeptide, are well known in the art and are variable depending on the host cell used (See for example, Molecular Cloning: A Laboratory Manual, second edition (Sambrook et al., 1989)).

It is to be understood that the embodiments of the present application which have been described are merely illustrative of some of the applications of the principles of the present application. Numerous modifications may be made by those skilled in the art based upon the teachings presented herein without departing from the true spirit and scope of the application.

The following examples are set forth as being representative of the present application. These examples are not to be construed as limiting the scope of the invention as these and other equivalent embodiments will be apparent in view of the present disclosure, figures, and accompanying embodiments.

EXAMPLES

Example 1. Selection and Design of Overlapping Fragments of the Viral Genome Synthetic Chimeric VACV ACAM2000 Containing VACV WR Strain Hairpin and Duplex Sequence (scVACV ACAM2000-WR DUP/HP)

Figure 1B:
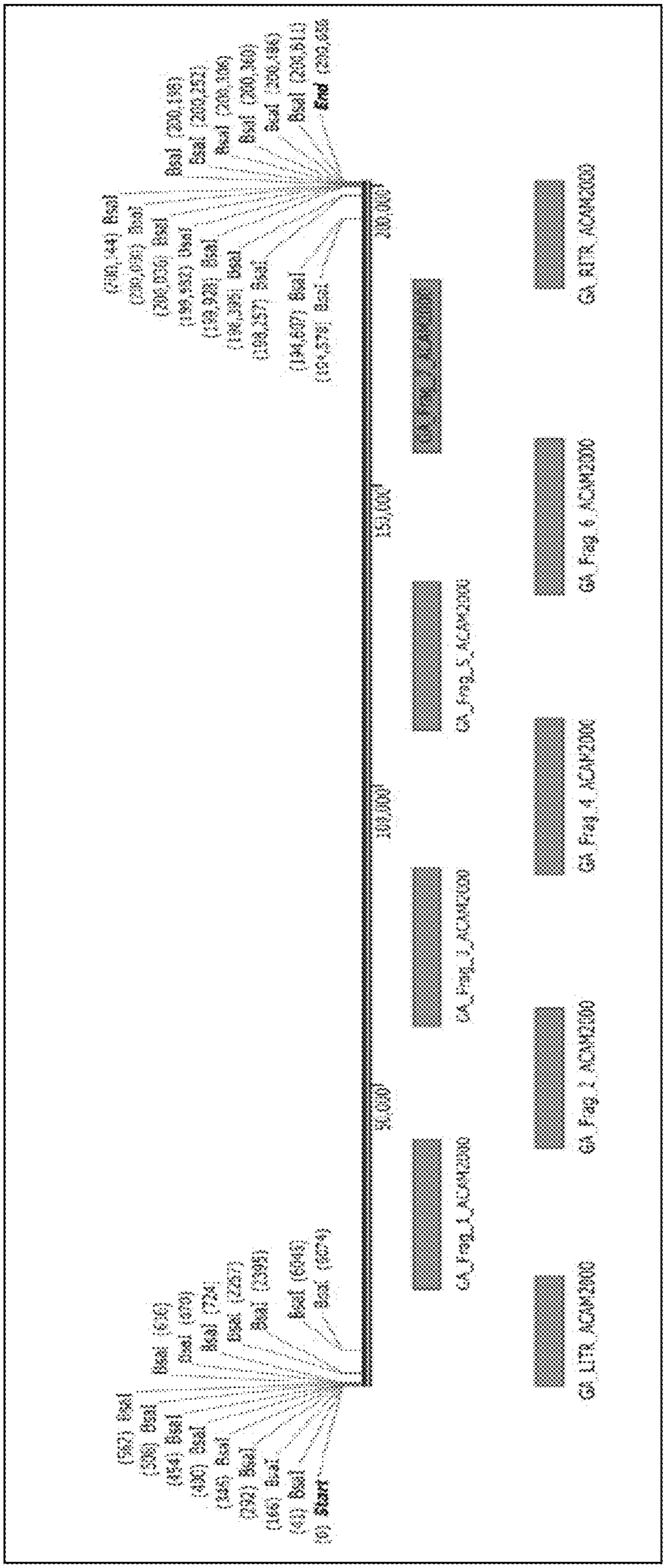

The design of the scVACV genome was based on the previously described genome sequence for VACV ACAM2000 [GenBank accession AY313847] (Osborne J D et al. Vaccine. 2007; 25 (52): 8807-32). The genome was divided into 9 overlapping fragments (FIG. 1). These fragments were designed so that they shared at least 1.0 kbp of overlapping sequence (i.e. homology) with each adjacent fragment, to provide sites where homologous recombination will drive the assembly of full-length genomes (Table 1). These overlapping sequences provided sufficient homology to accurately carry out recombination between the co-transfected fragments (Yao X D, Evans D H. Journal of Virology. 2003; 77 (13): 7281-90).

TABLE 1

The VACV ACAM2000 genome fragments used in this study. The size and the sequence within the VACV ACAM2000 genome [GenBank Accession AY313847] are described.

| Fragment Name | Size (bp) | Sequence |
|---|---|---|
| GA_LITR ACAM2000 | 18,525 | SEQ ID NO: 1 |
| GA_FRAG_1 ACAM2000 | 24,931 | SEQ ID NO: 2 |
| GA_FRAG_2 ACAM2000 | 23,333 | SEQ ID NO: 3 |
| GA_FRAG_3 ACAM2000 | 26,445 | SEQ ID NO: 4 |
| GA_FRAG_4 ACAM2000 | 26,077 | SEQ ID NO: 5 |
| GA_FRAG_5 ACAM2000 | 24,671 | SEQ ID NO: 6 |
| GA_FRAG_6 ACAM2000 | 25,970 | SEQ ID NO: 7 |
| GA_FRAG_7 ACAM2000 | 28,837 | SEQ ID NO: 8 |
| GA_RITR ACAM2000 | 17,641 | SEQ ID NO: 9 |

To assist with sub-cloning of these fragments, AarI and BsaI restriction sites were silently mutated in all the fragments, except for the two ITR-encoding fragments. The BsaI restriction sites in the two ITR-encoding fragments were not mutated, in case these regions contain nucleotide sequence-specific recognition sites that are important for efficient DNA replication and concatemer resolution.

A YFP/gpt cassette under the control of a poxvirus early late promoter was introduced into the thymidine kinase locus, so that reactivation of VACV ACAM2000 (VACV ACAM2000 YFP-gpt:: 105) was easy to visualize under a fluorescence microscope. The gpt locus also provided a potential tool for selecting reactivated viruses using drug selection.

Figure 2A:
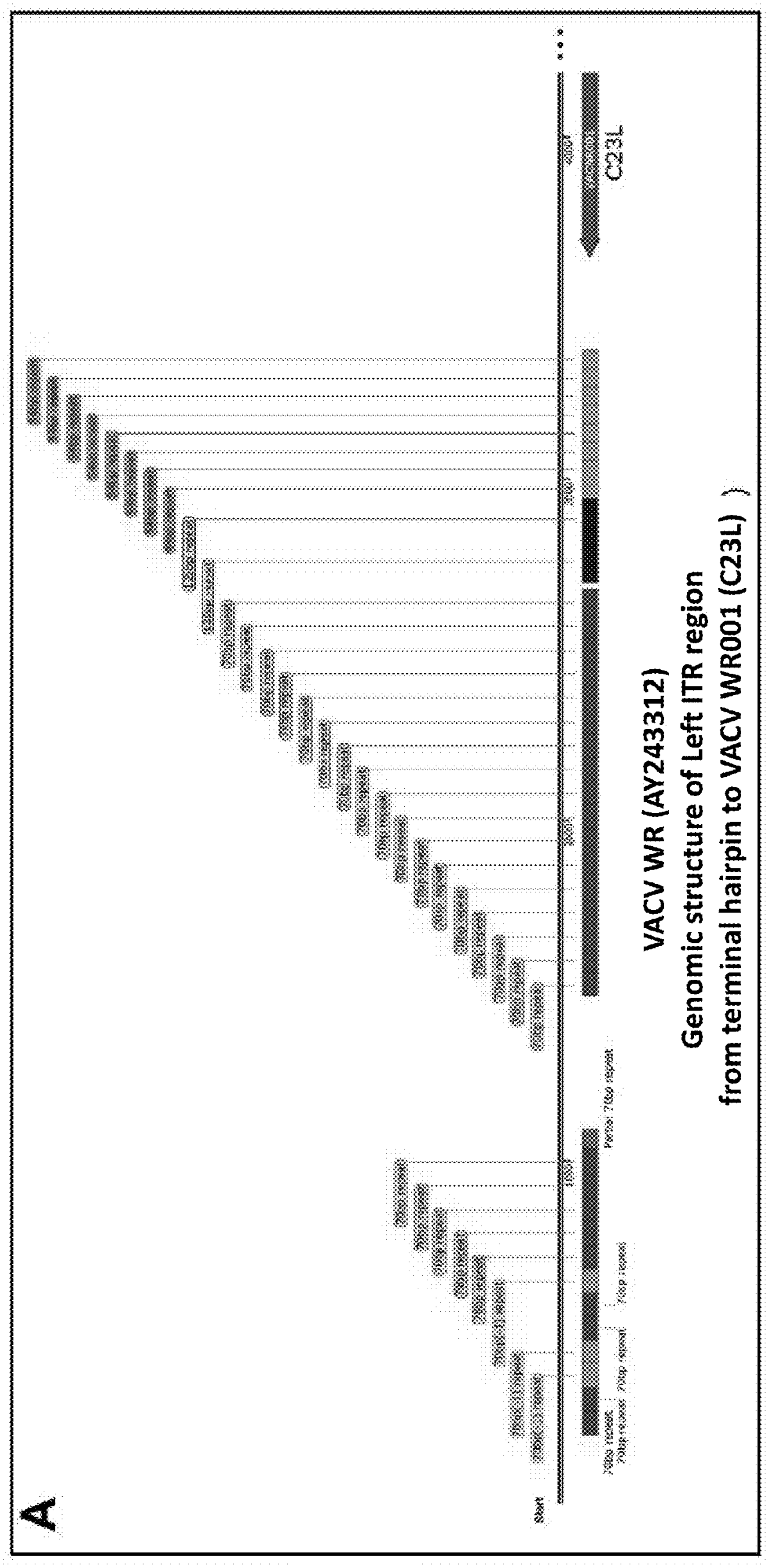
FIG. 2A-2C. Detailed schematic representation of the first ~1500-3000 bp of the published genomes of (A) VACV WR strain and (B) VACV ACAM2000. The tandem repeat regions are indicated in red (70 bp repeat), blue (125 bp repeat) and green (54 bp repeat) boxes. The ORF corresponding to gene C23L is also indicated in each of the genomes. (C) Schematic representation of the direct repeat region containing 70 bp repeat sequences in VACV WR. This sequence was synthesized to contain a SapI restriction site at the 5' terminus and an NheI restriction site at the 3' terminus to ligate the hairpin/duplex piece and the VACV ACAM2000 ITR fragments, respectively.
Figure 2B:
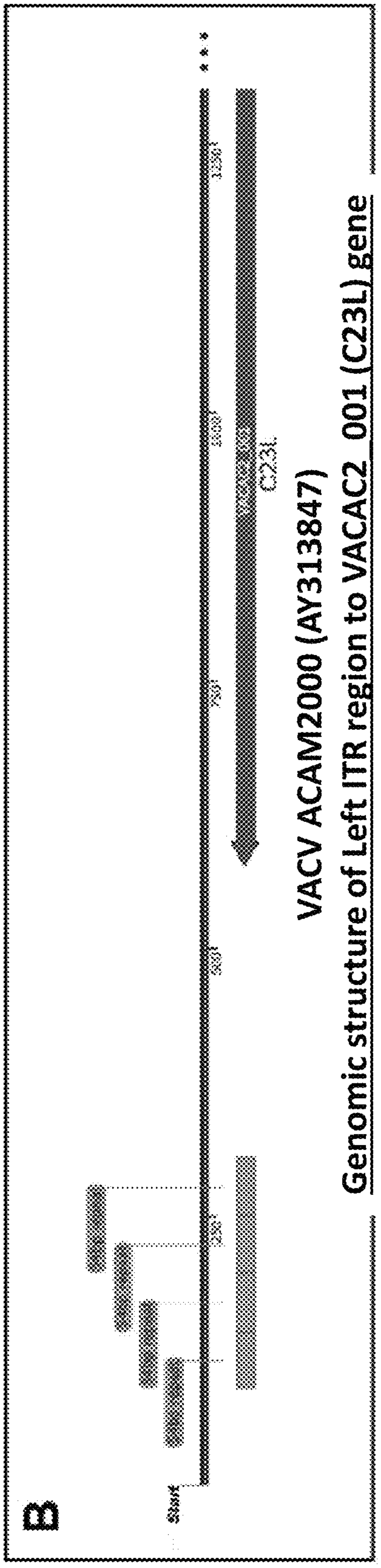

Traditionally, the terminal hairpins have been difficult to clone and sequence, hence, it is not surprising that the published sequence of the VACV ACAM2000 genome is not complete. Upon inspection of the very terminal region of the published VACV ACAM2000 strain, there appeared to be some differences between ACAM2000 and the very well characterized VACV WR strain (Genbank Accession #AY243312) (FIG. 2). In the WR strain, there are 70 bp tandem repeat sequences immediately downstream of the covalently closed hairpin loop that is located at the terminal 5' and 3' termini of the VACV genome. These are followed by two 125 bp repeat sequences and eight 54 bp repeat sequences (FIG. 2A). In the published VACV ACAM2000 sequence, however, only four 54 bp repeat sequences were identified (FIG. 2B). The presence of the 70 bp, 125 bp, and 54 bp repeat sequences was confirmed in a wild-type isolate of VACV ACAM2000 after sequencing (using Illumina), indicating that the current published sequence of ACAM2000 is incomplete. Due to the short-read lengths of the Illumina reads (<300 nucleotides), the inventors were unable to accurately determine what the actual ACAM2000 genomic sequence was in this ~ 3 kbp. Instead, the inventors decided to recreate a VACV ACAM2000 virus that had a similar sequence to VACV WR from the terminal hairpin to just before the stop codon of the C23L gene (FIG. 2). This included both the 125 bp and 54 bp tandem repeat sequences that, although not included in the published ACAM2000 sequence, were detected when next generation Illumina sequencing of the wtVACV ACAM2000 was performed. At the 5' termini of the modified VACV ACAM2000 left and right ITR fragments an NheI restriction site was also included, that would allow to directly attach the 70 bp tandem repeat sequence to the ITR ends (discussed on Example 2). The F and S terminal hairpin loop sequences of the wtVACV ACAM2000 are shown in FIG. 9 and SEQ ID NO: 20 and 19, respectively.

Synthetic Chimeric VACV ACAM2000 Containing VACV ACAM2000 Strain Hairpin and Duplex Sequence (scVACV ACAM2000-ACAM2000 DUP/HP)

The design of the scVACV genome was based on the previously described genome sequence for VACV ACAM2000 [GenBank accession AY313847] (Osborne J D et al. Vaccine. 2007; 25 (52): 8807-32). The genome was divided into 9 overlapping fragments (FIG. 1). These fragments were designed so that they shared at least 1.0 kbp of overlapping sequence (i.e. homology) with each adjacent fragment, to provide sites where homologous recombination will drive the assembly of full-length genomes (Table 1). These overlapping sequences provided sufficient homology to accurately carry out recombination between the co-transfected fragments (Yao X D, Evans D H. Journal of Virology. 2003; 77 (13): 7281-90).

To assist with sub-cloning of these fragments, AarI and BsaI restriction sites were silently mutated in all the fragments, except for the two ITR-encoding fragments. The BsaI restriction sites in the two ITR-encoding fragments were not mutated, in case these regions contain nucleotide sequence-specific recognition sites that are important for efficient DNA replication and concatemer resolution.

A YFP/gpt cassette under the control of a poxvirus early late promoter was introduced into the thymidine kinase locus, so that reactivation of VACV ACAM2000 (VACV ACAM2000 YFP-gpt:: 105) was easy to visualize under a fluorescence microscope. The gpt locus also provided a potential tool for selecting reactivated viruses using drug selection.

The F and S terminal hairpin loop sequences of the wtVACV ACAM2000 are shown in FIG. 9 and SEQ ID NO: 20 and 19, respectively.

Example 2

Figure 2C:
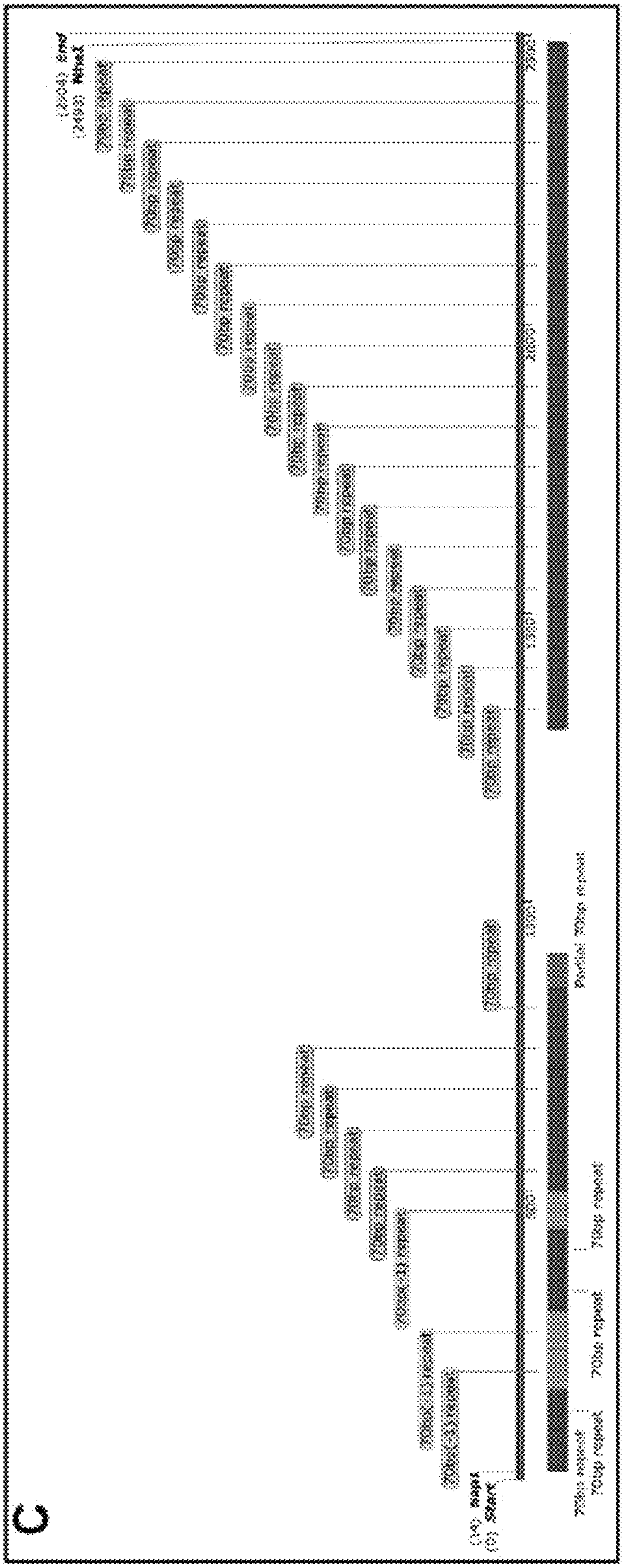
Figure 3B:
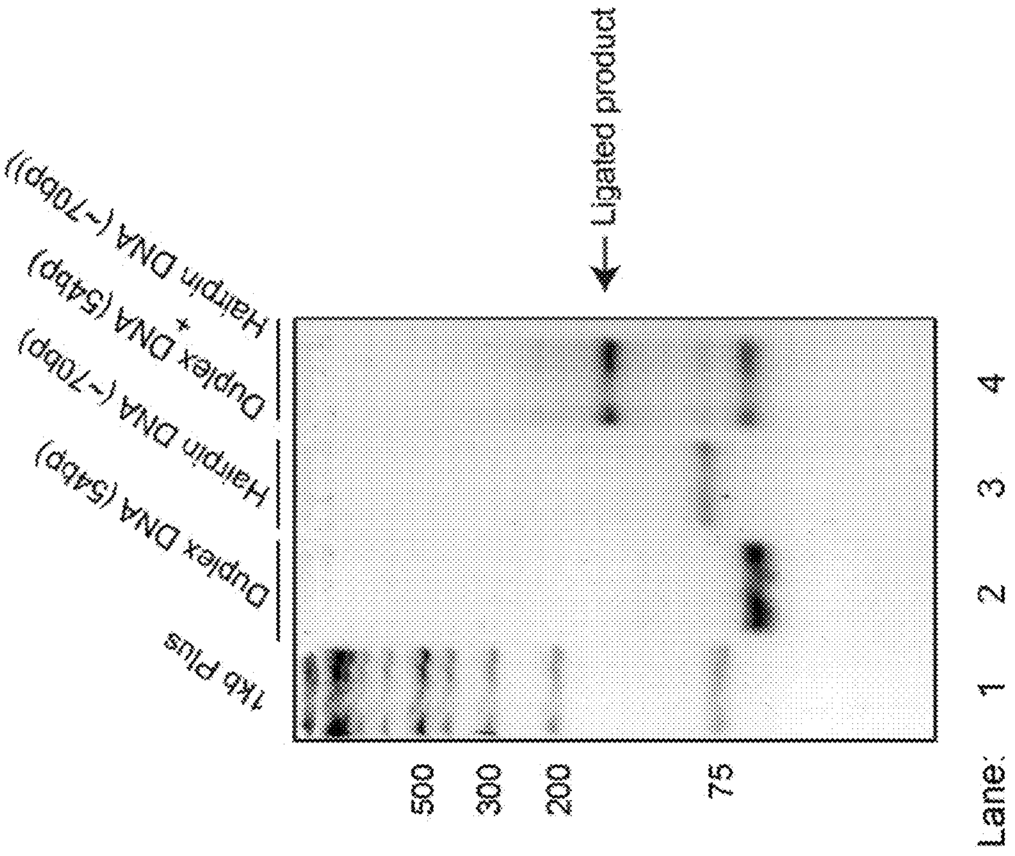
Figure 4:
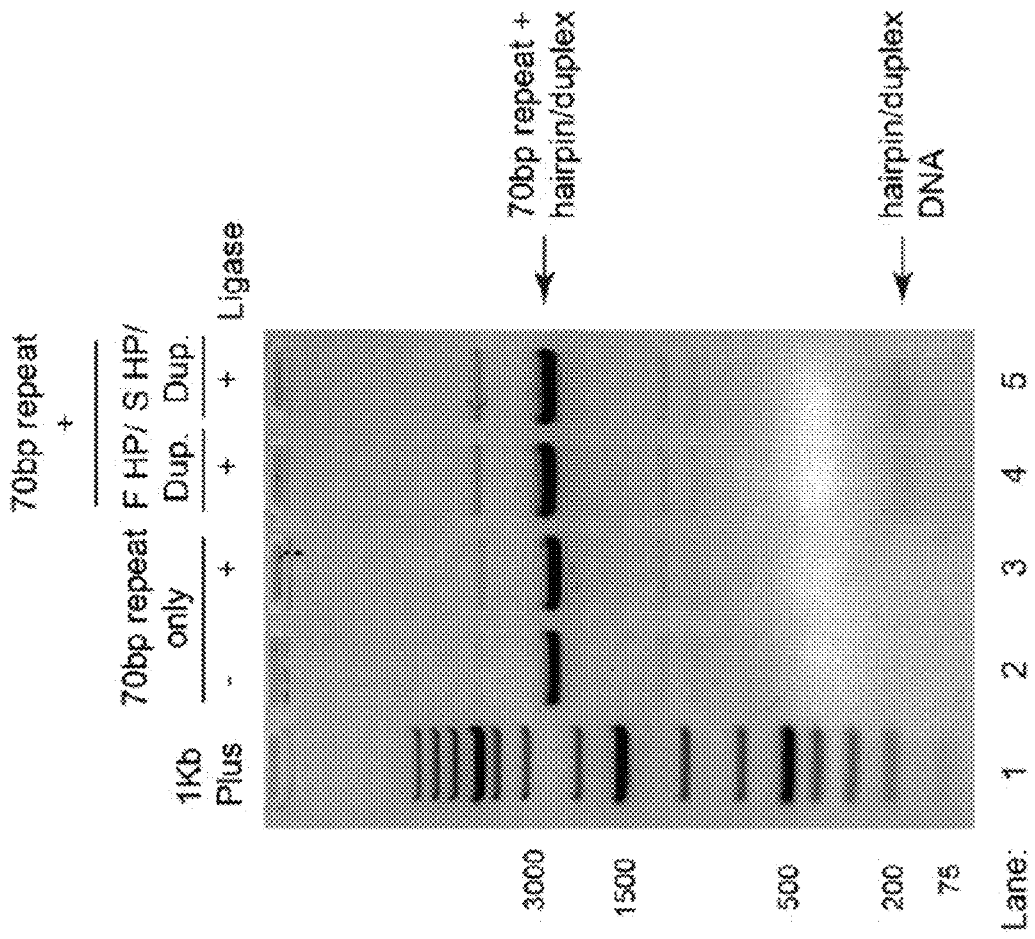
FIG. 4. Ligation of SapI/NheI digested 70 bp repeat fragment to WR strain hairpin/duplex DNA fragment. The 70 bp repeat fragment was digested with SapI and NheI and then gel-purified prior to ligating with the hairpin/duplex DNA fragments at a molar ratio of 5:1 of hairpin/duplex DNA to the 70 bp fragment. The shift upwards in the band at approximately 2300 bp in lane 4 and lane 5 indicates the successful addition of the hairpin/duplex fragment. These bands were subsequently gel extracted from the gel prior to ligation to the digested VACV ACAM2000 ITR fragments.

Ligation of the VACV WR F and S Terminal Hairpin Loops onto the VACV ACAM2000 Right and Left ITR Fragments A 70 bp repeat fragment that was identical to the VACV WR strain was synthesized (FIG. 2C; SEQ ID NO: 10). SapI and NheI restriction sites were included at the 5' and 3' terminus of the 70 bp tandem repeat fragment to facilitate the ligation onto the VACV WR hairpin sequence and the VACV ACAM2000 right and left ITR fragments, respectively. Before the VACV WR terminal hairpin loops could be ligated onto the 70 bp tandem repeat fragment, the loop had to be extended an additional 58 bp using a duplex sequence synthesized by IDT Technologies (FIG. 3A). This was due to the extra sequence being immediately downstream of the concatemer resolution site, prior to the first 70 bp repeat sequence found in VACV strain WR. The duplex sequence was produced by synthesizing two single-stranded DNA molecules that, when annealed together, would produce a duplex DNA molecule with a 5'-TGT overhang at the 5' end and a 5'-GGT overhang at the 3' end (FIG. 3A; SEQ ID NO: 11 and SEQ ID NO: 12). Since the VACV WR F and S terminal hairpin loops generate a 3'-ACA overhang at their terminal loops, the 58 bp duplex was ligated to the hairpins to generate an ~130 bp terminal hairpin loop that looked identical to the sequence found in the VACV WR strain up until the beginning of the 70 bp repeat sequence (FIG. 3B). This hairpin/duplex fragment was gel purified and then subsequently ligated onto the SapI digested end of the 70 bp repeat fragment. Digesting the 70 bp tandem repeat fragment with SapI created a three-base overhang (5'-CCA), complementary to the 5'GGT overhang in the terminal hairpin/duplex structure. The 70 bp tandem repeat was mixed with either an F terminal hairpin/duplex structure (FIG. 4, lane 4) or a S terminal hairpin/duplex structure (FIG. 4, lane 5) at a ~5-fold molar excess relative to the 70 bp tandem repeat fragment in the presence of DNA ligase. This produced an upward shift in the DNA electrophoresis gel compared to the 70 bp only reaction (FIG. 4, lane 3), indicating that the terminal hairpin/duplex was successfully ligated onto the 70 bp tandem repeat fragment (FIG. 4).

This terminal hairpin/duplex/70 bp tandem repeat fragment was subsequently ligated onto the 70 bp ACAM2000 left or right ITR fragment that had been previously modified at their terminal ends to include the NheI restriction site. When this fragment was digested, a 5'-CTAG overhang was left at their 5' termini. At the 3' terminus of the 70 bp tandem repeat fragment, the NheI site is used to directly ligate this fragment to the LITR and RITR regions of the VACV ACAM2000 DNA fragments. Following digestion of the VACV ACAM2000 left and right ITR fragments, the S terminal hairpin/duplex/70 bp tandem repeat fragment or the F terminal hairpin/duplex/70 bp tandem repeat fragment were separately ligated to either the left or right ITR fragment using DNA ligase at a 1:1 molar ratio overnight at 16° C. The DNA ligase was subsequently heat inactivated at 65° C. prior to being transfected into Shope Fibroma virus (SFV)-infected BGMK cells.

Ligation of the VACV ACAM2000 F and S Terminal Hairpin Loops onto the VACV ACAM2000 Right and Left ITR Fragments A 70 bp repeat fragment that was identical to the VACV ACAM2000 strain was synthesized. SapI and NheI restriction sites were included at the 5' and 3' terminus of the 70 bp tandem repeat fragment to facilitate the ligation onto the VACV ACAM2000 hairpin sequence and the VACV ACAM2000 right and left ITR fragments, respectively. Before the VACV ACAM2000 terminal hairpin loops could be ligated onto the 70 bp tandem repeat fragment, the loop had to be extended an additional 58 bp using a duplex sequence synthesized by IDT Technologies. This was due to the extra sequence being immediately downstream of the concatemer resolution site, prior to the first 70 bp repeat sequence found in VACV strain ACAM2000. The duplex sequence was produced by synthesizing two single-stranded DNA molecules that, when annealed together, would produce a duplex DNA molecule with a 5'-TGT overhang at the 5' end and a 5'-GGT overhang at the 3' end (SEQ ID NO: 21 and SEQ ID NO: 22). Since the VACV ACAM2000 F and S terminal hairpin loops generate a 3'-ACA overhang at their terminal loops, the 58 bp duplex was ligated to the hairpins to generate an ~130 bp terminal hairpin loop. This hairpin/duplex fragment was gel purified and then subsequently ligated onto the SapI digested end of the 70 bp repeat fragment. Digesting the 70 bp tandem repeat fragment with SapI created a three-base overhang (5'-CCA), complementary to the 5'GGT overhang in the terminal hairpin/duplex structure. The 70 bp tandem repeat was mixed with either an F terminal hairpin/duplex structure or a S terminal hairpin/duplex structure at a ~5-fold molar excess relative to the 70 bp tandem repeat fragment in the presence of DNA ligase. This produced an upward shift in the DNA electrophoresis gel compared to the 70 bp only reaction, indicating that the terminal hairpin/duplex was successfully ligated onto the 70 bp tandem repeat fragment.

This terminal hairpin/duplex/70 bp tandem repeat fragment was subsequently ligated onto the ACAM2000 left or right ITR fragment that had been previously modified at their terminal ends to include the NheI restriction site. When this left or right ITR fragment was digested, a 5'-CTAG overhang was left at their 5' termini. At the 3' terminus of the 70 bp tandem repeat fragment, the NheI site is used to directly ligate this fragment to the LITR and RITR regions of the VACV ACAM2000 DNA fragments. Following digestion of the VACV ACAM2000 left and right ITR fragments, the S terminal hairpin/duplex/70 bp tandem repeat fragment or the F terminal hairpin/duplex/70 bp tandem repeat fragment were separately ligated to either the left or right ITR fragment using DNA ligase at a 1:1 molar ratio overnight at 16° C. The DNA ligase was subsequently heat inactivated at 65° C. prior to being transfected into Shope Fibroma virus (SFV)-infected BGMK cells.

Example 3. Preparation of the VACV ACAM2000 Overlapping DNA Fragments

Figure 5:
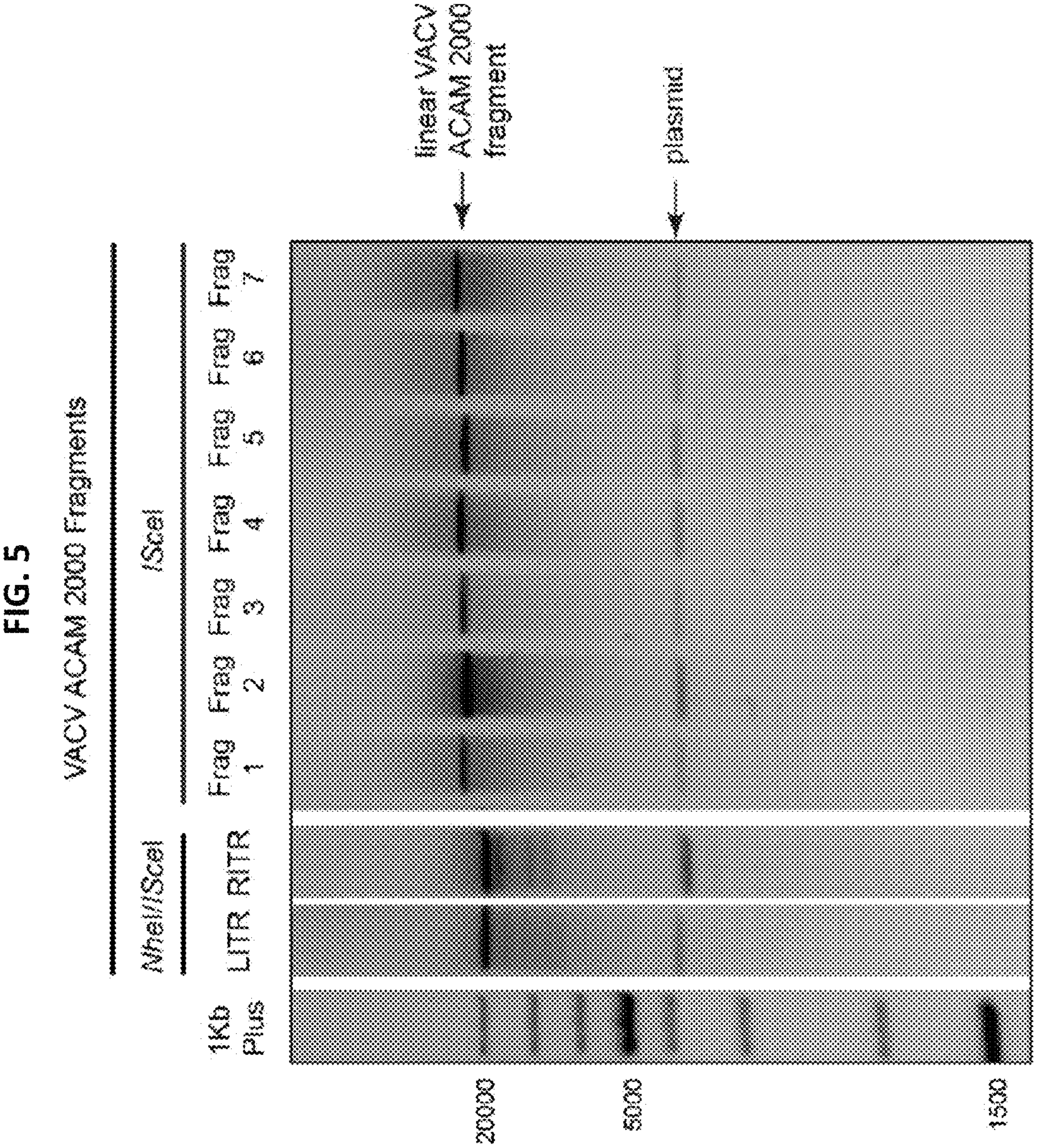
FIG. 5. Digestion of scVACV ACAM2000 fragments. ITR fragments were digested with both NheI/I-SceI for 2 h at 37° C. followed by dephosphorylation with alkaline phosphatase to remove the phosphate group and facilitate more efficient ligation of this fragment to the terminal hairpin loop/duplex/70 bp tandem repeat fragment. The other scVACV ACAM2000 DNA plasmids were linearized with I-SceI for 2 h at 37° C., followed by heat inactivation of the restriction enzyme at 65° C. for 10 minutes.

Each of the VACV ACAM2000 overlapping DNA fragments in Table 1 were cloned into a plasmid provided from GeneArt using the restriction enzyme I-SceI. Prior to transfection of these synthetic DNA fragments into BGMK cells, the plasmids were digested with I-SceI and the products were run on a gel to confirm that the DNA fragments were successfully linearized (FIG. 5). Following digestion at 37° C. for 2 h, the reactions were subsequently heat-inactivated at 65° C. Samples were stored on ice or at 4° C. until the terminal hairpin/duplex/70 bp tandem repeat/ITR fragments were created (as described above).

Example 4. Reactivation from Chemically Synthesized dsDNA Fragments

SFV strain Kasza and BSC-40 were originally obtained from the American Type Culture Collection. Buffalo green monkey kidney (BGMK) cells were obtained from G. McFadden (University of Florida). BSC-40 and BGMK cells are propagated at 37° C. in 5% $CO_2$ in minimal essential medium (MEM) supplemented with L-glutamine, nonessential amino acids, sodium pyruvate, antibiotics and antimycotics, and 5% fetal calf serum (FCS; ThermoFisher Scientific).

Reactivation of scVACV ACAM2000-WR DUP/HP or scVACV ACAM2000-ACAM2000 DUP/HP in Shope Fibroma Virus-Infected Cells Buffalo green monkey kidney (BGMK) cells were grown in MEM containing 60 mm tissue-culture dishes until they reached approximately 80% confluency. Cells were infected with Shope Fibroma Virus (SFV) in serum-free MEM at a MOI of 0.5 for 1 h at 37° C. The inoculum was replaced with 3 ml of warmed MEM containing 5% FCS and returned to the incubator for an additional hour. Meanwhile, transfection reactions were set up as follows. After approximately 2 h at 37° C., the linearized VACV ACAM2000 fragments were transfected (using Lipofectamine 2000) into the SFV-infected BGMK cells at molar equivalents based on the length of each fragment that comprised the VACV ACAM2000 genome. Different amounts of total DNA were tried and 5, 6, and 7.5 μg of DNA were able to successfully reactivate ACAM2000 from these overlapping DNA fragments. The complexes were incubated at room temperature for 10 minutes and then added dropwise to the BGMK cells previously infected with SFV. Approximately 24 h post infection, the media was replaced with fresh MEM containing 5% FCS. The cells were cultured for an additional 3-4 days (total of 4-5 days) at 37° C.

Virus particles were recovered by scraping the infected cells into the cell culture medium and performing three cycles of freezing and thawing. The crude extract was diluted 10-2 in serum-free MEM and 4 ml of the inoculum is plated on 9-16 150 mm tissue culture plates of BSC-40 cells to recover reactivated scVACV ACAM2000 YFP-gpt:: 105. One hour post infection, the inoculum was replaced with MEM containing 5% FCS and 0.9% Noble Agar. Yellow fluorescent plaques were visualized under an inverted microscope and individual plaques were picked for further analysis. scVACV ACAM2000 YFP-gpt:: 105 plaques were plaque purified three times with yellow fluorescence selection.

After 4 days, the infected plates containing both SFV and VACV ACAM2000 clones were harvested, followed by three freeze thaw cycles to release virus, and then serially diluted and plated onto BSC-40 cells, which preferentially promote growth of the VACV ACAM2000 viruses compared to the SFV viruses. Three rounds of plaque purification were performed followed by a bulkup of the virus stocks in 10-150 mm tissue culture plates. The virus was subsequently lysed from these cells and separated on a 36% sucrose cushion, followed by further purification on a 24%-40% sucrose density gradient. Genomic DNA was isolated from these purified genomes and next generation Illumina sequencing was performed to confirm the sequence of the synthetic virus genomes.

Example 4. Growth Properties Compared to Wild Type ACAM2000 Virus

Figure 6:
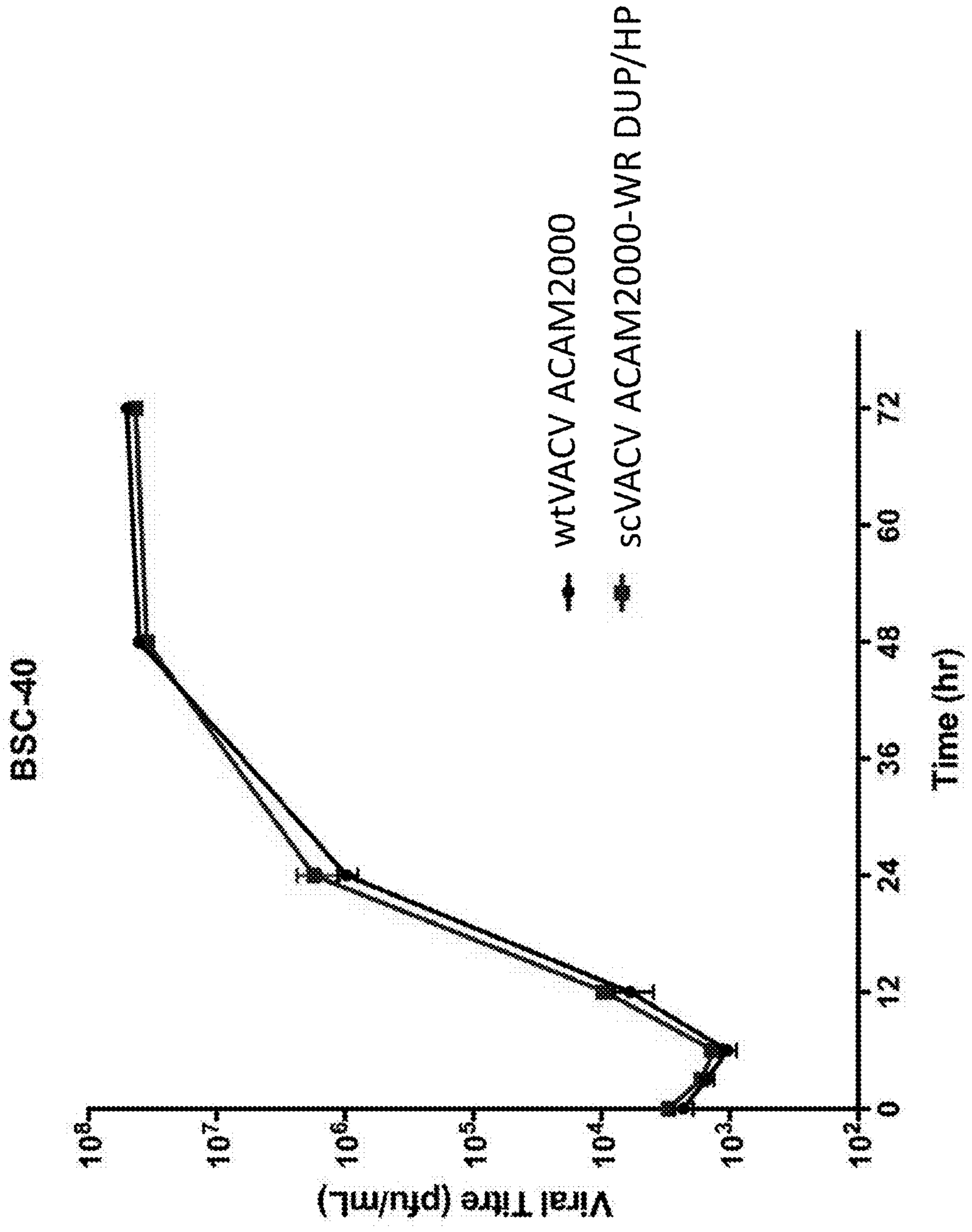
FIG. 6. Growth properties of scVACV ACAM2000-WR DUP/HP in vitro. Multi-step growth kinetics measured in monkey kidney epithelial cells (BSC-40). The cells were infected at a multiplicity of infection 0.03, the virus was harvested at the indicated times, and the virus was titrated on BSC-40 cells. The data represent three independent experiments. The error bars indicate standard error of the mean (SEM).

In vitro multi-step growth curves of the isolated synthetic chimeric VACV ACAM2000-WR DUP/HP, scVACV ACAM2000-ACAM2000 DUP/HP and the wild type VACV ACAM2000 virus were performed in monkey kidney epithelial (BSC-40) cells. The cells were infected at a multiplicity of infection 0.03, the virus was harvested at the indicated times (3 h, 6 h, 12 h, 21 h, 48 h and 72 h), and the virus was titrated on BSC-40 cells. The data shown in FIG. 6 represent three independent experiments. As shown in FIG. 6, scVACV ACAM2000-WR DUP/HP and wtVACV ACAM2000 viruses grew with indistinguishable growth kinetics over a 72 h period.

Figure 7:
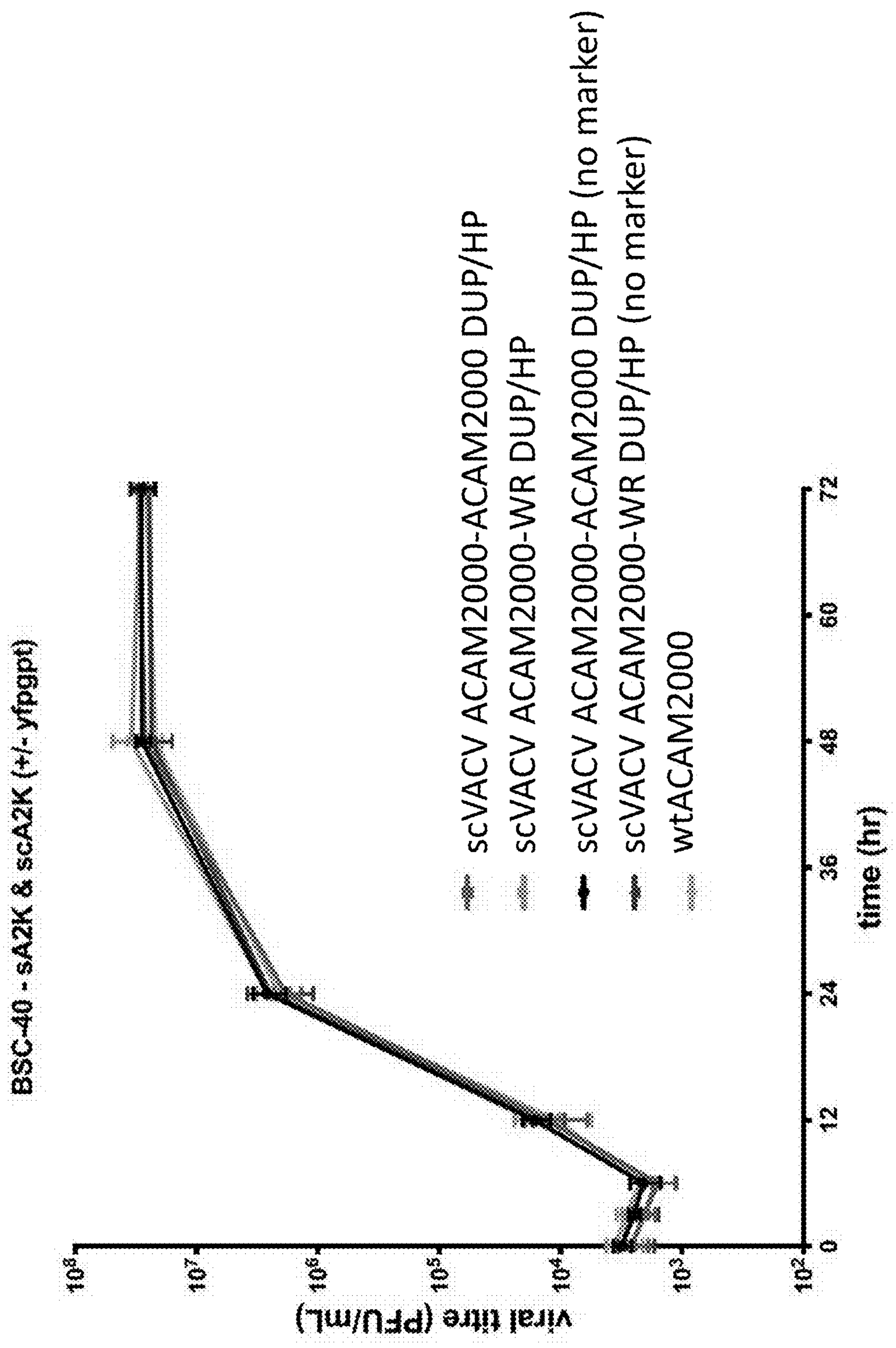
FIG. 7. Growth properties of scVACV ACAM2000-WR DUP/HP and scVACV ACAM2000-ACAM2000 DUP/HP in vitro, compared to scVACV ACAM2000-WR DUP/HP and scVACV ACAM2000-ACAM2000 DUP/HP where the YFP-gpt marker has been replaced with the J2R gene sequence (VAC_WRAJ2R) and wtVACV ACAM2000. Multi-step growth kinetics measured in monkey kidney epithelial cells (BSC-40). The cells were infected at a multiplicity of infection 0.03, the virus was harvested at the indicated times, and the virus was titrated on BSC-cells. The error bars indicate standard error of the mean (SEM).

A comparison between the growth curves of scVACV ACAM2000-WR DUP/HP(YFP-gpt marker), scVACV ACAM2000-ACAM2000 DUP/HP(YFP-gpt marker), scVACV ACAM2000-WR DUP/HP (no marker) (YFP-gpt marker replaced with J2R gene sequence), scVACV ACAM2000-ACAM2000 DUP/HP (no marker) (YFP-gpt marker replaced with J2R gene sequence) and wtVACV ACAM2000, shows that there is statistically no difference in the growth properties of these viruses as compared to the wtACAM2000 VACV (FIG. 7).

Figure 8:
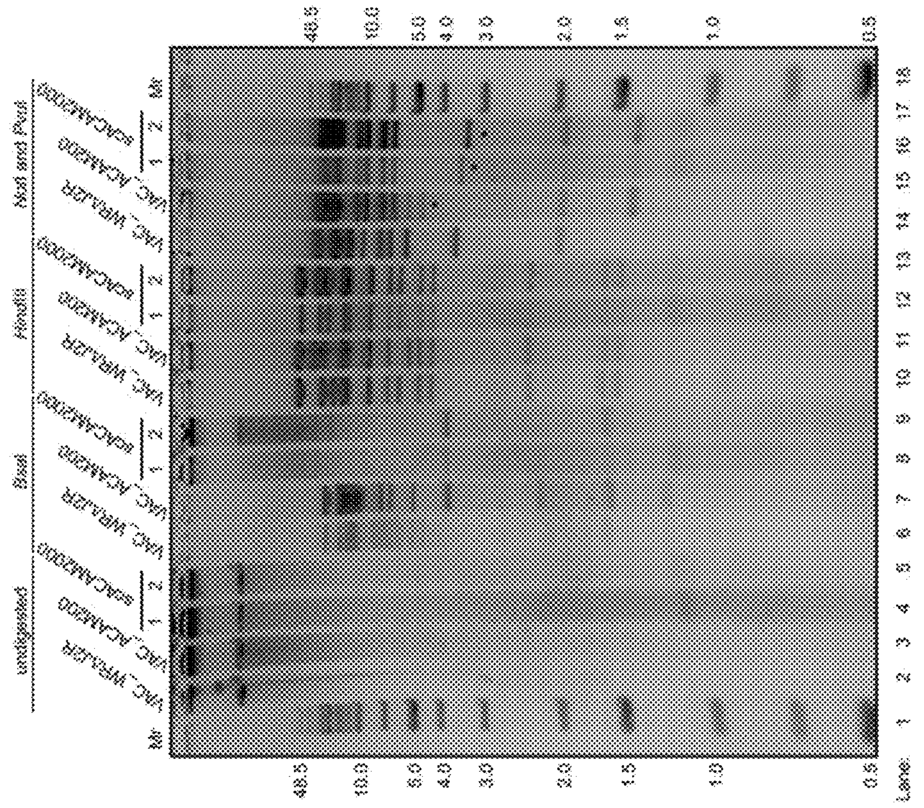
FIG. 8. Restriction endonuclease mapping of reactivated scVACV ACAM2000-WR DUP/HP clones. Pulsed field gel electrophoretic analysis. Two independent scVACV ACAM2000-WR DUP/HP clones plus a VACV WR control where the YFP-gpt marker has been replaced with the J2R gene sequence (VAC_WRAJ2R) and a wtVACV ACAM2000 control (VAC_ACAM2000) were purified and then left either undigested, digested with BsaI, HindIII, or NotI and PvuI. The expected absence of nearly all of the BsaI sites in the scVACV ACAM2000 clones was apparent. Minor differences in the HindIII digested scVACV ACAM2000 genomic DNA compared to VAC_WRAJ2R and VACV_ACAM2000 were observed. Genomic DNA digested with NotI and PvuI excises the 70 bp tandem repeat fragments found at the left and right ITR sequences. In VAC_WRAJ2R the ~size of the 70 bp repeats is close to 3.6 kbp. Interestingly, in the two independent scVACV ACAM2000 clones two different sized bands corresponding to the 70 bp tandem repeat were observed (marked with an *), even though a full-length 70 bp tandem repeat element was ligated to the ITR fragments. When ACAM2000 genomic DNA was digested with NotI and PvuI, a band at ~4.7 kbp was observed, which may indicate the size of the 70 bp repeats in ACAM2000.

Example 5. Confirmation of scVACV ACAM2000-WR DUP/HP YFP-Gpt:: 105 Genome Sequence by PCR and Restriction Fragment Analysis Further analysis of scVACV ACAM2000 YFP-gpt:: 105 genomes by restriction digestion followed by pulse-field gel electrophoresis (PFGE) was carried out on genomic DNA isolated using sucrose gradient purification (Yao X D, Evans D H. Methods Mol Biol. 2004; 269:51-64). Two independent scVACV ACAM2000-WR DUP/HP clones plus a VACV_WRAJ2R control where the J2R gene sequence has been replaced with a YFP-gpt marker, and a wtVACV ACAM2000 control (VAC_ACAM2000) were purified and then left either undigested, digested with BsaI, HindIII, or NotI and PvuI. The isolated genomic DNA from both scVACV ACAM2000-WR DUP/HP and wtVACV ACAM2000 were digested with BsaI and HindIII. Since most of the BsaI sites in the scVACV ACAM2000 genome had been silently mutated, a mostly intact ~200kbp fragment was observed following BsaI digestion (FIG. 8, lanes 8 and 9). This is unlike the wtVACV ACAM2000 and wtVACV WR control (VAC_WRAJ2R) genomes, which had been extensively digested when treated with BsaI (FIG. 8, lanes 6 and 7). To confirm that the scVACV ACAM2000-WR DUP/HP genome could still be digested with another enzyme, these genomes were digested with HindIII, which produced numerous bands from the scVACVACAM2000-WR DUP/HP clones (FIG. 8, lanes 12 and 13). To confirm the presence of the 70 bp tandem repeat elements within the ITR regions, the genomic DNA was digested with NotI and PvuI (FIG. 8, lanes 14 to 17).

In the wtVACV WR control (VAC_WRAJ2R) sample, a band at about 3.6 kbp (marked with asterisks) was detected, which encompasses all of the 70 bp tandem repeats in the WR strain of VAC. Given that the VACV WR strain used as a template to design the synthesis of the ITR repeat elements, it was expected that some bands were detected in the Not/PvuI treated scVACVACAM2000 clones at close to the same size as what was seen in strain WR. When the two scVACV ACAM2000-WR DUP/HP clones were compared, differences in the size of this region were observed, suggesting that not all of the 70 bp repeats were incorporated into each reconstructed genome (FIG. 7, lanes 16 and 17). This is not unexpected, given that others have shown that these repeat elements can expand and contract under selective pressure in cell culture (Paez and Esteban (1988). Virology; 163 (1): 145-54).

Overall, in vitro analysis of the scVACV ACAM2000-WR DUP/HP YFP-gpt:: 105 genome suggested that reactivation of VACV ACAM2000-WR DUP/HP from chemically synthesized DNA fragments was successful and that scVACV ACAM2000-WR DUP/HP virus behaved in vitro like the wtVACV ACAM2000 virus.

Example 6. Confirmation of scVACV ACAM2000 YFP-Gpt:: 105 Genome Sequence by Whole Genome Sequence Analysis Two clones of scVACV ACAM2000-WR DUP/HP and two clones of scVACV ACAM2000-ACAM2000 DUP/HP were sequenced. The Illumina reads were de novo assembled using CLC Genomics Workstation (version 11) with a word size of 35 or 61. Assembled contigs were then imported into Snapgene software and aligned onto a reference sequence of the expected scACAM2000 sequence based on the synthetic fragments that were provided by GeneArt.

For clone 1 of scVACV ACAM2000-WR DUP/HP, contig 1 was 16,317 bp, and corresponded to most of the ITR region (except for the tandem repeat sequences. Contig 2 was 167,020 bp, and aligned with the central conserved region of the genome (nucleotide positions 19,467 to 186, 486). For clone 2 of scVACV ACAM2000-WR DUP/HP, contig 3 was 16,322 bp, and corresponded to most of the ITR region (except for the tandem repeat sequences. Contig 1 was 167,020 bp, and aligned with the central conserved region of the genome (nucleotide positions 19,467 to 186, 486). There was a single nucleotide substitution (C to A) at nucleotide position 136791 of the contig of clone 2. This corresponded to nucleotide position 156,256 in the scACAM2000 genome sequence and resulted in an amino acid change from an Asp to Tyr in VAC_ACAM2000_177 (A41L).

For clone 1 of scVACV ACAM2000-ACAM2000 DUP/HP, contig 1 was 167,020 bp, and aligned with the central conserved region of the genome (nucleotide positions 19,469 to 186,488). Contig 2 was 16,150 bp, and corresponded to most of the ITR region (except for tandem repeat sequences). When this contig was mapped to the reference genome in Snapgene, gaps in the sequence were observed at positions 2633 to 3417 and nucleotide positions 15,175 to 15,220. The first gap region corresponds to the 54 bp repeat region and it is most likely due to the inability to accurately assemble these regions using de novo assembly tools. Mapping of the raw Illumina reads directly to the reference genome did not result in any gaps within either region. For clone 2 of scVACV ACAM2000-ACAM2000DUP/HP, contig 1 was 16,075 bp, and corresponded to most of the ITR region (except the tandem repeat sequences). Contig 2 was 167,078 bp and aligned with the central conserved region of the genome (nucleotide positions 19,469 to 186,546). There was a gap observed in contig 2 from nucleotide position 15,176 to 15,220. Mapping of the raw Illumina reads directly to the reference genome did not result in any gaps within this region, however. Neither sequenced clone of scVACV ACAM2000-ACAM2000 DUP/HP displayed any other nucleotide mutations at any position within the genome.

The Illumina reads were also mapped to a reference map in CLC Genomics. The Illumina reads covered the full length of the reference sequence with an average coverage of 1925 and 2533, for clone 1 and 2 of scVACV ACAM2000-WR DUP/HP, respectively, and an average coverage of 2195 and 1602 for clone 1 and 2 of scVACV ACAM2000-ACAM2000 DUP/HP, respectively.

Overall, the sequencing data corroborates the in vitro genomic analysis data and confirms that scVACV ACAM20000-WR DUP/HP and scVACV ACAM2000-ACAM2000 DUP/HP were successfully reactivated in SFV-infected cells.

Example 7. Removal of YFP/Gpt Selection Marker

Following reactivation of the scVACV ACAM2000 YFP-gpt:: 105, the yfp/gpt selection marker in the thymidine kinase locus can be removed.

Example 8. Nucleotide Sequence Variations Between Various VACV Strains within the Terminal Hairpin and Duplex Region in the ITRs Nucleotide sequence variations in the "duplex" region directly downstream of the concatemer resolution site in the VACV WR strain, ACAM 2000, Dryvax, and Copenhagen strains are shown in FIG. 9. Sequence variations are seen as 4 nucleotide substitutions and 3 nucleotide deletions between the wtACAM2000, Dryvax DPP15, TianTan, and Copenhagen strains, compared to the WR strain.

Example 9. Determination of Virulence in a Murine Intranasal Model or Via Tail Scarification The toxicity effects of scVACV ACAM20000-WR DUP/HP and scVACV ACAM2000-ACAM2000 DUP/HP are determined in this study. For this experiment, 6 groups of Balb/c mice are administered 3 different doses of scVACV ACAM20000-WR DUP/HP and scVACV ACAM2000-ACAM2000 DUP/HP described in Examples 1-7 and compared to a PBS control group, as well as a wtVACV (WR) control group and a wtVACV ACAM2000 control group (12 treatment groups in total). There are 3 additional mice included in this experiment that do not receive any treatment for the duration of the study. All mice are sampled for blood at predetermined points throughout the experiment and the additional mice serve as a baseline for serum analysis.

Prior to inoculation of Balb/c mice, all virus strains are grown in BSC-40 cells (African green monkey kidney), harvested by trypsinization, washed in PBS, extracted from cells by dounce homogenization, purified through a 36% sucrose cushion by ultracentrifugation, resuspended in PBS, and titered such that the final concentrations are between 107 PFU/ml and 109 PFU/ml.

The doses chosen for this study (105 PFU/dose, 106 PFU/dose, and 107 PFU/dose) are based on previous studies using known vaccine strains of VACV, including Dryvax and IOC (Medaglia M L, Moussatche N, Nitsche A, Dabrowski P W, Li Y, Damon I K, et al. Genomic Analysis, Phenotype, and Virulence of the Historical Brazilian Smallpox Vaccine Strain IOC: Implications for the Origins and Evolutionary Relationships of Vaccinia Virus. Journal of virology. 2015; 89 (23): 11909-25; Qin L, Favis N, Famulski J, Evans D H. Evolution of and evolutionary relationships between extant vaccinia virus strains. Journal of virology. 2015; 89 (3): 1809-24).

The viruses are administered intranasally or via tail scarification. See details on Examples and 11 below.

Example 10. Determine Whether scVACV Administered Via Intranasal Inoculation Confers Immune Protection Against a Lethal VACV-WR Challenge Since weight loss is used as a measurement of virulence in mice, wtVACV (strain WR) is administered intranasally at a dose of $5\times10^3$ PFU, which leads to approximately 20-30% weight loss. The VACV Dryvax clone, DPP15, is also administered intranasally at 107 PFU/dose, so that the virulence of this well-known Smallpox vaccine can be directly compared to the synthetic versions scVACV ACAM20000-WR DUP/HP and scVACV ACAM2000-ACAM2000 DUP/HP. Mice are purchased from Charles River Laboratories and once received, are acclimatized to their environment for at least one week prior to virus administration.

Each mouse receives a single dose of virus (~10 μl) administered via the intranasal injection while under anesthesia. Mice are monitored for signs of infection, such as swelling, discharge, or other abnormalities every day for a period of 30 days. Each mouse is specifically monitored for weight loss every day after virus administration. Mice that lose more than 25% of their body weight in addition to other morbidity factors are subjected to euthanasia in accordance with our animal health care facility protocols at the University of Alberta.

Even at the highest doses of scVACV ACAM20000-WR DUP/HP and scVACV ACAM2000-ACAM2000 DUP/HP tested, there may be no overt signs of illness in Balb/c mice. One of the VACV strains (Brazilian Smallpox Vaccine Strain IOC), in some cases produced no disease at 107 PFU (Medaglia M L, Moussatche N, Nitsche A, Dabrowski P W, Li Y, Damon I K, et al. Genomic Analysis, Phenotype, and Virulence of the Historical Brazilian Smallpox Vaccine Strain IOC: Implications for the Origins and Evolutionary Relationships of Vaccinia Virus. Journal of virology. 2015; 89 (23): 11909-25). It is impractical to test much higher doses than this due to the difficulty of making purified stocks with titers in excess of 109 PFU/mL.

Thirty days post virus inoculation, mice are subsequently challenged with a lethal dose of VACV-WR (106 PFU/dose) via intranasal inoculation. Mice are closely monitored for signs of infection as described above. Mice are weighed daily and mice that lose greater than 25% of their body weight in addition to other morbidity factors are subjected to euthanasia. It is expected that mice inoculated with PBS prior to administration of a lethal dose of VACV-WR show signs of significant weight loss and other morbidity factors within 7-10 days post inoculation. Approximately 14 days post lethal challenge with VACV-WR all mice are euthanized and blood is collected to confirm the presence of VACV-specific neutralizing antibodies in the serum by standard plaque reduction assays.

Example 11. Determine Whether scVACV Administered Via Tail Scarification Confers Immune Protection Against a Lethal VACV-WR Challenge Immunocompetent Balb/C animals are anesthesized prior to the start of the tail scarification procedure. At the base of the tail, a series of 15-20 scratches/pricks are made using the tip of a 25 gauge needle over a 1-2 cm length. A volume of 3-5 μL of the different viruses is applied to the scarification site.

The mouse is left anesthetized until the virus has had a chance to absorb into the site of scarification. Mice are monitored daily for signs of weight loss over a 28 day period. A pustule forms at the site of tail scarification (known as a "take") ~8-10 days post scarification.

Twenty-eight days post virus inoculation, mice are subsequently challenged with a lethal dose of VACV-WR (106 PFU/dose) via intranasal inoculation. Mice are closely monitored for signs of infection as described above. Mice are weighed daily and mice that lose greater than 25% of their body weight in addition to other morbidity factors are subjected to euthanasia. It is expected that mice inoculated with PBS prior to administration of a lethal dose of VACV-WR show signs of significant weight loss and other morbidity factors within 7-10 days post inoculation. Approximately 14 days post lethal challenge with VACV-WR all mice are euthanized and blood is collected to confirm the presence of VACV-specific neutralizing antibodies in the serum by standard plaque reduction assays.

All of the unvaccinated animals succumb to this lethal dose of VACV WR within 7 days post virus challenge.

The invention claimed is:

1. A synthetic chimeric vaccinia virus (scVACV) that is replicated and reactivated from DNA derived from chemically synthesized DNA, the genome of said scVACV comprising one or more modifications to eliminate one or more unique restriction sites or to add or repair one or more unique restriction sites relative to a wild type vaccinia virus genome, wherein the scVACV further comprises a left and a right terminal hairpin loop derived from chemically synthesized DNA, one or both of the terminal hairpin loops being heterologous relative to the wild type vaccinia virus genome, and wherein the one or both of the terminal hairpin loops comprise different tandem repeat regions or a different number thereof relative to the wild type form of the one or both of the terminal hairpin loops.

2. The scVACV of claim 1, wherein the one or more modifications to eliminate one or more unique restriction sites comprises eliminating one or more AarI restriction sites or one or more BsaI restriction sites.

3. The scVACV of claim 1, wherein the wild-type vaccinia virus genome is selected from the group of strains consisting of: Western Reserve, Clone 3, Tian Tan, Tian Tan clone TP5, Tian Tan clone TP3, NYCBH, NYCBH clone Acambis 2000, Wyeth, Copenhagen, Lister, Lister 107, Lister-LO, Lister GL-ONC1, Lister GL-ONC2, Lister GL-ONC3, Lister GL-ONC4, IHD-W, LC16m18, Lederle, Tashkent clone TKT3, Tashkent clone TKT4, USSR, Evans, Praha, L-IVP, V—VET1, LIVP 6.1.1, Ikeda, EM-63, Malbran, Duke, 3737, CV-1, Serro 2, CM-01, NYCBH Dryvax clone DPP13, NYCBH Dryvax clone DPP15, NYCBH Dryvax clone DPP20, NYCBH Dryvax clone DPP17, NYCBH Dryvax clone DPP21, VACV-IOC, Chorioallantois Vaccinia virus Ankara (CVA), Modified vaccinia Ankara (MVA), and MVA-BN.

4. The scVACV of claim 1, wherein the one or both of the terminal hairpin loops are independently selected from a slow form or a fast form of a terminal hairpin loop of the wild-type vaccinia virus.

5. The scVACV of claim 4, wherein:

(a) the slow form is independently selected from a group of nucleotide sequences that comprises a nucleotide sequence that is at least 85% identical to, that is at least 90% identical to, that is at least 95% identical to, and that consists of the nucleotide sequence of SEQ ID NO: 13 or SEQ ID NO: 19; and (b) the fast form is independently selected from a group of nucleotide sequences that comprises a nucleotide sequence that is at least 85% identical to, that is at least 90% identical to, that is at least 95% identical to, and that consists of the nucleotide sequence of SEQ ID NO: 14 or SEQ ID NO: 20.

6. The scVACV of claim 1, wherein the scVACV is replicated and reactivated from DNA derived from overlapping chemically synthesized DNA fragments comprising one or more modifications relative to the wild type vaccinia virus genome.

7. The scVACV of claim 1, wherein the scVACV is reactivated using leporipoxvirus-catalyzed recombination and reactivation, and wherein the leporipoxvirus is selected from the group consisting of: Shope fibroma virus (SFV), hare fibroma virus, rabbit fibroma virus, squirrel fibroma virus, and myxoma virus.

8. A method of producing a synthetic chimeric vaccinia virus (scVACV) that is replicated and reactivated from DNA derived from chemically synthesized DNA comprising the steps of:

(i) chemically synthesizing DNA fragments, the DNA fragments corresponding to the DNA that is replicated and reactivated and comprising one or more modifications to eliminate one or more unique restriction sites or to add or repair one or more unique restriction sites relative to a wild type vaccinia virus genome;

(ii) chemically synthesizing DNA corresponding to a left and a right terminal hairpin loop, one or both loops being heterologous relative to the wild type vaccinia virus genome and wherein one or both of the terminal hairpin loops comprise different tandem repeats regions, or a different number thereof, than a corresponding wild type terminal hairpin loop, and ligating the terminal hairpin loops derived from the chemically synthesized terminal hairpin loops to the corresponding left termini and right termini of the DNA fragments derived from the chemically synthesized DNA of step (i);

(iii) transfecting the ligated DNA fragments of step (ii) into helper virus-infected cells;

(iv) culturing said cells to produce a mixture of helper virus and scVACV particles in said cells; and (v) plating the mixture on host cells specific to the scVACV to recover the scVACV.

9. The method of claim 8, wherein the helper virus is selected from the group consisting of: a leporipoxvirus, a fowlpox virus and a psoralen-inactivated helper virus.

10. The method of claim 8, wherein the helper virus-infected cells are BGMK cells.

11. The method of claim 8, wherein the DNA fragments comprise:

(i) nucleotide sequences that are at least 85% identical to the sequences of SEQ ID NOs: 1-9;

(ii) nucleotide sequences that are at least 90% identical to the sequences of SEQ ID NOs: 1-9;

(iii) nucleotide sequences that are at least 95% identical to the sequences of SEQ ID NOs: 1-9; or (iv) nucleotide sequences that consist of the sequences of SEQ ID NOs: 1-9.

12. A pharmaceutical composition comprising an scVACV of claim 1 and a pharmaceutically acceptable carrier.

13. The pharmaceutical composition according to claim 12, wherein the scVACV is inactivated by heat, UV, or formalin.

14. A method of triggering or boosting an immune response or immunizing a human subject against vaccinia virus, variola virus, or monkeypox virus, comprising administering to a subject in need thereof the scVACV of claim 1 or a pharmaceutical composition comprising the scVACV and a pharmaceutically acceptable carrier.

15. A method of treating a variola virus infection or cancer, comprising administering to a subject in need thereof the scVACV of claim 1 or a pharmaceutical composition comprising the scVACV and a pharmaceutically acceptable carrier.

* * * * *